US010744164B2

(12) United States Patent
Mistry et al.

(10) Patent No.: US 10,744,164 B2
(45) Date of Patent: *Aug. 18, 2020

(54) REPAIR AND REGENERATION OF OCULAR TISSUE USING POSTPARTUM-DERIVED CELLS

(71) Applicant: DePuy Synthes Products, Inc., Raynham, MA (US)

(72) Inventors: Sanjay Mistry, Downingtown, PA (US); Darin J. Messina, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/992,431

(22) Filed: Jan. 11, 2016

(65) Prior Publication Data

US 2016/0193255 A1 Jul. 7, 2016

Related U.S. Application Data

(63) Continuation of application No. 14/444,689, filed on Jul. 28, 2014, now Pat. No. 9,234,172, which is a continuation of application No. 12/054,718, filed on Mar. 25, 2008, now Pat. No. 8,790,637, which is a continuation-in-part of application No. 10/877,541, filed on Jun. 25, 2004, now Pat. No. 7,413,734.

(60) Provisional application No. 60/483,264, filed on Jun. 27, 2003.

(51) Int. Cl.
  *A61K 35/12* (2015.01)
  *A61K 35/51* (2015.01)
  *A61K 9/00* (2006.01)
  *C12N 5/073* (2010.01)
  *C12N 5/074* (2010.01)
  *C12N 5/079* (2010.01)

(52) U.S. Cl.
  CPC ............ *A61K 35/51* (2013.01); *A61K 9/0048* (2013.01); *C12N 5/0605* (2013.01); *C12N 5/0607* (2013.01); *C12N 5/0618* (2013.01); *A61K 35/12* (2013.01); *C12N 2500/32* (2013.01); *C12N 2500/34* (2013.01); *C12N 2500/44* (2013.01); *C12N 2500/90* (2013.01); *C12N 2500/95* (2013.01); *C12N 2501/12* (2013.01); *C12N 2501/21* (2013.01); *C12N 2501/23* (2013.01); *C12N 2502/02* (2013.01); *C12N 2506/02* (2013.01); *C12N 2506/025* (2013.01); *C12N 2506/03* (2013.01); *C12N 2506/08* (2013.01); *C12N 2509/00* (2013.01); *C12N 2533/50* (2013.01)

(58) Field of Classification Search
  CPC .... A61K 35/51; C12N 5/0618; C12N 5/0619; C12N 5/0621; C12N 2506/025
  See application file for complete search history.

(56) References Cited

U.S. PATENT DOCUMENTS

| | | |
|---|---|---|
| 3,665,061 A | 5/1972 | Eberly, Jr. |
| 3,930,954 A | 1/1976 | Irie et al. |
| 4,193,992 A | 3/1980 | Fontaine et al. |
| 4,216,144 A | 8/1980 | Ashmead |
| 4,290,962 A | 9/1981 | Tachi et al. |
| 4,352,883 A | 10/1982 | Lim |
| 4,393,240 A | 7/1983 | Stille |
| 4,465,776 A | 8/1984 | Cidlowski et al. |
| 4,487,865 A | 12/1984 | Balazs et al. |
| 4,544,516 A | 10/1985 | Hughes et al. |
| 4,657,866 A | 4/1987 | Kumar et al. |
| 4,882,162 A | 11/1989 | Ikada et al. |
| 4,925,677 A | 5/1990 | Feijen |
| 4,963,489 A | 10/1990 | Naughton et al. |
| 5,004,681 A | 4/1991 | Boyse et al. |
| 5,192,553 A | 3/1993 | Boyse et al. |
| 5,248,608 A | 9/1993 | Van Dooren et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,466,233 A | 11/1995 | Weiner et al. |
| 5,486,359 A | 1/1996 | Caplan et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,693,332 A | 12/1997 | Hansbrough |
| 5,698,518 A | 12/1997 | Carson et al. |
| 5,707,643 A | 1/1998 | Ogura et al. |
| 5,718,922 A | 2/1998 | Herrero-Vanrell et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,843,781 A | 12/1998 | Ballermann et al. |

(Continued)

FOREIGN PATENT DOCUMENTS

| | | |
|---|---|---|
| CN | 1407088 | 2/2003 |
| EP | 0333328 | 9/1989 |

(Continued)

OTHER PUBLICATIONS

None (Year: 0000).*

(Continued)

*Primary Examiner* — Jennifer Dunston

(57) ABSTRACT

Cells derived from postpartum umbilicus and placenta are disclosed. Pharmaceutical compositions, devices and methods for the regeneration or repair of ocular tissue using the postpartum-derived cells are also disclosed.

16 Claims, 18 Drawing Sheets

Specification includes a Sequence Listing.

(56) References Cited

U.S. PATENT DOCUMENTS

| | | |
|---|---|---|
| 5,855,619 A | 1/1999 | Caplan et al. |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,928,214 A | 7/1999 | Rubinstein et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hotten et al. |
| 6,001,647 A | 12/1999 | Peck et al. |
| 6,022,743 A | 2/2000 | Naughton et al. |
| 6,059,968 A | 5/2000 | Wolf, Jr. |
| 6,140,039 A | 10/2000 | Naughton et al. |
| 6,153,591 A | 11/2000 | Cai et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,261,600 B1 | 7/2001 | Kirschner et al. |
| 6,261,841 B1 | 7/2001 | Cohen et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 8,658,152 B2 | 2/2014 | Messina et al. |
| 8,703,121 B2 | 4/2014 | Harris et al. |
| 8,741,638 B2 | 6/2014 | Harmon et al. |
| 8,790,637 B2 | 7/2014 | Mistry et al. |
| 8,815,587 B2 | 8/2014 | Harris et al. |
| 9,234,172 B2 | 1/2016 | Misty et al. |
| 9,498,501 B2 | 11/2016 | Misty et al. |
| 9,504,719 B2 | 11/2016 | Brown et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182241 A1 | 12/2002 | Borenstein et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0158089 A1 | 8/2003 | Gallop et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0204387 A1 | 10/2004 | McLaurin |
| 2004/0224401 A1 | 11/2004 | Ludwig et al. |
| 2005/0019865 A1 | 1/2005 | Kihm et al. |
| 2005/0032209 A1 | 2/2005 | Messina et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0058634 A1 | 3/2005 | Zhu |
| 2005/0074435 A1 | 4/2005 | Casper et al. |
| 2005/0089513 A1 | 4/2005 | Sakuragawa et al. |
| 2005/0118144 A1 | 6/2005 | Zhang et al. |

(56) References Cited

U.S. PATENT DOCUMENTS

| | | |
|---|---|---|
| 2005/0148074 A1 | 7/2005 | Davies et al. |
| 2005/0249731 A1 | 11/2005 | Aslan et al. |
| 2006/0094113 A1 | 5/2006 | Epstein et al. |
| 2006/0128014 A1 | 6/2006 | Haggblad et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0281793 A1 | 12/2006 | Gupta et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0264713 A1 | 11/2007 | Terstegge et al. |
| 2007/0275362 A1 | 11/2007 | Edinger et al. |
| 2008/0038782 A1 | 2/2008 | Borns |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2008/0226595 A1 | 9/2008 | Edinger et al. |
| 2008/0274087 A1 | 11/2008 | Li et al. |
| 2008/0305148 A1 | 12/2008 | Fu |
| 2009/0092653 A1 | 4/2009 | Colter et al. |
| 2009/0166178 A1 | 7/2009 | Harmon et al. |
| 2009/0169597 A1 | 7/2009 | Brown et al. |
| 2009/0186358 A1 | 7/2009 | Melville et al. |
| 2010/0158877 A1 | 6/2010 | Colter et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0247499 A1 | 9/2010 | Kihm et al. |
| 2010/0260843 A1 | 10/2010 | Messina et al. |
| 2010/0272803 A1 | 10/2010 | Mistry et al. |
| 2012/0315251 A1 | 12/2012 | Harris et al. |
| 2013/0022585 A1 | 1/2013 | Messina et al. |
| 2013/0216508 A1 | 8/2013 | Anversa et al. |
| 2014/0045263 A1 | 2/2014 | Mistry et al. |
| 2014/0154226 A1 | 6/2014 | Messina et al. |
| 2015/0064781 A1 | 3/2015 | Mistry et al. |
| 2016/0158293 A1 | 6/2016 | Harris et al. |
| 2016/0166619 A1 | 6/2016 | Harris et al. |
| 2017/0080033 A1 | 3/2017 | Harris et al. |
| 2017/0157179 A1 | 6/2017 | Harris et al. |

FOREIGN PATENT DOCUMENTS

| | | |
|---|---|---|
| EP | 1216718 | 6/2002 |
| EP | 1316322 | 6/2003 |
| EP | 1405649 | 4/2004 |
| JP | 2003235549 | 8/2003 |
| JP | 2004254682 | 9/2004 |
| WO | WO-9011354 | 10/1990 |
| WO | WO-9203917 | 3/1992 |
| WO | WO-9304169 | 3/1993 |
| WO | WO-9425584 | 11/1994 |
| WO | WO-9517911 | 7/1995 |
| WO | WO-95-23216 | 8/1995 |
| WO | WO-9601316 | 1/1996 |
| WO | WO-9605309 | 2/1996 |
| WO | WO-9817791 | 4/1998 |
| WO | WO-9851317 | 11/1998 |
| WO | WO-9903973 | 1/1999 |
| WO | WO-9928444 | 6/1999 |
| WO | WO-00009666 | 2/2000 |
| WO | WO-00038762 | 7/2000 |
| WO | WO-00046351 | 8/2000 |
| WO | WO-00073421 | 12/2000 |
| WO | WO-01011011 | 2/2001 |
| WO | WO-01019379 | 3/2001 |
| WO | WO-01034775 | 5/2001 |
| WO | WO-02036751 | 5/2002 |
| WO | WO-02046373 | 6/2002 |
| WO | WO-02059278 | 8/2002 |
| WO | WO-02061053 | 8/2002 |
| WO | WO-02062969 | 8/2002 |
| WO | WO-02063962 | 8/2002 |
| WO | WO-02064748 | 8/2002 |
| WO | WO-02064755 | 8/2002 |
| WO | WO-02086107 | 10/2002 |
| WO | WO-03023020 | 3/2003 |
| WO | WO-03025149 | 3/2003 |
| WO | WO-03029443 | 4/2003 |
| WO | WO-03029445 | 4/2003 |
| WO | WO-03039489 | 5/2003 |
| WO | WO-03042405 | 5/2003 |
| WO | WO-03048336 | 6/2003 |
| WO | WO-03054146 | 7/2003 |
| WO | WO-03055992 | 7/2003 |
| WO | WO-03064601 | 8/2003 |
| WO | WO-03066832 | 8/2003 |
| WO | WO-03068937 | 8/2003 |
| WO | WO-03070922 | 8/2003 |
| WO | WO-03072728 | 9/2003 |
| WO | WO-03080822 | 10/2003 |
| WO | WO-03087333 | 10/2003 |
| WO | WO-03087392 | 10/2003 |
| WO | WO-03089619 | 10/2003 |
| WO | WO-03100038 | 12/2003 |
| WO | WO-03102134 | 12/2003 |
| WO | WO-03102151 | 12/2003 |
| WO | WO-03104442 | 12/2003 |
| WO | WO-04011012 | 2/2004 |
| WO | WO-04011621 | 2/2004 |
| WO | WO-04016747 | 2/2004 |
| WO | WO-04023100 | 3/2004 |
| WO | WO-04072273 | 8/2004 |
| WO | WO-05001076 | 1/2005 |
| WO | WO-05001077 | 1/2005 |
| WO | WO-05001078 | 1/2005 |
| WO | WO-05001079 | 1/2005 |
| WO | WO-05001080 | 1/2005 |
| WO | WO-05003334 | 1/2005 |
| WO | WO-05021738 | 3/2005 |
| WO | WO-05038012 | 4/2005 |
| WO | WO-05042703 | 5/2005 |
| WO | WO-06027229 | 3/2006 |
| WO | WO-06036826 | 4/2006 |
| WO | WO-06071773 | 7/2006 |
| WO | WO-06071777 | 7/2006 |
| WO | WO-06071778 | 7/2006 |
| WO | WO-06071794 | 7/2006 |
| WO | WO-06071802 | 7/2006 |
| WO | 06/083394 | 8/2006 |
| WO | WO-06105152 | 10/2006 |
| WO | WO-07073552 | 6/2007 |
| WO | WO-07108003 | 9/2007 |
| WO | WO-08045498 | 4/2008 |
| WO | WO-08060541 | 5/2008 |
| WO | WO 08/085221 | 7/2008 |
| WO | WO 09/046335 | 4/2009 |
| WO | WO 09/085860 | 7/2009 |
| WO | WO 10/071862 | 6/2010 |
| WO | WO 10/071863 | 6/2010 |
| WO | WO 10/071864 | 7/2010 |
| WO | WO 10/080364 | 7/2010 |
| WO | WO 10/111663 | 9/2010 |
| WO | 16/090215 A2 | 6/2016 |
| WO | 16/099949 A2 | 6/2016 |

(56) References Cited

FOREIGN PATENT DOCUMENTS

| | | |
|---|---|---|
| WO | 2017095991 A1 | 6/2018 |
| WO | 2018102174 A1 | 6/2018 |

OTHER PUBLICATIONS

Baksh, D. et al., "Adult mesenchymal stem cells: characterization, differentiation, and application in cell and gene therapy", J Cell Mol Med., 2004; 8(3):301-16.
Broxmeyer, H.E. et al., "Growth characteristics and expansion of human umbilical cord blood and estimation of its potential for transplantation in adults," PNAS, 1992; 89(9): 4109-4113.
Cai, J. et al., "Stem cell and precursor cell therapy," NeuroMolecular Medicine, 2002; 3:233-249.
Caplan, A. I. et al., "Mesenchymal Stem Cells as Trophic Mediators," J Cell Biochem., 2006; 98:1076-84.
Das et al., "Retinal and Choroidal Angiogenesis: Pathophysiology and Strategies for Inhibition," Progress in Retinal and Eye Research, 2003; 22:721-748.
Diao et al., "Human Umbilical Cord Mesenchymal Stem Cells: Osteogenesis in Vivo as Seed Cells for Bone Tissue Engineering," J. BioMed Mater Res., 2009; 91A:123-131.
Haynesworth et al., "Cell Surface Antigens on Human Marrow-Derived Mesenchymal Cells are Detected by Monoclonal Antibodies," Bone, 1992; 13:69-80.
Henderson, GI, et al., "Inhibition of Placental Valine Uptake after Acute and Chronic Maternal Ethanol Consumption", J Pharmacol Exp Therap, 1981; 216:465-472.
Leventhal, C. et al. "Endothelial trophic support for neuronal production and recruitment from the adult mammalian subependyma," Molecular and Cellular Neuroscience, 1999; 13; 450-464.
Lund, R.D. et al., "Cell Isolated from Umbilical Cord Tissue Rescue Photoreceptors and Visual Functions in a Rodent Model of Retinal Disease," Stem Cells, 2007; 25:602-611.
Makino, S. et al., "Cardiomyocytes can be generated from marrow stromal cells in vitro," J. Clin. Invest., 1999; 103:697-705.
Mankikar, S.D., "Stem Cells: A New Paradigm in Medical Therapeutics," Journal of Long-Term Effects of Medical Implants, 2010; 20:219-250.
Naughton, B.A. et al., "Hematopoiesis on nylon mesh templates. I. Long-term culture of rat bone marrow cells.," Journal of Medicine, 1987; 18(3-4):219-50.
Naughton et al., "Cells isolated from Wharton's jelly of the human umbilical cord develop a cartilage phenotype when treated with TGF-b in vitro," FASEB J, 1997; 11:A19 (Abstract 108).
Otsuka, A. et al. "Lipopolysaccharide augments HLA-A,B,C molecule expression but inhibits interferon-gamma-induced HLA-DR molecule expression on cultured human endothelial cells," Immunology, 1991; 73; 428-432.
Secco, M. et al., "Multipotent Stem Cells from Umbilical Cord: Cord is Richer than Blood!" Stem Cells, 2008; 26:146-150.
Seiji, T. et al., Possibility of Regenerative Medicine Using Human Amniotic Cells, Regenerative Medicine, 2002; 1(2):79-85 (with English language Abstract).
Troyer, D. L. et al., "Concise Review: Wharton's Jelly-Derived Cells Are a Primitive Stromal Cell Population," Stem Cells, 2008; 26:591-599.
Wakitani, S. et al., "Mesenchymal cell-based repair of large, full-thickness defects of articular cartilage.", J Bone Joint Surg Am, 1994 ; 76(4): 579-592.
Wang, Y. et al., "Enhanced Recovery of Hematopoietic Progenitor and Stem Cells from Cultivated, Postpartum Human Placenta," Blood, 2001; 98(11): 183a (Abstract 769).
Weiss, M.L. et al., "Stem Cells in the Umbilical Cord," Stem Cell Rev., 2006; 2(2):155-162.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.

(56) References Cited

OTHER PUBLICATIONS

In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U.S. Patent and Trademark Office, Final Office Action in re: U.S. Appl. No. 11/315,898, dated Sep. 16, 2008, 8 pages.
In the U.S. Patent and Trademark Office, Non-Final Office Action in re: U.S. Appl. No. 11/317,574, dated Sep. 30, 2008, 23 pages.
In the U.S. Patent and Trademark Office, Non-Final Office Action in re: U.S. Appl. No. 11/315,969, dated Dec. 23, 2008, 11 pages.
In the U.S. Patent and Trademark Office, Non-Final Office Action in re: U.S. Appl. No. 11/321,864, dated Jan. 8, 2009, 10 pages.
In the U.S. Patent and Trademark Office, Final Office Action in re: U.S. Appl. No. 11/321,863, dated Feb. 12, 2009, 15 pages.
In the U.S. Patent and Trademark Office, Non-Final Office Action in re: U.S. Appl. No. 11/315,943, dated Feb. 20, 2009, 9 pages.
In the U.S. Patent and Trademark Office, Non-Final Office Action in re: U.S. Appl. No. 10/877,445, dated Mar. 19, 2009, 15 pages.
In the U.S. Patent and Trademark Office, Non-Final Office Action in re: U.S. Appl. No. 11/481,481, dated Mar. 20, 2009, 12 pages.
In the U.S. Patent and Trademark Office, Final Office Action in re: U.S. Appl. No. 11/315,897, dated Mar. 20, 2009, 13 pages.
In the U.S. Patent and Trademark Office, Non-Final Office Action in re: U.S. Appl. No. 11/481,480, dated Mar. 20, 2009, 13 pages.
In the U.S. Patent and Trademark Office, Final Office Action in re: U.S. Appl. No. 11/322,003 dated Feb. 13, 2009, 17 pages.
In the U.S. Patent and Trademark Office, Final Office Action in re: U.S. Appl. No. 10/876,998 dated Feb. 13, 2009, 10 pages.
In the U.S. Patent and Trademark Office, Final Office Action in re: U.S. Appl. No. 11/322,372 dated Feb. 13, 2009, 14 pages.
In the U.S. Patent and Trademark Office, Non-Final Office Action in re: U.S. Appl. No. 11/315,898 dated Feb. 18, 2009, 10 pages.
In the U.S. Patent and Trademark Office, Non-Final Office Action in re: U.S. Appl. No. 11/481,456 dated Apr. 16, 2009, 14 pages.
In the U.S. Patent and Trademark Office, Non-Final Office Action in re: U.S. Appl. No. 11/317,574 dated Apr. 29, 2009, 21 pages.
In the U.S. Patent and Trademark Office, Advisory Action in re: U.S. Appl. No. 11/315,969 dated Sep. 29, 2009, 8 pages.
In the U.S. Patent and Trademark Office, Advisory Action in re: U.S. Appl. No. 11/322,372 dated May 12, 2009, 10 pages.
In the U.S. Patent and Trademark Office, Non-Final Office Action in re: U.S. Appl. No. 10/877,446 dated Jun. 12, 2009, 16 pages.
In the U.S. Patent and Trademark Office, Final Office Action in re: U.S. Appl. No. 11/322,372 dated Aug. 6, 2009, 12 pages.
In the U.S. Patent and Trademark Office, Final Office Action in re: U.S. Appl. No. 11/617,346 dated Aug. 11, 2009, 12 pages.
In the U.S. Patent and Trademark Office, Final Office Action in re: U.S. Appl. No. 11/481,456 dated Oct. 9, 2009, 11 pages.
In the U.S. Patent and Trademark Office, Final Office Action in re: U.S. Appl. No. 10/877,445 dated Aug. 25, 2009, 18 pages.
In the U.S. Patent and Trademark Office, Final Office Action in re: U.S. Appl. No. 11/321,863 dated Aug. 7, 2009, 11 pages.
In the U.S. Patent and Trademark Office, Final Office Action in re: U.S. Appl. No. 11/321,864 dated Aug. 17, 2009, 13 pages.
In the U.S. Patent and Trademark Office, Final Office Action in re: U.S. Appl. No. 11/315,969 dated May 13, 2009, 11 pages.
In the U.S. Patent and Trademark Office, Non-Final Office Action in re: U.S. Appl. No. 11/317,574 dated Dec. 28, 2009, 26 pages.
In the U.S. Patent and Trademark Office, Non-Final Office Action in re: U.S. Appl. No. 11/321,863 dated Jan. 7, 2010, 13 pages.
In the U.S. Patent and Trademark Office, Non-Final Office Action in re: U.S. Appl. No. 11/321,864 dated Jan. 27, 2010, 12 pages.
In the U.S. Patent and Trademark Office, Non-Final Office Action in re: U.S. Appl. No. 11/315,969 dated Jan. 27, 2010, 12 pages.
In the U.S. Patent and Trademark Office, Non-Final Office Action in re: U.S. Appl. No. 11/315,943 dated Feb. 19, 2010, 13 pages.
In the U.S. Patent and Trademark Office, Final Office Action in re: U.S. Appl. No. 11/316,104 dated Mar. 24, 2010, 12 pages.
In the U.S. Patent and Trademark Office, Non-Final Office Action in re: U.S. Appl. No. 11/481,456 dated May 14, 2010, 9 pages.
In the U.S. Patent and Trademark Office, Non-Final Office Action in re: U.S. Appl. No. 11/481,481 dated May 13, 2010, 9 pages.
In the U.S. Patent and Trademark Office, Final Office Action in re: U.S. Appl. No. 11/315,897 dated May 14, 2010, 13 pages.
In the U.S. Patent and Trademark Office, Non-Final Office Action in re: U.S. Appl. No. 11/481,480 dated May 17, 2010, 10 pages.
In the U.S. Patent and Trademark Office, Final Office Action in re: U.S. Appl. No. 10/877,445 dated Jul. 8, 2010, 20 pages.
In the U.S. Patent and Trademark Office, Final Office Action in re: U.S. Appl. No. 10/876,998 dated Aug. 3, 2010, 14 pages.
In the U.S. Patent and Trademark Office, Non-Final Office Action in re: U.S. Appl. No. 11/321,863 dated Aug. 17, 2010, 15 pages.
In the U.S. Patent and Trademark Office, Final Office Action in re: U.S. Appl. No. 11/617,346 dated Aug. 20, 2010, 12 pages.
In the U.S. Patent and Trademark Office, Final Office Action in re: U.S. Appl. No. 11/321,864 dated Aug. 31, 2010, 7 pages.
In the U.S. Patent and Trademark Office, Final Office Action in re: U.S. Appl. No. 11/315,969 dated Aug. 31, 2010, 6 pages.
In the U.S. Patent and Trademark Office, Final Office Action in re: U.S. Appl. No. 11/322,372 dated Aug. 31, 2010, 11 pages.
In the U.S. Patent and Trademark Office, Non-Final Office Action in re: U.S. Appl. No. 12/245,571 dated Sep. 15, 2010, 8 pages.
In the U.S. Patent and Trademark Office, Non-Final Office Action in re: U.S. Appl. No. 11/316,104 dated Sep. 21, 2010, 13 pages.
In the U.S. Patent and Trademark Office, Final Office Action in re: U.S. Appl. No. 11/317,574 dated Oct. 6, 2010, 16 pages.
In the U.S. Patent and Trademark Office, Non-Final Office Action in re: U.S. Appl. No. 11/322,372 dated Jan. 21, 2010, 10 pages.
In the U.S. Patent and Trademark Office, Final Office Action in re: U.S. Appl. No. 11/481,481 dated Sep. 18, 2009, 11 pages.
In the U.S. Patent and Trademark Office, Advisory Action in re: U.S. Appl. No. 11/315,897 dated Jun. 30, 2009, 3 pages.
In the U.S. Patent and Trademark Office, Non-Final Office Action in re: U.S. Appl. No. 11/315,897 dated Sep. 2, 2009, 12 pages.
In the U.S. Patent and Trademark Office, Final Action in re: U.S. Appl. No. 11/481,480 dated Sep. 17, 2009, 12 pages.
In the U.S. Patent and Trademark Office, Final Action in re: U.S. Appl. No. 10/877,446 dated Jun. 4, 2010, 17 pages.
In the U.S. Patent and Trademark Office, Final Action in re: U.S. Appl. No. 11/617,346 dated Apr. 15, 2010, 7 pages.
In the U.S. Patent and Trademark Office, Non-Final Action in re: U.S. Appl. No. 11/316,104 dated Oct. 31, 2008, 15 pages.
In the U.S. Patent and Trademark Office, Final Action in re: U.S. Appl. No. 10/876,998 dated May 27, 2009, 14 pages.
In the U.S. Patent and Trademark Office, Non-Final Action in re: U.S. Appl. No. 10/876,998 dated Nov. 24, 2009, 7 pages.
In the U.S. Patent and Trademark Office, Final Action in re: U.S. Appl. No. 11/322,003 dated Feb. 13, 2009, 17 pages.
In the U.S. Patent and Trademark Office, Non-Final Office Action in re: U.S. Appl. No. 12/337,439 dated Jan. 6, 2011, 11 pages.
In the U.S. Patent and Trademark Office, Non-Final Action in re: U.S. Appl. No. 10/876,998 dated Feb. 1, 2011, 11 pages.
In the U.S. Patent and Trademark Office, Non-Final Action in re: U.S. Appl. No. 11/481,456 dated Feb. 3, 2011, 10 pages.
In the U.S. Patent and Trademark Office, Non-Final Action in re: U.S. Appl. No. 11/481,481 dated Feb. 3, 2011, 10 pages.
In the U.S. Patent and Trademark Office, Non-Final Action in re: U.S. Appl. No. 12/389,305 dated Feb. 8, 2011, 14 pages.
In the U.S. Patent and Trademark Office, Non-Final Action in re: U.S. Appl. No. 11/481,480 dated Feb. 3, 2011, 10 pages.
In the U.S. Patent and Trademark Office, Non-Final Office Action in re: U.S. Appl. No. 11/322,372 dated Jan. 16, 2014, 20 pages.

(56) References Cited

OTHER PUBLICATIONS

In the U.S. Patent and Trademark Office, Non-Final Office Action in re: U.S. Appl. No. 11/321,864 dated Jan. 29, 2014, 9 pages.
In the U.S. Patent and Trademark Office, Non-Final Office Action in re: U.S. Appl. No. 11/321,863 dated Jan. 31, 2014, 17 pages.
In the U.S. Patent and Trademark Office, Final Office Action in re: U.S. Appl. No. 11/317,574 dated Feb. 3, 2014, 16 pages.
In the U.S. Patent and Trademark Office, Non-Final Office Action in re: U.S. Appl. No. 10/876,998 dated Feb. 11, 2014, 14 pages.
In the U.S. Patent and Trademark Office, Non-Final Office Action in re: U.S. Appl. No. 12/389,305 dated Mar. 6, 2014, 38 pages.
In the U.S. Patent and Trademark Office, Non-Final Office Action in re: U.S. Appl. No. 11/316,104 dated Mar. 14, 2014, 11 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 22 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 17 pages.
In the U.S. Patent and Trademark Office, Final Office Action in re: U.S. Appl. No. 12/389,305 dated Aug. 6, 2014, 57 pages.
In the U.S. Patent and Trademark Office, Final Office Action in re: U.S. Appl. No. 10/877,446 dated Aug. 6, 2014, 35 pages.
In the U.S. Patent and Trademark Office, Final Office Action in re: U.S. Appl. No. 11/316,104 dated Aug. 6, 2014, 18 pages.
In the U.S. Patent and Trademark Office, Non-Final Office Action in re: U.S. Appl. No. 11/611,602 dated Oct. 9, 2014, 15 pages.
In the U.S. Patent and Trademark Office, Final Office Action in re: U.S. Appl. No. 11/317,574 dated Feb. 3, 2014, 12 pages.
In the U.S. Patent and Trademark Office, Final Office Action in re: U.S. Appl. No. 11/321,864 dated Nov. 3, 2014, 10 pages.
In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
Abbas, A.K. et al., *Cellular and Molecular Immunology*, 5th Ed. (2003) Saunders, Philadelphia, p. 171.
Aboody, K.S. et al., "Neural Stem Cells Display Extensive Tropism for Pathology in Adult Brain: Evidence From Intracranial Gliomase," *Proc. Natl. Acad. Sci. USA*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch Ophthalmol.*, 2001; 119(10): 1417-1436.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.

Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells,"*Biochem. & Biophys. Res. Comm.*, 2001; 288:156-164.
Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Baker, K.A. et al., "Intrastriatal and Intranigral Grafting of hNT Neurons in the 6-OHDA Rat Model of Parkinson's Disease," *Exper. Neurol.*, 2000; 162:350-360.
Baksh, D. et al., "Comparison of proliferative and multilineage differentiation potential of human mesenchymal stem cells derived from umbilical cord and bone marrow." *Stem Cells*, 2007; 25: 1384-1392.
Bakhshi, et al. "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Balis, F. et al., "Central Nervous System Pharmacology of Antileukemic Drugs," *Am. J. of Pediatric Hematol. Oncol.*, 1989; 11(1):74-86.
Balkema, G.W . et al., "Impaired Visual Thresholds in Hypopigmented Animals," *Visual Neuroscience*, 1991; 6:577-585.
Bao, Z.Z. et al., "Regulation of Chamber-Specific Gene Expression in the Developing Heart by IrX 4," *Science*, 1999; 283(5405):1161-1164 (Abstract 1 page).
Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.
Beck, R.W. et al., "A Clinical Comparison of Visual Field Testing With a New Automated Perimeter, The Humphrey Field Analyzer, and the Goldmann Perimeter," *Ophthalmology*, 1985; 92(1):77-82.
Bergers, G. et al., "The Role of Pericytes in Blood-Vessel Formation and Maintenance," *Neuro-Oncology*, 2005; 7:452-464.
Bhatia, R. et al., "A clinically suitable ex vivo expansion culture system for LTC-IC and CFC using stroma-conditioned medium," *Exp Hematol.*, 1997;25(9):980-91 (Abstract only).
Bhindi, R. et al., "Rat Models of Myocardial Infarction," *Thromb Haemost*, 2006; 96:602-610.
Björklund, L.M. et al., "Embryonic Stem Cells Develop Into Functional Dopaminergic Neurons After Transplantation in a Parkinson Rat Model," *Proc. Natl. Acad. Sci. USA*, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Boulton, A.J., "Diabetic neuropathy: classification, measurement and treatment," *Curr Opin Endocrinol Diabetes Obes*, 2007; 14(2):141-145.
Bradley, B.A., "The Role of HLA Matching in Transplantation," *Immunol. Lett.*, 1991; 29:55-59.
Brodsky, S.V., "Coagulation, Fibrinolysis and Angiogenesis: New Insights From Knockout Mice," *Exp. Nephrol.*, 2002; 10:299-306.
Brooks, P., "Inflammation As an Important Feature of Osteoarthritis," *Bull. World Health Org.*, 2003; 81(9):689-690.
Brown, J.A. et al., "Blockade of Programmed Death-1 Ligands on Dendritic Cells Enhances T Cell Activation and Cytokine Production," *J. Immunology*, 2003; 170:1257-1266.
Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.

(56) References Cited

OTHER PUBLICATIONS

Bussolati et al., "Isolation of Renal Progenitor Cells from Adult Human Kidney," *American Journal of Pathology*, 2005; 166(2):545-555.
Caballero, S. et al., "The Many Possible Roles of Stem Cells in Age-Related Macular Degeneration," *Graefe's Arch. Clin. Exp. Ophthalmol.*, 2004; 242:85-90.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.
Can et al., "Concise Review: Human Umbilical Cord Stroma with Regard to the Source of Fetus-Derived Stem Cells," *Stem Cells*, 2007; 25:2886-2895.
Cao, Q. et al., "Stem Cell Repair of Central Nervous System Injury," *J. of Neuroscience Res.*, 2002; 68:501-510.
Caplan, A.I. et al., "Mesenchymal Stem Cells: Building Blocks for Molecular Medicine in the 21st Century," *Trends in Molecular Med.*, 2001; 7(6):259-264.
Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.
Cell Isolation Theory, in Tissue Dissociation Guide, Worthington Biochemical, accessible at http://www.tissuedissociation.com, accessed Aug. 8, 2007.
Chader et al., "Animal Models in Research on Retinal Degenerations: Past Progress and Future Hope," *Vision Research*, 2002; 42:393-399.
Chagraoui, J. et al., "Fetal Liver Stroma Consists of Cells in Epithelial-To-Mesenchymal Transition," *Blood*, 2003; 101(8):2973-2982.
Chen, D., et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.
Chen, H. et al., "The Effect of Hypothermia on Transient Middle Cerebral Artery Occlusion in the Rat," *J. Cereb. Blood Flow Metab.*, 1992; 12(4):621-628.
Chen, J. et al., "Therapeutic Benefit of Intravenous Administration of Bone Marrow Stromal Cells after Cerebral Ischemia in Rats," *Stroke*, 2001; 32(4):1005-1011.
Chen, M. et al., "Synthesis of complement factor H by retinal pigment epithelial cells is down-regulated by oxidized photoreceptor outer segments," Experimental Eye Research, 2007 (EPub Dec. 21, 2006); 84(4):635-645.
Cheng, A., et al. "Nitric Oxide Acts in a Positive Feedback Loop With BDNF to Regulate Neural Progenitor Cell Proliferation and Differentiation in the Mammalian Brain," *Dev. Biol.*, 2003; 258:319-333.
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Constantini, S. et al., "The Effects of Methylprednisolone and the Ganglioside GM1 on Acute Spinal Cord Injury in Rats," *J. Neurosurg.*, 1994; 80(1):97-111.
Coumans, B. et al., "Lymphoid Cell Apoptosis Induced by Trophoblastic Cells: A Model of Active Foeto-Placental Tolerance," *J. of Immunological Methods*, 1999; 224:185-196.
Covas, D.T. et al., "Isolation and culture of umbilical vein mesenchymal stem cells." *Brazilian Journal of Medical and Biological Research*, 2003; 36: 1179-1183.
Curcio, C. et al., "Photoreceptor Loss in Age-Related Macular Degeneration," Investigative Ophthalmology & Visual Science, 1996; 37(7): 1236-1249.
D'Cruz, P.M. et al., "Mutation of the Receptor Tyrosine Kinase Gene Mertk in the Retinal Dystrophic RCS Rat," *Hum. Mol. Genet.*, 2000; 9(4):645-651.
Daley, G.Q. et al., "Realistic Prospects for Stem Cell Therapeutics," *Hematol.*, 2003; 398-418.

Danon, D. et al., "Macrophage Treatment of Pressure Sores in Paraplegia," *J. Wound Care*, 1998; 7(6):281-283.
Danon, D. et al., "Treatment of Human Ulcers by Application of Macrophages Prepared From a Blood Unit," *Exp. Gerontol.*, 1997; 32(6):633-641.
Davies, S.M. et al., "Engraftment and Survival After Unrelated-Donor Bone Marrow Transplantation: A Report From the National Marrow Donor Program," *Blood*, 2000; 96(13):4096-4102.
Dawson, T.M. et al., "Neuroprotective and Neurorestorative Strategies for Parkinson's Disease," *Nat. Neurosci.*, 2002; 5 Suppl.:1058-1061.
Deans, R.J. et al., "Mesenchymal stem cells: Biology and potential clinical uses," *Experimental Hematology, 2000; 28: 875-884*.
del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.
Dickinson, A.M. et al., "Non-HLA Immunogenetics in Hematopoietic Stem Cell Transplantation," *Curr. Opin. Immunol.*, 2005; 17(5):517-525.
Dimri, G.P. et al., "A Biomarker That Identifies Senescent Human Cells in Culture and in Aging Skin *In Vivo,*" *Proc. Natl. Acad. Sci. USA*, 1995; 92:9363-9367.
Domb, A. et al., "Degradable Polymers for Site-Specific Drug Delivery," *Polymers for Advanced Technologies*, 1992; 3:279-292.
Doshi, S.N. et al., "Evolving Role of Tissue Factor and Its Pathway Inhibitor," *Critical Care Med.*, 2002; 30(5):S241-250.
Doyle, J., "Spiraling Complexity, Robustness, and Fragility in Biology," http://www.cds.caltech.edu/~doyle/CmplxNets/Bio1.pdf, available online Feb. 28, 2004.
Draper et al., "Surface Antigens of Human Embryonic Stem Cells: Changes Upon Differentiation in Culture," *J. Anat.*, 2002; 200:249-258.
Du, Y. et al., "Functional Reconstruction of Rabbit Corneal Epithelium by Human Limbal Cells Cultured on Amniotic Membrane," *Molecular Vision*, 2003; 9:635-643.
Dykens, J. et al., "Photoreceptor Preservation in the S334ter Model of Retinitis Pigmentosa By a Novel Estradiol Analog", Biochemical Pharmacology, 2004; 68: 1971-1984.
Eagle, H., "The Specific Amino Acid Requirements of a Mammalian Cell (Strain L) in Tissue Culture," *J. Biol. Chem.*, 1955; 214(2):839-852.
Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).
Edelstein, M. L. et al., "Gene Therapy Clinical Trials Worldwide 1989-2004—An Overview," *J. Gene Med.*, 2004; 6(6):597-602.
Edlund, H., "Pancreatic Organogenesis—Developmental Mechanisms and Implications for Therapy," *Nat. Rev. Genet.*, 2002; 3:524-532.
Efrat, S. et al., "Cell Replacement Therapy for Type 1 Diabetes," *Trends in Molecular Medicine*, 2002; 8(7):334-339.
Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.
Ehtesham, M. et al., "The Use of Interleukin 12-Secreting Neural Stem Cells for the Treatment of Intracranial Glioma," *Cancer Res.*, 2002; 5657-5663.
Eisenhofer, G.E. et al., "Tyrosinase: A Developmentally Specific Major Determinant of Peripheral Dopamine," *FASEB J.*, 2003; 17:1248-1255.
Ende, N. et al., "Parkinson's Disease Mice and Human Umbilical Cord Blood," *J. Med.*, 2002; 33(1-4):173-180.
Engstad, C.S. et al., "The Effect of Soluble β -1,3-Glucan and Lipopolysaccharide on Cytokine Production and Coagulation Activation in Whole Blood," *Int. Immunopharmacol.*, 2002; 2:1585-1597.
Enzmann, V. et al., "Enhanced Induction of RPE Lineage Markers in Pluripotent Neural Stem Cells Engrafted Into the Adult Rat Subretinal Space," *Investig. Ophthalmol. Visual Sci.*, 2003; 44(12):5417-5422.
Erices et al., "Mesenchymal Progenitor Cells in Human Umbilical Cord Blood," *Br. J. Haematol.*, 2000; 109(1):235-242.

(56) References Cited

OTHER PUBLICATIONS

Fazleabas, A.T. et al., "Endometrial Function: Cell Specific Changes in the Uterine Environment," *Mol. & Cellular. Endo.*, 2002; 186:143-147.
Fernandes, A.M. et al., "Mouse Embryonic Stem Cell Expansion in a Microcarrier-based Stirred Culture System," *Journal of Biotechnology*, 2007; 132(2): 227-236.
Fiegel, H.C. et al., "Liver-Specific Gene Expression in Cultured Human Hematopoietic Stem Cells," *Stem Cells*, 2003;21:98-104.
Fields, G.B.,"Induction of Protein-Like Molecular Architecture by Self-Assembly Processes," *Bioorg. Med. Chem.*, 1999; 7(1):75-81.
Fischer, D. et al., "Counteracting the Nogo Receptor Enhances Optic Nerve Regeneration If Retinal Ganglion Cells Are in an Active Growth State," *J. Neurosci.*,2004; 24:1646-1651.
Fischer, D. et al., "Lens-Injury-Stimulated Axonal Regeneration Throughout the Optic Pathway of Adult Rats," *Exp. Neurol.*, 2001; 172:257-272.
Foley, A. et al., "Heart Induction: Embryology to Cardiomyocyte Regeneration," *Trends Cardiovasc. Med.*, 2004; 14(3):121-125.
Franc, S. et al., "Microfibrillar Composition of Umbilical Cord Matrix : Characterization of Fibrillin, Collagen VI and Intact Collagen V," *Placenta*, 1988; 19:95-104.
Freed, C.R. et al., "Transplantation of Embryonic Dopamine Neurons for Severe Parkinson's Disease," *N. Engl. J. Med.*, 2001; 344(10):710-719.
Frenkel, O. et al., "Activated Macrophages for Treating Skin Ulceration: Gene Expression in Human Monocytes After Hypo-Osmotic Shock," *Clin. Exp. Immunol.*, 2002; 128:59-66.
Friedman, J.A. et al., "Biodegradable Polymer Grafts for Surgical Repair of the Injured Spinal Cord," *Neurosurgery*, 2002; 51(3):742-751.
Fukuchi, Y. et al., "Human Placenta-Derived Cells Have Mesenchymal Stem/Progenitor Cell Potential," *Stem Cells*, 2004; 22(5):649-658.
Fukuda, K., "Reprogramming of Bone Marrow Mesenchymal Stem Cells Into Cardiomyocytes," *C.R. Biol.*, 2002; 325:1027-1038.
Gal, A. et al., "Mutations in MERTK, the human orthologue of the RCS rat retinal dystrophy gene, cause retinitis pigmentosa," *Nature Genet.*, 2000; 26(3):270-271.
Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Gökhan, S. et al., "Basic and Clinical Neuroscience Applications of Embryonic Stem Cells," *Anat. Rec. (New Anat)*, 2001; 265:142-156.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7: 581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.
Gottlieb, D.I. "Large-Scale Sources of Neural Stem Cells," *Annu. Rev. Neurosci.*, 2002; 25:381-407.
Gröhn, P. et al., "Collagen-Coated $BA^{2+}$-Alginate Microcarriers for the Culture of Anchorage-Dependent Mammalian Cells," *BioTechniques*, 1997; 22(5): 970-975.
Gupta, S. et al., "Isolation and Characterization of Kidney-Derived Stem Cells," *J. of Am. Soci. of Nephrol.*, 2006; 17(11):3028-3040.
Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.
Hanahan, D. "Heritable Formation of Pancreatic β -Cell Tumours in Transgenic Mice Expressing Recombinant Insulin/Simian Virus 40 Oncogenes," *Nature*, 1985; 315:115-122.
Hartgerink, J.D. et al., "Peptide-Amphiphile Nanofibers: A Versatile Scaffold for the Preparation of Self-Assembling Materials," *Proc. Natl. Acad. Sci. USA*, 2002; 99(8):5133-5138.

Haruta, M. et al., "In Vitro and in Vivo Characterization of Pigment Epithelial Cells Differentiated From Primate Embryonic Stem Cells," *Investig. Ophthalmol. & Visual Sci.*, 2004; 45(3):1020-1025.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Herrera, M.B. et al., "Mesenchymal Stem Cells Contribute to the Renal Repair of Acute Tubular Epithelial Injury," *Int. J. Mol. Med.*, 2004; 14(6):1035-1041.
Hill, D.P. et al., "Screening for Novel Pattern Formation Genes Using Gene Trap Approaches," *Methods in Enzymology*, 1993; 225:664-681.
Hill, M. et al., "Treatment for Swallowing Difficulties (Dysphagia) in Chronic Muscle Disease," *The Cochrane Library Cochrane Database Syst Rev.*, 2004; 2:1-12.
Hishikawa, K. et al., "Musculin/MyoR is Expressed in Kidney Side Population Cells and Can Regulate Their Function," *Journal of Cell Biology*, 2005; 169(6):921-928.
Ho, et al., "En Bloc Transfer of Extracellular Matrix In Vitro," *Curr. Eye Res.*, 1996; 15, pp. 991-997.
Ho, A.D. et al., "Heterogeneity of mesenchymal stromal cell preparations," *Cytotherapy*, 2008;10(4):320-30.
Holz, F.G. et al., "Intraocular Microablation of Choroidal Tissue by a 308 nm AIDA Excimer Laser for RPE-Transplantation in Patients With Age-Related Macular Degeneration," *BIOMED. TECH NIK, (Berlin)*, 2003; 48(4):82-85.
Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.
Hoynowski, S.M. et al., "Characterization and Differentiation of Equine Umbilical Cord-Derived Matrix Cells," *Biochemical and Biophysical Research Communications*, 2007; 362:347-353.
Hu, A. et al., "Hepatic Differentiation From Embryonic Stem Cells In Vitro," *Chin. Med. J.*, 2003; 116(12):1893-1897.
Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.
Hutmacher, D.W., "Scaffold Design and Fabrication Technologies for Engineering Tissues—State of the Art and Future Perspectives," *J. Biomater. Sci. Polymer Edn.*, 2001;12(1):107-124.
Igura et al. "Human Placental Derived Stem Cells Differentiate into Neural Cells," *Blood*, 2002; 100(11): 517A (Abstract 2021).
In't Anker, P., et al., "Isolation of Mesenchymal Stem Cells of Fetal or Maternal Origin from Human Placenta," *Stem Cells*, 2004; 22:1338-1345.
Isacson, O., "The Production and Use of Cells As Therapeutic Agents in Neurodegenerative Diseases," *The Lancet (Neurology)*, 2003; 2:417-424.
Isacson, O., et al., "Specific Axon Guidance Factors Persist in the Adult Brain As Demonstrated by Pig Neuroblasts Transplanted to the Rat," *Neurosci.*, 1996; 75(3):827-837.
Ishiba, Y., et al., "Targeted inactivation of synaptic HRG4 (UNC119) causes dysfunction in the distal photoreceptor and slow retinal degeneration, revealing a new function," *Experimental eye Research*, 2007; 84(3):473-85, Epub Dec. 2006.
Ishii, M. et al., "Molecular Markers Distinguish Bone Marrow Mesenchymal Stem Cells From Fibroblasts," *Biochemical and Biophysical Research Communications*, Jun. 24, 2005; 332(1):297-303.
Ito, Y. et al., "A Quantitative Assay Using Basement Membrane Ex tracts to Study Tumor Angiogenesis In Vivo," *Int. J. Cancer*, 1996; 67:148-152.
Iwasaki, T., "Recent Advances in the Treatment of Graft-Versus-Host Disease," *Clin. Med. Res.*, 2004; 2(4):243-252.
Jackson, K.A. et al., "Regeneration of Ischemic Cardiac Muscle and Vascular Endothelium by Adult Stem Cells," *J. Clin. Invest.*, 2001; 107:1395-1402.

(56) References Cited

OTHER PUBLICATIONS

Jaffe, E.A. et al., "Culture of Human Endothelial Cells Derived From Umbilical Veins; Identification by Morphologic and Immunologic Criteria" *J Clin Invest*, 1973; 52:2745-2756.

Jaiswal et al., Adult Human Mesenchymal Stem Cell Differentiation to the Osteogenic or Adipogenic Lineage is Regulated by Motogen-Activated Protein Kinase, *J. Biol. Chem.*, 2000; 275(13):9645-9652.

Janderová, L. et al., "Human Mesenchymal Stem Cells As an In Vitro Model for Human Adipogenesis," *Obes. Res.*, 2003; 11(1):65-74.

Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75:573-584.

Jeras, M., "The Role of *In Vitro* Alloreactive T-Cell Functional Tests in the Selection of HLA Matched and Mismatched Haematopoietic Stem Cell Donors," *Transpl. Immunol.*, 2002; 10(23):205-214.

Jikuhara, T. et al., "Left Atrial Function As a Reliable Predictor of Exercise Capacity in Patients With Recent Myocardial Infarction," *Chest*, 1997; 111(4):922-928.

Johe, K.K. et al., "Single Factors Direct the Differentiation of Stem Cells From the Fetal and Adult Central Nervous System," *Genes & Devel.*, 1996;10:3129-3140.

Johnstone, B. et al., "*In Vitro* Chondrogenesis of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2.

Jones, J. et al., "Insulin-Like Growth Factors and their Binding Proteins: Biological Actions," *Endocrine Review*, 1995; 16(1):3-34.

Jones-Villeneuve, E.M. et al., "Retinoic Acid-Induced Neural Differentiation of Embryonal Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.

Joussen, A.M. "Cell Transplantation in Age Related Macular Degeneration: Current Concepts and Future Hopes," *Graefe's Arch. Clin. Exp. Ophthalmol.*, 2004; 242:1-2.

Kadiyala, S. et al., "Culture Expanded Canine Mesenchymal Stem Cells Possess Osteochondrogenic Potential *In Vivo* and *In Vitro*," *Cell Transplant.*, 1997; 6(2):125-134.

Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, Sep. 1984; 160:633-651.

Kern, S. et al., "Comparative analysis of mesenchymal stem cells from bone marrow, umbilical cord blood, or adipose tissue," *Stem Cells*, 2006; 24(5):1294-301.

Kestendjieva, S. et al., "Characterization of mesenchymal stem cells isolated from the human umbilical cord." *Cell Biology International*, 2008; 32: 724-732.

Kicic, A. et al., "Differentiation of Marrow Stromal Cells Into Photoreceptors in the Rat Eye," *J. of Neurosci.*, 2003; 23(21):7742-7749.

Kim, J. et al., "Dopamine Neurons Derived From Embryonic Stem Cells Function in an Animal Model of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, S.K. et al., "Intercellular Signals Regulating Pancreas Development and Function," *Genes Dev.*, 2001; 15:111-127.

Kirschstein, R. et al., "Can Stem Cells Repair a Damaged Heart?" *Stem Cells: Scientific Progress and Future Research Directions*, 2001; 87-92.

Kisiday, J. et al., "Self-Assembling Peptide Hydrogel Fosters Chondrocyte Extracellular Matrix Production and Cell Division: Implications for Cartilage Tissue Repair," *Proc. Natl. Acad. Sci. USA*, 2002; 99(15):9996-10001.

Kitamura, S. et al., "Establishment and Characterization of Renal Progenitor Like Cells from S3 Segment of Nephron in Rat Adult Kidney," *The FASEB Journal: Official Publication of the Federation of American Societies for Experimental Biology*, 2005; 19(13).

Klahr, S et al., "Obstructive Nephropathy and Renal Fibrosis," *Am. J. Physiol. Renal. Physiol.*, 2002; 283(5):F861-875.

Klassen, H. et al., "Stem Cells and Retinal Repair," *Prog. Retin. Eye Res.*, 2004; 23(2):149-181.

Kusama et al., "Growth and morphogenesis of mouse prostate epithelial cells in collagen gel matrix culture" *Cell Biol Int Rep*, 1989; 13:569-575.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.

Laface, D. et al., "Gene Transfer Into Hematopoietic Progenitor Cells Mediated by an Adeno-Associated Virus Vector," *Virology*, 1998; 162:483-486.

Lang, K.J.D. et al., "Differentiation of Embryonic Stem Cells to a Neural Fate: A Route to Re-Building the Nervous System?" *J. of Neurosci. Res.*, 2004; 76:184-192.

Langeggen, H. et al., "HUVEC Take Up Opsonized Zymosan Particles and Secrete Cytokines IL-6 and IL-8 In Vitro," *FEMS Immunol. Med. Microbiol.*, 2003; 36:55-61.

Le Belle, J.E. et al., "Stem Cells for Neurodegenerative Disorders: Where Can We Go From Here?," *Biodrugs*, 2002; 16(6):389-401.

Le Blanc, K. et al., "Treatment of Severe Acute Graft-Versus-Host Disease With Third Party Haploidentical Mesenchymal Stem Cells," *Lancet*, 2004; 363(9419):1439-1441.

Le Bouteiller, P. et al., "Soluble HLA-G1 At the Materno-Foetal Interface-A Review," *Placenta*, 2003; 24 (Suppl. A):S10-S15.

Li, A. et al., "IL-8 Directly Enhanced Endothelial Cell Survival, Proliferation, and Matrix Metalloproteinases Production and Regulated Angiogenesis," *J. Immunol.*, 2003; 170(6):3369-3376.

Li, C.D. et al, "Mesenchymal Stem Cells Derived From Human Placenta Suppress Allogeneic Umbilical Cord Blood Lymphocyte Proliferation," *Cell Research*, 2005; 15(7):539-547.

Li, L.X. et al., "Inherited Retinal Dystrophy in the RCS Rat: Prevention of Photoreceptor Degeneration by Pigment Epithelial Cell Transplantation," *Exp. Eye Res.*, 1988; 47:911-917.

Li, Y. et al., "Intact, Injured, Necrotic and Apoptotic Cells after Focal Cerebral Ischemia in the Rat," *J. Neurol. Sci.*, 1998; 156(2):119-132.

Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.

Li, Y. et al., "Transplanted Olfactory Ensheathing Cells Promote Regeneration of Cut Adult at Optic Nerve Axons," *J. of Neuro.*, 2003; 23(21):7783-7788.

Li, Y. et al., "Ultrastructural and Light Microscopic Evidence of Apoptosis after Middle Cerebral Artery Occlusion in the Rat," *Am. J. Pathol.*, 1995; 146(5):1045-1051.

Lian, et al., "Human Umbilical Cord Wharton's Jelly-Derived Mesenchymal Stem Cells Differentiation into Nerve-Like Cells," *Chinese Medical Journal*, 2005; 118(23):1, pp. 1987-1993.

Lindenlaub, T. et al., "Partial Sciatic Nerve Transection as a Model of Neuropathic Pain: A Qualitative and Quantitative Study," PAIN, 2000; 89(1): 97-106.

Lindvall, O. et al., "Stem Cell Therapy for Human Neurodegenerative Disorders—How to Make It Work," *Nature Medicine*, 2004;10(Suppl.):S42-S50.

Liu, K. et al., "Constitutive and Regulated Expression of Telomerase Reverse Transcriptase (hTERT) in Human Lymphocytes," *Proc. Natl. Acad. Sci.*, 1999; 96:5147-5152.

Liu, Y. et al., "Molecular and Genetic Mechanisms of Obesity: Implications for Future Management," *Curr. Mol. Med.*, 2003; 3(A):325-340.

(56) References Cited

OTHER PUBLICATIONS

Lockhart, D.J. et al., "Expression Monitoring by Hybridization to High-Density Oligonucleotide Arrays," *Nat. Biotechnol.*, 1996;14(13):1675-1680.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.

Lonza (Cambrex), hMSC Human Mesenchymal Stem Cells, Lonza, 2014, http://www.lonza.com/products-services/bio-research/primary-and-stem-cells/adult-stem-cells-and-media/hmsc-mesenchymal-stem-cells.aspx; accessed Jan. 31, 2014.

Lund, R.D. et al., "Cell Transplantation As a Treatment for Retinal Disease," *Progress in Retinal and Eye Research*, 2001; 20(4):415-449.

Lund, R.D. et al., "Subretinal Transplantation of Genetically Modified Human Cell Lines Attenuates Loss of Visual Function in Dystrophic Rats," *Proc. Natl. Acad. Sci. USA*, 2001; 98(17):9942-9997.

Lund, R.D. et al., "Retinal Transplantation: Progress and Problems in Clinical Application," *J. Leukocyte Biol.*, 2003; 74:151-160.

Luo, D. et al., "Synthetic DNA Delivery Systems," *Nat. Biotechnol.*, 2000; 18(1):33-36.

Luyten, F.P. et al., "Skeletal Tissue Engineering: Opportunities and Challenges," *Best Pract. Res. Clin. Rheumatol.*, 2001; 15(5):759-769.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.

Ma, P.X. et al., "Synthetic Nano-Scale Fibrous Extracellular Matrix," *J. Biomed Mater Res.*, 1999; 46(1):60-72.

MacDonald, R.J. "Expression of the Pancreatic Elastase I Gene in Transgenic Mice," *Hepatology*, 1987; 7(1):42S-51S.

Mackay, A.M. et al., "Chondrogenic Differentiation of Cultured Human Mesenchymal Stem Cells From Marrow," *Tissue Engineering*, 1998; 4(4):415-428.

Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-198.

Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.

Mason, A.J. et al., "The Hypogonadal Mouse: Reproductive Functions Restored by Gene Therapy," *Science*, 1986; 234:1372-1378.

Mayer-Proschel, M. et al., "Isolation of Lineage-Restricted Neuronal Precursors From Multipotent Neuroepithelial Stem Cells," *Neuron.*, 1997; 19:773-785.

McAdams, T.A., et al., "Hematopoietic Cell Culture Therapies (Part I): Cell Culture Considerations," *TibTech*, 1996; 14:341-349.

McDonald, J.A. et al., "Diminished Responsiveness of Male Homosexual Chronic Hepatitis B Virus Carriers With HTLV-III Antibodies to Recombinant α-Interferon," *Hepatology*, 1987; 7(4):719-723.

McLaren, MJ. et al., "Double fluorescent vital assay of phagocytosis by cultured retinal pigment epithelial cells," *Invest Ophthalmol Vis Sci.*, 1993; 34(2):317-26.

McLaren, MJ. et al., "Kinetics of rod outer segment phagocytosis by cultured retinal pigment epithelial cells. Relationship to cell morphology," *Invest Ophthalmol Vis Sci.*, 1996; 37(7):1213-24.

McLaren MJ and Inana G., "Inherited retinal degeneration: basic FGF induces phagocytic competence in cultured RPE cells from RCS rats," *FEBS Lett.*, 1997; 412(1):21-29.

McLaren MJ, et al., "Analysis of basic fibroblast growth factor in rats with inherited retinal degeneration," *FEBS Lett.*, 1996; 387(1):63-70.

Medicetty, S. et al., "Transplantation of Human Umbilical Cord Matrix Stem Cells Alleviates Apomorphine-Induced Rotations in Parkinsonian Rats", 2003, XP-002383776, 1 page.

Melero-Martin, J. et al., "Optimal In-Vitro Expansion of Chondroprogenitor Cells in Monolayer Culture," *Biotechnology and Bioengineering*, 2006; 93(3):519-533.

Merriam Webster Medline Plus Online Medical Dictionary, definitions of "undifferentiated," and "differentiate," and "differentiation." Retrieved online Mar. 6, 2007, URL:www.nlm.nih.gov/medlineplus/mplusdictionary.html.

Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.

Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.

Mitchell, K.E. et al., "Matrix Cells From Wharton's Jelly Form Neurons and Glia," *Stem Cells*, 2003; 21:50-60.

Moll, S. et al., "Monitoring Warfarin Therapy in Patients With Lupus Anticoagulants," *Ann. Intern. Med.*, 1997; 127(3):177-185.

Mombaerts, P. et al., "Creation of a Large Genomic Deletion At the T-Cell Antigen Receptor β-Subunit Locus in Mouse Embryonic Stem Cells by Gene Targeting," *Proc. Nat. Acad. Sci. USA*, 1991; 88:3084-3087.

Moore, A.E. et al., "Parkinsonian Motor Deficits are Reflected by Proportional A9/A10 Dopamine Neuron Degeneration in the Rat," *Exp. Neurol.*, 2001; 172(2):363-376.

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-3596.

Mori, N., et al., "Truncation Mutation in HRG4 (UNC119) Leads to Mitochondrial ANT-1—Mediated Photoreceptor Synaptic and Retinal Degeneration by Apoptosis," *Invest Ophthalmol Vis Sci.*, 2006; 47:1281-1292.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Moulder, J.E., "Pharmacological Intervention to Prevent or Ameliorate Chronic Radiation Injuries," *Semin. Radiat. Oncol.*, 2003; 13(1):73-84.

Nakamura, T. et al., "Ocular Surface Reconstruction Using Cultivated Mucosal Epithelial Stem Cells," *Cornea*, 2003; 22(Supp. 1):S75-S80.

Newman, K.D. et al., "Poly(D,L lactic-co-glycolic acid) Microspheres as Biodegradable Microcarriers for Pluripotent Stem Cells," *Biomaterials*, 2004; 25:5763-5771.

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.

Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70(1):121-129.

Nishida, K. et al., "Functional Bioengineered Corneal Epithelial Sheet Grafts From Corneal Stem Cells Expanded Ex Vivo on a Temperature-Responsive Cell Culture Surface," *Transplantation*, 2004; 77(3):379-385.

Nishishita, T. et al., "A Potential Pro-Angiogenic Cell Therapy With Human Placenta-Derived Mesenchymal Cells," *Biochemical and Biophysical Research Communications*, 2004; 325:24-31.

Nixon, P.J. et al., "The Contribution of Cone Responses to Rat Electroretinograms," *Clin. Experiment Ophthalmol.*, 2001; 29(3):193-196.

Nordgaard, CL et al., "Proteomics of the retinal pigment epithelium reveals altered protein expression at progressive stages of age-related macular degeneration," *Invest Ophthalmol Vis Sci.*, 2006; 47(3):815-822.

(56) References Cited

OTHER PUBLICATIONS

Nork, T.M. et al., "Swelling and Loss of Photoreceptors in Chronic Human and Experimental Glaucomas," *Arch. Ophthalmol.*, 2000; 118:235-245.
Nowak, A.P. et al., "Rapidly Recovering Hydrogel Scaffolds From Self-Assembling Diblock Copolypeptide Amphilphiles," *Nature*, 2002; 417(6887):424-428.
Nusinowitz, S. et al., "Rod Multifocal Electroretinograms in Mice," *Invest Ophthalmol Vis. Sci.*, 1999; 40(12): 2848-2858.
Oh, S.H. et al., "Hepatocyte Growth Factor Induces Differentiation of Adult Rat Bone Marrow Cells Into a Hepatocyte Lineage *In Vitro*," *Biochem. & Biophys. Res. Comm.*, 2000; 279(2):500-504.
Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.
Oliver, J.A. et al., "The Renal Papilla is a Niche for Adult Kidney Stem Cells," *J. Clin Invest.*, 2004, 114(6):795-804.
Orlic, D. et al., "Stem Cells for Myocardial Regeneration," *Circ. Res.*, 2002; 91:1092-1102.
Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.
Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.
Palù, G. et al., "In Pursuit of New Developments for Gene Therapy of Human Diseases," *J. Biotechnol.*, 1999; 68(1):1-13.
Panepucci, R.A. et al., "Comparison of Gene Expression of Umbilical Cord Vein and Bone Marrow-Derived Mesenchymal Stem Cells," *Stem Cells*, 2004; 22(7):1263-1278.
Pera, M.F. et al., "Human Embryonic Stem Cells", *J. Cell Science*, 2000; 113:5-10.
Petersdorf, E.W., "HLA Matching in Allogeneic Stem Cell Transplantation," *Curr. Op. Hematol*, 2004; 11(6):386-391.
Phipps, J.A. et al., "Paired-Flash Identification of Rod and Cone Dysfunction in the Diabetic Rat," *Investigative Ophthalmology & Visual Science*, 2004; 45(12):4592-4600.
Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Mesenchymal Stem Cells and Their Potential as Cardiac Therapeutics," *Circ. Res.*, 2004; 95:9-20.
Pittenger, M.F. et al., "Multilineage Potential of Adult Human Mesenchymal Stem Cells," *Science*, 1999; 284:143-47 and seven pages of online supplementary material.
Pittenger, M.F. et al.; "Human mesenchymal stem cells: progenitor cells for cartilage, bone, fat and stroma," *Current Topics in Microbiology and Immunology*; 251:3-11. 2000.
Plaia, T., et al., "Characterization of a New Nih-Registered Variant Human Embryonic Stem Cell Line, BG01V: A Tool for Human Embryonic Stem Cell Research," *Stem Cells*, 2006: 24(3):531-546.
Pountos, I. et al., "Mesenchymal Stem Cell Tissue Engineering: Techniques for Isolation, Expansion and Application," *Injury*, 2007; 38(Supp. 4):S23-33.
Quaini, F. et al., "Chimerism of the Transplanted Heart," *NEJM*, 2002; 346:5-15.
Rabbany, S.Y. et al., "Molecular Pathways Regulating Mobilization of Marrow-Derived Stem Cells for Tissue Revascularization," *Trends in Molecular Med.*, 2003; 9(3):109-117.
Radeki, MJ et al., "Disease susceptibility of the human macula: differential gene transcription in the retinal pigmented epithelium/choroids," *Exp Eye Res.*, 2007; 85(3):366-80. Epub Jun. 14, 2007.
Rafii, S. et al., "Therapeutic Stem and Progenitor Cell Transplantation for Organ Vascularization and Regeneration," *Nature Med.*, 2003; 9(6):702-712.
Rahman, Z. et al., "Isolation and Primary Culture Urothelial Cells from Normal Human Bladder," *Urol. Research*, 1987; 15:315-320.

Ramon-Cueto, A. et al., "Functional Recovery of Paraplegic Rats and Motor Axon Regeneration in Their Spinal Cords by Olfactory Ensheathing Glia," *Neuron*, 2000; 25:425-435.
Readhead, C. et al., "Expression of a Myelin Basic Protein Gene in Transgenic Shiverer Mice: Correction of the Dysmyelinating Phenotype," *Cell*, 1987; 48(4):703-712.
Refaie, A. et al., "Experimental Islet Cell Transplantation in Rats: Optimization of the Transplantation Site," *Trans. Proc.*, 1998; 30:400-403.
Rehman, J. et al., "Secretion of Angiogenic and Antiapoptotic Factors by Human Adipose Stromal Cells," *Circulation*, 2004; 109:1292-1298.
Reubinoff, B.E. et al., "Neural Progenitors From Human Embryonic Stem Cells," *Nature Biotechnology*, 2001; 19:1134-1140.
Reyes, M. et al., "Purification and Ex Vivo Expansion of Postnatal Human Marrow Mesodermal Progenitor Cells," *Blood*, 2001; 98(9):2615-2625.
Rezai, K.A. et al., "Iris Pigment Epithelium Transplantation," *Graefe's Arch. Clin. Ophthalmol.*, 1997; 235:558-562.
Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.
Rios, M. et al., "Catecholamine Synthesis is Mediated by Tyrosinase in the Absence of Tyrosine Hydroxylase," *J. Neurosci.*, 1999, 19(9): 3519-3526.
Romanov, Y.A. et al., "Searching for Alternative Sources of Postnatal Human Mesenchymal Stem Cells," *Stem Cells*, 2003; 21:105-110.
Rosen, E.M. et al., "HGF/SF in Angiogenesis," *Ciba Found. Symp.*, 1997; 212:215-229.
Roskams, A.J. et al., "Directing Stem Cells and Progenitor Cells on the Stage of Spinal Cord Injury," *Exp. Neurol.*, 2005; 193:267-272.
Russo, E., Cultivating Policy from Cell Types, *The Scientist*, 2001; 15(11):6 (printout is numbered 1-6).
Rutherford, A. et al., "Eyeing-Up Stem Cell Transplantation," *Trends in Molecular Medicine*, 2003; 7(1):11.
Sagrinati, C. et al., "Isolation and Characterization of Multipotent Progenitor Cells from the Bowman's Capsule of Adult Human Kidney," *Journal of American Society of Nephrology*, 2006; 17(9)2443-2456.
Sahn, D.J. et al., "Recommendations Regarding Quantitation in M-Mode Echocardiography: Results of a Survey of Echocardiographic Measurements," *Circulation*, 1978; 58(6):1072-1083.
Sakariassen, K.S. et al., "Methods and Models to Evaluate Shear-Dependent and Surface Reactivity-Dependent Antithrombotic Efficacy," *Thromb. Res.*, 2001; 104:149-174.
Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, Aug. 2004; 4:743-765.
Sauve, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Schraermeyer, U. et al., "Subretinally Transplanted Embryonic Stem Cells Rescue Photoreceptor Cells From Degeneration in the RCS Rats," *Cell Transplantation*, 2001; 10:673-680.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-437.
Schwartz, R.E. et al., "Multipotent Adult Progenitor Cells From Bone Marrow Differentiate Into Functional Hepatocyte-Like Cells," *J. of Clin. Invest.*, 2002; 109(10):1291-1302.
Seaver et al. "The chick oviduct in tissue culture. I. Initial characterization of growing primary oviduct tissue cultures," *Exp. Cell Res.*, 1984; 155: 241-251.

(56) References Cited

OTHER PUBLICATIONS

Sebire, G. et al., "In Vitro Production of IL-6, IL-1 β, and Tumor Necrosis Factor-α by Human Embryonic Microglial and Neural Cells," *J. Immunol.*, 1993; 150(4):1517-1523.

Sethe, S. et al., "Aging of Mesenchymal Stem Cells," *Ageing Research Reviews*, 2006; 5:91-116.

Shake et al., "Mesenchymal stem cell implantation in a swine myocardial infarct model: engraftment and functional effects," *Ann Thorac Surg*, 2002; 73:1919-1926.

Shani, M., "Tissue-Specific Expression of Rat Myosin Light-Chain 2 Gene in Transgenic Mice," *Nature*, 1985; 314(6008):283-286.

Shimizu, T. et al., "Fabrication of Pulsatile Cardiac Tissue Grafts Using a Novel 3-Dimensional Cell Sheet Manipulation Technique and Temperature-Responsive Cell Culture Surfaces", *Circulation Research*, 2002; 90(3):e40-e48.

Shimizu, T. et al., "Cell Sheet Engineering for Myocardial Tissue Reconstruction," *Biomaterials*, 2003; 24:2309-2316.

Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.

Siminoff, R. et al., "Properties of Reptilian Cutaneous Mechanoreceptors," *Exp. Neurol.*, 1968; 20(3):403-414.

Sommer, et al., "Ocular Tissue Engineering," *Ad. Exptl. Med. Biol.*, 2007, 585, pp. 413-429.

Song, H. et al., "Astroglia Induce Neurogenesis From Adult Neural Stem Cells," *Nature*, 2002; 417(6884):39-44.

Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12:355-364.

Storch, T.G. "Oxygen Concentration Regulates 5-Azacytidine-Induced Myogenesis in $C_3H/10T1/2$cultures," *Biochim. Biophys. Acta*, 1990; 1055:126-129.

Strauss, O., "The retinal pigment epithelium in visual function," *Physiol Rev.*, 2005; 85(3):845-881.

Street, C.N. et al., "Stem Cells: A Promising Source of Pancreatic Islets for Transplantation in Type 1 Diabetes," *Curr. Top Dev. Biol.*, 2003; 58:111-136.

Sundelin, S. et al., "Lipofuscin accumulation in cultured retinal pigment epithelial cells reduces their phagocytic capacity," *Curr Eye Res.*, 1998; 17(8):851-857.

Svendsen, C.N. "The Amazing Astrocyte," *Nature*, 2002; 417:29-32.

Svendsen, C.N. et al., "Long-Term Survival of Human Central Nervous System Progenitor Cells Transplanted Into a Rat Model of Parkinson's Disease," *Experim. Neurol.*, 1997; 148:135-146.

Swanson, R.A. et al., "A Semiautomated Method for Measuring Brain Infarct Volume," *J. Cereb. Blood Flow Metab.*, 1990; 10(2):2902-93.

Swift, G.H. et al., "Tissue-Specific Expression of the Rat Pancreatic Elastase I Gene in Transgenic Mice," *Cell*, 1984; 38:639-646.

Tao, W., "Application of Encapsulated Cell Technology for Retinal Degenerative Disease", *Expert. Opin. Biol. Ther.*, 2006; 6(7): 717-726.

Taylor, D.A. et al., "Cardiac Chimerism As a Mechanism for Self-Repair: Does It Happen and If So to What Degree?" *Circulation*, 2002; 106(1):2-4.

Taylor, D.A. et al., "Regenerating Functional Myocardium: Improved Performance After Skeletal Myoblast Transplantation," *Nature Medicine*, Aug. 1998; 4(8):929-33 (Erratum in *Nature Medicine*, 1998; 4(10):1200).

Thorsby, E. et al., "Role of HLA Molecules in the Induction of Alloimmune Responses: Clinical Significance in the Cyclosporine Era," *Transplant Proc.*, 2004; 36(Suppl 2S):16S-21S.

Timmermans, F. et al., "Stem Cells for the Heart, Are We There Yet?", *Cardiology*, 2003; 100(4):1761-85.

Toma, C. et al., "Human Mesenchymal Stem Cells Differentiate to a Cardiomyocyte Phenotype in the Adult Murine Heart," *Circulation* 2002; 105:93-98.

Tomita, M. et al., "Bone Marrow-Derived Stem Cells Can Differentiate Into Retinal Cells in Injured Rat Retina," *Stem Cells*, 2002; 20:279-283.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001; 19:408-418.

Tresco, P.A. et al., "Cellular Transplants As Sources for Therapeutic Agents," *Advanced Drug Delivery Reviews*, 2000; 42:3-27.

Tsonis, P.A. et al., "Lens and Retina Regeneration: Transdifferentiation, Stem Cells and Clinical Applications," *Experim. Eye Res.*, 2004; 78:161-172.

Turner, D., "The Human Leucocyte Antigen (HLA) System," *Vox Sang.*, 2004; 87(Suppl 1):S87-S90.

Turner, J.F., "Inherited Retinal Dystrophy in the RCS Rat: Prevention of Photoreceptor Degeneration by Pigment Epithelial Cell Transplantation," *Exp. Eye Res.*, 1988; 47:911-917.

Tusher, V.G. et al., "Significance Analysis of Microarrays Applied to the Ionizing Radiation Response," *Proc. Natl. Acad. Sci. USA*, 2001; 98(9):5116-5121.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

"Unigene Entry for Hs.522632, *Homo Sapiens* TMP Metallopeptidase Inhibitor 1 (TIMP1)," printed from http://www.ncbi.nlm.nih.gov/UniGene on Oct. 12, 2006.

Urbich, C. et al., "Endothelial Progenitor Cells Characterization and Role in Vascular Biology,", *Circ. Res.*, 2004; 95:343-353.

Vajsar, J. et al., "Walker-Warburg syndrome," *Orphanet Journal of Rare Diseases*, 2006; 1:29.

Van Hoffelen, S.J. et al., "Incorporation of Murine Brain Progenitor Cells Into the Developing Mammalian Retina," *Invest. Ophthalmol. Vis. Sci.*, 2003; 44(1):426-434.

Vassliopoulos, G. et al., "Transplanted Bone Marrow Regenerates Liver by Cell Fusion," *Nature*, 2003(6934); 422:901-904.

Verma, I. M. et al., "Gene Therapy—Promises, Problems and Prospects," *Nature*, Sep. 1997; 389(6648):239-242.

Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.

Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.

Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.

von Koskull, H. et al., "Induction of Cytokeratin Expression in Human Mesenchymal Cells," *J. Cell Physiol.*, 1987; 133:321-329.

Walboomers, X .F. et al., "Cell and Tissue Behavior on Micro-Grooved Surfaces," *Odontology*, 2001; 89:2-11.

Wang, D. et al., "Synthesis and Characterization of a Novel Degradable Phosphate-Containing Hydrogel," *Biomaterials*, 2003; 24:3969-3980.

Wang, X. et al., "Cell Fusion Is the Principal Source of Bone-Marrow-Derived Hepatocytes," *Nature*, 2003; 422(6934):897-900.

Wegman, A. et al., "Nonsteroidal Anti-Inflammatory Drugs or Acetaminophen for Osteoarthritis of the Hip or Knee? A Synstematic Review of Evidence and Guidelines," *J. Rheumatol.*, 2004; 31(2):344-354.

Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.

Weiss, M.L. et al., "Transplantation of Porcine Umbilical Cord Matrix Cells Into the Rat Brain," *Exp. Neur.*, 2003; 182:288-299.

Wenning, G.K. et al., "Neural Transplantation in Animal Models of Multiple System Atrophy: A Review," *J. Nueral Transm.*, 1999; Suppl.(55):103-113.

(56) References Cited

OTHER PUBLICATIONS

Williams, J.T. et al., "Cells Isolated From Adult Human Skeletal Muscle Capable of Differentiating Into Multiple Mesodermal Phenotypes," *Am. Surg.*, 1999;:65(I):22-6.

Wobus, A.M. et al., "Retinoic Acid Accelerates Embryonic Stem Cell-Derived Cardiac Differentiation and Enhances Development of Ventricular Cardiomyocytes," *J. Mol. Cell Cardiol.*, 1997; 29(6):1525-1539.

Wolford, L.M. et al., "Considerations in Nerve Repair," *BUMC Proceedings*, 2003; 16:152-156.

Woodbury, D., et al., "Adult Rat and Human Bone Marrow Stromal Cells Differentiate Into Neurons," *J. Neurosci. Res.*, 2000; 61(4):364-370.

Wulf, G.G. et al., "Mesengenic Progenitor Cells Derived From Human Placenta," *Tissue Engineering*, 2004; 10(7/8):1136-1147.

Xu, C. et al., "Characterization and Enrichment of Cardiomyocytes Derived From Human Embryonic Stem Cells," *Circ. Res.*, 2002; 91(5):501-508.

Xu, Y. et al., "Dopamine, in the Presence of Tyrosinase, Covalently Modifies and Inactivates Tyrosine Hydroxylase," *J. Neurosci. Res.*, 1998; 54(5):691-697.

Yamashima, T., "Implication of Cysteine Proteases Calpain, Cathepsin and Caspase in Ischemic Neuronal Death of Primates," *Progress in Neurobiology*, 2000; 62:273-295.

Yang, C. et al., "Enhancement of Neovascularization With Cord Blood CD133+Cell-Derived Endothelial Progenitor Cell Transplantation," *Thrombosis and Haemostasis*, Jun. 2004; 91(6):1202-1212.

Yang, H. et al., "Region-Specific Differentiation of Neural Tube-Derived Neuronal Restricted Progenitor Cells After Heterotopic Transplantation," *Proc. Natl. Acad. Sci. USA*, 2000; 97(24):13366-13371.

Ye Q. et al., "Recovery of Placental-Derived Adherent Cells With Mesenchymal Stem Cell Characteristics", *Blood*, 2001; 98(11 Part 2):147B (Abstract No. 4260).

Yip, H.K. and So, K.F., "Axonal Regeneration of Retinal Ganglion Cells: Effect of Trophic Factors," *Prog. Retin Eye Res.*, 2000; 19(5):559-575.

Yokoo, T. et al., "Stem Cell Gene Therapy for Chronic Renal Failure," *Curr Gene Ther.*, 2003; 3:387-394.

Young et al., "Neuronal Differentiation and Morphological Integration of Hippocampal Progenitor Cells Transplanted to the Retina of Immature and Mature Dystrophic Rats," *Molecular and Cellular Neuroscience*, 2000; 16:197-205.

Yu, M. et al., "Mid-Trimester Fetal Blood-Derived Adherent Cells Share Characteristics Similar to Mesenchymal Stem Cells But Full-Term Umbilical Cord Blood Does Not," *British J. of Haematology*, 2004; 124:666-675.

Zangani, D. et al., "Multiple Differentiation Pathways of Rat Mammary Stromal Cells *In Vitro*: Acquisition of a Fibroblast, Adipocyte or Endothelial Phenotype Is Dependent on Hormonal and Extracellular Matrix Stimulation," *Differentiation*, 1999; 64(2):91-101.

Zarbin, MA, "Analysis of retinal pigment epithelium integrin expression and adhesion to aged submacular human Bruch's membrane," *Trans Am Ophthalmol Soc.*, 2003; 101:499-520.

Zeng, B.Y. et al., "Regenerative and Other Responses to Injury in the Retinal Stump of the Optic Nerve in Adult Albino Rats: Transection of the Intracranial Optic Nerve," *J. Anat.*, 1995; 186:495-508.

Zhang, L. et al., "A Test for Detecting Long-Term Sensorimotor Dysfunction in the Mouse after Focal Cerebral Ischemia," *J. Neurosci. Methods*, 2002; 117(2):207-214.

Zhang, S. et al., "*In Vitro* Differentiation of Transplantable Neural Precursors From Human Embryonic Stem Cells," *Nature Biotechnology*, 2001; 19:1129-1133.

Zhang, X. et al., "Efficient Adeno-Associated Virus-Mediated Gene Expression in Human Placenta-Derived Mesenchymal Cells," *Microbiol. Immunol.*, 2003; 47(1):109-116.

Zhang, Y. et al., "Comparison of Mesenchymal Stem Cells from Human Placenta and Bone Marrow," *Chinese Medical Journal*, 2004; 117(6):882-887.

Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-392.

Zimmerman, S. et al., "Lack of Telomerase Activity in Human Mesenchymal Stem Cells," *Leukemia*, 2003; 17:1146-1149.

Zuloff-Shani, A. et al., "Macrophage Suspensions Prepared From a Blood Unit for Treatment of Refractory Human Ulcers," *Transfus. Apheresis Sci.*, 2004; 30(2):163-167.

\* cited by examiner hUTC = Umbilicus-derived cells

REPAIR AND REGENERATION OF OCULAR TISSUE USING POSTPARTUM-DERIVED CELLS

CROSS-REFERENCE TO RELATED APPLICATIONS

This application is a continuation of U.S. application Ser. No. 14/444,689, filed Jul. 28, 2014, which issued as U.S. Pat. No. 9,234,172 on Jan. 12, 2016, and which is a continuation of Ser. No. 12/054,718, filed Mar. 25, 2008, which issued as U.S. Pat. No. 8,790,637 on Jul. 29, 2014, which is a continuation-in-part of U.S. application Ser. No. 10/877,541, filed Jun. 25, 2004, which issued as U.S. Pat. No. 7,413,734 on Aug. 19, 2008, which claims priority to U.S. Provisional Application No. 60/483,264, filed Jun. 27, 2003, the entire contents of each of which are incorporated by reference herein.

FIELD OF THE INVENTION

This invention relates to the field of cell-based or regenerative therapy for ophthalmic diseases and disorders. In particular, the invention provides pharmaceutical compositions, devices and methods for the regeneration or repair of cells and tissues of the eye, using postpartum derived cells.

BACKGROUND

Various patents and other publications are referred to throughout the specification. Each of these publications is incorporated by reference herein, in its entirety.

As a complex and sensitive organ of the body, the eye can experience numerous diseases and other deleterious conditions that affect its ability to function normally. Many of these conditions are associated with damage or degeneration of specific ocular cells, and tissues made up of those cells. As one example, diseases and degenerative conditions of the optic nerve and retina are the leading causes of blindness throughout the world. Damage or degeneration of the cornea, lens and associated ocular tissues represent another significant cause of vision loss worldwide.

The retina contains seven layers of alternating cells and processes that convert a light signal into a neural signal. The retinal photoreceptors and adjacent retinal pigment epithelium (RPE) form a functional unit that, in many disorders, becomes unbalanced due to genetic mutations or environmental conditions (including age). This results in loss of photoreceptors through apoptosis or secondary degeneration, which leads to progressive deterioration of vision and, in some instances, to blindness (for a review, see, e.g., Lund, R. D. et al. 2001, Progress in Retinal and Eye Research 20: 415-449). Two classes of ocular disorders that fall into this pattern are age-related macular degeneration (AMD) and retinitis pigmentosa (RP).

AMD is the most common cause of vision loss in the United States in those people whose ages are 50 or older, and its prevalence increases with age. The primary disorder in AMD appears to be due to RPE dysfunction and changes in Bruch's membranes, characterized by, among other things, lipid deposition, protein cross-linking and decreased permeability to nutrients (see Lund et al., 2001 supra). A variety of elements may contribute to macular degeneration, including genetic makeup, age, nutrition, smoking and exposure to sunlight.

AMD is broadly divided into two types. In the exudative-neovascular form, or "wet" AMD, which accounts for 10% of all cases, abnormal blood vessel growth occurs under the macula. These blood vessels leak fluid and blood into the retina and thus cause damage to the photoreceptors. The remaining 90% of AMD cases are the nonexudative, or "dry" form. In these patients there is a gradual disappearance of the retinal pigment epithelium (RPE), resulting in circumscribed areas of atrophy. Since photoreceptor loss follows the disappearance of RPE, the affected retinal areas have little or no visual function.

For example, Radeke, M. et al state "Macular degeneration is a blinding disease caused by the death of the photoreceptor cells in that part of the retina known as the macula (Radeke M et al, 2007). Radeke, M. et al further state, "Photoreceptors are critically dependent upon the RPE cells for their own survival" (Radeke M et al, 2007).

Current therapies for AMD involve procedures, such as, for example, laser therapy and pharmacological intervention. By transferring thermal energy, the laser beam destroys the leaky blood vessels under the macula, which slows the rate of vision loss. A disadvantage of this approach, however, is that the high thermal energy delivered by the beam also destroys healthy tissue nearby. Neuroscience $4^{th}$ edition, (Purves, D, et al. 2008) states "Currently there is no treatment for dry AMD."

RPE transplantation, following excision of choroid neovascularization is also one potential cell-based therapy for AMD. However, this has been unsuccessful in humans. For example, Zarbin, M, 2003 states, "With normal aging, human Bruch's membrane, especially in the submacular region, undergoes numerous changes (e.g., increased thickness, deposition of ECM and lipids, cross-linking of protein, non-enzymatic formation of advanced glycation end products). These changes and additional changes due to AMD could decrease the bioavailability of ECM ligands (e. g., laminin, fibronectin, and collagen IV) and cause the extremely poor survival of RPE cells in eyes with AMD. Thus, although human RPE cells express the integrins needed to attach to these ECM molecules, RPE cell survival on aged submacular human Bruch's membrane is impaired".

RP is mainly considered an inherited disease, with over 100 mutations being associated with photoreceptor loss (see Lund et al., 2001, supra). Though the majority of mutations target photoreceptors, some affect RPE cells directly. Together, these mutations affect such processes as molecular trafficking between photoreceptors and RPE cells and phototransduction, for example.

Other less common, but nonetheless debilitating retinopathies can also involve progressive cellular degeneration leading to vision loss and blindness. These include, for example, diabetic retinopathy and choroidal neovascular membrane (CNVM).

Diabetic retinopathy may be classified as (1) non-proliferative or background retinopathy, characterized by increased capillary permeability, edema, hemorrhage, microaneurysms, and exudates, or 2) proliferative retinopathy, characterized by neovascularization extending from the retina to the vitreous, scarring, fibrous tissue formation, and potential for retinal detachment.

In CNVM, abnormal blood vessels stemming from the choroid grow up through the retinal layers. The fragile new vessels break easily, causing blood and fluid to pool within the layers of the retina.

Damage or progressive degeneration of the optic nerve and related nerves of the eye constitutes another leading cause of vision loss and blindness. A prime example is glaucoma, a condition of the eye that is made up of a collection of eye diseases that cause vision loss by damage to the optic nerve. Elevated intraocular pressure (TOP) due to inadequate ocular drainage is a primary cause of glaucoma, but it can also develop in the absence of elevated TOP. Glaucoma can develop as the eye ages. It can also occur as the result of an eye injury, inflammation, tumor, or in advanced cases of cataract or diabetes, or it can be caused by certain drugs, such as, for example, steroids. The primary features of the optic neuropathy in glaucoma include characteristic changes in the optic nerve head, a decrease in number of surviving retinal ganglion cells, and loss of vision. It has been proposed that a cascade of events links degeneration of the optic nerve head with the slow death of retinal ganglion cells observed in the disease, and that this cascade of events can be slowed or prevented through the use of neuroprotective agents (Osborne et al., 2003, Eur. J. Ophthalmol. 13 (Supp 3): S19-S26).

Cellular damage and degenerative conditions also affect other parts of the eye. For example, cataracts result from gradual opacification of the crystalline lens of the eye. It is believed that once begun, cataract development proceeds along one or more common pathways that culminate in damage to lens fibers. This condition is presently treated by surgical removal and replacement of the affected lens. Another example concerns the cornea and surrounding conjuctiva that make up the ocular surface. The limbal epithelium, located between the cornea and the bulbar conjuctiva, contains corneal epithelial stem cells. Limbal epithelial cell deficiency (LECD) is a condition that occurs, for example, in Stevens-Johnson syndrome and thermal or chemical burns. LECD often leads to an imbalance between the corneal epithelium and the conjunctival epithelium in which the cornea is covered by invading conjunctival epithelial cells, which severely compromises the corneal surface and affects visual acuity (Nakamura, T. & Kinoshita, S., 2003. Cornea 22 (Supp. 1): S75-S80).

The recent advent of stem cell-based therapy for tissue repair and regeneration provides promising treatments for a number of aforementioned cell-degenerative pathologies and other ocular disorders. Stem cells are capable of self-renewal and differentiation to generate a variety of mature cell lineages. Transplantation of such cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of biotherapeutic agents to a target location via exogenously supplied living cells or cellular components that produce or contain those agents (For a review, see, for example, Tresco, P. A. et al., 2000, Advanced Drug Delivery Reviews 42: 2-37).

An obstacle to realization of the therapeutic potential of stem cell technology has been the difficulty in obtaining sufficient numbers of stem cells. One source of stem cells is embryonic or fetal tissue. Embryonic stem and progenitor cells have been isolated from a number of mammalian species, including humans, and several such cell types have been shown capable of self-renewal and expansion, as well differentiation into a variety of cell lineages. In animal model systems, embryonic stem cells have been reported to differentiate into a RPE cell phenotype, as well as to enhance the survival of host photoreceptors following transplantation (Haruta, M. et al., 2004, Investig. Ophthalml. Visual Sci. 45: 1020-1025; Schraermeyer, U. et al., 2001, Cell Transplantation 10: 673-680). But the derivation of stem cells from embryonic or fetal sources has raised many ethical issues that are desirable to avoid by identifying other sources of multipotent or pluripotent cells.

Adult tissue also can yield stem cells useful for cell-based ocular therapy. For instance, retinal and corneal stem cells themselves may be utilized for cell replacement therapy in the eye. In addition, neural stem cells from the hippocampus have been reported to integrate with the host retina, adopting certain neural and glial characteristics (see review of Lund, R. L. et al., 2003, J. Leukocyte Biol. 74: 151-160). Neural stem cells prepared from fetal rat cortex were shown to differentiate along an RPE cell pathway following transplantation into the adult rat subretinal space (Enzmann, V. et al., 2003, Investig. Ophthalmol. Visual Sci. 44: 5417-5422). Bone marrow stem cells have been reported to differentiate into retinal neural cells and photo receptors following transplantation into host retinas (Tomita, M. et al., 2002, Stem Cells 20: 279-283; Kicic, A. et al., 2003, J. Neurosci. 23: 7742-7749). An ocular surface reconstruction in a rabbit model system, utilizing cultured mucosal epithelial stem cells, has also been reported (Nakamura, T. & Kinoshita, S., 2003, supra). While these reports show promise for the use of adult progenitor and stem cells in cell-based therapy for the eye, it must be noted that adult stem cell populations are comparatively rare and are often obtainable only by invasive procedures. Further, adult stem cells may have a more limited ability to expand in culture than do embryonic stem cells.

Thus, a need exists for alternative sources of adequate supplies of cells having the ability to support, augment or replace lost cellular function in the eye. A reliable, well-characterized and plentiful supply of substantially homogeneous populations of such cells would be an advantage in a variety of diagnostic and therapeutic applications in ocular repair and regeneration, including drug screening assays, ex vivo or in vitro trophic support of ocular and other useful cell types, and in vivo cell-based therapy.

SUMMARY

This invention provides compositions and methods applicable to cell-based or regenerative therapy for ophthalmic diseases and disorders. In particular, the invention features pharmaceutical compositions, devices and methods for the regeneration or repair of ocular tissue using postpartum-derived cells.

One aspect of the invention features an isolated postpartum-derived cell, derived from human placental or umbilical cord tissue substantially free of blood, wherein the cell is capable of self-renewal and expansion in culture and has the potential to differentiate into a cell of a neural phenotype; wherein the cell requires L-valine for growth and is capable of growth in at least about 5% oxygen. This cell further comprises one or more of the following characteristics: (a) potential for at least about 40 doublings in culture; (b) attachment and expansion on a coated or uncoated tissue culture vessel, wherein the coated tissue culture vessel comprises a coating of gelatin, laminin, collagen, polyomithine, vitronectin, or fibronectin; (c) production of at least one of tissue factor, vimentin, and alpha-smooth muscle actin; (d) production of at least one of CD10, CD13, CD44, CD73, CD90, PDGFr-alpha, PD-L2 and HLA-A,B,C; (e) lack of production of at least one of CD31, CD34, CD45, CD80, CD86, CD117, CD141, CD178, B7-H2, HLA-G, and HLA-DR,DP,DQ, as detected by flow cytometry; (f) expression of a gene, which relative to a human cell that is a fibroblast, a mesenchymal stem cell, or an iliac crest bone marrow cell, is increased for at least one of a gene encoding: interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; downregulated in ovarian cancer 1; and *Homo sapiens* gene from clone DKFZp547k1113; (g) expression of a gene, which relative to a human cell that is a fibroblast, a mesenchymal stem cell, or an iliac crest bone marrow cell, is reduced for at least one of a gene encoding: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (T AZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; cytochrome c oxidase subunit VIIa polypeptide 1 (muscle); similar to neuralin 1; B cell translocation gene 1; hypothetical protein FLJ23191; and DKFZp586L151; (h) secretion of at least one of MCP-1, IL-6, IL-8, GCP-2, HGF, KGF, FGF, HB-EGF, BDNF, TPO, MIP1a, RANTES, and TIMP1; and (i) lack of secretion of at least one of TGF-beta2, ANG2, PDGFbb, MIP1b, I309, MDC, and VEGF, as detected by ELISA.

In certain embodiments, the postpartum-derived cell is an umbilicus-derived cell. In other embodiments it is a placenta-derived cell. In specific embodiments, the cell has all identifying features of anyone of: cell type PLA 071003 (P8) (ATCC Accession No. PTA-6074); cell type PLA 071003 (P11) (ATCC Accession No. PTA-6075); cell type PLA 071003 (P16) (ATCC Accession No. PTA-6079); cell type UMB 022803 (P7) (ATCC Accession No. PTA-6067); or cell type UMB 022803 (P17) (ATCC Accession No. PTA-6068).

In certain embodiments, postpartum-derived cells are isolated in the presence of one or more enzyme activities comprising metalloprotease activity, mucolytic activity and neutral protease activity. Preferably, the cells have a normal karyotype, which is maintained as the cells are passaged in culture. In preferred embodiments, the postpartum-derived cells comprise each of CD10, CD13, CD44, CD73, CD90, PDGFr-alpha, and HLA-A,B,C and does not comprise any of CD31, CD34, CD45, CD117, CD141, or HLA-DR,DP, DQ, as detected by flow cytometry.

Another aspect of the invention features a cell population comprising the postpartum-derived cells as described above. In one embodiment, the population is a substantially homogeneous population of the postpartum-derived cells. In a specific embodiment, the population comprises a clonal cell line of the postpartum-derived cells. In another embodiment, the population is a heterogeneous population comprising the postpartum-derived cells and at least one other cell type. In certain embodiments, the other cell type is an astrocyte, oligodendrocyte, neuron, neural progenitor, neural stem cell, retinal epithelial stem cell, corneal epithelial stem cell or other multipotent or pluripotent stem cell. In other embodiments, the cell population is cultured in contact with one or more factors that stimulate stem cell differentiation toward a neural or epithelial lineage.

Also featured in accordance with the present invention is a cell lysate prepared from postpartum-derived cells. The cell lysate may be separated into a membrane enriched fraction and a soluble cell fraction. The invention also features an extracellular matrix produced by the postpartum-derived cells, as well as a conditioned medium in which the cells have been grown.

Another aspect of the invention features a method of treating a patient having an ocular degenerative condition, which comprises administering to the patient multipotent or pluripotent cells isolated from a postpartum placenta or umbilical cord, in an amount effective to treat the ocular degenerative condition. Preferably the cells are postpartum-derived cells, as described above. In certain embodiments, the ocular degenerative condition is an acute ocular degenerative condition such as brain trauma, optic nerve trauma or ocular lesion. In other embodiments, it is a chronic or progressive degenerative condition, such as macular degeneration, retinitis pigmentosa, diabetic retinopathy, glaucoma or limbal epithelial cell deficiency. In certain embodiments, the cells are induced in vitro to differentiate into a neural or epithelial lineage cells prior to administration.

In certain embodiments, the cells are administered with at least one other cell type, such as an astrocyte, oligodendrocyte, neuron, neural progenitor, neural stem cell, retinal epithelial stem cell, corneal epithelial stem cell, or other multipotent or pluripotent stem cell. In these embodiments, the other cell type can be administered simultaneously with, or before, or after, the postpartum-derived cells. Likewise, in these and other embodiments, the cells are administered with at least one other agent, such as a drug for ocular therapy, or another beneficial adjunctive agent such as an anti-inflammatory agent, anti-apoptotic agents, antioxidants or growth factors. In these embodiments, the other agent can be administered simultaneously with, or before, or after, the postpartum cells.

In various embodiments, the cells are administered to the surface of an eye, or they are administered to the interior of an eye or to a location in proximity to the eye, e.g., behind the eye. The cells can be administered through a cannula or from a device implanted in the patient's body within or in proximity to the eye, or they may be administered by implantation of a matrix or scaffold containing the cells.

Another aspect of the invention features a pharmaceutical composition for treating a patient having an ocular degenerative condition, comprising a pharmaceutically acceptable carrier and multipotent or pluripotent cells isolated from a postpartum placenta or umbilical cord in an amount effective to treat the ocular degenerative condition. Preferably the postpartum cells are postpartum-derived cells as described above. The ocular degenerative condition may be an acute, chronic or progressive condition. In certain embodiments, the composition comprises cells that have been induced in vitro to differentiate into a neural or epithelial lineage cells prior to formulation of the composition.

In certain embodiments, the pharmaceutical composition comprises at least one other cell type, such as an astrocyte, oligodendrocyte, neuron, neural progenitor, neural stem cell, retinal epithelial stem cell, corneal epithelial stem cell, or other multipotent or pluripotent stem cell. In these or other embodiments, the pharmaceutical composition comprises at least one other agent, such as a drug for treating the ocular degenerative disorder or other beneficial adjunctive agents, e.g., anti-inflammatory agents, anti-apoptotic agents, antioxidants or growth factors.

In certain embodiments, the pharmaceutical compositions are formulated for administration to the surface of an eye. Alternatively, they can be formulated for administration to the interior of an eye or in proximity to the eye (e.g., behind the eye). The compositions also can be formulated as a matrix or scaffold containing the cells.

According to yet another aspect of the invention, a kit is provided for treating a patient having an ocular degenerative condition. The kit comprises a pharmaceutically acceptable carrier, a population of multipotent or pluripotent cells isolated from postpartum placenta or umbilicus, preferably the postpartum-derived cells described above, and instructions for using the kit in a method of treating the patient. The kit may also contain one or more additional components, such as reagents and instructions for culturing the cells, or a population of at least one other cell type, or one or more agents useful in the treatment of an ocular degenerative condition.

According to another aspect of the invention, a method is provided for treating a patient having an ocular degenerative condition, which comprises administering to the patient a preparation made from multipotent or pluripotent cells isolated from a postpartum placenta or umbilical cord, in an amount effective to treat the ocular degenerative condition, wherein the preparation comprises a cell lysate of the cells (or fraction thereof), or a conditioned medium in which the cells were grown, or an extracellular matrix of the cells. Preferably, the cells are the postpartum-derived cells described above. In another aspect, the invention features a pharmaceutical composition comprising a pharmaceutically acceptable carrier and a preparation made from the postpartum cells, which may be a cell lysate (or fraction thereof) of the postpartum cells, an extracellular matrix of the postpartum cells or a conditioned medium in which the postpartum cells were grown. Kits for practicing this aspect of the invention are also provided. These may include the one or more of a pharmaceutically acceptable carrier or other agent or reagent, one or more of a cell lysate or fraction thereof, an extracellular matrix or a conditioned medium from the postpartum cells, and instructions for use of the kit components.

Another aspect of the invention features a method for increasing the survival, growth or activity of cells for transplantation to treat an ocular degenerative disorder. The method comprises co-culturing the cells for transplantation with cultured cells derived from postpartum placental or umbilical tissue, under conditions effective to increase the survival, growth or activity of the cells for transplantation. Preferably, the postpartum cells are the postpartum-derived cells described above. A kit for practicing the method is also provided. The kit comprises the cultured postpartum cells and instructions for co-culturing the cells for transplantation with the postpartum cells under conditions effective to increase the survival, growth or activity of the cells for transplantation.

In one embodiment, the present invention provides a method for treating a patient having a retinopathy or a retinal/macular disorder, the method comprising administering to the patient's eye umbilicus-derived cells, in an amount effective to treat the retinopathy or a retinal/macular disorder, wherein the cells are capable of self-renewal and expansion in culture, have the potential to differentiate into cells of at least a neural phenotype, and have the following characteristics:
  a. Potential for at least 40 population doublings in culture;
  b. Attachment and expansion on a coated or uncoated tissue culture vessel, wherein the coated tissue culture vessel comprises a coating of gelatin, laminin, collagen, polyornithine, vitronectin, or fibronectin;
  c. Production of vimentin and alpha-smooth muscle actin;
  d. Production of CD10, CD13, CD44, CD73, and CD90; and
  e. Increased expression of genes, encoding interleukin 8 and reticulon 1 relative to a human cell that is a fibroblast, a mesenchymal stem cell, or an iliac crest bone marrow cell.

In one embodiment, the umbilicus-derived cells are positive for HLA-A,B,C, and negative for CD31, CD34, CD45, CD117, and CD141. In one embodiment, the umbilicus-derived cells are expanded in culture prior to administering to the patient's eye.

In one embodiment, the retinopathy or a retinal/macular disorder is age-related macular degeneration. In an alternate embodiment, the retinopathy or a retinal/macular disorder is glaucoma.

In one embodiment, the present invention provides a method for preventing the loss of photoreceptor cells associated with a retinopathy or a retinal/macular disorder in a patient, the method comprising administering to the patient's eye umbilicus-derived cells, in an amount effective to prevent the loss of photoreceptor cells, wherein the cells are capable of self-renewal and expansion in culture, have the potential to differentiate into cells of at least a neural phenotype, and have the following characteristics:
  a. Potential for at least 40 population doublings in culture;
  b. Attachment and expansion on a coated or uncoated tissue culture vessel, wherein the coated tissue culture vessel comprises a coating of gelatin, laminin, collagen, polyornithine, vitronectin, or fibronectin;
  c. Production of vimentin and alpha-smooth muscle actin;
  d. Production of CD10, CD13, CD44, CD73, and CD90; and
  e. Increased expression of genes, encoding interleukin 8 and reticulon 1 relative to a human cell that is a fibroblast, a mesenchymal stem cell, or an iliac crest bone marrow cell.

In one embodiment, the umbilicus-derived cells are positive for HLA-A,B,C, and negative for CD31, CD34, CD45, CD117, and CD141. In one embodiment, the umbilicus-derived cells are expanded in culture prior to administering to the patient's eye.

In one embodiment, the retinopathy or a retinal/macular disorder is age-related macular degeneration. In an alternate embodiment, the retinopathy or a retinal/macular disorder is glaucoma.

In one embodiment, the loss of photoreceptor cells is prevented by inhibiting the apoptosis of the photoreceptor cells. In an alternate embodiment, the loss of photoreceptor cells is prevented by stimulating the phagocytosis of shed photoreceptor fragments.

In one embodiment, the umbilicus-derived cells phagocytose the shed photoreceptor fragments. In an alternate embodiment, the umbilicus-derived cells stimulate the phagocytosis of shed photoreceptor fragments by RPE cells.

In one embodiment, the loss of photoreceptor cells is prevented by replacing the photoreceptor cells. In one embodiment, the photoreceptor cells are replaced by the umbilicus-derived cells differentiating retinal progenitor cells into photoreceptor cells.

In one embodiment, the loss of photoreceptor cells is prevented by resurfacing Bruch's membrane.

Figure 1:
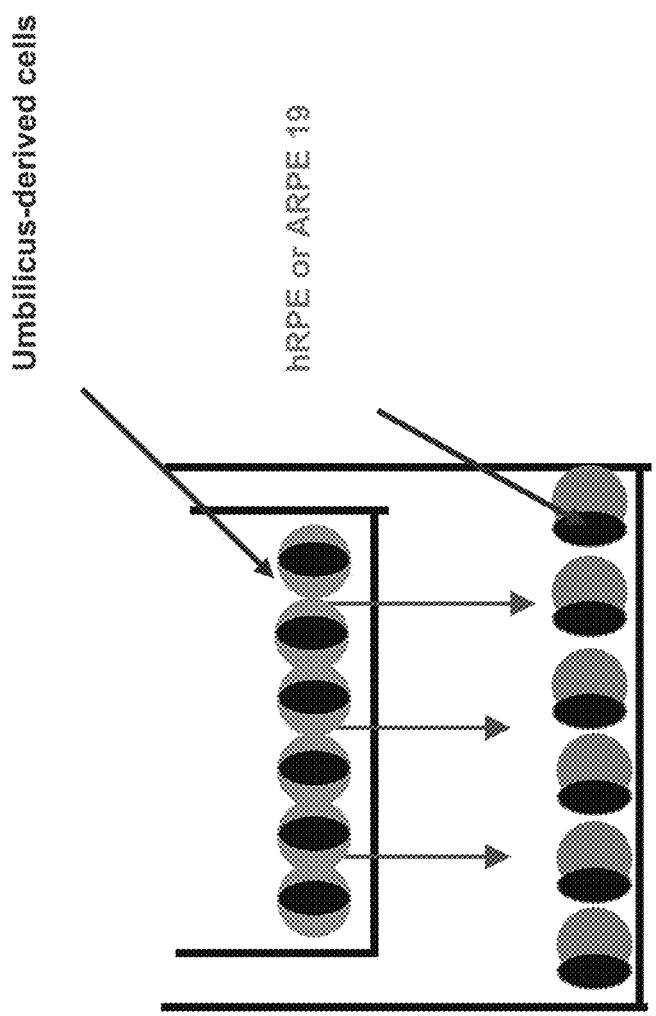
FIG. 1 shows a graphical representation of the layout of the cells in a typical transwell experiment.

Other features and advantages of the invention will be apparent from the detailed description and examples that follow.

DETAILED DESCRIPTION

Various patents and other publications are referred to throughout the specification. Each of these publications is incorporated by reference herein, in its entirety.

Definitions

Various terms used throughout the specification and claims are defined as set forth below.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into an ocular lineage or phenotype refers to a cell that becomes partially or fully committed to a specific ocular phenotype, including without limitation, retinal and corneal stem cells, pigment epithelial cells of the retina and iris, photoreceptors, retinal ganglia and other optic neural lineages (e.g., retinal glia, microglia, astrocytes, Mueller cells), cells forming the crystalline lens, and epithelial cells of the sclera, cornea, limbus and conjunctiva. The phrase differentiates into a neural lineage or phenotype refers to a cell that becomes partially or fully committed to a specific neural phenotype of the CNS or PNS, i.e., a neuron or a glial cell, the latter category including without limitation astrocytes, oligodendrocytes, Schwann cells and microglia.

The cells exemplified herein and preferred for use in present invention are generally referred to as postpartum-derived cells (or PPDCs). They also may sometimes be referred to more specifically as umbilicus-derived cells or placenta-derived cells (UDCs or PDCs). In addition, the cells may be described as being stem or progenitor cells, the latter term being used in the broad sense. The term derived is used to indicate that the cells have been obtained from their biological source and grown in vitro (e.g., cultured in a Growth Medium to expand the population and! or to produce a cell line). The in vitro manipulations of umbilical stem cells and the unique features of the umbilicus-derived cells of the present invention are described in detail below. Cells isolated from postpartum placenta and umbilicus by other means is also considered suitable for use in the present invention. These other cells are referred to herein as postpartum cells (rather than postpartum-derived cells).

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a Growth Medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes survival, growth, differentiation, proliferation and/or maturation of a cell, or stimulates increased activity of a cell. The interaction between cells via trophic factors may occur between cells of different types. Cell interaction by way of trophic factors is found in essentially all cell types, and is a particularly significant means of communication among neural cell types. Trophic factors also can function in an autocrine fashion, i.e., a cell may produce trophic factors that affect its own survival, growth, differentiation, proliferation and/or maturation.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are alive and metabolically active, but they do not divide. The nondividing state of senescent cells has not yet been found to be reversible by any biological, chemical, or viral agent.

The terms ocular, ophthalmic and optic are used interchangeably herein to define "of, or about, or related to the eye."

The term ocular degenerative condition (or disorder) is an inclusive term encompassing acute and chronic conditions, disorders or diseases of the eye, inclusive of the neural connection between the eye and the brain, involving cell damage, degeneration or loss. An ocular degenerative condition may be age-related, or it may result from injury or trauma, or it may be related to a specific disease or disorder. Acute ocular degenerative conditions include, but are not limited to, conditions associated with cell death or compromise affecting the eye including conditions arising from cerebrovascular insufficiency, focal or diffuse brain trauma, diffuse brain damage, infection or inflammatory conditions of the eye, retinal tearing or detachment, intra-ocular lesions (contusion penetration, compression, laceration) or other physical injury (e.g., physical or chemical burns). Chronic ocular degenerative conditions (including progressive conditions) include, but are not limited to, retinopathies and other retinal/macular disorders such as retinitis pigmentosa (RP), age-related macular degeneration (AMD), choroidal neovascular membrane (CNVM); retinopathies such as diabetic retinopathy, occlusive retinopathy, sickle cell retinopathy and hypertensive retinopathy, central retinal vein occlusion, stenosis of the carotid artery, optic neuropathies such as glaucoma and related syndromes; disorders of the lens and outer eye, e.g., limbal stem cell deficiency (LSCD), also referred to as limbal epithelial cell deficiency (LECD), such as occurs in chemical or thermal injury, Steven-Johnson syndrome, contact lens-induced keratopathy, ocular cicatricial pemphigoid, congenital diseases of aniridia or ectodermal dysplasia, and multiple endocrine deficiency-associated keratitis.

The term treating (or treatment of) an ocular degenerative condition refers to ameliorating the effects of, or delaying, halting or reversing the progress of, or delaying or preventing the onset of, an ocular degenerative condition as defined herein.

The term effective amount refers to a concentration or amount of a reagent or pharmaceutical composition, such as a growth factor, differentiation agent, trophic factor, cell population or other agent, that is effective for producing an intended result, including cell growth and/or differentiation in vitro or in vivo, or treatment of ocular degenerative conditions, as described herein. With respect to growth factors, an effective amount may range from about 1 nanogram/milliliter to about 1 microgram/milliliter. With respect to PPDCs as administered to a patient in vivo, an effective amount may range from as few as several hundred or fewer, to as many as several million or more. In specific embodiments, an effective amount may range from $10^3$ to $11^{11}$, more specifically at least about $10^4$ cells. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or pharmaceutical composition to achieve its intended result.

The term patient or subject refers to animals, including mammals, preferably humans, who are treated with the pharmaceutical compositions or in accordance with the methods described herein.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

Several terms are used herein with respect to cell replacement therapy. The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy. Transplantation as used herein refers to the introduction of autologous, or allogeneic donor cell replacement therapy into a recipient.

DESCRIPTION

Ocular degenerative conditions, which encompass acute, chronic and progressive disorders and diseases having divergent causes, have as a common feature the dysfunction or loss of a specific or vulnerable group of ocular cells. This commonality enables development of similar therapeutic approaches for the repair or regeneration of vulnerable, damaged or lost ocular tissue, one of which is cell-based therapy. Development of cell therapy for ocular degenerative conditions heretofore has been limited to a comparatively few types of stem or progenitor cells, including ocular-derived stem cells themselves (e.g., retinal and corneal stem cells), embryonic stem cells and a few types of adult stem or progenitor cells (e.g., neural, mucosal epithelial and bone marrow stem cells). The present inventors have identified a significant new source of stem cells for this purpose, namely, cells isolated from the postpartum placenta and umbilical cord. Accordingly, in its various embodiments described herein, the present invention features methods and pharmaceutical compositions for repair and regeneration of ocular tissues, which utilize progenitor cells and cell populations isolated from postpartum tissues. The invention is applicable to any ocular degenerative condition, but is expected to be particularly suitable for a number of ocular disorders for which treatment or cure heretofore has been difficult or unavailable. These include, without limitation, age-related macular degeneration, retinitis pigmentosa, diabetic and other retinopathies, glaucoma and other optic neuropathies, and disorders associated with limbal stem cell deficiency.

Stem or progenitor cells isolated from postpartum placenta or umbilical cord in accordance with any method known in the art are expected to be suitable for use in the present invention. In a one embodiment, however, the invention utilizes postpartum-derived cells (PPDCs) as defined above, which are derived from placental or umbilical cord tissue that has been rendered substantially free of blood, preferably in accordance with the method set forth below. The PPDCs are capable of self-renewal and expansion in culture and have the potential to differentiate into cells of other phenotypes. Certain embodiments features populations comprising such cells, pharmaceutical compositions comprising the cells or components or products thereof, and methods of using the pharmaceutical compositions for treatment of patients with acute or chronic ocular degenerative conditions. The postpartum-derived cells of the present invention have been characterized by their growth properties in culture, by their cell surface markers, by their gene expression, by their ability to produce certain biochemical trophic factors, and by their immunological properties.

Preparation of PPDCs

According to the methods described herein, a mammalian placenta and umbilical cord are recovered upon or shortly after termination of either a full-term or pre-term pregnancy, for example, after expulsion after birth. The postpartum tissue may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of PPDCs. It is even more preferable that the tissue not be frozen prior to extraction of PPDCs.

Isolation of PPDCs preferably occurs in an aseptic environment. The umbilical cord may be separated from the placenta by means known in the art. Alternatively, the umbilical cord and placenta are used without separation. Blood and debris are preferably removed from the postpartum tissue prior to isolation of PPDCs. For example, the postpartum tissue may be washed with buffer solution, such as but not limited to phosphate buffered saline. The wash buffer also may comprise one or more antimycotic and/or antibiotic agents, such as but not limited to penicillin, streptomycin, amphotericin B, gentamicin, and nystatin.

Postpartum tissue comprising a whole placenta or a fragment or section thereof is disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Ranging from weakly digestive (e.g. deoxyribonucleases and the neutral protease, dispase) to strongly digestive (e.g. papain and trypsin), such enzymes are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest singlestranded DNA and can minimize cell clumping during isolation. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. More preferred are those methods that employ digestion in the presence of at least one collagenase from *Clostridium histolyticum*, and either of the protease activities, dispase and thermo lysin. Still more preferred are methods employing digestion with both collagenase and dispase enzyme activities. Also preferred are methods that include digestion with a hyaluronidase activity in addition to collagenase and dispase activities. The skilled artisan will appreciate that many such enzyme treatments are known in the art for isolating cells from various tissue sources. For example, the LIBERASE™ Blendzyme 3 (Roche) series of enzyme combinations are suitable for use in the instant methods. Other sources of enzymes are known, and the skilled artisan may also obtain such enzymes directly from their natural sources. The skilled artisan is also well equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, postpartum tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome.

Isolated cells or postpartum tissue from which PPDCs grow out may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. PPDCs are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, and cellgro FREE™. The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth Medium (DMEM-low glucose, serum, BME, and an antibiotic agent).

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent O$_2$ in air. The cells preferably are cultured at about 25 to about 40° C. and more preferably are cultured at 37° C. The cells are preferably cultured in an incubator. The medium in the culture vessel can be static or agitated, for example, using a bioreactor. PPDCs preferably are grown under low oxidative stress (e.g., with addition of glutathione, Vitamin C, Catalase, Vitamin E, N-Acetylcysteine). "Low oxidative stress", as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

After culturing the isolated cells or tissue fragments for a sufficient period of time, PPDCs will have grown out, either as a result of migration from the postpartum tissue or cell division, or both. In some embodiments of the invention, PPDCs are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in postpartum tissue are fractionated into subpopulations from which the PPDCs can be isolated. This may be accomplished using standard techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS). For a review of clonal selection and cell separation techniques, see Freshney, 1994, CULTURE OF ANIMAL CELLS: A MANUAL OF BASIC TECHNIQUES, 3rd Ed., Wiley-Liss, Inc., New York, which is incorporated herein by reference.

The culture medium is changed as necessary, for example, by carefully aspirating the medium from the dish, for example, with a pipette, and replenishing with fresh medium. Incubation is continued until a sufficient number or density of cells accumulates in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be PPDCs.

PPDCs may be cryopreserved. Accordingly, in a preferred embodiment described in greater detail below, PPDCs for autologous transfer (for either the mother or child) may be derived from appropriate postpartum tissues following the birth of a child, then cryopreserved so as to be available in the event they are later needed for transplantation.

Characteristics of PPDCs

PPDCs may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of PPDCs derived from placental tissue were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079. Examples of PPDCs derived from umbilicus tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the PPDCs possess one or more of the following growth features (1) they require L-valine for growth in culture; (2) they are capable of growth in atmospheres containing oxygen from about 5% to at least about 20% (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyomithine, vitronectin or fibronectin.

In certain embodiments the PPDCs possess a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the PPDCs may be characterized by production of certain proteins, including (1) production of at least one of tissue factor, vimentin, and alpha-smooth muscle actin; and (2) production of at least one of CD10, CD13, CD44, CD73, CD90, PDGFr-alpha, PD-L2 and HLA-A,B, C cell surface markers, as detected by flow cytometry. In other embodiments, the PPDCs may be characterized by lack of production of at least one of CD31, CD34, CD45, CD80, CD86, CD117, CD141, CD178, B7-H2, HLA-G, and HLA-DR,DP,DQ cell surface markers, as detected by flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the PPDCs may be characterized by gene expression, which relative to a human cell that is a fibroblast, a mesenchymal stem cell, or an iliac crest bone marrow cell, is increased for a gene encoding at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; Homo sapiens clone IMAGE:4179671; protein kinase C zeta; hypothetical protein DKFZp564F013; downregulated in ovarian cancer 1; and Homo sapiens gene from clone DKFZp547k1113.

In yet other embodiments, the PPDCs may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); Homo sapiens mRNA; cDNA DKFZp586M2022 (from clone DKFZp586M2022); mesenchyme homeo box 2 (growth arrest-specific homeo box); sine oculis homeobox homolog 1 (Drosophila); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (Drosophila); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; Homo sapiens cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); Homo sapiens mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; Homo sapiens mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the PPDCs may be characterized by secretion of at least one of MCP-1, IL-6, IL-8, GCP-2, HGF, KGF, FGF, HB-EGF, BDNF, TPO, MIP1a, RANTES, and TIMP1. In alternative embodiments, the PPDCs may be characterized by lack of secretion of at least one of TGF-beta2, ANG2, PDGFbb, MIP1b, I309, MDC, and VEGF, as detected by ELISA.

In preferred embodiments, the cell comprises two or more of the above-listed growth, protein/surface marker production, gene expression or substance-secretion characteristics. More preferred are those cells comprising, three, four, or five or more of the characteristics. Still more preferred are PPDCs comprising six, seven, or eight or more of the characteristics. Still more preferred presently are those cells comprising all of above characteristics.

Among cells that are presently preferred for use with the invention in several of its aspects are postpartum cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by flow cytometry.

Certain cells having the potential to differentiate along lines leading to various phenotypes are unstable and thus can spontaneously differentiate. Presently preferred for use with the invention are cells that do not spontaneously differentiate, for example along neural lines. Preferred cells, when grown in Growth Medium, are substantially stable with respect to the cell markers produced on their surface, and with respect to the expression pattern of various genes, for example as determined using an Affymetrix GENECHIP. The cells remain substantially constant, for example in their surface marker characteristics over passaging, through multiple population doublings.

However, one feature of PPDCs is that they may be deliberately induced to differentiate into various lineage phenotypes by subjecting them to differentiation-inducing cell culture conditions. Of use in treatment of certain ocular degenerative conditions, the PPDCs may be induced to differentiate into neural phenotypes using one or more methods known in the art. For instance, as exemplified herein, PPDCs may be plated on flasks coated with laminin in Neurobasal-A medium (Invitrogen, Carlsbad, Calif.) containing B27 (B27 supplement, Invitrogen), L-glutamine and Penicillin/Streptomycin, the combination of which is referred to herein as Neural Progenitor Expansion (NPE) medium. NPE media may be further supplemented with bFGF and/or EGF. Alternatively, PPDCs may be induced to differentiate in vitro by (1) co-culturing the PPDCs with neural progenitor cells, or (2) growing the PPDCs in neural progenitor cell-conditioned medium.

Differentiation of the PPDCs into neural phenotypes may be demonstrated by a bipolar cell morphology with extended processes. The induced cell populations may stain positive for the presence of nestin. Differentiated PPDCs may be assessed by detection of nestin, TuJ1 (BIII tubulin), GFAP, tyrosine hydroxylase, GABA, 04 and/or MBP. In some embodiments, PPDCs have exhibited the ability to form three-dimensional bodies characteristic of neuronal stem cell formation of neurospheres.

Cell Populations, Modifications, Components and Products

Another aspect of the invention features populations of cells isolated from placental or umbilical tissue. In a preferred embodiment, the populations comprise the PPDCs described above, and these cell populations are described in the section below. In some embodiments, the cell population is heterogeneous. A heterogeneous cell population of the invention may comprise at least about 5%, 10%, 20%, 30%, 40%, 50%, 60%, 70%, 80%, 90%, or 95% PPDCs. The heterogeneous cell populations of the invention may further comprise stem cells or other progenitor cells, such as epithelial or neural progenitor cells, or it may further comprise fully differentiated cells. In some embodiments, the population is substantially homogeneous, i.e., comprises substantially only PPDCs (preferably at least about 96%, 97%, 98%, 99% or more PPDCs). The homogeneous cell population of the invention may comprise umbilicus- or placenta-derived cells. Homogeneous populations of umbilicus-derived cells are preferably free of cells of maternal lineage. Homogeneous populations of placenta-derived cells may be of neonatal or maternal lineage. Homogeneity of a cell population may be achieved by any method known in the art, for example, by cell sorting (e.g., flow cytometry) or by clonal expansion in accordance with known methods. Thus, preferred homogeneous PPDC populations may comprise a clonal cell line of postpartum-derived cells. Such populations are particularly useful when a cell clone with highly desirable functionality has been isolated.

Also provided herein are populations of cells incubated in the presence of one or more factors, or under conditions, that stimulate stem cell differentiation along a desired pathway (e.g., neural, epithelial). Such factors are known in the art and the skilled artisan will appreciate that determination of suitable conditions for differentiation can be accomplished with routine experimentation. Optimization of such conditions can be accomplished by statistical experimental design and analysis, for example response surface methodology allows simultaneous optimization of multiple variables, for example in a biological culture. Presently preferred factors include, but are not limited to factors, such as growth or trophic factors, demethylating agents, co-culture with neural or epithelial lineage cells or culture in neural or epithelial lineage cell-conditioned medium, as well other conditions known in the art to stimulate stem cell differentiation along these pathways (for factors useful in neural differentiation, see, e.g., Lang, K. J. D. et al., 2004, J. Neurosci. Res. 76: 184-192; Johe, K. K. et al., 1996, Genes Devel. 10: 3129-3140; Gottleib, D., 2002, Ann. Rev. Neurosci. 25: 381-407).

Postpartum cells, preferably PPDCs, may also be genetically modified to produce therapeutically useful gene products, or to produce antineoplastic agents for treatment of tumors, for example. Genetic modification may be accomplished using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV40, papillomavirus, Epstein-Barr virus or elastin gene promoter. In some embodiments, the control elements used to control expression of the gene of interest can allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

Cells may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a neuron or glial cell can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, Proc. Nat. Acad. Sci. U.S.A. 88:3084-3087). Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, BASIC METHODS IN MOLECULAR BIOLOGY, 2nd ed., Appleton & Lange, Norwalk, Conn.

In other aspects, the invention provides cell lysates and cell soluble fractions prepared from postpartum stem cells, preferably PPDCs, or heterogeneous or homogeneous cell populations comprising PPDCs, as well as PPDCs or populations thereof that have been genetically modified or that have been stimulated to differentiate along a neurogenic pathway. Such lysates and fractions thereof have many utilities. Use of the cell lysate soluble fraction (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well known in the art and include various means of mechanical disruption, enzymatic disruption, or chemical disruption, or combinations thereof. Such cell lysates may be prepared from cells directly in their Growth Medium and thus containing secreted growth factors and the like, or may be prepared from cells washed free of medium in, for example, PBS or other solution. Washed cells may be resuspended at concentrations greater than the original population density if preferred.

In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods.

Cell lysates or cell soluble fractions prepared from populations of postpartum-derived cells may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Cell lysates or fractions thereof may be used in vitro or in vivo, alone or for example, with autologous or syngeneic live cells. The lysates, if introduced in vivo, may be introduced locally at a site of treatment, or remotely to provide, for example needed cellular growth factors to a patient.

In a further embodiment, postpartum cells, preferably PPDCs, can be cultured in vitro to produce biological products in high yield. For example, such cells, which either naturally produce a particular biological product of interest (e.g., a trophic factor), or have been genetically engineered to produce a biological product, can be clonally expanded using the culture techniques described herein. Alternatively, cells may be expanded in a medium that induces differentiation to a desired lineage. In either case, biological products produced by the cell and secreted into the medium can be readily isolated from the conditioned medium using standard separation techniques, e.g., such as differential protein precipitation, ion-exchange chromatography, gel filtration chromatography, electrophoresis, and HPLC, to name a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed, as described above. The biological product may then be purified using anyone or more of the above-listed techniques.

In other embodiments, the invention provides conditioned medium from cultured postpartum cells, preferably PPDCs, for use in vitro and in vivo as described below. Use of such conditioned medium allows the beneficial trophic factors secreted by the postpartum cells to be used allogeneically in a patient without introducing intact cells that could trigger rejection, or other adverse immunological responses. Conditioned medium is prepared by culturing cells in a culture medium, then removing the cells from the medium.

Conditioned medium prepared from populations of postpartum-derived cells may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Conditioned medium may be used in vitro or in vivo, alone or for example, with autologous or syngeneic live cells. The conditioned medium, if introduced in vivo, may be introduced locally at a site of treatment, or remotely to provide, for example needed cellular growth or trophic factors to a patient.

In another embodiment, an extracellular matrix (ECM) produced by culturing postpartum cells (preferably PPDCs) on liquid, solid or semi-solid substrates is prepared, collected and utilized as an alternative to implanting live cells into a subject in need of tissue repair or replacement. The cells are cultured in vitro, on a three dimensional framework as described elsewhere herein, under conditions such that a desired amount of ECM is secreted onto the framework. The cells and the framework are removed, and the ECM processed for further use, for example, as an injectable preparation. To accomplish this, cells on the framework are killed and any cellular debris removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure.

Once the cells have been killed, the cellular membranes may be disrupted and cellular debris removed by treatment with a mild detergent rinse, such as EDTA, CHAPS or a zwitterionic detergent. Alternatively, the tissue can be enzymatically digested and/or extracted with reagents that break down cellular membranes and allow removal of cell contents. Example of such enzymes include, but are not limited to, hyaluronidase, dispase, proteases, and nucleases. Examples of detergents include non-ionic detergents such as, for example, alkylaryl polyether alcohol (TRITON X-100), octylphenoxy polyethoxy-ethanol (Rohm and Haas Philadelphia, Pa.), BRIJ-35, a polyethoxyethanollauryl ether (Atlas Chemical Co., San Diego, Calif.), polysorbate 20 (TWEEN 20), a polyethoxyethanol sorbitan mono laureate (Rohm and Haas), polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending, for example, on whether the new tissue has been formed on a three-dimensional framework that is biodegradable or non-biodegradable. For example, if the framework is non-biodegradable, the ECM can be removed by subjecting the framework to sonication, high-pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in tow for subsequent injection. Alternatively, the ECM can be removed from the biodegradable framework by any of the methods described above for collection of ECM from a non-biodegradable framework. All collection processes are preferably designed so as not to denature the ECM.

After it has been collected, the ECM may be processed further. For example, the ECM can be homogenized to fine particles using techniques well known in the art such as by sonication, so that it can pass through a surgical needle. The components of the ECM can be crosslinked, if desired, by gamma irradiation. Preferably, the ECM can be irradiated between 0.25 to 2 mega rads to sterilize and cross link the ECM. Chemical crosslinking using agents that are toxic, such as glutaraldehyde, is possible but not generally preferred.

The amounts and/or ratios of proteins, such as the various types of collagen present in the ECM, may be adjusted by mixing the ECM produced by the cells of the invention with ECM of one or more other cell types. In addition, biologically active substances such as proteins, growth factors and/or drugs, can be incorporated into the ECM. Exemplary biologically active substances include tissue growth factors, such as TGF-beta, and the like, which promote healing and tissue repair at the site of the injection. Such additional agents may be utilized in any of the embodiments described herein above, e.g., with whole cell lysates, soluble cell fractions, or further purified components and products produced by the cells.

In another embodiment, postpartum cells (preferably PPDCs) are used to re-surface Bruch's membrane that has undergone modifications due to age. Such modifications include, for example, increased thickness, deposition of extracellular matrix and lipids, cross-linking of protein, non-enzymatic formation of advanced glycation end products. In one embodiment, the age-related changes in Bruch's membrane cause dissociation of RPE cells from the Bruch's membrane, and ultimately result in photoreceptor cell death. In one aspect of the present invention, the resurfacing of Bruch's membrane by postpartum cells (preferably PPDCs) prevents the dissociation of RPE cells from the Bruch's membrane. In an alternate embodiment, the postpartum cells promote the attachment of RPE cells to Bruch's membrane. The RPE cells may be endogenous, or they may be transplanted RPE cells.

Pharmaceutical Compositions

In another aspect, the invention provides pharmaceutical compositions that utilize postpartum cells, preferably PPDCs, cell populations and cell components and products in various methods for treatment of ocular degenerative conditions. Certain embodiments encompass pharmaceutical compositions comprising live cells (e.g., PPDCs alone or admixed with other cell types). Other embodiments encompass pharmaceutical compositions comprising PPDC cellular components (e.g., cell lysates, soluble cell fractions, conditioned medium, ECM, or components of any of the foregoing) or products (e.g., trophic and other biological factors produced naturally by PPDCs or through genetic modification, conditioned medium from PPDC culture). In either case, the pharmaceutical composition may further comprise other active agents, such as anti-inflammatory agents, anti-apoptotic agents, antioxidants, growth factors, neurotrophic factors or neuroregenerative, neuroprotective or ophthalmic drugs as known in the art.

Examples of other components that may be added to PPDC pharmaceutical compositions include, but are not limited to: (1) other neuroprotective or neurobeneficial drugs; (2) selected extracellular matrix components, such as one or more types of collagen known in the art, and/or growth factors, platelet-rich plasma, and drugs (alternatively, PPDCs may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, PEMIROLAST, TRANILAST, REMICADE, SIROLIMUS, and non-steroidal anti-inflammatory drugs (NSAIDS) (such as TEPDXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (6) local anesthetics, to name a few.

Pharmaceutical compositions of the invention comprise postpartum cells (preferably PPDCs), or components or products thereof, formulated with a pharmaceutically acceptable carrier or medium. Suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Typically, but not exclusively, pharmaceutical compositions comprising cellular components or products, but not live cells, are formulated as liquids. Pharmaceutical compositions comprising PPDC live cells are typically formulated as liquids, semisolids (e.g., gels) or solids (e.g., matrices, scaffolds and the like, as appropriate for ophthalmic tissue engineering).

Pharmaceutical compositions may comprise auxiliary components as would be familiar to medicinal chemists or biologists. For example, they may contain antioxidants in ranges that vary depending on the kind of antioxidant used. Reasonable ranges for commonly used antioxidants are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. Other representative compounds include mercaptopropionyl glycine, N-acetyl cysteine, beta-mercaptoethylamine, glutathione and similar species, although other antioxidant agents suitable for ocular administration, e.g. ascorbic acid and its salts or sulfite or sodium metabisulfite may also be employed.

A buffering agent may be used to maintain the pH of eye drop formulations in the range of about 4.0 to about 8.0; so as to minimize irritation of the eye. For direct intravitreal or intraocular injection, formulations should be at pH 7.2 to 7.5, preferably at pH 7.3-7.4. The ophthalmologic compositions may also include tonicity agents suitable for administration to the eye. Among those suitable is sodium chloride to make formulations approximately isotonic with 0.9% saline solution.

In certain embodiments, pharmaceutical compositions are formulated with viscosity enhancing agents. Exemplary agents are hydroxyethylcellulose, hydroxypropylcellulose, methylcellulose, and polyvinylpyrrolidone. The pharmaceutical compositions may have cosolvents added if needed. Suitable cosolvents may include glycerin, polyethylene glycol (PEG), polysorbate, propylene glycol, and polyvinyl alcohol. Preservatives may also be included, e.g., benzalkonium chloride, benzethonium chloride, chlorobutanol, phenylmercuric acetate or nitrate, thimerosal, or methyl or propylparabens.

Formulations for injection are preferably designed for single-use administration and do not contain preservatives.

Injectable solutions should have isotonicity equivalent to 0.9% sodium chloride solution (osmolality of 290-300 milliosmoles). This may be attained by addition of sodium chloride or other co-solvents as listed above, or excipients such as buffering agents and antioxidants, as listed above.

The tissues of the anterior chamber of the eye are bathed by the aqueous humor, while the retina is under continuous exposure to the vitreous. These fluids/gels exist in a highly reducing redox state because they contain antioxidant compounds and enzymes. Therefore, it may be advantageous to include a reducing agent in the ophthalmologic compositions. Suitable reducing agents include N-acetylcysteine, ascorbic acid or a salt form, and sodium sulfite or metabisulfite, with ascorbic acid and/or N-acetylcysteine or glutathione being particularly suitable for injectable solutions.

Pharmaceutical compositions comprising cells, cell components or cell products may be delivered to the eye of a patient in one or more of several delivery modes known in the art. In one embodiment that may be suitable for use in some instances, the compositions are topically delivered to the eye in eye drops or washes. In another embodiment, the compositions may be delivered to various locations within the eye via periodic intraocular injection or by infusion in an irrigating solution such as BSS or BSS PLUS (Alcon USA, Fort Worth, Tex.). Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. In another embodiment, the composition may be delivered to or through the lens of an eye in need of treatment via a contact lens (e.g. Lidofilcon B, Bausch & Lomb CW79 or DELTACON (Deltafilcon A) or other object temporarily resident upon the surface of the eye. In other embodiments, supports such as a collagen corneal shield (e.g. BIO-COR dissolvable corneal shields, Summit Technology, Watertown, Mass.) can be employed. The compositions can also be administered by infusion into the eyeball, either through a cannula from an osmotic pump (ALZET, Alza Corp., Palo Alto, Calif.) or by implantation of timed-release capsules (OCCUSENT) or biodegradable disks (OCULEX, OCUSERT). These routes of administration have the advantage of providing a continuous supply of the pharmaceutical composition to the eye. This may be an advantage for local delivery to the cornea, for example.

Pharmaceutical compositions comprising live cells in a semi-solid or solid carrier are typically formulated for surgical implantation at the site of ocular damage or distress. It will be appreciated that liquid compositions also may be administered by surgical procedures. In particular embodiments, semi-solid or solid pharmaceutical compositions may comprise semi-permeable gels, lattices, cellular scaffolds and the like, which may be non-biodegradable or biodegradable. For example, in certain embodiments, it may be desirable or appropriate to sequester the exogenous cells from their surroundings, yet enable the cells to secrete and deliver biological molecules to surrounding cells. In these embodiments, cells may be formulated as autonomous implants comprising living PPDCs or cell population comprising PPDCs surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression (for a review of such devices and methods, see, e.g., P. A. Tresco et al., 2000, Adv. Drug Delivery Rev. 42: 3-27).

In other embodiments, different varieties of degradable gels and networks are utilized for the pharmaceutical compositions of the invention. For example, degradable materials particularly suitable for sustained release formulations include biocompatible polymers, such as poly (lactic acid), poly (lactic-co-glycolic acid), methylcellulose, hyaluronic acid, collagen, and the like. The structure, selection and use of degradable polymers in drug delivery vehicles have been reviewed in several publications, including, A. Domb et al., 1992, Polymers for Advanced Technologies 3:279-291. U.S. Pat. No. 5,869,079 to Wong et al. disclose combinations of hydrophilic and hydrophobic entities in a biodegradable sustained release ocular implant. In addition, U.S. Pat. No. 6,375,972 to Guo et al., U.S. Pat. No. 5,902,598 to Chen et al., U.S. Pat. No. 6,331,313 to Wong et al., U.S. Pat. No. 5,707,643 to Ogura et al., U.S. Pat. No. 5,466,233 to Weiner et al. and U.S. Pat. No. 6,251,090 to Avery et al. each describes intraocular implant devices and systems that may be used to deliver pharmaceutical compositions.

In other embodiments, e.g., for repair of neural lesions, such as a damaged or severed optic nerve, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established (see, e.g., P. A. Tresco et al., 2000, supra; see also D. W. Hutmacher, 2001, J. Biomater. Sci. Polymer Edn. 12: 107-174).

Examples of scaffold or matrix (sometimes referred to collectively as "framework") material that may be used in the present invention include nonwoven mats, porous foams, or self-assembling peptides. Nonwoven mats may, for example, be formed using fibers comprised of a synthetic absorbable copolymer of glycolic and lactic acids (PGA/PLA), sold under the trade name VICRYL (Ethic on, Inc., Somerville, N.J), Foams, composed of, for example, poly (epsilon-caprolactone)/poly (glycolic acid) (PCL/PGA) copolymer, formed by processes such as freeze-drying, or lyophilized, as discussed in U.S. Pat. No. 6,355,699 also may be utilized. Hydrogels such as self-assembling peptides (e.g., RAD16) may also be used. In situ-forming degradable networks are also suitable for use in the invention (see, e.g., Anseth, K. S. et al., 2002, J. Controlled Release 78: 199-209; Wang, D. et al., 2003, Biomaterials 24: 3969-3980; U.S. Patent Publication 2002/0022676 to He et al.). These materials are formulated as fluids suitable for injection, and then may be induced by a variety of means (e.g., change in temperature, pH, exposure to light) to form degradable hydrogel networks in situ or in vivo.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures.

In many of the abovementioned embodiments, the framework may be molded into a useful shape. Furthermore, it will be appreciated that PPDCs may be cultured on pre-formed, non-degradable surgical or implantable devices, e.g., in a manner corresponding to that used for preparing fibroblast-containing GDC endovascular coils, for instance (Marx, W. F. et al., 2001, Am. J. Neuroradiol. 22: 323-333).

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

Frameworks containing living cells are prepared according to methods known in the art. For example, cells can be grown freely in a culture vessel to sub-confluency or confluency, lifted from the culture and inoculated onto the framework. Growth factors may be added to the culture medium prior to, during, or subsequent to inoculation of the cells to trigger differentiation and tissue formation, if desired. Alternatively, the frameworks themselves may be modified so that the growth of cells thereon is enhanced, or so that the risk of rejection of the implant is reduced. Thus, one or more biologically active compounds, including, but not limited to, anti-inflammatory agents, immunosuppressants or growth factors, may be added to the framework for local release.

Methods of Use

Postpartum cells, preferably PPDCs, or cell populations, components of or products produced by such cells, may be used in a variety of ways to support and facilitate repair and regeneration of ocular cells and tissues. Such utilities encompass in vitro, ex vivo and in vivo methods. The methods set forth below are directed to PPDCs, but other postpartum cells may also be suitable for use in those methods.

In Vitro and Ex Vivo Methods

In one embodiment, PPDCs may be used in vitro to screen a wide variety of compounds for effectiveness and cytotoxicity of pharmaceutical agents, growth factors, regulatory factors, and the like. For example, such screening may be performed on substantially homogeneous populations of PPDCs to assess the efficacy or toxicity of candidate compounds to be formulated with, or co-administered with, the PPDCs, for treatment of a an ocular condition. Alternatively, such screening may be performed on PPDCs that have been stimulated to differentiate into a cell type found in the eye, or progenitor thereof, for the purpose of evaluating the efficacy of new pharmaceutical drug candidates. In this embodiment, the PPDCs are maintained in vitro and exposed to the compound to be tested. The activity of a potentially cytotoxic compound can be measured by its ability to damage or kill cells in culture. This may readily be assessed by vital staining techniques. The effect of growth or regulatory factors may be assessed by analyzing the number or robustness of the cultured cells, as compared with cells not exposed to the factors. This may be accomplished using standard cytological and/or histological techniques, including the use of immunocytochemical techniques employing antibodies that define type-specific cellular antigens.

In a further embodiment, as discussed above, PPDCs can be cultured in vitro to produce biological products that are either naturally produced by the cells, or produced by the cells when induced to differentiate into other lineages, or produced by the cells via genetic modification. For instance, TIMP1, TPO, KGF, HGF, FGF, HBEGF, BDNF, MIP1b, MCP1, RANTES, 1309, TARC, MDC, and IL-8 were found to be secreted from umbilicus-derived cells grown in Growth Medium. TIMP1, TPO, KGF, HGF, HBEGF, BDNF, MIP1a, MCP-1, RANTES, TARC, Eotaxin, and IL-8 were found to be secreted from placenta-derived PPDCs cultured in Growth Medium (see Examples). Some of these trophic factors, such as BDNF and IL-6, have important roles in neural regeneration. Other trophic factors, as yet undetected or unexamined, of use in repair and regeneration of ocular tissues, are likely to be produced by PPDCs and possibly secreted into the medium.

In this regard, another embodiment of the invention features use of PPDCs for production of conditioned medium, either from undifferentiated PPDCs or from PPDCs incubated under conditions that stimulate differentiation. Such conditioned media are contemplated for use in in vitro or ex vivo culture of epithelial or neural precursor cells, for example, or in vivo to support transplanted cells comprising homogeneous populations of PPDCs or heterogeneous populations comprising PPDCs and other progenitors, for example.

Yet another embodiment comprises the use of PPCD cell lysates, soluble cell fractions or components thereof, or ECM or components thereof, for a variety of purposes. As mentioned above, some of these components may be used in pharmaceutical compositions. In other embodiments, a cell lysate or ECM is used to coat or otherwise treat substances or devices to be used surgically, or for implantation, or for ex vivo purposes, to promote healing or survival of cells or tissues contacted in the course of such treatments.

As described in Examples 13 and 15, PPDCs have demonstrated the ability to support survival, growth and differentiation of adult neural progenitor cells when grown in co-culture with those cells. Likewise, the experimental results set forth in Example 18 indicates that PPDCs may function to support cells of the retina via trophic mechanisms. Accordingly, in another embodiment, PPDCs are used advantageously in co-cultures in vitro to provide trophic support to other cells, in particular neural cells and neural and ocular progenitors (e.g., neural stem cells and retinal or corneal epithelial stem cells). For co-culture, it may be desirable for the PPDCs and the desired other cells to be co-cultured under conditions in which the two cell types are in contact. This can be achieved, for example, by seeding the cells as a heterogeneous population of cells in culture medium or onto a suitable culture substrate. Alternatively, the PPDCs can first be grown to confluence, and then will serve as a substrate for the second desired cell type in culture. In this latter embodiment, the cells may further be physically separated, e.g., by a membrane or similar device, such that the other cell type may be removed and used separately, following the co-culture period. Use of PPDCs in co-culture to promote expansion and differentiation of neural or ocular cell types may find applicability in research and in clinical/therapeutic areas. For instance, PPDC co-culture may be utilized to facilitate growth and differentiation of such cells in culture, for basic research purposes or for use in drug screening assays, for example. PPDC co-culture may also be utilized for ex vivo expansion of neural or ocular progenitors for later administration for therapeutic purposes. For example, neural or ocular progenitor cells may be harvested from an individual, expanded ex vivo in co-culture with PPDCs, then returned to that individual (autologous transfer) or another individual (syngeneic or allogeneic transfer). In these embodiments, it will be appreciated that, following ex vivo expansion, the mixed population of cells comprising the PPDCs and progenitors could be administered to a patient in need of treatment. Alternatively, in situations where autologous transfer is appropriate or desirable, the co-cultured cell populations may be physically separated in culture, enabling removal of the autologous progenitors for administration to the patient.

In Vivo Methods

As set forth in Examples 16, 17, and 18, PPDCs have been shown to be effectively transplanted into the body, and to supply lost neural or retinal function in animal models accepted for their predictability of efficacy in humans. These results support a preferred embodiment of the invention, wherein PPDCs are used in cell therapy for treating an ocular degenerative condition. Once transplanted into a target location in the eye, PPDCs may themselves differentiate into one or more phenotypes, or they may provide trophic support for ocular cells in situ, or they may exert a beneficial effect in both of those fashions, among others.

PPDCs may be administered alone (e.g., as substantially homogeneous populations) or as admixtures with other cells. As described above, PPDCs may be administered as formulated in a pharmaceutical preparation with a matrix or scaffold, or with conventional pharmaceutically acceptable carriers. Where PPDCs are administered with other cells, they may be administered simultaneously or sequentially with the other cells (either before or after the other cells). Cells that may be administered in conjunction with PPDCs include, but are not limited to, neurons, astrocytes, oligodendrocytes, neural progenitor cells, neural stem cells, ocular progenitor cells, retinal or corneal epithelial stem cells and/or other multipotent or pluripotent stem cells. The cells of different types may be admixed with the PPDCs immediately or shortly prior to administration, or they may be co-cultured together for a period of time prior to administration.

The PPDCs may be administered with other beneficial drugs, biological molecules, such as growth factors, trophic factors, conditioned medium (from postpartum cells or from progenitor or differentiated cell cultures), or other active agents, such as anti-inflammatory agents, anti-apoptotic agents, antioxidants, growth factors, neurotrophic factors or neuroregenerative or neuroprotective drugs as known in the art. When PPDCs are administered with other agents, they may be administered together in a single pharmaceutical composition, or in separate pharmaceutical compositions, simultaneously or sequentially with the other agents (either before or after administration of the other agents).

Examples of other components that may be administered with postpartum cells include, but are not limited to: (1) other neuroprotective or neurobeneficial drugs; (2) selected extracellular matrix components, such as one or more types of collagen known in the art, and/or growth factors, platelet-rich plasma, and drugs (alternatively, the cells may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-I inhibitors, PEMIROLAST, TRANILAST, REMICADE, SIROLIMUS, and non-steroidal anti-inflammatory drugs (NSAIDS) (such as TEPDXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (6) local anesthetics, to name a few.

In one embodiment, PPDCs are administered as undifferentiated cells, i.e., as cultured in Growth Medium. Alternatively, PPDCs may be administered following exposure in culture to conditions that stimulate differentiation toward a desired phenotype.

The cells may be surgically implanted, injected or otherwise administered directly or indirectly to the site of ocular damage or distress. When cells are administered in semi-solid or solid devices, surgical implantation into a precise location in the body is typically a suitable means of administration. Liquid or fluid pharmaceutical compositions, however, may be administered to a more general location in the eye (e.g., topically or intra-ocularly).

Other embodiments encompass methods of treating ocular degenerative conditions by administering pharmaceutical compositions comprising PPDC cellular components (e.g., cell lysates or components thereof) or products (e.g., trophic and other biological factors produced naturally by PPDCs or through genetic modification, conditioned medium from PPDC culture). Again, these methods may further comprise administering other active agents, such as growth factors, neurotrophic factors or neuroregenerative or neuroprotective drugs as known in the art.

Dosage forms and regimes for administering PPDCs or any of the other pharmaceutical compositions described herein are developed in accordance with good medical practice, taking into account the condition of the individual patient, e.g., nature and extent of the ocular degenerative condition, age, sex, body weight and general medical condition, and other factors known to medical practitioners. Thus, the effective amount of a pharmaceutical composition to be administered to a patient is determined by these considerations as known in the art.

It may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above. These and other means for reducing or eliminating an immune response to the transplanted cells are known in the art. As an alternative, PPDCs may be genetically modified to reduce their immunogenicity, as mentioned above.

Survival of transplanted cells in a living patient can be determined through the use of a variety of scanning techniques, e.g., computerized axial tomography (CAT or CT) scan, magnetic resonance imaging (MRI) or positron emission tomography (PET) scans.

Determination of transplant survival can also be done post mortem by removing the tissue and examining it visually or through a microscope. Alternatively, cells can be treated with stains that are specific for neural or ocular cells or products thereof, e.g., neurotransmitters. Transplanted cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

Functional integration of transplanted cells into ocular tissue of a subject can be assessed by examining restoration of the ocular function that was damaged or diseased. For example, effectiveness in the treatment of macular degeneration or other retinopathies may be determined by improvement of visual acuity and evaluation for abnormalities and grading of stereoscopic color fundus photographs. (Age-Related Eye Disease Study Research Group, NEI, NIH, AREDS Report No. 8, 2001, Arch. Ophthalmol. 119: 1417-1436).

Kits and Banks

In another aspect, the invention provides kits that utilize postpartum cells, preferably PPDCs, cell populations, components and products thereof in various methods for ocular regeneration and repair as described above. Where used for treatment of ocular degenerative conditions, or other scheduled treatment, the kits may include one or more cell populations, including at least postpartum cells and a pharmaceutically acceptable carrier (liquid, semi-solid or solid). The kits also optionally may include a means of administering the cells, for example by injection. The kits further may include instructions for use of the cells. Kits prepared for field hospital use, such as for military use may include full-procedure supplies including tissue scaffolds, surgical sutures, and the like, where the cells are to be used in conjunction with repair of acute injuries. Kits for assays and in vitro methods as described herein may contain, for example, one or more of (1) PPDCs or components or products of PPDCs, (2) reagents for practicing the in vitro method, (3) other cells or cell populations, as appropriate, and (4) instructions for conducting the in vitro method.

In yet another aspect, the invention also provides for banking of tissues, cells, cellular components and cell populations of the invention. As discussed above, the cells are readily cryopreserved. The invention therefore provides methods of cryopreserving the cells in a bank, wherein the cells are stored frozen and associated with a complete characterization of the cells based on immunological, biochemical and genetic properties of the cells. The frozen cells can be thawed and expanded or used directly for autologous, syngeneic, or allogeneic therapy, depending on the requirements of the procedure and the needs of the patient. Preferably, the information on each cryopreserved sample is stored in a computer, which is searchable based on the requirements of the surgeon, procedure and patient with suitable matches being made based on the characterization of the cells or populations. Preferably, the cells of the invention are grown and expanded to the desired quantity of cells and therapeutic cell compositions are prepared either separately or as co-cultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a source or donor with a recipient of such cells, for immunological purposes, the bank system makes it easy to match, for example, desirable biochemical or genetic properties of the banked cells to the therapeutic needs. Upon matching of the desired properties with a banked sample, the sample is retrieved and prepared for therapeutic use. Cell lysates, ECM or cellular components prepared as described herein may also be cryopreserved or otherwise preserved (e.g., by lyophilization) and banked in accordance with the present invention.

The following examples are provided to describe the invention in greater detail. They are intended to illustrate, not to limit, the invention.

As used in the following examples and elsewhere in the specification, the term Growth Medium generally refers to a medium sufficient for the culturing of PPDCs. In particular, one presently preferred medium for the culturing of the cells of the invention in comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics ((preferably 50-100 Units/milliliter penicillin, 50-100 microgram/milliliter streptomycin, and 0-0.25 microgram/milliliter amphotericin B; Invitrogen, Carlsbad, Calif.)), and 0.001% (v/v) 2-mercaptoethanol (Sigma, St. Louis Mo.). As used in the Examples below, Growth Medium refers to DMEM-low glucose with 15% fetal bovine serum and antibiotics/antimycotics (when penicillin/streptomycin are included, it is preferably at 50 U/ml and 50 microgram/ml respectively; when penicillin/streptomycin/amphotericin Bare use, it is preferably at 100 U/ml, 100 microgram/ml and 0.25 microgram/ml, respectively). In some cases different growth media are used, or different supplementations are provided, and these are normally indicated in the text as supplementations to Growth Medium.

The following abbreviations may appear in the examples and elsewhere in the specification and claims: ANG2 (or Ang2) for angiopoietin 2; APC for antigen-presenting cells; BDNF for brain-derived neurotrophic factor; bFGF for basic fibroblast growth factor; bid (BID) for "bis in die" (twice per day); CK18 for cytokeratin 18; CNS for central nervous system; CXC ligand 3 for chemokine receptor ligand 3; DMEM for Dulbecco's Minimal Essential Medium; DMEM:lg (or DMEM:Lg, DMEM:LG) for DMEM with low glucose; EDTA for ethylene diamine tetraacetic acid; EGF (or E) for epidermal growth factor; FACS for fluorescent activated cell sorting; FBS for fetal bovine serum; FGF (or F) for fibroblast growth factor; GCP-2 for granulocyte chemotactic protein-2; GF AP for glial fibrillary acidic protein; HB-EGF for heparin-binding epidermal growth factor; HCAEC for Human coronary artery endothelial cells; HGF for hepatocyte growth factor; hMSC for Human mesenchymal stem cells; HNF-1alpha for hepatocyte-specific transcription factor; HVVEC for Human umbilical vein endothelial cells; 1309 for a chemokine and the ligand for the CCR8 receptor; IGF-1 for insulin-like growth factor 1; 1L-6 for interleukin-6; 1L-8 for interleukin 8; K19 for keratin 19; K8 for keratin 8; KGF for keratinocyte growth factor; LIF for leukemia inhibitory factor; MBP for myelin basic protein; MCP-1 for monocyte chemotactic protein 1; MDC for macrophage-derived chemokine; MIP1alpha for macrophage inflammatory protein 1 alpha; MIP1beta for macrophage inflammatory protein 1 beta; MMP for matrix metalloprotease (MMP); MSC for mesenchymal stem cells; NHDF for Normal Human Dermal Fibroblasts; NPE for Neural Progenitor Expansion media; 04 for oligodendrocyte or glial differentiation marker 04; PBMC for Peripheral blood mononuclear cell; PBS for phosphate buffered saline; PDGFbb for platelet derived growth factor; PO for "per os" (by mouth); PNS for peripheral nervous system; Rantes (or RANTES) for regulated on activation, normal T cell expressed and secreted; rhGDF-5 for recombinant human growth and differentiation factor 5; SC for subcutaneously; SDF-1alpha for stromal-derived factor 1 alpha; SHH for sonic hedgehog; SOP for standard operating procedure; TARC for thymus and activation-regulated chemokine; TCP for Tissue culture plastic; TCPS for tissue culture polystyrene; TGFbeta2 for transforming growth factor beta2; TGF beta-3 for transforming growth factor beta-3; TIMP1 for tissue inhibitor of matrix metalloproteinase 1; TPO for thrombopoietin; TUJ1 for BIII Tubulin; VEGF for vascular endothelial growth factor; vWF for von Willebrand factor; and alphaFP for alpha-fetoprotein.

The present invention is further illustrated, but not limited by, the following examples.

Example 1 Derivation of Cells from Postpartum Tissue

This example describes the preparation of postpartum-derived cells from placental and umbilical cord tissues. Postpartum umbilical cords and placentae were obtained upon birth of either a full term or pre-term pregnancy. Cells were harvested from five separate donors of umbilicus and placental tissue. Different methods of cell isolation were tested for their ability to yield cells with: 1) the potential to differentiate into cells with different phenotypes, a characteristic common to stem cells, or 2) the potential to provide trophic factors useful for other cells and tissues.

Methods & Materials

Umbilical Cell Isolation:

Umbilical cords were obtained from National Disease Research Interchange (NDR1, Philadelphia, Pa.). The tissues were obtained following normal deliveries. The cell isolation protocol was performed aseptically in a laminar flow hood. To remove blood and debris, the cord was washed in phosphate buffered saline (PBS; Invitrogen, Carlsbad, Calif.) in the presence of antimycotic and antibiotic (100 units/milliliter penicillin, 100 micrograms/milliliter streptomycin, 0.25 micrograms/milliliter amphotericin B). The tissues were then mechanically dissociated in 150 cm$^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic as described above. In some experiments, an enzyme mixture of collagenase and dispase was used ("C: D") collagenase (Sigma, St Louis, Mo.), 500 Units/milliliter; and dispase (Invitrogen), 50 Units/milliliter in DMEM-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150$^x$ g for 5 minutes, and the supernatant was aspirated. The pellet was resuspended in 20 milliliters of Growth Medium (DMEM-Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 1 milliliter per 100 milliliters of antibiotic/antimycotic as described above. The cell suspension was filtered through a 70-micrometer nylon cell strainer (BD Biosciences). An additional 5 milliliters rinse comprising Growth Medium was passed through the strainer. The cell suspension was then passed through a 40-micrometer nylon cell strainer (BD Biosciences) and chased with a rinse of an additional 5 milliliters of Growth Medium.

The filtrate was resuspended in Growth Medium (total volume 50 milliliters) and centrifuged at 150$^x$ g for 5 minutes. The supernatant was aspirated and the cells were resuspended in 50 milliliters of fresh Growth Medium. This process was repeated twice more.

Upon the final centrifugation supernatant was aspirated and the cell pellet was resuspended in 5 milliliters of fresh Growth Medium. The number of viable cells was determined using Trypan Blue staining. Cells were then cultured under standard conditions.

The cells isolated from umbilical cords were seeded at 5,000 cells/cm$^2$ onto gelatin-coated T-75 cm$^2$ flasks (Corning Inc., Corning, N.Y.) in Growth Medium with antibiotics/antimycotics as described above. After 2 days (in various experiments, cells were incubated from 2-4 days), spent medium was aspirated from the flasks. Cells were washed with PBS three times to remove debris and blood-derived cells. Cells were then replenished with Growth Medium and allowed to grow to confluence (about 10 days from passage 0) to passage 1. On subsequent passages (from passage 1 to 2 and so on), cells reached sub-confluence (75-85 percent confluence) in 4-5 days. For these subsequent passages, cells were seeded at 5000 cells/cm$^2$. Cells were grown in a humidified incubator with 5 percent carbon dioxide and atmospheric oxygen, at 37° C.

Placental Cell Isolation:

Placental tissue was obtained from NDRI (Philadelphia, Pa.). The tissues were from a pregnancy and were obtained at the time of a normal surgical delivery. Placental cells were isolated as described for umbilical cell isolation.

The following example applies to the isolation of separate populations of maternal-derived and neonatal-derived cells from placental tissue.

The cell isolation protocol was performed aseptically in a laminar flow hood. The placental tissue was washed in phosphate buffered saline (PBS; Invitrogen, Carlsbad, Calif.) in the presence of antimycotic and antibiotic (as described above) to remove blood and debris. The placental tissue was then dissected into three sections: top-line (neonatal side or aspect), midline (mixed cell isolation neonatal and maternal) and bottom line (maternal side or aspect).

The separated sections were individually washed several times in PBS with antibiotic/antimycotic to further remove blood and debris. Each section was then mechanically dissociated in 150 cm$^2$ tissue culture plates in the presence of 50 milliliters of DMEM-Low glucose, to a fine pulp. The pulp was transferred to 50 milliliter conical tubes. Each tube contained approximately 5 grams of tissue. The tissue was digested in either DMEM-Low glucose or DMEM-High glucose medium containing antimycotic and antibiotic (100 U/milliliter penicillin, 100 micrograms/milliliter streptomycin, 0.25 micrograms/milliliter amphotericin B) and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliter in DMEM-Low glucose medium. In other experiments a mixture of collagenase, dispase and hyaluronidase (C:D:H) was used (collagenase, 500 Units/milliliter; dispase, 50 Units/milliliter; and hyaluronidase (Sigma), 5 Units/milliliter in DMEM- Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at $150^x$ g for 5 minutes, the resultant supernatant was aspirated off. The pellet was resuspended in 20 milliliters of Growth Medium with penicillin/streptomycin/amphotericin B. The cell suspension was filtered through a 70 micometer nylon cell strainer (BD Biosciences), chased by a rinse with an additional 5 milliliters of Growth Medium. The total cell suspension was passed through a 40 micometer nylon cell strainer (BD Biosciences) followed with an additional 5 milliliters of Growth Medium as a rinse.

The filtrate was resuspended in Growth Medium (total volume 50 milliliters) and centrifuged at $150^x$ g for 5 minutes. The supernatant was aspirated and the cell pellet was resuspended in 50 milliliters of fresh Growth Medium. This process was repeated twice more. After the final centrifugation, supernatant was aspirated and the cell pellet was resuspended in 5 milliliters of fresh Growth Medium. A cell count was determined using the Trypan Blue Exclusion test. Cells were then cultured at standard conditions.

LIBERASE Cell Isolation:

Cells were isolated from umbilicus tissues in DMEM-Low glucose medium with LIBERASE (Boehringer Mannheim Corp., Indianapolis, Ind.) (2.5 milligrams per milliliter, Blendzyme 3; Roche Applied Sciences, Indianapolis, Ind.) and hyaluronidase (5 Units/milliliter, Sigma). Digestion of the tissue and isolation of the cells was as described for other protease digestions above, using the LIBERASE/hyaluronidase mixture in place of the C:D or C:D:H enzyme mixture. Tissue digestion with LIBERASE resulted in the isolation of cell populations from postpartum tissues that expanded readily.

Cell Isolation Using Other Enzyme Combinations:

Procedures were compared for isolating cells from the umbilical cord using differing enzyme combinations. Enzymes compared for digestion included: i) collagenase; ii) dispase; iii) hyaluronidase; iv) collagenase: dispase mixture (C:D); v) collagenase: hyaluronidase mixture (C:H); vi) dispase: hyaluronidase mixture (D:H); and vii) collagenase: dispase: hyaluronidase mixture (C:D:H). Differences in cell isolation utilizing these different enzyme digestion conditions were observed (Table 1-1).

Isolation of Cells from Residual Blood in the Cords:

Other attempts were made to isolate pools of cells from umbilical cord by different approaches. In one instance umbilical cord was sliced and washed with Growth Medium to dislodge the blood clots and gelatinous material. The mixture of blood, gelatinous material and Growth Medium was collected and centrifuged at $150^x$ g. The pellet was resuspended and seeded onto gelatin-coated flasks in Growth Medium. From these experiments a cell population was isolated that readily expanded.

Isolation of Cells from Cord Blood:

Cells have also been isolated from cord blood samples attained from NDR1. The isolation protocol used here was that of International Patent Application PCT/US2002/029971 by Ho et al (Ho, T. W. et al., WO2003025149 A2). Samples (50 milliliter and 10.5 milliliters, respectively) of umbilical cord blood (NDR1, Philadelphia Pa.) were mixed with lysis buffer (filter-sterilized 155 mM ammonium chloride, 10 millimolar potassium bicarbonate, 0.1 millimolar EDT A buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at $200^x$ g). The cell pellet was resuspended in complete minimal essential medium (Gibco, Carlsbad Calif.) containing 10 percent fetal bovine serum (Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at $200^x$ g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

Isolation of Cells Using Different Enzyme Combinations and Growth Conditions:

To determine whether cell populations could be isolated under different conditions and expanded under a variety of conditions immediately after isolation, cells were digested in Growth Medium with or without 0.001 percent (v/v) 2-mercaptoethanol (Sigma, St. Louis, Mo.), using the enzyme combination of C:D:H, according to the procedures provided above. Placental-derived cells so isolated were seeded under a variety of conditions. All cells were grown in the presence of penicillin/streptomycin. (Table 1-2).

Isolation of Cells Using Different Enzyme Combinations and Growth Conditions:

In all conditions cells attached and expanded well between passage 0 and 1 (Table 1-2). Cells in conditions 5-8 and 13-16 were demonstrated to proliferate well up to 4 passages after seeding at which point they were cryopreserved and banked.

Results

Cell Isolation Using Different Enzyme Combinations:

The combination of C:D:H, provided the best cell yield following isolation, and generated cells, which expanded for many more generations in culture than the other conditions (Table 1-1). An expandable cell population was not attained using collagenase or hyaluronidase alone. No attempt was made to determine if this result is specific to the collagen that was tested.

Isolation of Cells Using Different Enzyme Combinations and Growth Conditions:

Cells attached and expanded well between passage 0 and 1 under all conditions tested for enzyme digestion and growth (Table 1-2). Cells in experimental conditions 5-8 and 13-16 proliferated well up to 4 passages after seeding, at which point they were cryopreserved. All cells were banked for further investigation.

Isolation of Cells from Residual Blood in the Cords:

Nucleated cells attached and grew rapidly. These cells were analyzed by flow cytometry and were similar to cells obtained by enzyme digestion.

Isolation of Cells from Cord Blood:

The preparations contained red blood cells and platelets. No nucleated cells attached and divided during the first 3 weeks. The medium was changed 3 weeks after seeding and no cells were observed to attach and grow.

Summary:

Populations of cells can be derived from umbilical cord and placental tissue efficiently using the enzyme combination collagenase (a matrix metalloprotease), dispase (a neutral protease) and hyaluronidase (a mucolytic enzyme that breaks down hyaluronic acid). LIBERASE, which is a Blendzyme, may also be used. Specifically, Blendzyme 3, which is collagenase (4 Wunsch units/g) and thermolysin (1714 casein Units/g) was also used together with hyaluronidase to isolate cells. These cells expanded readily over many passages when cultured in Growth Medium on gelatin-coated plastic.

Cells were also isolated from residual blood in the cords, but not cord blood. The presence of cells in blood clots washed from the tissue that adhere and grow under the conditions used may be due to cells being released during the dissection process.

Example 2 Growth Characteristics of Postpartum-Derived Cells

The cell expansion potential of postpartum-derived cells (PPDCs) was compared to other populations of isolated stem cells. The process of cell expansion to senescence is referred to as Hayflick's limit (Hayflick L. 1974a, 1974b). Postpartum-derived cells are highly suited for therapeutic use because they can be readily expanded to sufficient cell numbers.

Materials and Methods

Gelatin-Coating Flasks:
Tissue culture plastic flasks were coated by adding 20 milliliters 2% (w/v) porcine gelatin (Type B: 225 Bloom; Sigma, St Louis, Mo.) to a T75 flask (Corning Inc., Corning, N.Y.) for 20 minutes at room temperature. After removing the gelatin solution, 10 milliliters phosphatebuffered saline (PBS) (Invitrogen, Carlsbad, Calif.) was added and then aspirated.

Comparison of Expansion Potential of PPDCs with Other Cell Populations:
For comparison of growth expansion potential the following cell populations were utilized; i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot #9F0844; Cambrex, Walkersville, Md.); iv) Umbilicus-derived cells; and v) Placenta-derived cells. Cells were initially seeded at 5,000 cells/cm$^2$ on gelatin-coated T75 flasks in Growth Medium with penicillin/streptomycin/amphotericin B. For subsequent passages, cell cultures were treated as follows. After trypsinization, viable cells were counted after Trypan Blue staining. Cell suspension (50 microliters) was combined with Trypan Blue (50 milliliters, Sigma, St. Louis Mo.). Viable cell numbers were estimated using a hemocytometer.

Following counting, cells were seeded at 5,000 cells/cm$^2$ onto gelatin-coated T75 flasks in 25 milliliters of fresh Growth Medium. Cells were grown under standard conditions at 37° C. The Growth Medium was changed twice per week. When cells reached about 85 percent confluence they were passaged; this process was repeated until the cells reached senescence.

At each passage, cells were trypsinized and counted. The viable cell yield, population doubling [ln (cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion Potential of Cell Banks at Low Density:
The expansion potential of cells banked at passage 10 was also tested, using a different set of conditions. Normal dermal skin fibroblasts (cc-2509 lot #9F0844; Cambrex, Walkersville, Md.), umbilicus-derived cells, and placenta-derived cells were tested. These cell populations had been banked at passage 10 previously, having been cultured at 5,000 cells/cm$^2$ and grown to confluence at each passage to that point. The effect of cell density on the cell populations following cell thaw at passage 10 was determined. Cells were thawed under standard conditions and counted using Trypan Blue staining. Thawed cells were then seeded at 1000 cells/cm$^2$ in DMEM-Low glucose Growth Medium with antibiotic/antimycotic as described above. Cells were grown under standard atmospheric conditions at 37° C. Growth Medium was changed twice a week and cells were passaged as they reached about 85% confluence. Cells were subsequently passaged until senescence, i.e., until they could not be expanded any further. Cells were trypsinized and counted at each passage. The cell yield, population doubling (ln (cell final/cell initial)/ln 2) and doubling time (time in culture (h)/population doubling). The total cell yield per passage was determined by multiplying total yield for the previous passage by the expansion factor for each passage (i.e., expansion factor=cell final/cell initial).

Expansion of PPDCs at Low Density from Initial Cell Seeding:
The expansion potential of freshly isolated PPDCs under low cell seeding conditions was tested. PPDDs were prepared as described herein. Cells were seeded at 1000 cells/cm$^2$ and passaged as described above until senescence. Cells were grown under standard atmospheric conditions at 37° C. Growth Medium was changed twice per week. Cells were passaged as they reached about 85% confluence. At each passage, cells were trypsinized and counted by Trypan Blue staining. The cell yield, population doubling (ln (cell final/cell initial)/ln 2) and doubling time (time in culture (h)/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of Clonal Neonatal Placenta-Derived Cells:
Cloning was used in order to expand a population of neonatal cells from placental tissue. Following isolation of three differential cell populations from the placenta (as described herein), these cell populations were expanded under standard growth conditions and then karyotyped to reveal the identity of the isolated cell populations. Because the cells were isolated from a mother who delivered a boy, it was straightforward to distinguish between the male and female chromosomes by performing metaphase spreads. These experiments demonstrated that fetal-aspect cells were karyotype positive for neonatal phenotype, mid-layer cells were karyotype positive for both neonatal and maternal phenotypes and maternal-aspect cells were karyotype positive for maternal cells.

Expansion of Cells in Low Oxygen Culture Conditions:
It has been demonstrated that low oxygen cell culture conditions can improve cell expansion in certain circumstances (US20040005704). To determine if cell expansion of PPDCs could be improved by altering cell culture conditions, cultures of umbilical-derived cells were grown in low oxygen conditions. Cells were seeded at 5000 cells/cm$^2$ in Growth Medium on gelatin coated flasks. Cells were initially cultured under standard atmospheric conditions through passage 5, at which point they were transferred to low oxygen (5% O$_2$) culture conditions.

Other Growth Conditions:

In other protocols, cells were expanded on non-coated, collagen-coated, fibronectin-coated, laminin-coated and extracellular matrix protein-coated plates. Cultures have been demonstrated to expand well on these different matrices.

Results

Comparison of Expansion Potential of PPDCs with Other Stem Cell and Non-Stem Cell Populations:

Both umbilical-derived and placenta-derived cells expanded for greater than 40 passages generating cell yields of greater than $1E^{17}$ cells in 60 days. In contrast, MSCs and fibroblasts senesced after less than 25 days and less than 60 days, respectively. Although adipose-derived cells expanded for almost 60 days they generated total cell yields of $4.5E^{12}$. Thus, when seeded at 5000 cells/$cm^2$ under the experimental conditions utilized, postpartum-derived cells expanded much better than the other cell types grown under the same conditions (Table 2-1).

Expansion Potential of Cell Banks at Low Density:

Umbilicus-derived, placenta-derived and fibroblast cells expanded for greater than 10 passages generating cell yields of greater than $1E^{11}$ cells in 60 days (Table 2-2). After 60 days under these conditions the fibroblasts became senescent whereas the umbilicus-derived and placenta-derived cell populations senesced after 80 days, completing greater than 50 and greater than 40 population doublings respectively.

Expansion of PPDCs at low density from initial cell seeding. PPDCs were expanded at low density (1,000 cells/$cm^2$) on gelatin-coated and uncoated plates or flasks. Growth potential of these cells under these conditions was good. The cells expanded readily in a log phase growth. The rate of cell expansion was similar to that observed when placenta-derived cells were seeded at 5000 cells/$cm^2$ on gelatin-coated flasks in Growth Medium. No differences were observed in cell expansion potential between culturing on either uncoated flasks or gelatin-coated flasks. However, cells appeared phenotypically much smaller on gelatin-coated flasks and more larger cell phenotypes were observed on uncoated flasks.

Expansion of Clonal Neonatal or Maternal Placenta-Derived Cells:

A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin coated plates. From this initial cloning, expansive clones are identified, trypsinized, and reseeded in 12-well gelatin-coated plates in Growth medium and then subsequently passaged into T25 gelatin-coated flasks at 5,000 cells/$cm^2$ in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells $cm^2$ 1 flask. Cells are passaged at 5,000 cells $cm^2$/T75 flask. The growth characteristics of a clone may be plotted to demonstrate cell expansion. Karyotyping analysis can confirm that the clone is either neonatal or maternal.

Expansion of Cells in Low Oxygen Culture Conditions:

Cells expanded well under the reduced oxygen conditions, however, culturing under low oxygen conditions did not appear to have a significant effect on cell expansion of PPDCs under the conditions used.

Summary:

Cell expansion conditions comprising growing isolated postpartum-derived cells at densities of about 5000 cells/$cm^2$, in Growth Medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1000 cells/$cm^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

Example 3 Evaluation of Growth Media for Placenta-Derived Cells

Several cell culture media were evaluated for their ability to support the growth of placenta-derived cells. The growth of placenta-derived cells in normal (20%) and low (5%) oxygen was assessed after 3 days using the MTS calorimetric assay.

Methods & Materials

Placenta-derived cells at passage 8 (P8) were seeded at $1 \times 10^3$ cells/well in 96 well plates in Growth Medium with penicillin/streptomycin. After 8 hours the medium was changed as described below and cells were incubated in normal (atmospheric) or low (5%, v/v) oxygen at 37° C., 5% $CO_2$ for 48 hours. MTS was added to the culture medium (CellTiter 96® AQueous One Solution Cell Proliferation Assay, Promega, Madison, Wis.) for 3 hours and the absorbance measured at 490 nanometers (Molecular Devices, Sunnyvale Calif.).

Results

Standard curves for the MTS assay established a linear correlation between an increase in absorbance and an increase in cell number. The absorbance values obtained were converted into estimated cell numbers and the change (%) relative to the initial seeding was calculated.

The Effect of Serum:

The addition of serum to media at normal oxygen conditions resulted in a reproducible dose-dependent increase in absorbance and thus the viable cell number. The addition of serum to complete MSCGM resulted in a dose-dependent decrease in absorbance. In the media without added serum, cells only grew appreciably in cellgro FREE™ Ham's F10 and DMEM.

The Effect of Oxygen:

Reduced oxygen appeared to increase the growth rate of cells in Growth Medium, Ham's F10, and MSCGM. In decreasing order of growth, the media resulting in the best growth of the cells were Growth Medium, greater than MSCGM, greater than Iscove's+10% FBS, equal to DMEM-H+10% FBS, equal to Ham's F12+10% FBS, equal to RPMI 1640+10% FBS.

Summary:

Placenta-derived cells may be grown in a variety of culture media in normal or low oxygen. Short-term growth of placenta-derived cells was determined in twelve basal media with 0.2 and 10% (v/v) serum in 5% or atmospheric oxygen. In general, placenta-derived cells did not grow as well in serum-free conditions with the exception of Ham's F10 and cellgro FREE™, which are also protein-free. Growth in these serum-free media was about 25-33% of the maximal growth observed with media containing 15% serum.

Example 4 Growth of Postpartum-Derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). It was not previously known whether postpartum-derived cells could grow in medium containing D-valine.

Methods & Materials

Placenta-derived cells (P3), fibroblasts (P9) and umbilical-derived cells (P5) were seeded at $5 \times 10^3$ cells/cm$^2$ in gelatin-coated T75 flasks (Corning Inc., Corning, N.Y.). After 24 hours the medium was removed and the cells were washed with phosphate buffered saline (PBS) (Gibco, Carlsbad, Calif.) to remove residual medium. The medium was replaced with a Modified Growth Medium (DMEM with D-valine (special order Gibco), 15% (v/v) dialyzed fetal bovine serum (Hyclone, Logan, Utah), 0.001% (v/v) beta-mercaptoethanol (Sigma), penicillin/streptomycin (Gibco)).

Results

Placenta-derived, umbilical-derived, and fibroblast cells seeded in the D-valine-containing medium did not proliferate, unlike cells seeded in Growth Medium containing dialyzed serum. Fibroblasts cells changed morphologically, increasing in size and changing shape. All of the cells died and eventually detached from the flask surface after 4 weeks. These results indicate that medium containing D-valine is not suitable for selectively growing postpartum-derived cells.

Example 5 Cryopreservation Media for Placenta-Derived Cells

Cryopreservation media for the cryopreservation of placenta-derived cells were evaluated.

Methods & Materials

Placenta-derived cells grown in Growth Medium in a gelatin-coated T75 flask were washed with PBS and trypsinized using 1 milliliter Trypsin/EDTA (Gibco). The trypsinization was stopped by adding 10 milliliters Growth Medium. The cells were centrifuged at 150$^x$ g, supernatant removed, and the cell pellet was resuspended in 1 milliliter Growth Medium. An aliquot of cell suspension, 60 microliters, was removed and added to 60 microliters trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

a. Growth Medium+10% (v/v) DMSO (Hybrimax, Sigma, St. Louis, Mo.)
   b. Cell Freezing medium w/DMSO, w/methyl cellulose, serum-free (C6295, Sigma, St. Louis, Mo.)
   c. Cell Freezing medium serum-free (C2639, Sigma, St. Louis, Mo.)
   d. Cell Freezing Medium w/glycerol (C6039, Sigma, St. Louis, Mo.)

The cells were cooled at approximately-1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliters Growth Medium and centrifuged before the cell number and viability was estimated. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%. The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary:

The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is the preferred medium of those compared for cryopreservation of placenta-derived cells.

Example 6 Karyotype Analysis of Postpartum-Derived Cells

Cell lines used in cell therapy are preferably homogeneous and free from any contaminating cell type. Cells used in cell therapy should have a normal chromosome number (46) and structure. To identify placenta- and umbilicus-derived cell lines that are homogeneous and free from cells of non-postpartum tissue origin, karyotypes of cell samples were analyzed.

Methods & Materials

PPDCs from postpartum tissue of a male neonate were cultured in Growth Medium containing penicillin/streptomycin. Postpartum tissue from a male neonate (X,Y) was selected to allow distinction between neonatal-derived cells and maternal derived cells (X,X). Cells were seeded at 5,000 cells per square centimeter in Growth Medium in a T25 flask (Corning Inc., Corning, N.Y.) and expanded to 80% confluence. A T25 flask containing cells was filled to the neck with Growth Medium. Samples were delivered to a clinical cytogenetics laboratory by courier (estimated lab to lab transport time is one hour). Cells were analyzed during metaphase when the chromosomes are best visualized. Of 20 cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted as exhibiting a normal appearance. Three of the 16 cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

Summary:

Chromosome analysis identified placenta- and umbilicus-derived cells whose karyotypes appeared normal as interpreted by a clinical cytogenetic laboratory. Karyotype analysis also identified cell lines free from maternal cells, as determined by homogeneous karyotype.

Example 7 Evaluation of Human Postpartum-Derived Cell Surface Markers by Flow Cytometry Characterization of cell surface proteins or "markers" by flow cytometry can be used to determine a cell line's identity. The consistency of expression can be determined from multiple donors, and in cells exposed to different processing and culturing conditions. Postpartum-derived cell (PPDC) lines isolated from the placenta and umbilicus were characterized (by flow cytometry), providing a profile for the identification of these cell lines.

Methods & Materials

Media and Culture Vessels:

Cells were cultured in Growth Medium (Gibco Carlsbad, Calif.) with penicillin/streptomycin. Cells were cultured in plasma-treated T75, T150, and T225 tissue culture flasks (Corning Inc., Corning, N.Y.) until confluent. The growth surfaces of the flasks were coated with gelatin by incubating 2% (w/v) gelatin (Sigma, St. Louis, Mo.) for 20 minutes at room temperature.

Antibody Staining and Flow Cytometry Analysis:

Adherent cells in flasks were washed in PBS and detached with Trypsin/EDTA. Cells were harvested, centrifuged, and resuspended in 3% (v/v) FBS in PBS at a cell concentration of $1 \times 10^7$ per milliliter. In accordance with the manufacture's specifications, antibody to the cell surface marker of interest (see below) was added to one hundred microliters of cell suspension and the mixture was incubated in the dark for 30 minutes at 4° C. After incubation, cells were washed with PBS and centrifuged to remove unbound antibody. Cells were resuspended in 500 microliter PBS and analyzed by flow cytometry. Flow cytometry analysis was performed with a FACScalibur™ instrument (Becton Dickinson, San Jose, Calif.). Table 7 lists the antibodies to cell surface markers that were used.

Placenta and Umbilicus Comparison:

Placenta-derived cells were compared to umbilicus-derive cells at passage 8.

Passage to Passage Comparison:

Placenta- and umbilicus-derived cells were analyzed at passages 8, 15, and 20.

Donor to Donor Comparison:

To compare differences among donors, placenta-derived cells from different donors were compared to each other, and umbilicus-derived cells from different donors were compared to each other.

Surface Coating Comparison:

Placenta-derived cells cultured on gelatin-coated flasks was compared to placenta-derived cells cultured on uncoated flasks. Umbilicus-derived cells cultured on gelatin-coated flasks was compared to umbilicus-derived cells cultured on uncoated flasks.

Digestion Enzyme Comparison:

Four treatments used for isolation and preparation of cells were compared. Cells isolated from placenta by treatment with 1) collagenase; 2) collagenase/dispase; 3) collagenase/hyaluronidase; and 4) collagenase/hyaluronidase/dispase were compared.

Placental Layer Comparison:

Cells derived from the maternal aspect of placental tissue were compared to cells derived from the villous region of placental tissue and cells derived from the neonatal fetal aspect of placenta.

Results

Placenta Vs. Umbilicus Comparison:

Placenta- and umbilicus-derived cells analyzed by flow cytometry showed positive expression of CD10, CD13, CD44, CD73, CD90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in fluorescence values of positive curves were accounted for. The mean (i.e. CD13) and range (i.e. CD90) of the positive curves showed some variation, but the curves appeared normal, confirming a homogenous population. Both curves individually exhibited values greater than the IgG control.

Passage to Passage Comparison—Placenta-Derived Cells:

Placenta-derived cells at passages 8, 15, and 20 analyzed by flow cytometry all were positive for expression of CD10, CD13, CD44, CD73, CD90, PDGFr-alpha and HLAA, B, C, as reflected in the increased value of fluorescence relative to the IgG control. The cells were negative for expression of CD31, CD34, CD45, CD117, CD141, and HLA-DR, D P, DQ having fluorescence values consistent with the IgG control.

Passage to Passage Comparison—Umbilicus-Derived Cells:

Umbilicus-derived cells at passage 8, 15, and 20 analyzed by flow cytometry all expressed CD10, CD13, CD44, CD73, CD90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Donor to Donor Comparison—Placenta-Derived Cells:

Placenta-derived cells isolated from separate donors analyzed by flow cytometry each expressed CD10, CD13, CD44, CD73, CD90, PDGFr-alpha and HLA-A, B, C, with increased values of fluorescence relative to the IgG control. The cells were negative for expression of CD31, CD34, CD45, CD117, CD141, and HLA-DR, DP, DQ as indicated by fluorescence value consistent with the IgG control.

Donor to Donor Comparison—Umbilicus Derived Cells:

Umbilicus-derived cells isolated from separate donors analyzed by flow cytometry each showed positive expression of CD10, CD13, CD44, CD73, CD90, PDGFr-alpha and HLA-A, B, C, reflected in the increased values of fluorescence relative to the IgG control. These cells were negative for expression of CD31, CD34, CD45, CD117, CD141, and HLA-DR, DP, DQ with fluorescence values consistent with the IgG control.

The Effect of Surface Coating with Gelatin on Placenta-Derived Cells:

Placenta-derived cells expanded on either gelatin-coated or uncoated flasks analyzed by flow cytometry all expressed of CD10, CD13, CD44, CD73, CD90, PDGFr-alpha and HLA-A, B, C, reflected in the increased values of fluorescence relative to the IgG control. These cells were negative for expression of CD31, CD34, CD45, CD117, CD141, and HLA-DR, DP, DQ indicated by fluorescence values consistent with the IgG control.

The Effect of Surface Coating with Gelatin on Umbilicus-Derived Cells:

Umbilicus-derived cells expanded on gelatin and uncoated flasks analyzed by flow cytometry all were positive for expression of CD10, CD13, CD44, CD73, CD90, PDGFr-alpha and HLA-A, B, C, with increased values of fluorescence relative to the IgG control. These cells were negative for expression of CD31, CD34, CD45, CD117, CD141, and HLA-DR, DP, DQ, with fluorescence values consistent with the IgG control.

Effect of Enzyme Digestion Procedure Used for Preparation of the Cells on the Cell Surface Marker Profile:

Placenta-derived cells isolated using various digestion enzymes analyzed by flow cytometry all expressed CD10, CD13, CD44, CD73, CD90, PDGFr-alpha and HLA-A, B, C, as indicated by the increased values of fluorescence relative to the IgG control. These cells were negative for expression of CD31, CD34, CD45, CD117, CD141, and HLADR, DP, DQ as indicated by fluorescence values consistent with the IgG control.

Placental Layer Comparison:

Cells isolated from the maternal, villous, and neonatal layers of the placenta, respectively, analyzed by flow cytometry showed positive expression of CD10, CD13, CD44, CD73, CD90, PDGFr-alpha and HLA-A, B, C, as indicated by the increased value of fluorescence relative to the IgG control. These cells were negative for expression of CD31, CD34, CD45, CD117, CD141, and HLA-DR, DP, DQ as indicated by fluorescence values consistent with the IgG control.

Summary:

Analysis of placenta- and umbilicus-derived cells by flow cytometry has established of an identity of these cell lines. Placenta- and umbilicus-derived cells are positive for CD10, CD13, CD44, CD73, CD90, PDGFr-alpha, HLA-A,B,C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges was observed, but all positive curves under all conditions tested were normal and expressed fluorescence values greater than the IgG control, thus confirming that the cells comprise a homogenous population that has positive expression of the markers.

Example 8 Immunohistochemical Characterization of Postpartum Tissue Phenotypes

The phenotypes of cells found within human postpartum tissues, namely umbilical cord and placenta, was analyzed by immunohistochemistry.

Methods & Materials

Tissue Preparation:

Human umbilical cord and placenta tissue was harvested and immersion fixed in 4% (w/v) paraformaldehyde overnight at 4° C. Immunohistochemistry was performed using antibodies directed against the following epitopes: vimentin (1:500; Sigma, St. Louis, Mo.), desmin (1:150, raised against rabbit; Sigma; or 1:300, raised against mouse; Chemic on, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: antihuman GROalpha-PE (1:100; Becton Dickinson, Franklin Lakes, N.J), antihuman GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 μm thick) using a standard cryostat (Leica Microsystems) and mounted onto glass slides for staining.

Immunohistochemistry:

Immunohistochemistry was performed similar to previous studies (e.g., Messina, et al., 2003, Exper. Neurol. 184: 816-829). Tissue sections were washed with phosphate-buffered saline (PBS) and exposed to a protein blocking solution containing PBS, 4% (v/v) goat serum (Chemic on, Temecula, Calif.), and 0.3% (v/v) Triton (Triton X-100; Sigma) for 1 hour to access intracellular antigens. In instances where the epitope of interest would be located on the cell surface (CD34, ox-LDL R1), Triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical Cord Characterization:
Vimentin, desmin, SMA, CKI8, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta Characterization:
Vimentin, desmin, SMA, CKI8, vWF, and CD34 were all observed within the placenta and regionally specific.

GROalpha, GCP-2, Ox-LDL RI, and NOGO-A Tissue Expression:
None of these markers were observed within umbilical cord or placental tissue.

Summary:
Vimentin, desmin, alpha-smooth muscle actin, cytokeratin 18, von Willebrand Factor, and CD34 are expressed in cells within human umbilical cord and placenta.

Example 9 Analysis of Postpartum Tissue-Derived Cells Using Oligonucleotide Arrays Affymetrix GENECHIP arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Methods & Materials

Isolation and Culture of Cells:
Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium (using DMEM-LG) on gelatin-coated tissue culture plastic flasks. The cultures were incubated at 37° C. with 5% $CO_2$.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen). The cells were grown on standard tissue-treated plastic.

Human mesenchymal stem cells (hMSC) were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human iliac crest bone marrow was received from the NDRI with patient consent. The marrow was processed according to the method outlined by Ho, et al. (WO03/025149). The marrow was mixed with lysis buffer (155 mM NH 4Cl, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at $500^x$ g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at $5 \times 10^4$ cells/$cm^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and GENECHIP Analysis:
Actively growing cultures of cells were removed from the flasks with a cell scraper in cold PBS. The cells were centrifuged for 5 minutes at $300^x$ g. The supernatant was removed and the cells were resuspended in fresh PBS and centrifuged again. The supernatant was removed and the cell pellet was immediately frozen and stored at −80° C. Cellular mRNA was extracted and transcribed into cDNA, which was then transcribed into and biotin-labeled. The biotin-labeled cRNA was hybridized with HG-U133A GENECHIP oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University; Tusher, V. G. et al., 2001, Proc. Natl. Acad. Sci. USA 98: 5116-5121).

Results

Fourteen different populations of cells were analyzed. The cells along with passage information, culture substrate, and culture media are listed in Table 9-1.

The data were evaluated by a Principle Component Analysis, analyzing the 290 genes that were differentially expressed in the cells. This analysis allows for a relative comparison for the similarities between the populations. Table 9-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes (i.e., the greater the distance, the less similarity exists).

Tables 9-3, 9-4, and 9-5 show the expression of genes increased in placenta-derived cells (Table 9-3), increased in umbilicus-derived cells (Table 9-4), and reduced in umbilicus- and placenta-derived cells (Table 9-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

Tables 9-6, 9-7, and 9-8 show the expression of genes increased in human fibroblasts (Table 9-6), ICBM cells (Table 9-7), and MSCs (Table 9-8).

Summary:

The present examination was performed to provide a molecular characterization of the postpartum cells derived from umbilical cord and placenta. This analysis included cells derived from three different umbilical cords and three different placentas. The examination also included two different lines of dermal fibroblasts, three lines of mesenchymal stem cells, and three lines of iliac crest bone marrow cells. The mRNA that was expressed by these cells was analyzed using an oligonucleotide array that contained probes for 22,000 genes. Results showed that 290 genes are differentially expressed in these five different cell types. These genes include ten genes that are specifically increased in the placenta-derived cells and seven genes specifically increased in the umbilical cord-derived cells. Fifty-four genes were found to have specifically lower expression levels in placenta and umbilical cord, as compared with the other cell types. The expression of selected genes has been confirmed by PCR (see the example that follows). These results demonstrate that the postpartum-derived cells have a distinct gene expression profile, for example, as compared to bone marrow-derived cells and fibroblasts.

Example 10 Cell Markers in Postpartum-Derived Cells

In the preceding example, similarities and differences in cells derived from the human placenta and the human umbilical cord were assessed by comparing their gene expression profiles with those of cells derived from other sources (using an oligonucleotide array). Six "signature" genes were identified: oxidized LDL receptor 1, interleukin-8, rennin, reticulon, chemokine receptor ligand 3 (CXC ligand 3), and granulocyte chemotactic protein 2 (GCP-2). These "signature" genes were expressed at relatively high levels in postpartum-derived cells.

The procedures described in this example were conducted to verify the microarray data and find concordance/discordance between gene and protein expression, as well as to establish a series of reliable assay for detection of unique identifiers for placenta- and umbilicus-derived cells.

Methods & Materials

Cells:

Placenta-derived cells (three isolates, including one isolate predominately neonatal as identified by karyotyping analysis), umbilicus-derived cells (four isolates), and Normal Human Dermal Fibroblasts (NHDF; neonatal and adult) grown in Growth Medium with penicillin/streptomycin in a gelatin-coated T75 flask. Mesechymal Stem Cells (MSCS) were grown in Mesenchymal Stem Cell Growth Medium Bullet kit (MSCGM; Cambrex, Walkerville, Md.).

For the IL-8 protocol, cells were thawed from liquid nitrogen and plated in gelatin-coated flasks at 5,000 cells/$cm^2$, grown for 48 hours in Growth Medium and then grown for further 8 hours in 10 milliliters of serum starvation medium [DMEM—low glucose (Gibco, Carlsbad, Calif.), penicillin/streptomycin (Gibco, Carlsbad, Calif.) and 0.1% (w/v) Bovine Serum Albumin (BSA; Sigma, St. Louis, Mo.)]. After this treatment RNA was extracted and the supernatants were centrifuged at $150^x$ g for 5 minutes to remove cellular debris. Supernatants were then frozen at $-80°$ C. for ELISA analysis.

Cell Culture for ELISA Assay:

Postpartum cells derived from placenta and umbilicus, as well as human fibroblasts derived from human neonatal foreskin were cultured in Growth Medium in gelatin-coated T75 flasks. Cells were frozen at passage 11 in liquid nitrogen. Cells were thawed and transferred to 15-milliliter centrifuge tubes. After centrifugation at $150^x$ g for 5 minutes, the supernatant was discarded. Cells were resuspended in 4 milliliters culture medium and counted. Cells were grown in a 75 $cm^2$ flask containing 15 milliliters of Growth Medium at 375,000 cells/flask for 24 hours. The medium was changed to a serum starvation medium for 8 hours. Serum starvation medium was collected at the end of incubation, centrifuged at $14,000^x$ g for 5 minutes (and stored at $-20°$ C.).

To estimate the number of cells in each flask, 2 milliliters of tyrpsin/EDTA (Gibco, Carlsbad, Calif.) was added each flask. After cells detached from the flask, trypsin activity was neutralized with 8 milliliters of Growth Medium. Cells were transferred to a 15 milliliters centrifuge tube and centrifuged at $150^x$ g for 5 minutes. Supernatant was removed and 1 milliliter Growth Medium was added to each tube to resuspend the cells. Cell number was estimated using a hemocytometer.

ELISA Assay:

The amount of IL-8 secreted by the cells into serum starvation medium was analyzed using ELISA assays (R&D Systems, Minneapolis, Minn.). All assays were tested according to the instructions provided by the manufacturer.

Total RNA Isolation:

RNA was extracted from confluent postpartum-derived cells and fibroblasts or for IL-8 expression from cells treated as described above. Cells were lysed with 350 microliters buffer RLT containing beta-mercaptoethanol (Sigma, St. Louis, Mo.) according to the manufacturer's instructions (RNeasy® Mini Kit; Qiagen, Valencia, Calif.). RNA was extracted according to the manufacturer's instructions (RNeasy® Mini Kit; Qiagen, Valencia, Calif.) and subjected to DNase treatment (2.7 U/sample) (Sigma St. Louis, Mo.). RNA was eluted with 50 microliters DEPC-treated water and stored at $-80°$ C.

Reverse Transcription:

RNA was also extracted from human placenta and umbilicus. Tissue (30 milligram) was suspended in 700 microliters of buffer RLT containing 2-mercaptoethanol. Samples were mechanically homogenized and the RNA extraction proceeded according to manufacturer's specification. RNA was extracted with 50 microliters of DEPC-treated water and stored at $-80°$ C. RNA was reversed transcribed using random hexamers with the TaqMan® reverse transcription reagents (Applied Biosystems, Foster City, Calif.) at $25°$ C. for 10 minutes, $37°$ C. for 60 minutes, and $95°$ C. for 10 minutes. Samples were stored at $-20°$ C.

Genes identified by cDNA microarray as uniquely regulated in postpartum cells (signature genes—including oxidized LDL receptor, interleukin-8, rennin and reticulon), were further investigated using real-time and conventional PCR.

Real-Time PCR:

PCR was performed on cDNA samples using Assays-on-Demand® gene expression products: oxidized LDL receptor (Hs00234028); rennin (Hs00166915); reticulon (Hs003825 15); CXC ligand 3 (Hs00171061); GCP-2 (Hs00605742); IL-8 (Hs00174103); and GAPDH (Applied Biosystems, Foster City, Calif.) were mixed with cDNA and TaqMan® Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 min and 95° C. for 10 min, followed by 40 cycles of 95° C. for 15 sec and 60° C. for 1 min. PCR data was analyzed according to manufacturer's specifications (User Bulletin #2 from Applied Biosystems for ABI Prism 7700 Sequence Detection System).

Conventional PCR:

Conventional PCR was performed using an ABI PRISM 7700 (Perkin Elmer Applied Biosystems, Boston, Mass., USA) to confirm the results from real-time PCR. PCR was performed using 2 microliters of cDNA solution, $1^x$ Ampli-Taq Gold universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for rennin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 10. Primer concentration in the final PCR reaction was 1 micromolar except for GAPDH, which was 0.5 micromolar. GAPDH primers were the same as real-time PCR, except that the manufacturer's TaqMan® probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal length Polaroid camera (VWR International, South Plainfield, N.J.).

Immunofluorescence:

PPDCs were fixed with cold 4% (w/v) paraformaldehyde (Sigma-Aldrich, St. Louis, Mo.) for 10 minutes at room temperature. One isolate each of umbilicus- and placenta-derived cells at passage 0 (P0) (directly after isolation) and passage 11 (P 11) (two isolates of placenta-derived, two isolates of umbilicus-derived cells) and fibroblasts (P 11) were used. Immunocytochemistry was performed using antibodies directed against the following epitopes: vimentin (1:500, Sigma, St. Louis, Mo.), desmin (1:150; Sigma—raised against rabbit; or 1:300; Chemic on, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GRO alpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemic on, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of Cells for FACS Analysis:

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$ per milliliter. One hundred microliter aliquots were delivered to conical tubes. Cells stained for intracellular antigens were permeabilized with Perm/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliters PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), Donkey against Goat IgG (sc-3743; Santa Cruz, Biotech.). Flow cytometry analysis was performed with FACScalibur™ (Becton Dickinson San Jose, Calif.).

Results

Results of real-time PCR for selected "signature" genes performed on cDNA from cells derived from human placentae, adult and neonatal fibroblasts and Mesenchymal Stem Cells (MSCs) indicate that both oxidized LDL receptor and rennin were expressed at higher level in the placenta-derived cells as compared to other cells. The data obtained from real-time PCR were analyzed by the AACT method and expressed on a logarithmic scale. Levels of reticulon and oxidized LDL receptor expression were higher in umbilicus-derived cells as compared to other cells. No significant difference in the expression levels of CXC ligand 3 and GCP-2 were found between postpartum-derived cells and controls. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed above.

The production of the cytokine, IL-8 in postpartum was elevated in both Growth Medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilical cells and some isolates of placenta cells (Table 10-1). No IL-8 was detected in medium derived from human dermal fibroblasts.

Placenta-derived cells were also examined for the production of oxidized LDL receptor, GCP-2 and GROalpha by FACS analysis. Cells tested positive for GCP-2. Oxidized LDL receptor and GRO were not detected by this method.

Placenta-derived cells were also tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilicus-derived cells were positive for alpha-smooth muscle actin and vimentin, with the staining pattern consistent through passage 11.

Summary:

Concordance between gene expression levels measured by microarray and PCR (both real-time and conventional) has been established for four genes: oxidized LDL receptor 1, rennin, reticulon, and IL-8. The expression of these genes was differentially regulated at the mRNA level in PPDCs, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level, however GCP-2 was detected at the protein level by FACS analysis in the placenta-derived cells. Although this result is not reflected by data originally obtained from the micro array experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, in the Growth Medium and under the conditions utilized in these procedures. Cells derived from the human umbilical cord at passage 0 were probed for the expression of alpha-smooth muscle actin and vimentin, and were positive for both. The staining pattern was preserved through passage 11.

Example 11 In Vitro Immunological Evaluation of Postpartum-Derived Cells

Postpartum-derived cells (PPDCs) were evaluated in vitro for their immunological characteristics in an effort to predict the immunological response, if any, these cells would elicit upon in vivo transplantation. PPDCs were assayed by flow cytometry for the presence of HLA-DR, HLA-DP, HLA-DQ, CD80, CD86, and B7-H2. These proteins are expressed by antigen-presenting cells (APe) and are required for the direct stimulation of naïve CD4+T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, 2003, supra), CD 178 (Coumans, et al., (1999) Journal of Immunological Methods 224, 185-196), and PD-L2 (Abbas & Lichtman, 2003, supra; Brown, et. al. (2003) The Journal of Immunology 170, 1257-1266). The expression of these proteins by cells residing in placental tissues is thought to mediate the immuno-privileged status of placental tissues in utero. To predict the extent to which placenta- and umbilicus-derived cell lines elicit an immune response in vivo, the cell lines were tested in a one-way mixed lymphocyte reaction (MLR).

Methods & Materials

Cell Culture:

Cells were cultured to confluence in Growth Medium containing penicillin/streptomycin in T75 flasks (Corning Inc., Corning, N.Y.) coated with 2% gelatin (Sigma, St. Louis, Mo.).

Antibody Staining:

Cells were washed in phosphate buffered saline (PBS) (Gibco, Carlsbad, Calif.) and detached with Trypsin/EDTA (Gibco, Carlsbad, Mo.). Cells were harvested, centrifuged, and re-suspended in 3% (v/v) FBS in PBS at a cell concentration of $1 \times 10^7$ per milliliter. Antibody (Table 11-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur™ instrument (Becton Dickinson, San Jose, Calif.).

Mixed Lymphocyte Reaction:

Cryopreserved vials of passage 10 umbilicus-derived cells labeled as cell line A and passage 11 placenta-derived cells labeled as cell line B were sent on dry ice to CTBR (Senneville, Quebec) to conduct a mixed lymphocyte reaction using CTBR SOP No. CAC-031. Peripheral blood mononuclear cells (PBMCs) were collected from multiple male and female volunteer donors. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]-thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the PPDCs was calculated as the mean proliferation of the receiver plus mitomycin C-treated postpartum cell line divided by the baseline proliferation of the receiver.

Results

Mixed Lymphocyte Reaction—Placenta-Derived Cells:

Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 11-2). The average stimulation index ranged from 1.3 (plate 2) to 3 (plate 1) and the allogeneic donor positive controls ranged from 46.25 (plate 2) to 279 (plate 1) (Table 11-3).

Mixed Lymphocyte Reaction—Umbilicus-Derived Cells:

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and placenta cell lines were mitomycin C-treated and cultured in a mixed lymphocyte reaction with the five individual allogeneic receivers. Reactions were performed in triplicate using two cell culture plates with three receivers per plate (Table 11-4). The average stimulation index ranged from 6.5 (plate 1) to 9 (plate 2) and the allogeneic donor positive controls ranged from 42.75 (plate 1) to 70 (plate 2) (Table 11-5).

Antigen Presenting Cell Markers—Placenta-Derived Cells:

Histograms of placenta-derived cells analyzed by flow cytometry show negative expression of HLA-DR, DP, DQ, CD80, CD86, and B7-H2, as noted by fluorescence value consistent with the IgG control, indicating that placental cell lines lack the cell surface molecules required to directly stimulate CD4+T cells.

Immunomodulating Markers—Placenta-Derived Cells:

Histograms of placenta-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Antigen Presenting Cell Markers—Umbilicus-Derived Cells:

Histograms of umbilicus-derived cells analyzed by flow cytometry show negative expression of HLA-DR, DP, DQ, CD80, CD86, and B7-H2, as noted by fluorescence value consistent with the IgG control, indicating that umbilical cell lines lack the cell surface molecules required to directly stimulate CD4+T cells.

Immunomodulating Cell Markers—Umbilicus-Derived Cells:

Histograms of umbilicus-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary:

In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilicus-derived cell lines the average stimulation index ranged from 6.5 to 9, and that of the allogeneic positive controls ranged from 42.75 to 70. Placenta- and umbilicus-derived cell lines were negative for the expression of the stimulating proteins HLA-DR, HLA-DP, HLA-DQ, CD80, CD86, and B7-H2, as measured by flow cytometry. Placenta- and umbilicus-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DR, DQ, CD8, CD86, and B 7-H2, thereby allowing for the stimulation of naïve CD4+T cells. The absence of antigen-presenting cell surface molecules on placenta- and umbilicus-derived cells required for the direct stimulation of naïve CD4+T cells and the presence of PD-L2, an immunomodulating protein, may account for the low stimulation index exhibited by these cells in a MLR as compared to allogeneic controls.

Example 12 Secretion of Trophic Factors by Postpartum-Derived Cells

The secretion of selected trophic factors from placenta- and umbilicus-derived cells was measured. Factors selected for detection included: (1) those known to have angiogenic activity, such as hepatocyte growth factor (HGF) (Rosen et al. (1997) Ciba Found. Symp. 212:215-26), monocyte chemotactic protein 1 (MCP-1) (Salcedo et al. (2000) Blood 96; 34-40), interleukin-8 (IL-8) (Li et al. (2003) J. Immunol. 170:3369-76), keratinocyte growth factor (KGF), basic fibroblast growth factor (bFGF), vascular endothelial growth factor (VEGF) (Hughes et al. (2004) Ann. Thorac. Surg. 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1alpha (SDF-1alpha); (2) those known to have neurotrophic/neuroprotective activity, such as brain-derived neurotrophic factor (BDNF) (Cheng et al. (2003) Dev. Biol. 258; 319-33), interleukin-6 (IL-6), granulocyte chemotactic protein-2 (GCP-2), transforming growth factor beta2 (TGFbeta2); and (3) those known to have chemokine activity, such as macrophage inflammatory protein 1alpha (MIP1a), macrophage inflammatory protein 1 beta (MIP1b), monocyte chemoattractant-1 (MCP-1), Rantes (regulated on activation, normal T cell expressed and secreted), 1309, thymus and activation-regulated chemokine (TARe), Eotaxin, macrophage-derived chemokine (MDC), IL-8).

Methods & Materials

Cell Culture:

PPDCs from placenta and umbilicus as well as human fibroblasts derived from human neonatal foreskin were cultured in Growth Medium with penicillin/streptomycin on gelatin-coated T75 flasks. Cells were cryopreserved at passage 11 and stored in liquid nitrogen. After thawing of the cells, Growth Medium was added to the cells followed by transfer to a 15 milliliter centrifuge tube and centrifugation of the cells at $150^x$ g for 5 minutes. The supernatant was discarded. The cell pellet was resuspended in 4 milliliters Growth Medium, and cells were counted. Cells were seeded at 375,000 cells/75 $cm^2$ flask containing 15 milliliters of Growth Medium and cultured for 24 hours. The medium was changed to a serum-free medium (DMEM-low glucose (Gibco), 0.1% (w/v) bovine serum albumin (Sigma), penicillin/streptomycin (Gibco)) for 8 hours. Conditioned serum-free medium was collected at the end of incubation by centrifugation at 14,000$^x$ g for 5 minutes and stored at −20° C. To estimate the number of cells in each flask, cells were washed with PBS and detached using 2 milliliters trypsin/EDTA. Trypsin activity was inhibited by addition of 8 milliliters Growth Medium. Cells were centrifuged at 150$^x$ g for 5 minutes. Supernatant was removed, and cells were resuspended in 1 milliliter Growth Medium. Cell number was estimated using a hemocytometer.

ELISA Assay:

Cells were grown at 37° C. in 5% carbon dioxide and atmospheric oxygen. Placenta-derived cells (batch 101503) also were grown in 5% oxygen or beta-mercaptoethanol (BME). The amount of MCP-1, IL-6, VEGF, SDF-1alpha, GCP-2, IL-8, and TGF-beta 2 produced by each cell sample was measured by an ELISA assay (R&D Systems, Minneapolis, Minn.). All assays were performed according to the manufacturer's instructions.

SearchLight™ Multiplexed ELISA Assay:

Chemokines (MIP1a, MIP1b, MCP-1, Rantes, 1309, TARC, Eotaxin, MDC, IL8), BDNF, and angiogenic factors (HGF, KGF, bFGF, VEGF, TIMP1, ANG2, PDGF-bb, TPO, HB-EGF were measured using SearchLight™ Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA Assay:

MCP-1 and IL-6 were secreted by placenta- and umbilicus-derived cells and dermal fibroblasts (Table 12-1). SDF-1alpha was secreted by placenta-derived cells cultured in 5% O 2 and by fibroblasts. GCP-2 and IL-8 were secreted by umbilicus-derived cells and by placenta-derived cells cultured in the presence of BME or 5% O2. GCP-2 also was secreted by human fibroblasts. TGF-beta2 was not detectable by ELISA assay.

SearchLight™ Multiplexed ELISA Assay:

TIMP1, TPO, KGF, HGF, FGF, HBEGF, BDNF, MIP1b, MCP1, RANTES, 1309, TARC, MDC, and IL-8 were secreted from umbilicus-derived cells (Tables 12-2 and 12-3). TIMP1, TPO, KGF, HGF, HBEGF, BDNF, MIP1a, MCP-1, RANTES, TARC, Eotaxin, and IL-8 were secreted from placenta-derived cells (Tables 12-2 and 12-3). No Ang2, VEGF, or PDGF-bb were detected.

Summary:

Umbilicus- and placenta-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

Example 13 Short-Term Neural Differentiation of Postpartum-Derived Cells

The ability of placenta- and umbilicus-derived cells (collectively postpartum-derived cells or PPDCs) to differentiate into neural lineage cells was examined.

Methods & Materials

Isolation and Expansion of Postpartum Cells:

PPDCs from placental and umbilical tissues were isolated and expanded as described in Example 1.

Modified Woodbury-Black Protocol (A):

This assay was adapted from an assay originally performed to test the neural induction potential of bone marrow stromal cells (1). Umbilicus-derived cells (022803) P4 and placenta-derived cells (042203) P3 were thawed and culture expanded in Growth Media at 5,000 cells/cm$^2$ until sub-confluence (75%) was reached. Cells were then trypsinized and seeded at 6,000 cells per well of a Titretek II glass slide (VWR International, Bristol, Conn.). As controls, mesenchymal stem cells (P3; 1F2155; Cambrex, Walkersville, Md.), osteoblasts (P5; CC2538; Cambrex), adipose-derived cells (Artecel, U.S. Pat. No. 6,555,374 B1) (P6; Donor 2) and neonatal human dermal fibroblasts (P6; CC2509; Cambrex) were also seeded under the same conditions.

All cells were initially expanded for 4 days in DMEM/F12 medium (Invitrogen, Carlsbad, Calif.) containing 15% (v/v) fetal bovine serum (FBS; Hyclone, Logan, Utah), basic fibroblast growth factor (bFGF; 20 nanograms/milliliter; Peprotech, Rocky Hill, N.J.), epidermal growth factor (EGF; 20 nanograms/milliliter; Peprotech) and penicillin/streptomycin (Invitrogen). After four days, cells were rinsed in phosphate-buffered saline (PBS; Invitrogen) and were subsequently cultured in DMEM/F12 medium+20% (v/v) FBS+penicillin/streptomycin for 24 hours. After 24 hours, cells were rinsed with PBS. Cells were then cultured for 1-6 hours in an induction medium which was comprised of DMEM/F12 (serum-free) containing 200 mM butylated hydroxyanisole, 10 µM potassium chloride, 5 milligram/milliliter insulin, 10 µM forskolin, 4 µM valproic acid, and 2 µM hydrocortisone (all chemicals from Sigma, St. Louis, Mo.). Cells were then fixed in 100% ice-cold methanol and immunocytochemistry was performed (see methods below) to assess human nestin protein expression.

Modified Woodbury-Black Protocol (B):

PPDCs (umbilicus (022803) P11; placenta (042203) P11 and adult human dermal fibroblasts (1F1853, P11) were thawed and culture expanded in Growth Medium at 5,000 cells/cm$^2$ until sub-confluence (75%) was reached. Cells were then trypsinized and seeded at similar density as in (A), but onto (1) 24 well tissue culture-treated plates (TCP, Falcon brand, VWR International), (2) TCP wells+2% (w/v) gelatin adsorbed for 1 hour at room temperature, or (3) TCP wells+20 µg/milliliter adsorbed mouse laminin (adsorbed for a minimum of 2 hours at 37° C.; Invitrogen).

Exactly as in (A), cells were initially expanded and media switched at the aforementioned timeframes. One set of cultures was fixed, as before, at 5 days and 6 hours, this time with ice-cold 4% (w/v) paraformaldehyde (Sigma) for 10 minutes at room temperature. In the second set of cultures, medium was removed and switched to Neural Progenitor Expansion medium (NPE) consisting of Neurobasal-A medium (Invitrogen) containing B27 (B27 supplement; Invitrogen), L-glutamine (4 mM), and penicillin/streptomycin (Invitrogen). NPE medium was further supplemented with retinoic acid (RA; 1 µM; Sigma). This medium was removed 4 days later and cultures were fixed with ice-cold 4% (w/v) paraformaldehyde (Sigma) for 10 minutes at room temperature, and stained for nestin, GFAP, and TuJ1 protein expression (see Table 13-1).

Two Stage Differentiation Protocol:

PPDCs (umbilicus (042203) P11, placenta (022803) P11), adult human dermal fibroblasts (P11; 1F1853; Cambrex)

were thawed and culture expanded in Growth Medium at 5,000 cells/cm² until sub-confluence (75%) was reached. Cells were then trypsinized and seeded at 2,000 cells/cm², but onto 24 well plates coated with laminin (BD Biosciences, Franklin Lakes, N.J.) in the presence of NPE media supplemented with bFGF (20 nanograms/milliliter; Peprotech, Rocky Hill, N.J.) and EGF (20 nanograms/milliliter; Peprotech) [whole media composition further referred to as NPE+F+E]. At the same time, adult rat neural progenitors isolated from hippocampus (P4; (062603) were also plated onto 24 welliaminin-coated plates in NPE+F+E media. All cultures were maintained in such conditions for a period of 6 days (cells were fed once during that time) at which time media was switched to the differentiation conditions listed in Table 13-2 for an additional period of 7 days. Cultures were fixed with ice-cold 4% (w/v) paraformaldehyde (Sigma) for 10 minutes at room temperature, and stained for human or rat nestin, GF AP, and TuJ1protein expression.

Multiple Growth Factor Protocol:

Umbilicus-derived cells (P11; (042203)) were thawed and culture expanded in Growth Medium at 5,000 cells/cm² until sub-confluence (75%) was reached. Cells were then trypsinized and seeded at 2,000 cells/cm², onto 24 welliaminin-coated plates (BD Biosciences) in the presence of NPE+F (20 nanograms/milliliter)+E (20 nanograms/milliliter). In addition, some wells contained NPE+F+E+2% FBS or 10% FBS. After four days of "pre-differentiation" conditions, all media were removed and samples were switched to NPE medium supplemented with sonic hedgehog (SHH; 200 nanograms/milliliter; Sigma, St. Louis, Mo.), FGF8 (100 nanograms/milliliter; Peprotech), BDNF (40 nanograms/milliliter; Sigma), GDNF (20 nanograms/milliliter; Sigma), and retinoic acid (1 µM; Sigma). Seven days post medium change, cultures were fixed with ice-cold 4% (w/v) paraformaldehyde (Sigma) for 10 minutes at room temperature, and stained for human nestin, GFAP, TuJ1, desmin, and alpha-smooth muscle actin expression.

Neural Progenitor Co-Culture Protocol:

Adult rat hippocampal progenitors (062603) were plated as neurospheres or single cells (10,000 cells/well) onto laminin-coated 24 well dishes (BD Biosciences) in NPE+F (20 nanograms/milliliter)+E (20 nanograms/milliliter). Separately, umbilicus-derived cells (042203) P11 and placenta-derived cells (022803) P11 were thawed and culture expanded in NPE+F (20 nanograms/milliliter)+E (20 nanograms/milliliter) at 5,000 cells/cm² for a period of 48 hours. Cells were then trypsinized and seeded at 2,500 cells/well onto existing cultures of neural progenitors. At that time, existing medium was exchanged for fresh medium. Four days later, cultures were fixed with ice-cold 4% (w/v) paraformaldehyde (Sigma) for 10 minutes at room temperature, and stained for human nuclear protein (hNuc; Chemic on) (Table 13-1 above) to identify PPDCs.

Immunocytochemistry:

Immunocytochemistry was performed using the antibodies listed in Table 13-1. Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Modified Woodbury-Black Protocol (A):

Upon incubation in this neural induction composition, all cell types transformed into cells with bipolar morphologies and extended processes. Other larger non-bipolar morphologies were also observed. Furthermore, the induced cell populations stained positively for nestin, a marker of multipotent neural stem and progenitor cells.

Modified Woodbury-Black Protocol (B):

When repeated on tissue culture plastic (TCP) dishes, nestin expression was not observed unless laminin was pre-adsorbed to the culture surface. To further assess whether nestin-expressing cells could then go on to generate mature neurons, PPDCs and fibroblasts were exposed to NPE+RA (1 µM), a media composition known to induce the differentiation of neural stem and progenitor cells into such cells (2, 3, 4). Cells were stained for TuJ1, a marker for immature and mature neurons, GFAP, a marker of astrocytes, and nestin. Under no conditions was TuJ1 detected, nor were cells with neuronal morphology observed, suggesting that neurons were not generated in the short term. Furthermore, nestin and GF AP were no longer expressed by PPDCs, as determined by immunocytochemistry.

Two-Stage Differentiation:

Umbilicus and placenta PPDC isolates (as well as human fibroblasts and rodent neural progenitors as negative and positive control cell types, respectively) were plated on laminin (neural promoting)-coated dishes and exposed to 13 different growth conditions (and two control conditions) known to promote differentiation of neural progenitors into neurons and astrocytes. In addition, two conditions were added to examine the influence of GDF5, and BMP7 on PPDC differentiation. Generally, a two-step differentiation approach was taken, where the cells were first placed in neural progenitor expansion conditions for a period of 6 days, followed by full differentiation conditions for 7 days. Morphologically, both umbilicus- and placenta-derived cells exhibited fundamental changes in cell morphology throughout the time-course of this procedure. However, neuronal or astrocytic-shaped cells were not observed except for in control, neural progenitor-plated conditions. Immunocytochemistry, negative for human nestin, TuJ1, and GFAP confirmed the morphological observations.

Multiple Growth Factors:

Following one week's exposure to a variety of neural differentiation agents, cells were stained for markers indicative of neural progenitors (human nestin), neurons (TuJ1), and astrocytes (GFAP). Cells grown in the first stage in non-serum containing media had different morphologies than those cells in serum containing (2% or 10%) media, indicating potential neural differentiation. Specifically, following a two step procedure of exposing umbilicus-derived cells to EGF and bFGF, followed by SHH, FGF8, GDNF, BDNF, and retinoic acid, cells showed long extended processes similar to the morphology of cultured astrocytes. When 2% FBS or 10% FBS was included in the first stage of differentiation, cell number was increased and cell morphology was unchanged from control cultures at high density. Potential neural differentiation was not evidenced by immunocytochemical analysis for human nestin, TuJ1, or GFAP.

Neural Progenitor and PPDC Co-Culture:

PPDCs were plated onto cultures of rat neural progenitors seeded two days earlier in neural expansion conditions (NPE+F+E). While visual confirmation of plated PPDCs proved that these cells were plated as single cells, human-specific nuclear staining (hNuc) 4 days post-plating (6 days total) showed that they tended to ball up and avoid contact with the neural progenitors. Furthermore, where PPDCs attached, these cells spread out and appeared to be innervated by differentiated neurons that were of rat origin, suggesting that the PPDCs may have differentiated into muscle cells. This observation was based upon morphology under phase contrast microscopy. Another observation was that typically large cell bodies (larger than neural progenitors) possessed morphologies resembling neural progenitors, with thin processes spanning out in multiple directions. hNuc staining (found in one half of the cell's nucleus) suggested that in some cases these human cells may have fused with rat progenitors and assumed their phenotype. Control wells containing only neural progenitors had fewer total progenitors and apparent differentiated cells than did co-culture wells containing umbilicus or placenta PPDCs, further indicating that both umbilicus- and placenta-derived cells influenced the differentiation and behavior of neural progenitors, either by release of chemokines and cytokines, or by contact-mediated effects.

Summary:

Multiple protocols were conducted to determine the short term potential of PPDCs to differentiate into neural lineage cells. These included phase contrast imaging of morphology in combination with immunocytochemistry for nestin, TuJ1, and GFAP, proteins associated with multipotent neural stem and progenitor cells, immature and mature neurons, and astrocytes, respectively. Evidence was observed to suggest that neural differentiation occurred in certain instances in these short-term protocols.

Several notable observations were made in co-cultures of PPDCs with neural progenitors. This approach, using human PPDCs along with a xenogeneic cell type allowed for absolute determination of the origin of each cell in these cultures. First, some cells were observed in these cultures where the cell cytoplasm was enlarged, with neurite-like processes extending away from the cell body, yet only half of the body labeled with hNuc protein. Those cells may have been human PPDCs that had differentiated into neural lineage cells or they may have been PPDCs that had fused with neural progenitors. Second, it appeared that neural progenitors extended neurites to PPDCs in a way that indicates the progenitors differentiated into neurons and innervated the PPDCs. Third, cultures of neural progenitors and PPDCs had more cells of rat origin and larger amounts of differentiation than control cultures of neural progenitors alone, further indicating that plated PPDCs provided soluble factors and or contact-dependent mechanisms that stimulated neural progenitor survival, proliferation, and/or differentiation.

Example 14 Long-Term Neural Differentiation of Postpartum-Derived Cells

The ability of umbilicus and placenta-derived cells (collectively postpartum-derived cells or PPDCs) to undergo long-term differentiation into neural lineage cells was evaluated.

Methods & Materials

Isolation and Expansion of PPDCs:

PPDCs were isolated and expanded as described in previous Examples.

PPDC Cell Thaw and Plating:

Frozen aliquots of PPDCs (umbilicus (022803) P11; (042203) P11; (071003) P12; placenta (101503) P7) previously grown in Growth Medium were thawed and plated at 5,000 cells/cm 2 in T-75 flasks coated with laminin (BD, Franklin Lakes, N.J.) in Neurobasal-A medium (Invitrogen, Carlsbad, Calif.) containing B27 (B27 supplement, Invitrogen), L-glutamine (4 mM), and Penicillin/Streptomycin (10 milliliters), the combination of which is herein referred to as Neural Progenitor Expansion (NPE) media. NPE media was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Control Cell Plating:

In addition, adult human dermal fibroblasts (P11, Cambrex, Walkersville, Md.) and mesenchymal stem cells (P5, Cambrex) were thawed and plated at the same cell seeding density on laminin-coated T-75 flasks in NPE+bFGF+EGF. As a further control, fibroblasts, umbilicus, and placenta PPDCs were grown in Growth Medium for the period specified for all cultures.

Cell Expansion:

Media from all cultures were replaced with fresh media once a week and cells observed for expansion. In general, each culture was passaged one time over a period of one month because of limited growth in NPE+bFGF+EGF.

Immunocytochemistry:

After a period of one month, all flasks were fixed with cold 4% (w/v) paraformaldehyde (Sigma) for 10 minutes at room temperature.

Immunocytochemistry was performed using antibodies directed against TuJ1 (BIII Tubulin; 1:500; Sigma, St. Louis, Mo.) and GFAP (glial fibrillary acidic protein; 1:2000; DakoCytomation, Carpinteria, Calif.). Briefly, cultures were washed with phosphate-buffered saline (PBS) and exposed to a protein blocking solution containing PBS, 4% (v/v) goat serum (Chemic on, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing block along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

NPE+bFGF+EGF media slows proliferation of PPDCs and alters their morphology. Immediately following plating, a subset of PPDCs attached to the culture flasks coated with laminin. This may have been due to cell death as a function of the freeze/thaw process or because of the new growth conditions. Cells that did attach adopted morphologies different from those observed in Growth Media.

Upon confluence, cultures were passaged and observed for growth. Very little expansion took place of those cells that survived passage. At this point, very small cells with no spread morphology and with phase-bright characteristics began to appear in cultures of umbilicus-derived cells. These areas of the flask were followed over time. From these small cells, bifurcating processes emerged with varicosities along their lengths, features very similar to previously described PSA-NCAM+neuronal progenitors and TuJ1+immature neurons derived from brain and spinal cord (1, 2). With time, these cells became more numerous, yet still were only found in clones.

Clones of Umbilicus-Derived Cells Express Neuronal Proteins:

Cultures were fixed at one month post-thawing/plating and stained for the neuronal protein TuJ1 and GFAP, an intermediate filament found in astrocytes. While all control cultures grown in Growth Medium and human fibroblasts and MSCs grown in NPE+bFGF+EGF medium were found to be TuJ1-/GFAP-, TuJ1 was detected in the umbilicus and placenta PPDCs. Expression was observed in cells with and without neuronal-like morphologies. No expression of GFAP was observed in either culture. The percentage of cells expressing TuJ1 with neuronal-like morphologies was less than or equal to 1% of the total population (n=3 umbilicus-derived cell isolates tested). While not quantified, the percentage of TuJ1+cells without neuronal morphologies was higher in umbilicus-derived cell cultures than placenta-derived cell cultures. These results appeared specific as age-matched controls in Growth Medium did not express TuJ1.

Summary:

Methods for generating differentiated neurons (based on TuJ1 expression and neuronal morphology) from umbilicus-derived cells were developed. While expression for TuJ1 was not examined earlier than one month in vitro, it is clear that at least a small population of umbilicus-derived cells can give rise to neurons either through default differentiation or through long-term induction following one month's exposure to a minimal media supplemented with L-glutamine, basic FGF, and EGF.

Example 15 PPDC Trophic Factors for Neural Progenitor Support

The influence of umbilicus- and placenta-derived cells (collectively postpartum-derived cells or PPDCs) on adult neural stem and progenitor cell survival and differentiation through non-contact dependent (trophic) mechanisms was examined.

Methods & Materials

Adult Neural Stem and Progenitor Cell Isolation:

Fisher 344 adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (Paxinos, G. & Watson, C. 1997. The Rat Brain in Stereotaxic Coordinates). Tissue was washed in Neurobasal-A medium (Invitrogen, Carlsbad, Calif.) containing B27 (B27 supplement; Invitrogen), L-glutamine (4 mM; Invitrogen), and penicillin/streptomycin (Invitrogen), the combination of which is herein referred to as Neural Progenitor Expansion (NPE) medium. NPE medium was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNase (100 microliters per 8 milliliters total volume, Sigma, St. Louis, Mo.) was also added. Next, the tissue/media was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250 g. Supernatant was removed, fresh NPE+bFGF+EGF was added and the pellet resuspended. The resultant cell suspension was passed through a 40 micrometer cell strainer (Becton Dickinson), plated on laminin-coated T-75 flasks (Becton Dickinson) or low cluster 24-well plates (Becton Dickinson), and grown in NPE+bFGF+EGF media until sufficient cell numbers were obtained for the studies outlined.

PPDC Plating:

Postpartum-derived cells (umbilicus (022803) P12, (042103) P12, (071003) P12; placenta (042203) P12) previously grown in Growth Medium were plated at 5,000 cells/transwell insert (sized for 24 well plate) and grown for a period of one week in Growth Medium in inserts to achieve confluence.

Adult Neural Progenitor Plating:

Neural progenitors, grown as neurospheres or as single cells, were seeded onto laminin-coated 24 well plates at an approximate density of 2,000 cells/well in NPE+bFGF+EGF for a period of one day to promote cellular attachment. One day later, transwell inserts containing postpartum cells were added according to the following scheme:

a. Transwell (umbilicus-derived cells in Growth Media, 200 microliters)+neural progenitors (NPE+bFGF+EGF, 1 milliliter)
b. Transwell (placenta-derived cells in Growth Media, 200 microliters)+neural progenitors (NPE+bFGF+EGF, 1 milliliter)
c. Transwell (adult human dermal fibroblasts [1 F 1853; Cambrex, Walkersville, Md.] P12 in Growth Media, 200 microliters)+neural progenitors (NPE+bFGF+EGF, 1 milliliter)
d. Control: neural progenitors alone (NPE+bFGF+EGF, 1 milliliter)
e. Control: neural progenitors alone (NPE only, 1 milliliter)

Immunocytochemistry:

After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 15-1. Briefly, cultures were washed with phosphate-buffered saline (PBS) and exposed to a protein blocking solution containing PBS, 4% (v/v) goat serum (Chemic on, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Quantitative Analysis of Neural Progenitor Differentiation:

Quantification of hippocampal neural progenitor differentiation was examined. A minimum of 1000 cells were counted per condition or if less, the total number of cells observed in that condition. The percentage of cells positive for a given stain was assessed by dividing the number of positive cells by the total number of cells as determined by DAPI (nuclear) staining.

Mass Spectrometry Analysis & 2D Gel Electrophoresis:

In order to identify unique, secreted factors as a result of co-culture, conditioned media samples taken prior to culture fixation were frozen down at −80° C. overnight. Samples were then applied to ultrafiltration spin devices (MW cutoff 30 kD). Retentate was applied to immunoaffinity chromatography (anti-Hu-albumin; IgY) (immunoaffinity did not remove albumin from the samples). Filtrate was analyzed by MALDI. The pass through was applied to Cibachron Blue affinity chromatography. Samples were analyzed by SDS-PAGE and 2D gel electrophoresis.

Results

PPDC Co-Culture Stimulates Adult Neural Progenitor Differentiation:

Following culture with umbilicus- or placenta-derived cells, co-cultured neural progenitor cells derived from adult rat hippocampus exhibited significant differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells. While both umbilicus- and placenta-derived cells induced cell differentiation, the degree of differentiation for all three lineages was less in co-cultures with placenta-derived cells than in co-cultures with umbilicus-derived cells.

The percentage of differentiated neural progenitors following co-culture with umbilicus-derived cells was quantified (Table 15-2). Umbilicus-derived cells significantly enhanced the number of mature oligodendrocytes (MBP) (24.0% vs. 0% in both control conditions). Furthermore, co-culture enhanced the number of GFAP+astrocytes and TuJ1+neurons in culture (47.2% and 8.7% respectively). These results were confirmed by nestin staining indicating that progenitor status was lost following co-culture (13.4% vs. 71.4% in control condition 4).

Though differentiation also appeared to be influenced by adult human fibroblasts, such cells were not able to promote the differentiation of mature oligodendrocytes nor were they able to generate an appreciable quantity of neurons. Though not quantified, fibroblasts did however, appear to enhance the survival of neural progenitors.

Identification of Unique Compounds:

Conditioned media from umbilicus- and placenta-derived co-cultures, along with the appropriate controls (NPE media±I.7% serum, media from co-culture with fibroblasts), were examined for differences. Potentially unique compounds were identified and excised from their respective 2D gels.

Summary:

Co-culture of adult neural progenitor cells with umbilicus or placenta PPDCs results in differentiation of those cells. Results presented in this example indicate that the differentiation of adult neural progenitor cells following co-culture with umbilicus-derived cells is particularly profound. Specifically, a significant percentage of mature oligodendrocytes was generated in co-cultures of umbilicus-derived cells. In view of the lack of contact between the umbilicus-derived cells and the neural progenitors, this result appears to be a function of soluble factors released from the umbilicus-derived cells (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+(indicative of astrocytes). This may be due to the fact that such significant expansion occurred throughout the course of the procedure that contact between progenitors induced this differentiation (Song, H. et al. 2002. Nature 417: 39-44).

Example 16 Transplantation of Postpartum-Derived Cells

Cells derived from the postpartum umbilicus and placenta are useful for regenerative therapies. The tissue produced by postpartum-derived cells (PPDCs) transplanted into SCID mice with a biodegradable material was evaluated. The materials evaluated were Vicryl non-woven, 35/65 PCL/PGA foam, and RAD 16 self-assembling peptide hydrogel.

Methods & Material

Cell Culture:

Placenta- and umbilicus-derived cells were grown in Growth Medium (DMEM-low glucose (Gibco, Carlsbad Calif.), 15% (v/v) fetal bovine serum (Cat. #SH30070.03; Hyclone, Logan, Utah), 0.001% (v/v) betamercaptoethanol (Sigma, St. Louis, Mo.), penicillin/streptomycin (Gibco)) in a gelatin-coated flasks.

Sample Preparation:

One million viable cells were seeded in 15 microliters Growth Medium onto 5 mm diameter, 2.25 mm thick Vicryl non-woven scaffolds (64.33 milligrams/cc; Lot#3547-47-1) or 5 mm diameter 35/65 PCL/PGA foam (Lot#3415-53). Cells were allowed to attach for two hours before adding more Growth Medium to cover the scaffolds. Cells were grown on scaffolds overnight. Scaffolds without cells were also incubated in medium.

RAD16 self-assembling peptides (3D Matrix, Cambridge, Mass. under a material transfer agreement) was obtained as a sterile 1% (w/v) solution in water, which was mixed 1:1 with $1 \times 10^6$ cells in 10% (w/v) sucrose (Sigma, St Louis, Mo.), 10 mM HEPES in Dulbecco's modified medium (DMEM; Gibco) immediately before use. The final concentration of cells in RAD 16 hydrogel was $1 \times 10^6$ cells/100 microliters.

Test Material (N=4/Rx)
a. Vicryl non-woven+$1 \times 10^6$ umbilicus-derived cells
b. 35/65 PCL/PGA foam+$1 \times 10^6$ umbilicus-derived cells
c. RAD 16 self-assembling peptide+$1 \times 10^6$ umbilicus-derived cells
d. Vicryl non-woven+$1 \times 10^6$ placenta-derived cells
e. 35/65 PCL/PGA foam+$1 \times 10^6$ placenta-derived cells
f. RAD 16 self-assembling peptide+$1 \times 10^6$ placenta-derived cells
g. 35/65 PCL/PGA foam
h. Vicryl non-woven Animal Preparation:

The animals were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (*Mus Musculus*)/Fox Chase SCID/Male (Harlan Sprague Dawley, Inc., Indianapolis, Ind.), 5 Weeks of Age:

All handling of the SCID mice took place under a hood. The mice were individually weighed and anesthetized with an intraperitoneal injection of a mixture of 60 milligrams/kg KETASET (ketamine hydrochloride, Aveco Co., Inc., Fort Dodge, Iowa) and 10 milligrams/kg ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique:

Four skin incisions, each approximately 1.0 cm in length, were made on the dorsum of the mice. Two cranial sites were located transversely over the dorsal lateral thoracic region, about 5-mm caudal to the palpated inferior edge of the scapula, with one to the left and one to the right of the vertebral column. Another two were placed transversely over the gluteal muscle area at the caudal sacro-lumbar level, about 5-mm caudal to the palpated iliac crest, with one on either side of the midline. Implants were randomly placed in these sites in accordance with the experimental design. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing:

Mice were individually housed in micro isolator cages throughout the course of the study within a temperature range of 64° F.-79° F. and relative humidity of 30% to 70%, and maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology:

Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five-micron tissue sections were obtained by microtome and stained with hematoxylin and eosin (Poly Scientific Bay Shore, N.Y.) using routine methods.

Results

There was minimal ingrowth of tissue into foams (without cells) implanted subcutaneously in SCID mice after 30 days. In contrast there was extensive tissue fill in foams implanted with umbilical-derived cells or placenta-derived cells. Some tissue ingrowth was observed in Vicryl non-woven scaffolds. Non-woven scaffolds seeded with umbilicus- or placenta-derived cells showed increased matrix deposition and mature blood vessels.

Summary:

Synthetic absorbable non-woven/foam discs (5.0 mm diameter×1.0 mm thick) or self-assembling peptide hydrogel were seeded with either cells derived from human umbilicus or placenta and implanted subcutaneously bilaterally in the dorsal spine region of SCID mice. The results demonstrated that postpartum-derived cells could dramatically increase good quality tissue formation in biodegradable scaffolds.

Retinal ganglion cell (RGC) lesions have been extensively used as models for various repair strategies in the adult mammalian CNS. It has been demonstrated that retrobulbar section of adult rodent RGC axons results in abortive sprouting (Zeng et al., 1995) and progressive death of the parent cell population (Villegas-Perez et al., 1993). Numerous studies have demonstrated the stimulatory effects of various exogenous and endogenous factors on the survival of axotomized RGC's and regeneration of their axons (Yip and So, 2000; Fischer et al., 2001). Furthermore, other studies have demonstrated that cell transplants can be used to promote regeneration of severed nerve axons (Li et al., 2003; Ramon-Cueto et al., 2000). Thus, these and other studies have demonstrated that cell based therapy can be utilized for the treatment of neural disorders that affect the spinal cord, peripheral nerves, pudendal nerves, optic nerves or other diseases/trauma due to injury in which nervous damage can occur.

Self-assembling peptides (PuraMatrix®, U.S. Pat. Nos. 5,670,483, 5,955,343, US/PCT applications US2002/0160471, WO02/062969) have been developed to act as a scaffold for cell-attachment to encapsulate cells in 3-D, plate cells in 2-D coatings, or as microcarriers in suspension cultures. Three-dimensional cell culture has required either animal-derived materials (mouse sarcoma extract), with their inherent reproducibility and cell signaling issues, or much larger synthetic scaffolds, which fail to approximate the physical nanometer-scale and chemical attributes of native ECM. RAD16 (NH2-(RADA) 3-COOH) (SEQ ID NO: 11) and KLD (NH2-(KLDL)3-COOH) (SEQ ID NO: 12) are synthesized in small (RAD16 is 5 nanometers) oligopeptide fragments that self-assemble into nanofibers on a scale similar to the in vivo extracellular matrix (ECM) (3D Matrix, Inc Cambridge, Mass.). The self-assembly is initiated by mono- or di-valent cations found in culture media or the physiological environment. In the protocols described in this example, RAD16 was used as a microcarrier for the implantation of postpartum cells into the ocular defect. In this example, it is demonstrated that transplants of postpartum-derived cells PPDCs) can provide efficacy in an adult rat optic nerve axonal regeneration model.

Cells:

Cultures of human adult PPDCs (umbilicus and placenta) and fibroblast cells (passage 10) were expanded for 1 passage. All cells were initially seeded at 5,000 cells/cm$^2$ on gelatin-coated T75 flasks in Growth Medium with 100 Units per milliliter penicillin, 100 micrograms per milliliter streptomycin, 0.25 micrograms per milliliter amphotericin B (Invitrogen, Carlsbad, Calif.). At passage 11 cells were trypsinized and viability was determined using trypan blue staining. Briefly, 50 microliters of cell suspension was combined with 50 microliters of 0.04% w/v trypan blue (Sigma, St. Louis Mo.) and the viable cell number, was estimated using a hemocytometer. Cells were then washed three times in supplement free-Leibovitz's L-15 medium (Invitrogen, Carlsbad, Calif.). Cells were then suspended at a concentration of 200,000 cells in 25 microliters of RAD16 (3DM Inc., Cambridge, Mass.), which was buffered and made isotonic as per manufacturer's recommendations. One hundred microliters of supplement free Leibovitz's L-15 medium was added above the cell/matrix suspension to keep it wet till use. These cell/matrix cultures were maintained under standard atmospheric conditions until transplantation occurred. At the point of transplantation the excess medium was removed.

Animals and Surgery:

Long Evans female rats (220-240 gram body weight) were used. Under intraperitoneal tribromoethanol anesthesia (20 milligram/100 grams body weight), the optic nerve was exposed, and the optic sheath was incised intraorbitally at approximately 2 millimeters from the optic disc, the nerve was lifted from the sheath to allow complete trans section with fine scissors (Li et al., 2003). The completeness of trans section was confirmed by visually observing complete separation of the proximal and distal stumps. The control group consisted of lesioned rats without transplants. In transplant rats cultured postpartum cells seeded in RAD16 were inserted between the proximal and distal stumps using a pair of microforceps. Approximately 75,000 cells in RAD16 were implanted into the severed optic nerve. Cell/matrix was smeared into the severed cut using a pair of fine microforceps. The severed optic nerve sheath was closed with 10/0 black monofilament nylon (Ethicon, Inc., Edinburgh, UK). Thus, the gap was closed by drawing the cut proximal and distal ends of the nerve in proximity with each other.

After cell injections were performed, animals were injected with dexamethasone (2 milligrams/kilogram) for 10 days post transplantation. For the duration of the study, animals were maintained on oral cyclosporine A (210 milligrams/liter of drinking water; resulting blood concentration: 250-300 micrograms/liter) (Bedford Labs, Bedford, Ohio) from 2 days pre-transplantation until end of the study. Food and water were available ad libitum. Animals were sacrificed at either 30 or 60 days post transplantation.

eTB Application:

Three days before animals were sacrificed, under anesthesia, a glass micropipette with a 30-50 millimeter tip was inserted tangentially through the sclera behind the lens, and two 4-5 microliter aliquots of a 1% retrograde tracer-cholera toxin B (CTB) aqueous solution (List Biologic, Campbell, Calif.) was injected into the vitreous. Animals were perfused with fixative and optic nerves were collected in the same fixative for 1 hour. The optic nerves were transferred into sucrose overnight. Twenty micrometer cryostat sections were incubated in 0.1 molar glycine for 30 minutes and blocked in a PBS solution containing 2.5% bovine serum albumin (BSA) (Boeringer Mannheim, Mannheim, Germany) and 0.5% Triton-X100 (Sigma, St. Louis, Mo.), followed by a solution containing goat anti-CTB antibody (List Biologic, Campbell, Calif.) diluted 1:4000 in a PBS containing 2% normal rabbit serum (NRS) (Invitrogen, Carlsbad, Calif.), 2.5% BSA, and 2% Triton X-I00 (Sigma, St. Louis, Mo.) in PBS, and incubated in biotinylated rabbit anti-goat IgG antibody (Vector Laboratories, Burlinghame, Calif.) diluted 1:200 in 2% Triton-X100 in PBS for 2 hours at room temperature. This was followed by staining in 1:200 streptavidin-green (Alexa Flour 438; Molecular Probes, Eugene, Oreg.) in PBS for 2 hours at room temperature. Stained sections were then washed in PBS and counterstained with propidium iodide for confocal microscopy.

Histology Preparation:

Briefly, 5 days after CTB injection, rats were perfused with 4% paraformaldehyde. Rats were given 4 cubic centimeters of urethane and were then perfused with PBS (0.1 molar) then with 4% Para formaldehyde. The spinal cord was cut and the bone removed from the head to expose the colliculus. The colliculus was then removed and placed in 4% paraformaldehyde. The eye was removed by cutting around the outside of the eye and going as far back as possible. Care was given not to cut the optic nerve that lies on the underside of the eye. The eye was removed and the muscles were cut exposing the optic nerve this was then placed in 4% paraformaldehyde.

Results

Lesions Alone:

One month after retrotubular section of the optic nerve, a number of CTB-labeled axons were identified in the nerve segment attached to the retina. In the 200 micrometers nearest the cut, axons were seen to emit a number of collaterals at right angles to the main axis and terminate as a neuromatous tangle at the cut surface. In this cut between the proximal and distal stumps, the gap was observed to be progressively bridged by a 2-3 millimeter segment of vascularized connective tissue; however, no axons were seen to advance into this bridged area. Thus, in animals that received lesion alone no axonal growth was observed to reach the distal stump.

Rad16 Transplantation:

Following transplantation of RAD16 into the cut, visible ingrowth of vascularized connective tissue was observed. However, no axonal in growth was observed between the proximal and distal stumps. The results demonstrate that application of RAD16 alone is not sufficient for inducing axonal regeneration in this situation.

Transplantation of Postpartum-Derived Cells:

Transplantation of postpartum-derived cells into the severed optic nerve stimulated optic nerve regrowth. Some regrowth was also observed in conditions in which fibroblast cells were implanted, although this was minimal as compared with the regrowth observed with the transplanted placenta-derived cells. Optic nerve regrowth was observed in 4/5 animals transplanted with placenta-derived cells, 3/6 animals transplanted with adult dermal fibroblasts and in 1/4 animals transplanted with umbilicus-derived cells. In situations where regrowth was observed, CTB labeling confirmed regeneration of retinal ganglion cell axons, which were demonstrated to penetrate through the transplant area. GFAP labeling was also performed to determine the level of glial scarring. The GFAP expression was intensified at the proximal stump with some immunostaining being observed through the reinervated graft.

Summary:

These results demonstrate that transplanted human adult postpartum-derived cells are able to stimulate and guide regeneration of cut retinal ganglion cell axons.

Example 18 Use of Postpartum-Derived Cells in the Treatment of Retinitis Pigmentosa Currently no real treatment exists for blinding disorders that stem from the degeneration of cells in the retina. Loss of photoreceptors as a result of apoptosis or secondary degeneration lead to progressive deterioration of vision, and ultimately to blindness. Diseases in which this occurs include age-related macular degeneration (AMD) and retinitis pigmentosa (RP). RP is most commonly associated with a single gene mutation, which contributes to photoreceptor cell death.

The retinal photoreceptors and adjacent retinal pigment epithelium form a functional unit. The Royal College of Surgeons (RCS) rat presents with a tyrosine receptor kinase (Merkt) defect affecting outer segment phagocytosis, leading to photoreceptor cell death. Transplantation of retinal pigment epithelial (RPE) cells into the subretinal space of RCS rats was found to limit the progress of photoreceptor loss and preserve visual function. In this example, it is demonstrated that postpartum-derived cells can be used to promote photoreceptor rescue and thus preserve photoreceptors in an RCS model.

Methods & Materials

Cell Transplants:

Cultures of human adult umbilicus-derived cells, placental-derived cells and fibroblast cells (passage 10) were expanded for 1 passage. All cells were initially seeded at 5,000 cells/cm$^2$ on gelatin-coated T75 flasks in Growth Medium. For subsequent passages, all cells were treated as follows. After trypsinization, viable cells were counted after trypan blue staining. Briefly, 50 microliters of cell suspension was combined with 50 microliters of 0.04% w/v trypan blue (Sigma, St. Louis Mo.) and the viable cell number was estimated using a hemocytometer. Cells were trypsinized and washed three times in supplement free-DMEM:Low glucose medium (Invitrogen, Carlsbad, Calif.). Cultures of human adult umbilicus-derived cells, placental-derived cells and fibroblast cells at passage 11 were trypsinized and washed twice in Leibovitz's L-15 medium (Invitrogen, Carlsbad, Calif.). For the transplantation procedure, dystrophic RCS rats were anesthetized with xylazine-ketamine (1 mg/kg i.p. of the following mixture: 2.5 ml xylazine at 20 mg/ml, 5 ml ketamine at 100 mg/ml, and 0.5 ml distilled water) and their heads secured by a nose bar. Cells devoid of serum were resuspended (2×10$^5$ cells per injection) in 2 microliters of Leibovitz, L-15 medium (Invitrogen, Carlsbad, Calif.) and transplanted using a fine glass pipette (internal diameter 75-150 micrometers) trans-scerally. Cells were delivered into the dorso-temporal subretinal space of anesthetized 3 week old dystrophic-pigmented RCS rats (total N=10/cell type).

Cells were injected unilaterally into the right eye, while the left eye was injected with carrier medium alone (Sham control; Leibovitz's L-15 medium). Viability of residual transplant cells remained at greater than 95% as assessed by trypan blue exclusion at the end of the transplant session. After cell injections were performed, animals were injected with dexamethasone (2 mg/kg) for 10 days post transplantation. For the duration of the study, animals were maintained on oral cyclosporine A (210 mg/L of drinking water; resulting blood concentration: 250-300 micrograms/L) (Bedford Labs, Bedford, Ohio) from 2 days pre-transplantation until end of the study. Food and water were available ad libitum. Animals were sacrificed at 60 or 90 days post-operatively, with some animals being sacrificed at earlier timepoints for histological assessment of short-term changes associated with cell transplantation.

ERG Recordings:

Following overnight dark adaptation, animals were prepared for ERG recording under dim red light, as described in (Sauve, Y. et al., 2004, Vision Res. 44: 9-18). In brief, under anesthesia (with a mixture of 150 mg/kg i.p ketamine, and 10 mg/kg i.p. xylazine) the head was secured with a stereotaxic head holder and the body temperature monitored through a rectal thermometer and maintained at 38° C. using a homeothermic blanket. Pupils were dilated using equal parts of topical 2.5% phenylephrine and 1% tropicamide. Topical anesthesia with 0.75% bupivacaine was used to prevent any corneal reflexes and a drop of 0.9% saline was frequently applied on the cornea to prevent its dehydration and allow electrical contact with the recording electrode (gold wire loop). A 25-gauge needle inserted under the scalp, between the two eyes, served as the reference electrode. Amplification (at 1-1000 Hz bandpass, without notch filtering), stimulus presentation, and data acquisition were provided by the UTAS-3000 system from LKC Technologies (Gaithersburg, Md.). ERGs were recorded at 60 and 90 days of age in the umbilicus-derived cell groups and at 60 days only in the placental-derived cell and fibroblast cell groups.

Mixed a- and b-Wave Recording, Measuring Total Rod and Cone Contribution:

For the quantification of dark-adapted b-waves, recordings consisted of single flash presentations (10 μsec duration), repeated 3 to 5 times to verify the response reliability and improve the signal-to-noise ratio, if required. Stimuli were presented at six increasing intensities in one log unit steps varying from −3.6 to 1.4 log candila/m$^2$ in luminance.

To minimize the potential bleaching of rods, inter-stimulus intervals were increased as the stimulus luminance was elevated from 10 sec at lowest stimulus intensity to 2 minutes at highest stimulus intensity. The maximum b-wave amplitude was defined as that obtained from the flash intensity series, regardless of the stimulus intensity. The true $V_{max}$ from fitting the data with a Naka-Rushton curve was not used because ERG responses were often erratic at higher luminance levels in dystrophic animals and showed tendencies for depressed responses around 0.4 and 1.4 log candila/m². In order to determine the age at which ERG components were obtained or lost, criterion amplitudes were used: 20 μV for a- and b-waves, and 10 μV for STR-like responses. The amplitude of the b-wave was measured from the a-wave negative peak up to the b-wave positive apex, and not up to the peak of oscillations, which can exceed the b-wave apex. In these experiments as disease progresses in this model the ERG's are effectively abnormal. Thus, ERG measurements are taken on the lower end of normal visual function. This in turn can make measurements noisy as you reach the limits of threshold sensitivity.

Isolation of Rod and Cone Responses:

The double flash protocol, as described in (Nixon, P. J. et al., 2001, Clin Experiment Ophthalmol. 29: 193-196) was used to determine the isolation of rod and cone responses. A probe flash was presented 1 sec after a conditioning flash, using a specific feature of the UTAS-3000 system (LKC Technologies) with calibrated ganzfeld; assuring complete recharge of the stimulator under the conditions used. The role of the conditioning flash in the procedure was to transiently saturate rods so that they were rendered unresponsive to the probe flash. Response to the probe flash was taken as reflecting cone-driven activity. A rod-driven b-wave was obtained by subtracting the cone-driven response from the mixed response (obtained following presentation of a probe flash alone, i.e. not preceded by any conditioning flash).

Functional Assessment:

Physiological retinal sensitivity testing was performed to demonstrate retinal response to dim light. Animals were anesthetized with a recovery dose of urethane at 1.25 g/kg i.p. Physiological assessment in the animals was tested post graft in animals at 90 days by recording multiunit extracellular activity in the superior colliculus to illumination of respective visual receptive fields, using the method disclosed in (Lund, R. D. et al., 2001, Proc. Natl. Acad. Sci. USA. 98: 9942-9947). This procedure was repeated for 20 independent points (spaced 200 mm apart, with each step corresponding to approximately 10-150 displacements in the visual field), covering the visual field. Visual thresholds were measured as the increase in intensity over background and maintained at 0.02 candila/m² (luminescence unit) [at least 2.6 logarithm units below rod saturation], required for activating units in the superficial 200 μm of the superior colliculus. Response parameters were compared between transplanted and sham control eyes that received vehicle alone.

Histology:

Animals were sacrificed with an overdose of urethane (12.5 g/kg). The orientation of the eye was maintained by placing a 6.0 suture through the superior rectus muscle prior to enucleation. After making a corneal incision, the eyes were fixed with 2.5% parafomaldehyde, 2.5% glutaraldehyde, 0.01% picric acid in 0.1 M cacodylate buffer (pH7.4) (Sigma, St. Louis, Mo.). After fixation, the cornea and lens were removed by cutting around the ciliary body. A small nick was made in the periphery of the dorsal retina prior to removal of the superior rectus to assist in maintaining orientation. The retinas were then post-fixed in 1% osmium tetroxide for 1 h. After dehydration through a series of alcohols to epoxypropane, the retinas were embedded in TAAB embedding resin (TAAB Laboratories, Aldemarston, UK). Semi-thin sections were stained with 1% toluidine Blue in 1% borate buffer and the ultra thin sections were contrasted with uranyl acetate and lead citrate.

For Nissl staining, sections were stained with 0.75% cresyl violet (Sigma, St. Louis, Mo.) after which they were dehydrated through graded alcohols at 70, 95 and 100% twice. They were then placed in xylene (Sigma, St. Louis, Mo.), rinsed with PBS (pH 7.4) (Invitrogen, Carlsbad, Calif.), coverslipped and mounted with DPX mountant (Sigma, St. Louis, Mo.).

Results

ERG Recordings:

Animals that received umbilicus-derived cell injections exhibited relative preservation of visual response properties 60 and 90 days post-operatively (Table 18-1). The response observed in these animals was greater than that seen with placental-derived cell, fibroblast cell or sham treated animals. Placental-derived cell transplants (n=4) at 60 days showed no improvement in a-wave (20±20) versus sham controls (0), but showed some improvement in mixed b-wave (81±72) versus sham controls (1.5±2), and good improvement in cone-b-wave (50±19) versus sham controls (7±7), and in rod contribution (30%) versus sham controls (O). These results indicated some improvement in visual responsiveness when compared to sham controls.

Umbilicus-derived cell-transplanted animals (n=6) demonstrated good improvement in all outcome measures tested at 60 days (Table 18-1), a-wave (27±11) versus sham controls (O), mixed b-wave (117±67) versus sham controls (18±13), cone-b-wave (55±25) versus sham controls (28±11), and in rod contribution (49±16%) versus sham controls (6±7%). Furthermore, at 90 days, improved responses were measured in two animals tested, with measures including: a-wave (15±7) versus sham controls (O), mixed b-wave (37±15) versus sham controls (O), cone-b-wave (16±11) versus sham controls (7±5), and in rod contribution (58±39%) versus sham controls (0%). These results indicate that visual responsiveness was improved in umbilicus-derived cell transplanted animals with evidence for photoreceptor preservation in the RCS model. Although a diminution in responsiveness to ERG was observed in the 90 day animals tested, their preservation of visual function in comparison to sham-treated controls was good.

In contrast to either umbilicus-derived or placental-derived cells, fibroblast transplantations showed no improvement in any of the parameters tested, with values less than or equal to sham-treated controls.

Histology:

Following transplantation, there was no histological evidence of an inflammatory reaction and infiltrating immune cells were not observed in Nissl-stained sections in the postpartum cell groups. However, fibroblast implantations resulted in animal death (n=7) and indications of early stage inflammatory responses. Histologically at the 90 day time point in the umbilicus-derived cell transplanted animals anatomical rescue of photoreceptors was clearly demonstrated. The photoreceptors formed a thick layer separated by a gap from the inner nuclear layer, made up of other retinal cells. By comparison, the width of the outer layer in the sham control was, at best, a discontinuous single layer as opposed to around 5 cells thick in the grafted eye. In comparison to a normal animal this is marginally more than half the thickness of photoreceptor cell layers normally observed.

Functional Assessment:

Efficacy of transplants in preventing visual loss was monitored by assessment of electrophysiological responsiveness in two animals. The threshold sensitivity response to light was used to define the area of visual field rescue in sham-injected control eyes versus eyes transplanted with umbilicus-derived cells. In nondystrophic rats, visual thresholds never exceeded 0.5 log candila/m$^2$ above background. In non-operated dystrophic rats, the thresholds are usually in the magnitude of 4 log candila/m$^2$ units. By contrast, in non-operated sham injected dystrophic rats, the thresholds were in the order of 2.9-4.9 log candila/m$^2$ units with an average threshold of 4.0 log candila/m$^2$ units, in some instances no recording could be attained. Thus, the sham-injected rats showed some highly localized functional rescue in the temporal retina. However, the human umbilicus-derived cell transplanted rats exhibited substantially greater levels of visual preservation with thresholds ranging from 0.8 to 2.1 log candila/m$^2$ units, with an average threshold of 1.3 log candila/m$^2$ units.

Summary:

Transplantation of umbilicus-derived cells into dystrophic RCS rats was shown to preserve photoreceptors. To a lesser degree this response was also seen following transplantation with placental-derived cells although improvement was seen in a-wave responsiveness was not observed. In this degenerative model, one would expect the a-wave to disappear within 30 to 60 days and the b-wave to disappear within 3 months. Thus, a retained a-wave indicates that real and normal rod function is preserved. Rod contribution to b-wave suggests abnormal rod function is still possible. The sustained non-rod b-wave is the measure of how much cone function is maintained, which is a real measure of vision. Thus, the level of improvement assessed both physiologically and anatomically following umbilicus-derived cell transplantation is well defined here. ERG measurements provide an assessment of visual function after photoreceptor loss, indicating changes in electrical activity in the retina. However, ERG does not provide direct information as to image forming capability. The measurement of collicular threshold sensitivity used in this study provides an indication of relative preservation of visual fields. The importance of this measure is based on a correlation between the amounts of functional rescue and anatomical preservation and that the data collected compares with visual field perimetry testing in humans. The transplantation has demonstrated a retardation of the disease process in the test animals. Thus, the results presented herein demonstrate clear evidence of functional efficacy of grafting human PPDCs into the subretinal space, and that rescue occurs in the general region in which the grafted cells are located.

Example 19 Use of Postpartum Derived Cells in the Treatment of Glaucoma

Glaucoma is a group of eye diseases causing optic nerve damage. The optic nerve carries images from the retina, which is the specialized light sensing tissue, to the brain so we can see. In glaucoma, eye pressure plays a role in damaging the delicate nerve fibers of the optic nerve. When a significant number of nerve fibers are damaged, blind spots develop in the field of vision. Once nerve damage and visual loss occur, it is permanent. Most people don't notice these blind areas until much of the optic nerve damage has already occurred. If the entire nerve is destroyed, blindness results. Furthermore, this damage to the optic nerve leads to damage of retinal ganglion cell elements, which correspondingly lead to loss of photoreceptors and a subsequent loss of vision. Glaucoma is a leading cause of blindness in the world, especially in older people. Thus, if a therapy can be provided, that can either regenerate new nerve fibers or replace existing ones, the potential to repair the degenerative process in Glaucoma exists. In the following example we describe the potential of umbilicus-derived cells to stimulate the generation of neurons and oligodendrocytes. The generation of these cell types in vivo would enable replacement of lost nerve fibers.

Methods & Materials

Adult Neural Stem and Progenitor Cell Isolation:

Fisher adult rats were sacrificed by $CO_2$ asphyxiation followed by cervical dislocation. Whole brains were removed intact using bone rongeurs and hippocampus tissue dissected based on coronal incisions posterior to the motor and somatosensory regions of the brain (Paxinos, G. & Watson, C. 1997. The Rat Brain in Stereotaxic Coordinates). Tissue was washed in Neurobasal-A medium (Invitrogen, Carlsbad, Calif.) containing B27 (B27 supplement; Invitrogen), L-glutamine (4 mM; Invitrogen), and penicillin/streptomycin (Invitrogen), the combination of which is herein referred to as Neural Progenitor Expansion (NPE) medium. NPE medium was further supplemented with bFGF (20 nanograms/milliliter, Peprotech, Rocky Hill, N.J.) and EGF (20 nanograms/milliliter, Peprotech, Rocky Hill, N.J.), herein referred to as NPE+bFGF+EGF.

Following wash, the overlying meninges were removed, and the tissue minced with a scalpel. Minced tissue was collected and trypsin/EDTA (Invitrogen) added as 75% of the total volume. DNAse (100 microliters per 8 milliliters total volume, Sigma, St. Louis, Mo.) was also added. Next, the tissue/media was sequentially passed through an 18 gauge needle, 20 gauge needle, and finally a 25 gauge needle one time each (all needles from Becton Dickinson, Franklin Lakes, N.J.). The mixture was centrifuged for 3 minutes at 250 g. Supernatant was removed, fresh NPE+bFGF+EGF was added and the pellet resuspended. The resultant cell suspension was passed through a 40 micrometer cell strainer (Becton Dickinson), plated on laminin-coated T-75 flasks (Becton Dickinson) or low cluster 24-well plates (Becton Dickinson), and grown in NPE+bFGF+EGF media until sufficient cell numbers were obtained for the studies outlined.

PPDC Plating:

Postpartum-derived cells (umbilicus (022803) P12, (042103) P12, (071003) P12; placenta (042203) P12) previously grown in Growth Medium were plated at 5,000 cells/transwell insert (sized for 24 well plate) and grown for a period of one week in Growth Medium in inserts to achieve confluence.

Adult Neural Progenitor Plating:

Neural progenitors, grown as neurospheres or as single cells, were seeded onto laminin-coated 24 well plates at an approximate density of 2,000 cells/well in NPE+bFGF+EGF for a period of one day to promote cellular attachment. One day later, trans well inserts containing postpartum cells were added according to the following scheme:

1. Transwell (umbilicus-derived cells in Growth Media, 200 microliters)+neural progenitors (NPE+bFGF+EGF, 1 milliliter)
2. Transwell (placenta-derived cells in Growth Media, 200 microliters)+neural progenitors (NPE+bFGF+EGF, 1 milliliter)
3. Transwell (adult human dermal fibroblasts [1 F 1853; Cambrex, Walkersville, Md.] P12 in Growth Media, 200 microliters)+neural progenitors (NPE+bFGF+EGF, 1 milliliter)

4. Control: neural progenitors alone (NPE+bFGF+EGF, 1 milliliter)
5. Control: neural progenitors alone (NPE only, 1 milliliter)

Immunocytochemistry:

After 7 days in co-culture, all conditions were fixed with cold 4% (w/v) paraformaldehyde (Sigma) for a period of 10 minutes at room temperature. Immunocytochemistry was performed using antibodies directed against the epitopes listed in Table 19-1. Briefly, cultures were washed with phosphate-buffered saline (PBS) and exposed to a protein blocking solution containing PBS, 4% (v/v) goat serum (Chemic on, Temecula, Calif.), and 0.3% (v/v) Triton (Triton X-100; Sigma) for 30 minutes to access intracellular antigens. Primary antibodies, diluted in blocking solution, were then applied to the cultures for a period of 1 hour at room temperature. Next, primary antibodies solutions were removed and cultures washed with PBS prior to application of secondary antibody solutions (1 hour at room temperature) containing blocking solution along with goat anti-mouse IgG—Texas Red (1:250; Molecular Probes, Eugene, Oreg.) and goat anti-rabbit IgG—Alexa 488 (1:250; Molecular Probes). Cultures were then washed and 10 micromolar DAPI (Molecular Probes) applied for 10 minutes to visualize cell nuclei.

Following immunostaining, fluorescence was visualized using the appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Quantitative Analysis of Neural Progenitor Differentiation:

Quantification of hippocampal neural progenitor differentiation was examined. A minimum of 1000 cells were counted per condition or if less, the total number of cells observed in that condition. The percentage of cells positive for a given stain was assessed by dividing the number of positive cells by the total number of cells as determined by DAPI (nuclear) staining.

Mass Spectrometry Analysis & 2D Gel Electrophoresis:

In order to identify unique, secreted factors as a result of co-culture, conditioned media samples taken prior to culture fixation were frozen down at −80° C. overnight. Samples were then applied to ultrafiltration spin devices (MW cutoff 30 kD). Retentate was applied to immunoaffinity chromatography (anti-Hu-albumin; IgY) (immunoaffinity did not remove albumin from the samples). Filtrate was analyzed by MALDI. The pass through was applied to Cibachron Blue affinity chromatography. Samples were analyzed by SDS-PAGE and 2D gel electrophoresis.

Results

PPDC Co-Culture Stimulates Adult Neural Progenitor Differentiation.

Following culture with umbilicus- or placenta-derived cells, co-cultured neural progenitor cells derived from adult rat hippocampus exhibited significant differentiation along all three major lineages in the central nervous system. This effect was clearly observed after five days in co-culture, with numerous cells elaborating complex processes and losing their phase bright features characteristic of dividing progenitor cells. Conversely, neural progenitors grown alone in the absence of bFGF and EGF appeared unhealthy and survival was limited.

After completion of the procedure, cultures were stained for markers indicative of undifferentiated stem and progenitor cells (nestin), immature and mature neurons (TuJ1), astrocytes (GFAP), and mature oligodendrocytes (MBP). Differentiation along all three lineages was confirmed while control conditions did not exhibit significant differentiation as evidenced by retention of nestin-positive staining amongst the majority of cells. While both umbilicus- and placenta-derived cells induced cell differentiation, the degree of differentiation for all three lineages was less in co-cultures with placenta-derived cells than in co-cultures with umbilicus-derived cells.

The percentage of differentiated neural progenitors following co-culture with umbilicus-derived cells was quantified (Table 19-2). Umbilicus-derived cells significantly enhanced the number of mature oligodendrocytes (MBP) (24.0% vs. 0% in both control conditions). Furthermore, co-culture enhanced the number of GFAP+astrocytes and TuJ1+neurons in culture (47.2% and 8.7% respectively). These results were confirmed by nestin staining indicating that progenitor status was lost following co-culture (13.4% vs. 71.4% in control condition 4).

Though differentiation also appeared to be influenced by adult human fibroblasts, such cells were not able to promote the differentiation of mature oligodendrocytes nor were they able to generate an appreciable quantity of neurons. Though not quantified, fibroblasts did, however, appear to enhance the survival of neural progenitors.

Identification of Unique Compounds:

Conditioned media from umbilicus- and placenta-derived co-cultures, along with the appropriate controls (NPE media±1.7% serum, media from co-culture with fibroblasts), were examined for differences. Potentially unique compounds were identified and excised from their respective 2D gels.

Summary:

Co-culture of adult neural progenitor cells with umbilicus or placenta PPDCs results in differentiation of those cells. Results presented in this example indicate that the differentiation of adult neural progenitor cells following co-culture with umbilicus-derived cells is particularly profound. Specifically, a significant percentage of mature oligodendrocytes was generated in co-cultures of umbilicus-derived cells. In view of the lack of contact between the umbilicus-derived cells and the neural progenitors, this result appears to be a function of soluble factors released from the umbilicus-derived cells (trophic effect).

Several other observations were made. First, there were very few cells in the control condition where EGF and bFGF were removed. Most cells died and on average, there were about 100 cells or fewer per well. Second, it is to be expected that there would be very little differentiation in the control condition where EGF and bFGF was retained in the medium throughout, since this is normally an expansion medium. While approximately 70% of the cells were observed to retain their progenitor status (nestin+), about 30% were GFAP+(indicative of astrocytes). This may be due to the fact that such significant expansion occurred throughout the course of the procedure that contact between progenitors induced this differentiation (Song, H. et al. 2002. Nature 417:39-44).

The demonstration that postpartum cells derived from umbilicus tissue can promote the differentiation of neural stem cells into neurons and oligodendrocytes suggests that the cells may promote axonal regeneration (see Example 20) or remyelination. These data suggest that postpartum cells derived from umbilicus tissue may be protective in glaucoma. Furthermore, if postpartum cells derived from umbilicus tissue are injected in combination with neural stem cells they would have the potential to remyelinate lost neural elements in the retina, which support vision.

Example 20 Use of Postpartum-Derived Cells in Optic Nerve Repair for the Treatment of Glaucoma Glaucoma is a group of eye diseases causing optic nerve damage. The optic nerve carries images from the retina, which is the specialized light sensing tissue, to the brain so we can see. In glaucoma, eye pressure plays a role in damaging the delicate nerve fibers of the optic nerve. When a significant number of nerve fibers are damaged, blind spots develop in the field of vision. Once nerve damage and visual loss occur, it is permanent. Most people don't notice these blind areas until much of the optic nerve damage has already occurred. If the entire nerve is destroyed, blindness results. Glaucoma is a leading cause of blindness in the world, especially in older people. Thus, if you are able to provide a therapy that can either regenerate new nerve fibers or replace existing ones, the potential to repair the degenerative process in Glaucoma exists. The following Example demonstrates the ability of umbilicus-derived cells to cause axonal re-growth through a severed optic nerve head. Such growth in vivo could provide the level of axonal regeneration required to repair vision loss.

Retinal ganglion cell (RGC) lesions have been extensively used as models for various repair strategies in the adult mammalian CNS. It has been demonstrated that retrobulbar section of adult rodent RGC axons results in abortive sprouting (Zeng et al., 1995) and progressive death of the parent cell population (Villegas-Perez et al., 1993). Numerous studies have demonstrated the stimulatory effects of various exogenous and endogenous factors on the survival of axotomized RGC's and regeneration of their axons (Yip and So, 2000; Fischer et al., 2001). Furthermore, other studies have demonstrated that cell transplants can be used to promote regeneration of severed nerve axons (Li et al., 2003; Ramon-Cueto et al., 2000). Thus, these and other studies have demonstrated that cell based therapy can be utilized for the treatment of neural disorders that affect the spinal cord, peripheral nerves, pudendal nerves, optic nerves or other diseases/trauma due to injury in which nervous damage can occur.

Self-assembling peptides (PuraMatrix®, U.S. Pat. Nos. 5,670,483, 5,955,343, US/PCT applications US2002/0160471, WO02/062969) have been developed to act as a scaffold for cell-attachment to encapsulate cells in 3-D, plate cells in 2-D coatings, or as microcarriers in suspension cultures. Three-dimensional cell culture has required either animal-derived materials (mouse sarcoma extract), with their inherent reproducibility and cell signaling issues, or much larger synthetic scaffolds, which fail to approximate the physical nanometer-scale and chemical attributes of native ECM. RAD16 (NH2-(RADA) 3-COOH) (SEQ ID NO: 11) and KLD (NH2-(KLDL)3-COOH) (SEQ ID NO: 12) are synthesized in small (RAD16 is 5 nanometers) oligopeptide fragments that self-assemble into nanofibers on a scale similar to the in vivo extracellular matrix (ECM) (3D Matrix, Inc Cambridge, Mass.). The self-assembly is initiated by mono- or di-valent cations found in culture media or the physiological environment. In the protocols described in this example, RAD16 was used as a microcarrier for the implantation of postpartum cells into the ocular defect. In this example, it is demonstrated that transplants of postpartum-derived cells PPDCs) can provide efficacy in an adult rat optic nerve axonal regeneration model.

Methods & Materials

Cells.

Cultures of human adult PPDCs (umbilicus and placenta) and fibroblast cells (passage 10) were expanded for 1 passage. All cells were initially seeded at 5,000 cells/cm 2 on gelatin-coated T75 flasks in Growth Medium with 100 Units per milliliter penicillin, 100 micrograms per milliliter streptomycin, 0.25 micrograms per milliliter amphotericin B (Invitrogen, Carlsbad, Calif.). At passage 11 cells were trypsinized and viability was determined using trypan blue staining. Briefly, 50 microliters of cell suspension was combined with 50 microliters of 0.04% w/v trypan blue (Sigma, St. Louis Mo.) and the viable cell number, was estimated using a hemocytometer. Cells were then washed three times in supplement free-Leibovitz's L-15 medium (Invitrogen, Carlsbad, Calif.). Cells were then suspended at a concentration of 200,000 cells in 25 microliters of RAD16 (3DM Inc., Cambridge, Mass.), which was buffered and made isotonic as per manufacturer's recommendations. One hundred microliters of supplement free Leibovitz's L-15 medium was added above the cell/matrix suspension to keep it wet till use. These cell/matrix cultures were maintained under standard atmospheric conditions until transplantation occurred. At the point of transplantation the excess medium was removed.

Animals and Surgery:

Long Evans female rats (220-240 gram body weight) were used. Under intraperitoneal tribromoethanol anesthesia (20 milligram/100 grams body weight), the optic nerve was exposed, and the optic sheath was incised intraorbitally at approximately 2 millimeters from the optic disc, the nerve was lifted from the sheath to allow complete trans section with fine scissors (Li et al., 2003). The completeness of trans section was confirmed by visually observing complete separation of the proximal and distal stumps. The control group consisted of lesioned rats without transplants. In transplant rats cultured postpartum cells seeded in RAD16 were inserted between the proximal and distal stumps using a pair of microforceps. Approximately 75,000 cells in RAD16 were implanted into the severed optic nerve. Cell/matrix was smeared into the severed cut using a pair of fine microforceps. The severed optic nerve sheath was closed with 10/0 black monofilament nylon (Ethicon, Inc., Edinburgh, UK). Thus, the gap was closed by drawing the cut proximal and distal ends of the nerve in proximity with each other.

After cell injections were performed, animals were injected with dexamethasone (2 milligrams/kilogram) for 10 days post transplantation. For the duration of the study, animals were maintained on oral cyclosporine A (210 milligrams/liter of drinking water; resulting blood concentration: 250-300 micrograms/liter) (Bedford Labs, Bedford, Ohio) from 2 days pre-transplantation until end of the study. Food and water were available ad libitum. Animals were sacrificed at either 30 or 60 days post transplantation.

eTB Application:

Three days before animals were sacrificed, under anesthesia, a glass micropipette with a 30-50 millimeter tip was inserted tangentially through the sclera behind the lens, and two 4-5 microliter aliquots of a 1% retrograde tracer-cholera toxin B (CTB) aqueous solution (List Biologic, Campbell, Calif.) was injected into the vitreous. Animals were perfused with fixative and optic nerves were collected in the same fixative for 1 hour. The optic nerves were transferred into sucrose overnight. Twenty micrometer cryostat sections were incubated in 0.1 molar glycine for 30 minutes and blocked in a PBS solution containing 2.5% bovine serum albumin (BSA) (Boeringer Mannheim, Mannheim, Germany) and 0.5% triton X-100 (Sigma, St. Louis, Mo.), followed by a solution containing goat anti-CTB antibody (List Biologic, Campbell, Calif.) diluted 1:4000 in a PBS containing 2% normal rabbit serum (NRS) (Invitrogen, Carlsbad, Calif.), 2.5% BSA, and 2% Triton X-100 (Sigma, St. Louis, Mo.) in PBS, and incubated in biotinylated rabbit anti-goat IgG antibody (Vector Laboratories, Burlinghame, Calif.) diluted 1:200 in 2% Triton-X100 in PBS for 2 hours at room temperature. This was followed by staining in 1:200 streptavidin-green (Alexa Flour 438; Molecular Probes, Eugene, Oreg.) in PBS for 2 hours at room temperature. Stained sections were then washed in PBS and counterstained with propidium iodide for confocal microscopy.

Histology Preparation:

Briefly, 5 days after CTB injection, rats were perfused with 4% paraformaldehyde. Rats were given 4 cubic centimeters of urethane and were then perfused with PBS (0.1 molar) then with 4% Para formaldehyde. The spinal cord was cut and the bone removed from the head to expose the colliculus. The colliculus was then removed and placed in 4% paraformaldehyde. The eye was removed by cutting around the outside of the eye and going as far back as possible. Care was given not to cut the optic nerve that lies on the underside of the eye. The eye was removed and the muscles were cut exposing the optic nerve this was then placed in 4% paraformaldehyde.

Results

Lesions Alone:

One month after retrotubular section of the optic nerve, a number of CTB-labeled axons were identified in the nerve segment attached to the retina. In the 200 micrometers nearest the cut, axons were seen to emit a number of collaterals at right angles to the main axis and terminate as a neuromatous tangle at the cut surface. In this cut between the proximal and distal stumps, the gap was observed to be progressively bridged by a 2-3 millimeter segment of vascularized connective tissue; however, no axons were seen to advance into this bridged area. Thus, in animals that received lesion alone no axonal growth was observed to reach the distal stump.

RAD16 Transplantation:

Following transplantation of RAD16 into the cut, visible ingrowth of vascularized connective tissue was observed. However, no axonal in growth was observed between the proximal and distal stumps. The results demonstrate that application of RAD-16 alone is not sufficient for inducing axonal regeneration in this situation.

Transplantation of postpartum-derived cells: Transplantation of postpartum-derived cells into the severed optic nerve stimulated optic nerve regrowth. Some regrowth was also observed in conditions in which fibroblast cells were implanted, although this was minimal as compared with the regrowth observed with the transplanted placenta-derived cells. Optic nerve regrowth was observed in 4/5 animals transplanted with placenta-derived cells, 3/6 animals transplanted with adult dermal fibroblasts and in 1/4 animals transplanted with umbilicus-derived cells. In situations where regrowth was observed, CTB labeling confirmed regeneration of retinal ganglion cell axons, which were demonstrated to penetrate through the transplant area. GFAP labeling was also performed to determine the level of glial scarring. The GFAP expression was intensified at the proximal stump with some immunostaining being observed through the reinervated graft.

Summary:

These results demonstrate that transplanted human adult postpartum-derived cells are able to stimulate and guide regeneration of cut retinal ganglion cell axons. Thus, an ability to promote axonal regeneration from the optic nerve has the potential to repair a primary defect associated to vision loss with glaucoma.

Example 21 Evaluation of the Ability of Umbilicus-Derived Cells to Protect Photo Receptors in Royal College of Surgeons Rat Model of Retinal Degeneration The central unifying aspect of disease progression in all forms of retinal degeneration is photoreceptor cell death leading to permanent blindness. With few exceptions such as retinal trauma, this death is mediated through a process termed apoptosis or programmed cell death in all of these diseases.

In order to assess whether application of umbilicus-derived cells could rescue photoreceptors from apoptosis, umbilicus-derived cells were transplanted and assessed for their ability to reduce the number of apoptotic cells in the Royal College of Surgeon's rat model of retinal degeneration (RCS). In this model, a mutation in retinal pigmented epithelial (RPE) cells leads to build up of the otherwise phagocytosed outer segments of photoreceptors. As a result of this buildup, photoreceptors become uncoupled from RPE and undergo apoptosis.

One of the characteristics of apoptosis is the degradation of DNA after the activation of Ca/Mg dependent endonucleases. This DNA cleavage leads to strand breakage within the DNA. One accepted measure of detecting apoptosis in histological sections is called TUNEL (terminal deoxynucleotidyl transferase biotin-dUTP nick end labeling). TUNEL identifies apoptotic cells in situ by using terminal deoxynucleotidyl transferase (TdT) to transfer biotin-dUTP to these strand breaks of cleaved DNA. The biotin labeled cleavage sites are then detected by reaction with fluorophore-conjugated streptavidin and visualized using an epifluorescent microscope. In this study, TUNEL labeling was used to assess the percentage of positive apoptotic photoreceptor cells relative to total nuclei in the outer nuclear layer.

Materials and Methods

Cell Transplants:

Frozen vials of previously expanded umbilicus-derived cells (passage 10) were thawed, washed with PBS, and concentrated in Dulbecco's Modified Eagles Medium (DMEM; Invitrogen, Grand Island, N.Y.) to 20,000 cells per microliter. Prior to this, cells were isolated/expanded and cryopreserved in Growth Medium as previously described in Example 5.

For the transplantation procedure, dystrophic RCS rats were anesthetized with xylazine-ketamine (1 mg/kg i.p. of the following mixture: 2.5 ml xylazine at 20 mg/ml, 5 ml ketamine at 100 mg/ml, and 0.5 ml distilled water) and their heads secured by a nose bar. Cells were transplanted using a fine glass pipette (internal diameter 75-150 micrometers) trans-sclerally. Cells were delivered via single injections into the dorso-temporal subretinal space of anesthetized 3 week old dystrophic-pigmented RCS rats (total N=2/group). As controls, sets of RCS animals underwent either a sham injection procedure containing DMEM only or were left untreated. Congenic, non-dystrophic rats were included as a third control group to evaluate the level of normal apoptosis in healthy eyes.

After cell injections were performed, animals were injected with dexamethasone (2 mg/kg) for 10 days post transplantation. For the duration of the study, animals were maintained on oral cyclosporine A (210 mg/L of drinking water; resulting blood concentration: 250-300 micrograms/L) (Bedford Labs, Bedford, Ohio) from 2 days pre-transplantation until end of the study. Food and water were available ad libitum. Animals were sacrificed at 8 days (dystrophic-untreated, dystrophic-sham injected, dystrophic-cell injected, congenic control) or 67 days postoperatively (dystrophic-untreated, dystrophic-cell injected) for histological analysis.

Histology:

Animals were sacrificed with an overdose of urethane (12.5 g/kg). The orientation of the eye was maintained by placing a 6.0 suture through the superior rectus muscle prior to enucleation. The cornea and lens were next removed by cutting around the ciliary body. Eyes were then fixed with Davidson's fix containing 22% (v/v) formalin, 33% (v/v) alcohol, 11% (v/v) glacial acetic acid, and 33% (v/v) water. After 24 hours, eyes were removed from fix and washed/retained in PBS for sectioning.

Eye samples were oriented, embedded in OCT (Sakura, Torrence, Calif.), and cryostat sectioned (10/μm). TUNEL staining was performed using an in situ apoptosis detection kit whereby fragmented DNA was labeled with TdT and biotin-dUTP. A streptavidin-FITC system was used to visualize labeling. Sections were counterstained with DAPI (10/μM, Invitrogen) to visualize cell nuclei and covers lipped.

Imaging & Analysis:

Tiled images of TUNEL and DAPI stained retina were taken at 20× using a scanning stage and TURBOSCAN software (Media Cybernetics Inc, Bethesda, Md.). ImagePro Software (Media Cybernetics Inc.) was then used to quantitatively analyze the area of DAPI positive nuclei and TUNEL+ nuclei in the outer nuclear layer (ONL) after calibrating images to square micron area. A minimum of 8 tissue sections was analyzed per eye and averaged to generate mean+/−standard deviation values per section. TUNEL+ area was next divided by DAPI+ area to assess the percentage of nuclei undergoing apoptosis as determined by TUNEL. Post-hoc statistic analysis was performed to assess whether treatment with postpartum cells derived from umbilical tissue significantly reduced the number of TUNEL+figures versus controls (untreated or sham injected). One-tailed, paired t-tests were performed to evaluate this possibility.

Results

TUNEL+ area in the photoreceptor specific outer nuclear layer (ONL) was assessed as a function of DAPI+ area in RCS animals that were untreated, sham injected, or umbilicus-derived cell treated at two different timepoints, 8 and 67 days post injection (post natal day 29 and 88 respectively). Congenic-untreated controls at P29 were used to assess the level of apoptosis in healthy retina. Results of this analysis are summarized in Table 22-1.

At post natal day 29, congenic eyes had very few TUNEL+FIGS. 0.2±0.2% of total DAPI+ area) in the ONL, while 16.0±2.3% of the ONL was TUNEL+ in sham injected dystrophic rats. Umbilicus-derived cell treated animals, however, exhibited a significant decrease in TUNEL+ area (6.6±0.5%, p<0.05, vs. dystrophic-sham). This decrease was not seen in the overall DAPI+ area at this time, suggesting that changes in apoptotic figures had not had an impact on overall photoreceptor number in the ONL at this timepoint.

In contrast, at P88, there was a significant increase in the DAPI+ area of untreated vs. umbilicus-derived cell treated animals (p<0.05, dystrophic untreated vs. umbilicus-derived cell) (Table 22-2). This difference was shadowed by differences in the percent of TUNEL+ cells (35.9±9.0% dystrophic untreated vs. 3.8%±1.4% in dystrophic-umbilicus-derived cell treated) indicating that at 67 days post injection, there was a lasting effect on preservation of photoreceptors in umbilicus-derived cell treated animals.

Summary:

Decreases in TUNEL+ area, indicative of decreased apoptosis, were observed as early as 8 days post injection and as late as 67 days following single dose subretinal administration of umbilicus-derived cells (20,000 cells). This difference is confirmed by an overall significant increase in the total area of DAPI+ cells with time in umbilicus-derived cell treated animals, indicating an overall preservation of photo receptors as late as post natal day 88. To briefly summarize, umbilicus-derived cell treatment has an overall positive effect in the retina, decreasing the overall TUNEL+ area (and presumable number of cells). This effect is lasting and maintained at 67 days post injection.

Example 22 Evaluation of the Ability of Umbilicus-Derived Cells to Stimulate RPE Phagocytosis In Vitro One of the prominent characteristics of retinal pigmented epithelial cells (RPE) is to phagocytose the shed outer segments of photoreceptors on a daily basis. This feature is well characterized and important in maintaining a healthy retina. However, there are numerous other functions of RPE that are well described and important to maintaining homeostasis in the eye (reviewed in Strauss et al., 2005). RPE transport ions, water, and metabolic products to the blood, they transport non-endogenous factors as well as secrete endogenous factors that maintain the integrity of photo receptors as well as choriocapillaris. RPE also secrete immunosuppressive agents that establish immune privilege in the eye. A failure of anyone of these functions can lead to degeneration of the retina, loss of visual function, and eventually blindness.

There is considerable building evidence to suggest that defects in RPE ability to perform these functions can trigger known human diseases like Retinitis Pigmentosa and the dry form of age-related macular degeneration (AMD) (Gal et al., 2000; Inana et al., 2005; Inana et al., 2007; Nordgaard et al., 2006; Sundelin et al., 1998; Strauss et al., 2005). There is further evidence to support that, while not the initial trigger, such defects participate in the pathogenesis of other retinal degenerative diseases like Stargardts, Bests, and Lebers Amaurosis (Boulton, et al., 2007).

Restoring or augmenting any of these processes may ameliorate or prevent the further deterioration of the retina by minimizing the progression of photoreceptor degeneration. Doing so would ultimately protect individuals from the possibility of further blindness.

In this study, the ability of umbilicus-derived cells to augment phagocytosis was assessed in an in vitro model that mimics properties of the back of the eye.

Materials and Methods

Cells:

Frozen vials of previously expanded human adult RPE (ARPE-19, American Type Culture Collection, Manassas, Va.) or primary human RPE isolated from donor cadaver eyes (National Disease Resource Interchange, Philadelphia, Pa.) were plated onto 24 well tissue culture treated plastic plates in Growth Medium at 20,000 cells/well.

Frozen vials of previously expanded umbilicus-derived cells (passage 7-10) were thawed, washed with PBS, and plated into transwells at 10,000 or 30,000/well in Growth Medium (0.4 µm pore size PET track-etched membrane cell culture inserts, BD Falcon). The transwells were then added above the existing RPE cultures in the multiwell plate. In addition, previously expanded human dermal fibroblasts (passage 7-10, Cambrex, Walkersville, Md.) were used as a comparison to umbilicus-derived cells.

Co-cultures were maintained at 37 deg C., 5% $CO_2$ in incubators for 3 days to allow for growth factors to be transferred across the membrane between postpartum cells derived from umbilical tissue and RPE cells. After that time, (1) transwells were either removed and the phagocytosis assay performed, or (2) transwells were removed and well containing RPE alone were maintain for 1 or 4 more days by themselves prior to performing the phagocytosis assay.

Phagocytosis Assay:

This assay was performed utilizing a commercially available kit (Vybrant Phagocytosis Assay, V-6694, Invitrogen), designed to provide a model system for quantitating the effects of drugs or other environmental factors on phagocytic function. Following removal of transwells, left over media in bottom of wells was removed and 200 µl of E. coli reagent was added to each well. This solution contained fluorescently tagged, heat inactivated E. coli prepared as described in the kit directions. The plate was placed back in the 37° C. incubator for 2-3 hours. Following incubation, plates were removed, E. coli particle solution removed from each well, and trypan blue (200 µl) added to each well for 1 minute at room temperature to quench any undigested fluorescent E. coli. Next, trypan blue was removed and wells were washed with PBS one time. Fresh PBS was added and ingested E. coli was quantitated by measuring fluorescent activity utilizing a plate reader (SpectraMax® M5, Molecular Devices, limits of excitation 480 nm, emission 520 nm, cutoff 515 nm). Plate reader results were normalized to media only controls and quantitatively represented as percentage of the control cell condition, RPE alone, where 100% of control would represent equal levels of phagocytosis between compared conditions.

Results

Figure 2:
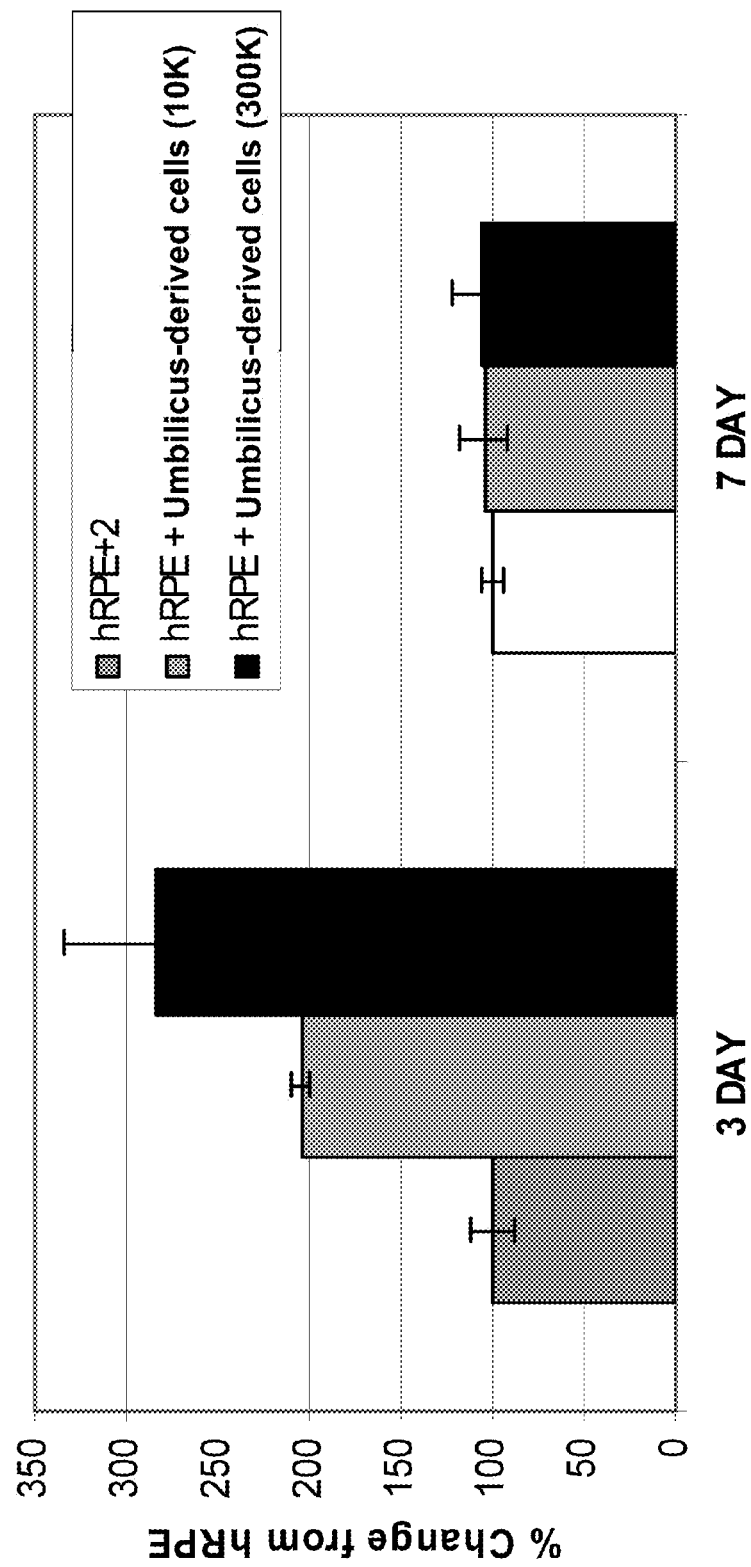
FIG. 2 shows the effect of umbilicus-derived cells on phagocytosis observed in aged primary human RPE cells.

An analysis of phagocytosis was performed assessing the ability of umbilicus-derived cells to effect levels of phagocytosis in cadaveric primary human RPE (age 76 donor) or a human cell line (ARPE-19, ATCC). Both low passage (passage 2) primary human RPE and ARPE-19 behaved similarly when co-cultured with umbilicus-derived cells in this transwell format assay (for a schematic view, see FIG. 1). Umbilicus-derived cells stimulated phagocytosis versus RPE alone in a dose dependent manner after three days co-culture (10,000 umbilicus-derived cells=approx doubling in amount of phagocytosed particles; 30,000 umbilicus-derived cells greater than 2.5 times increase in phagocytosis versus control) (FIG. 2). These values were statistically significant over control, hRPE alone (*p<0.05). However, when umbilicus-derived cells were removed after three days, and the RPE cultures maintained for another 4 days (7 day assay total), overall levels of phagocytosis went down to control levels (FIG. 2).

Figure 3:
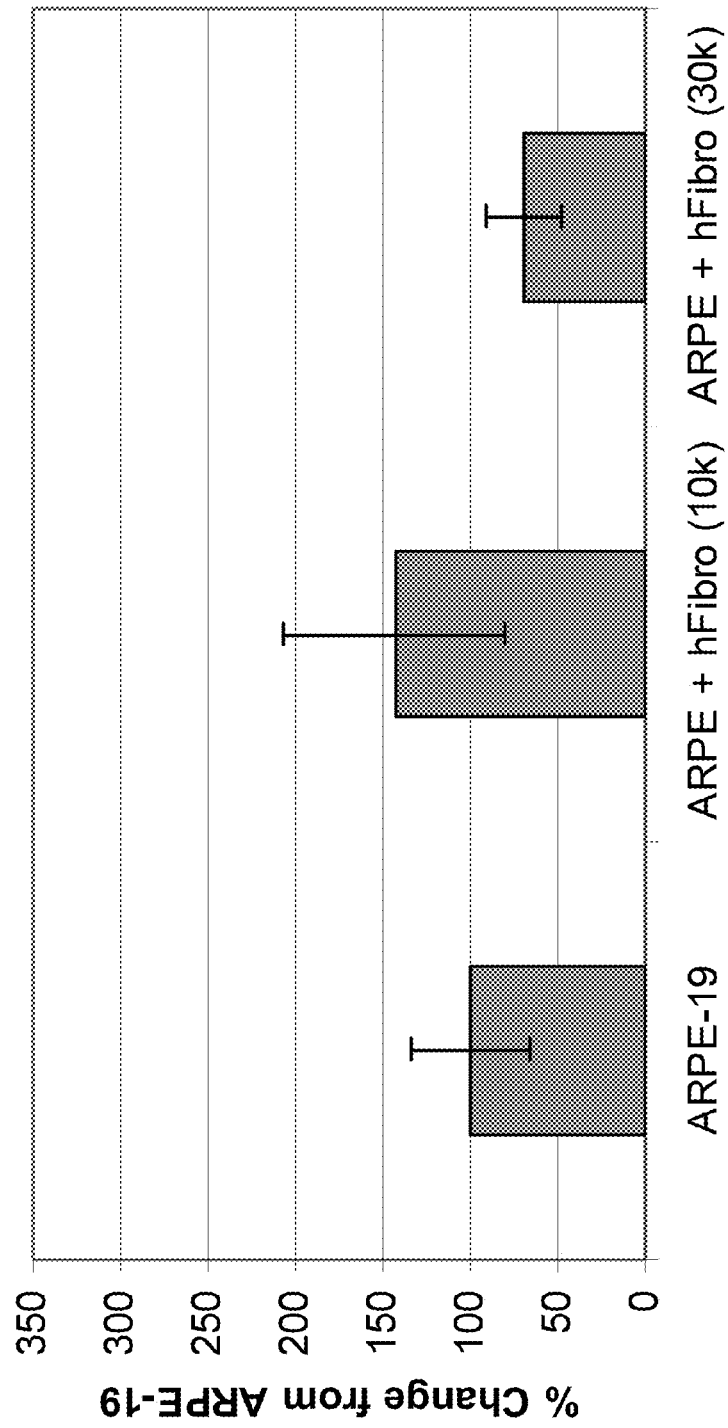
FIG. 3 shows the analysis of human dermal fibroblast stimulated phagocytosis.

In addition, we assessed whether other cell types could stimulate phagocytosis similar to umbilicus-derived cells. In particular we examined expanded human dermal fibroblasts (Cambrex Biosciences, Walkersville, Md.). In contrast to umbilicus-derived cells treatment, 3 day treatment with human dermal fibroblasts led to no changes in phagocytosis above control, RPE alone (FIG. 3, * p<0.05).

Summary:

A dose dependent, significant increase in phagocytosis was observed after three days co-culture of umbilicus-derived cells with aged (76 year old donor) primary human RPE or an expanded human cell line ARPE-19. The transwell assay performed here suggests that this effect was mediated through trophic means rather than cell contact. This result was lost after removal of umbilicus-derived cells for a period of 4 days further implicating trophic factors in the mechanism of action since most growth factors are labile and would not be expected to have an impact after a further four days in culture. Finally, the observed effect of umbilicus-derived cells on RPE phagocytosis could not be replicated using human dermal fibroblasts suggesting that the effect was cell type specific. These results suggest that umbilicus-derived cells secrete growth factors that stimulate phagocytosis in human retinal pigmented epithelial (RPE) cells.

Example 23 Evaluation of the Ability of Umbilicus-Derived Cells to Rescue Phagocytic Function In Vitro Using Cells from the RCS Loss of Function Mutant The details of the RCS model of retinal degeneration are well described earlier in this patent application. The merTK defect associated with this model renders these rats incompetent to phagocytose the shed outer segments of photoreceptors. Previously in Example 22 we have shown the ability of umbilicus-derived cells to stimulate human RPE phagocytosis in aged, but otherwise healthy RPE or similar cell lines. Here we tested whether we could rescue this function utilizing RPE cells from the RCS rodent, a model in which the RPE have a mutation that severely limits this phagocytic function and has a known orthologue in humans that causes retinitis pigmentosa (Gal et al., 2000).

Materials and Methods

Cells:

Primary rat RPE from RCS-dystrophic rats (post natal day 11) were isolated and plated as previously described (McLaren et al. IOVS 1993:34; 317-326; McLaren IOVS 1996:37; 1213-1224). They were cultured for one week until confluent prior to co-culture with umbilicus-derived cells. RPE from congenic, healthy rodents were harvested and utilized as a control.

Phagocytosis Assay:

Previously expanded and frozen umbilicus-derived cells (passage 7-10) were next plated on top of RCS-RPE in a similar trans well format as in Example 22. Co-cultures (in the absence of contact between the two cell types) were maintained for 24 hours at 37 deg C., 5% $CO_2$. FITC-labeled photoreceptor outer segments (POS) were next applied to cultures for 3-6 hours at 37 deg C. Cultures were then analyzed under an epifluorescent microscope for ingestion of FITC-POS at 12.3 hours total assay time post application of FITC-POS.

Quantitation:

Quantitative analysis of ingested FITC-POS was performed manually as previously described (McLaren et al. IOVS 1993:34; 317-326; McLaren IOVS 1996:37; 1213-1224). Briefly, random fields of type I RPE were taken and the number of ingested particles counted. Control congenic (n=6) conditions were compared to dystrophic untreated (n=5) and dystrophic-umbilicus-derived cells treated (n=5) at 40× power. Group means were analyzed for differences using a student's t-test (*p<0.05). Results shown were normalized to congenic controls (100%) for visual comparison.

Figure 4:
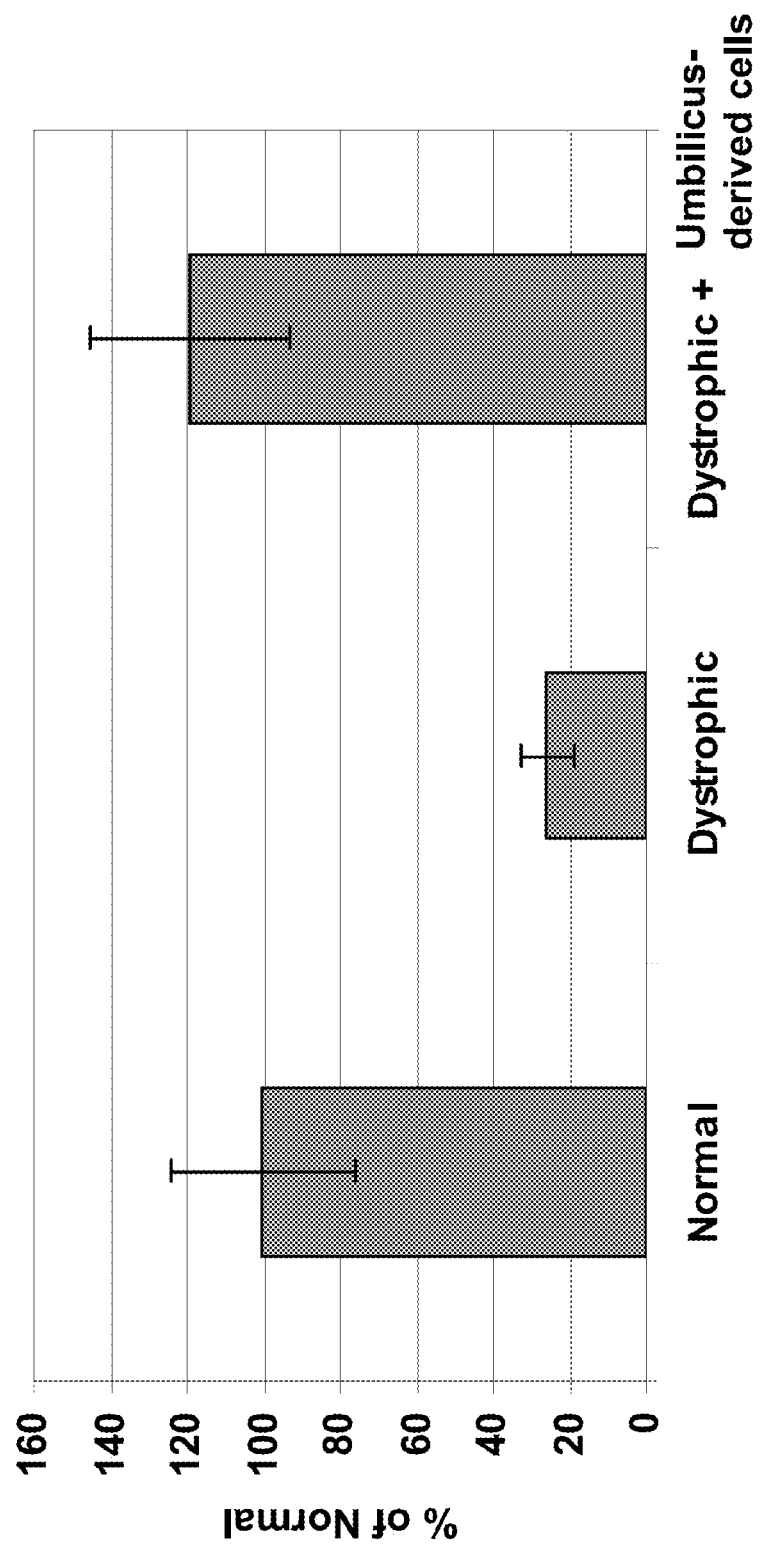
FIG. 4 shows the effects of umbilicus-derived cells on the phagocytosis of fluorescein isothiocyanate-photoreceptor outer segments observed in normal and dystrophic RPE cells.

A quantitative analysis photoreceptor outer segment phagocytosis was performed to evaluate the ability of umbilicus-derived cells to stimulate phagocytosis in otherwise defective RPE from the RCS rat. Normalized to congenic control levels (normal), dystrophic untreated RPE had a drastic decrease in ability to phagocytose the FITC-POS further confirming the mutation leading to loss of function in the RCS model (25.7% of control) (FIG. 4). However, after 24 hours co-culture with umbilicus-derived cells, phagocytosis was restored to normal congenic levels in dystrophic RPE (119.2% of control, p=0.0015 vs. dystrophic untreated).

Summary:

In this study, the ability of umbilicus-derived cells to stimulate RPE phagocytosis was assessed. Uniquely, this model allowed us to evaluate the effect of umbilicus-derived cells trophic factors on RPE with a defect in a phagocytic gene. Further, this model allowed us to use the physiologic photoreceptor outer segments to evaluate phagocytosis. These results suggest that trophic factors secreted by umbilicus-derived cells rescue the loss of function inherent in the RPE cells in the RCS model of retinal degeneration. These results further implicate umbilicus-derived cells in treating a variety of retinal degenerations associated with phagocytic defects in RPE (Gal et al., 2000; Inana et al., 2004; Inana et al., 2007).

Example 24: Attachment of Umbilicus-Derived Cells to Aged Bruch's Membrane: Ability to Repopulate Degenerate Retina and Sustain RPE Cell Survival or Act Like RPE in the Prevention of AMD Aging changes occur more prominently in submacular Bruch's membrane. Thus, because AMD related changes predominate in the macular region we sought to examine the ability of umbilicus-derived cells to survive and grow on submacular Bruch's membrane. A demonstration of umbilicus-derived cells to attach to submacular membranes would provide evidence that these cells could survive in this environment in vivo. The attachment of umbilicus-derived cells would provide a potential to integrate and function like RPE or alternately provide a matrix platform on which RPE could repopulate and function.

Previous studies utilizing a Bruch's membrane explant model system show that retinal pigment epithelial cells have limited capacity to survive on aged Bruch's membrane, even when a robust fetal cell line is used. These results predict that RPE transplant in patients, particularly patients with age-related macular degeneration (AMD), will not be effective. In fact, combined RPE transplantation and choridal neovascular membrane excision has been attempted in AMD eyes, but it has not led to significant visual improvement in most patients. In contrast, RPE transplantation in animal models of retinal degeneration has been proved to rescue photoreceptors and preserve visual acuity. Although animal studies validate cell transplantation as a means of achieving photoreceptor rescue, laboratory animals in which RPE transplantation has been successful do not accurately reproduce the age-related modifications of Bruch's membrane in human eyes, which may have a significant effect on cell graft survival.

With normal aging, human Bruch's membrane, especially in the submacular region, undergoes numerous changes (e.g., increased thickness, deposition of extracellular matrix and lipids, cross-linking of protein, non-enzymatic formation of advanced glycation end products). BM thickness appears to increase linearly with aging. Membranous debris, filamentous material, and coated vesicles accumulate primarily in the inner collagenous layer by early adulthood and continue to do so throughout adult life and by late middle age, lipid deposition in BM is apparent. Basal laminar deposit, which comprises mostly wide-spaced collagen and other materials including laminin, membrane-bound vesicles, and fibronectin, is present in the 7th decade during normal aging. Lipid accumulation in BM begins to increase significantly after age 40 years.

The results of RPE cell attachment and survival on aged Bruch's membrane and similar preliminary data using putative RPE derived from embryonic stem (RPE-ES) cells indicate poor survival may not be unique to RPE. Additionally, morphology of RPE-ES indicates that some of the cells may be dedifferentiating or trans differentiating following seeding onto Bruch's membrane. These results indicate the importance of studying the behavior of postpartum cells derived from umbilical tissue on Bruch's membrane to determine applicability to treating patients with AMD.

Materials and Methods

The external surface of donor human eyes was trimmed to remove muscle, connective tissue and fat, and the globes were immersed in 10% povidone iodine briefly. This was followed by washing in BSS. This was followed by two 10-minute incubations in Dulbecco's modification of Eagle's Medium (DMEM) containing 2.5 mg/ml amphotericin B. The anterior segment, vitreous, and the retina are dissected out. Posterior segments were trimmed to include submacular Bruch's membrane.

The RPE were gently removed from Bruch's membrane without damaging the RPE basement membrane. After dissecting out the anterior segment, vitreous, and retina from donor eyes, submacular RPE was debrided gently using a microsurgical sponge (Alcon, Fort Worth, Tex.) to create a surface with intact native RPE basement membrane.

Umbilicus-derived cells were seeded at a density of 3146 cells/$mm^2$ onto the submacular explants. Supplemented DMEM was changed every other day for 1, 2, 7 or 14 days. After culture of postpartum cells derived from umbilical tissue on submacular explants, they were fixed in 2% paraformaldehyde and 2.5% glutaraldehyde. Explants were bisected following minimum overnight fixation and then examined by light microscopy or scanning electron microscopy (SEM). SEM image acquisition was performed on a JEOL 35C equipped with a digital image acquisition system (Gatan Inc., Pleasanton, Calif.). SEM analysis focused on comparing surface morphology of the two cells, confirming the presence of RPE basement membrane, and determining the extent of cell coverage.

Results

Figure 5:
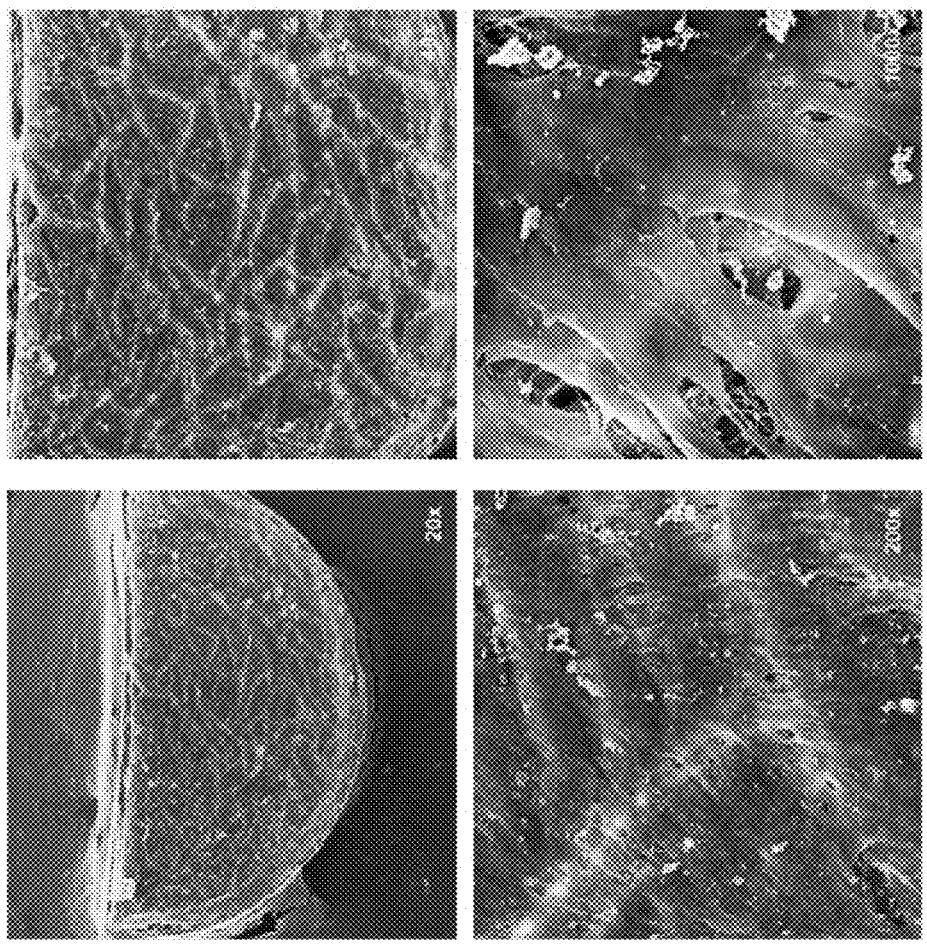
FIG. 5 shows the adherence and integration of umbilicus-derived cells on aged explants of human Bruch's membrane after 7 days.

Umbilicus-derived cells survived and grew to confluence on explants for up to 14 days in vitro (FIG. 5). These results demonstrated that umbilicus-derived cells can repopulate aged Bruch's membrane and thus, providing a potential platform to support RPE repopulation or alternately a replacement for lost RPE.

Summary:

Umbilicus-derived cells can repopulate aged Bruch's membrane and thus, provide a potential platform to support RPE repopulation or alternately a replacement for lost RPE.

Example 25 Comparison of Integrin Expression Profiles of Umbilicus-Derived Cells with RPE Umbilicus-derived cells and ARPE-19 were analyzed for the expression of several integrins to determine if umbilicus-derived cells share similar characteristics to RPE.

Materials and Methods

Single cell suspensions of cultured human umbilicus-derived cells and adult retinal pigment epithelial (ARPE-19) cells were prepared by detaching cells from culture dishes with trypsin 0.5%-EDTA solution (Invitrogen, Carlsbad, Calif.). Cells were incubated with FACSFlow™ Buffer (Becton Dickinson, Franklin Lakes, N.J.) containing 3% fetal calf serum (blocking solution) for 30 minutes at 4° C. with one of the following mouse monoclonal antibodies (Table 25-1): $\alpha 1$, $\alpha 2$, $\alpha 3$, $\alpha 4$, $\alpha 5$, $\alpha v\beta 3$, $\alpha 2\beta 1$, $\beta 1$ and $\alpha 5\beta 1$. All washes and incubations were done in blocking solution at 4° C. Non-conjugated primary antibody labeled cells were washed and incubated in PE-conjugated goat anti-mouse secondary antibody f( )r 15 minutes. Isotype controls contained cells incubated in PE-conjugated goat anti-mouse secondary antibodies (Table 25-2). At least 10,000 cells were analyzed with a Becton Dickinson FACSCalibur™ flow cytometer (Becton Dickinson, Franklin Lakes, N.J.).

Results

The results demonstrated that umbilicus-derived cells express several integrins associated with both fetal and adult RPE (Table 25-1). These results clearly demonstrate that umbilicus-derived cells express the natural matrix molecules that would allow them to integrate and adhere to Bruch's membrane as was demonstrated in Example 24. Furthermore, the integrin expression is similar to that previously published for fetal RPE.

Summary:

These data suggest that umbilicus-derived cells administration to the eye may enhance the grafting of an adult RPE cell transplantation. Furthermore, the results confirm that umbilicus-derived cells express the relative cell surface markers necessary for them to adhere to Bruch's membrane.

Example 26 Effect of Umbilicus-Derived Cell Treatment on Phagocytosis in Aged Human RPE-Gene Expression Analysis Age-related macular degeneration (AMD) affects approximately fifteen million people over the age of sixty and two million new cases are diagnosed each year. Those stricken by this disease experience a decrease in visual function, leading to blindness.

In this condition, both retinal pigment epithelium cells (RPE) and photoreceptors are affected. The interaction of the RPE and photoreceptor outer segments is crucial for the function and survival of the photoreceptors. Normally, RPE function to synthesize and secrete complement factor H (CFH) as well as to ingest and degrade shed photoreceptor outer segments. Failure of RPE in phagocytosis leads to photoreceptor cell death, as observed in the Royal College of Surgeons (RCS) rat (Dowling and Sidman, 1962). In the RCS model, a mutation in the gene Mertk results in the normal binding of photoreceptor outer segments but the inability to ingest shed tips of photoreceptor outer segments. As oxidized shed segments build up, synthesis and secretion of CFH by RPE is affected. The role of CFH is to regulate complement activation. If inhibited, CFH-mediated protection of RPE cells may be reduced thus leading to the onset of AMD (Chen, 2007).

In order to assess the impact umbilicus-derived cell application has on human aged RPE, differences in host gene expression were examined. Ruman aged RPE were used in this study for the following reasons: [1] AMD generally affects people over the age of sixty and [2] evidence suggests that with age, lipofuscin build-up occurs. Lipofuscin build-up in the lysosomal compartment of RPE may cause insufficient synthesis of CFH thus resulting a lack of protection against complement damage. Therefore, a panel of genes associated with phagocytosis, proteosomal degradation and inflammation was established and subsequent gene expression levels were compared.

Materials and Methods

Human Retinal Pigmented Epithelium (hRPE) Isolation:

The hRPE was dissected from one set of human eyes (75 year old Caucasian female). The donor had no known diagnosed eye disease. However, after examining the gross appearance of the retina and RPE, small retinal hemorrhages were noted (hallmark characteristic of those affected by AMD). The eyes were obtained through the National Disease Research Interchange (NDRI). After removing the sclera from both eyes, the hRPE was dissected away from the retina. The hRPE was cut into pieces and enzymatically digested for 30 minutes in a solution containing trypsin (JRH Bioscience), kynurenic acid ([20 mg], Sigma) and vitrase ([200 units], ISTA Pharmaceuticals). To further disassociate the tissue, cells were triturated and then briefly vortexed. To stop the digestion process, DMEM-low glucose media (Invitrogen, Carlsbad, Calif.) containing 15 percent (v/v) fetal bovine serum (FBS; Hyclone, Logan, Utah) was added. After that cells were forced through a 100 µm nylon cell strainer (BD Falcon). The resulting solution was then centrifuged for 5 minutes at 250×g. The supernatant was removed and the cells were resuspended in complete medium containing DMEM-low glucose (Invitrogen, Carlsbad, Calif.), 15 percent (v/v) fetal bovine serum (FBS; Hyclone, Logan, Utah), 0.001% (v/v) 2-mercaptoethanol (Sigma, St. Louis, Mo.), and penicillin/streptomycin (5,000 Units/mL). Cells were counted with a hemocytometer and plated (concentration of 1×105 cells/well) into a six-welliaminin coated plate (BD Biosciences). The plate was then placed into a 37° C. incubator.

Preparation of Umbilicus-Derived Cells and Co-Culture Assay:

Frozen aliquots of previously expanded umbilicus-derived cells (passage 7) were thawed, washed, counted and seeded ($5 \times 10^4$ cells/inserts) into either a 6-well cell culture plate (Corning) or into cell culture inserts (pore size: 0.4 µm, BD Biosciences, Franklin Lakes, N.J.). All cells were grown in the same complete medium as hRPE. The umbilicus-derived cells inserts were placed directly on top of three wells containing hRPE. The plates were then placed into a 37° C. incubator for 3 days.

RNA Isolation:

After 3 days, the inserts were removed and all cells (hRPE and umbilicus-derived cells) were trypsinized, centrifuged, resuspended and counted. The untreated hRPE and treated hRPE were lysed by addition of 350 µL RLT Buffer (RNeasy® Mini kit, QIAGEN). The lysate was applied onto a QIAshredder spin column and placed in a 2 mL collection tube and then centrifuged for 2 minutes at maximum speed (18,000 g; Microfuge 18 Centrifuge, Beckman-Coulter Cat#367160). One volume of 70% ethanol (200 proof, Sigma, Cat # E7023-500ML) was added to the homogenized lysate and applied to an RNeasy® mini column placed in a 2 mL collection tube (supplied). The column was centrifuged for 15 seconds at greater than or equal to 8000×g (greater than or equal to 10,000 rpm). The flow through was discarded. Buffer RWI (700 µL) was added to the RNeasy® column and centrifuged for 15 seconds at greater than or equal to 8000×g (greater than or equal to 10,000 rpm) to wash the column. The flow through was discarded. The RNeasy® column was transferred into a new 2 mL collection tube (supplied) and 500 llL Buffer RPE was applied to the RNeasy® column. The column was centrifuged for 15 seconds at greater than or equal to 8000×g (greater than or equal to 10,000 rpm). The flow through was discarded. Another 500 µL of Buffer RPE was applied to the RNeasy® column and centrifuge for 2 minutes at greater than or equal to 8000×g (greater than or equal to 10,000 rpm) to dry the RNeasy® column. The RNeasy® column was transferred to a new 1.8 mL collection tube (DNA LoBind tube 1.5 mL 22 43 102-1, Eppendorf AG) and centrifuged in a microcentrifuge at full speed for 1 minute. To elute the RNA from the RNeasy® column, the column was transferred to a new 1.5 mL collection tube (supplied) and 30 µL RNase-free water was applied. The tube was then centrifuged for 1 minute at greater than or equal to 8000×g (greater than or equal to 10,000 rpm). After centrifugation, the tube was removed, capped and labeled and then transferred to a −80° C. freezer.

RNA Quality and Quantification:

The quantity and quality of RNA was determined using SOFTMAX Pro software on the SPECTRAMAX M5 spectrophotometer (Molecular Devices). Deionized water (dH20) was used as a blank and was loaded into the first well of a 96-well UV plate (Costar, Corning). Diluted RNA samples (1:20) were loaded into subsequent wells and the reading was taken. The RNA concentration was calculated: (µg/mL)=(OD260)×(dilution factor)×(40 µg RNA/ml). Then 10 µL of each diluted RNA sample was loaded into an agarose E-gel (Invitrogen) along with 10 µL of TrackIt (50 bp DNA ladder, Invitrogen). Samples were run for 15 minutes. After time had expired, images were taken of the gel using the Chemi Doc XRS camera system (Bio-Rad).

First Strand cDNA Synthesis:

The synthesis of cDNA was performed using the SUPERSCRIPT III First-Strand Synthesis System (Invitrogen, Carlsbad, Calif., USA). Reagents were combined and added to each tube as shown in Table 26-1.

Tubes were then transferred to a Thermal Cycler (Bio-Rad Cat#170-9703), incubated at 65° C. for 5 minutes and then cooled to 4° C. Next, 20 µL of cDNA Synthesis Mix (Table 26-2) was added to each tube. The tubes were then heated to 50° C. for 50 minutes, followed by another 85° C. cycle, which lasted for 5 minutes, and finally a cooling 4° C. cycle for 15 minutes. At this time, 1 µL of RNase H was added to each tube. The tubes were again incubated for 20 minutes at 37° C. At the end of this cycle, the cDNA synthesis reaction was used immediately for RT-PCR.

Real-Time Quantitative RT-PCR:

The mRNA levels of the analyzed genes were quantified by real time RT-PCR. Master mix was made (Table 26-3) and then pipetted into a Fast Thermal Cycler Optical 96-well plate (Applied Biosystems).

The RT-PCR reaction was performed using the 7900HT Fast Real-Time PCR System (Applied Biosystems). Thermal cycle conditions were as follows: 50° C. for 2 minutes, 95° C. for 10 minutes followed by 40 cycles of 95° C. for 15 seconds and 60° C. for 1 minute. At the completion of the reaction, the data was saved and then analyzed with the SDS 2.2.2 system software (Applied Biosystems).

Results

Genes Used for Analysis:

The names of the genes that were chosen for this analysis, their abbreviation, catalogue number and proposed function in the eye are summarized in Table 26-4. The genes were chosen based on their importance in functions for RPE.

Real Time RT-PCR:

For the calibration of mRNA expression levels, GAPDH was selected to serve as the endogenous control. Thus for analysis, the expression levels of all genes were normalized to GAPDH.

In this analysis, the gene expression levels of untreated RPE were compared to umbilicus-derived cell treated RPE (Table 26-5). In hRPE co-cultured with umbilicus-derived cells, increases expression in the following genes were observed: MERTK, CRALBP, INTAV, CATHD and CFH. (2.8±0.2 co-culture vs. 8.2±0.2 control, *p<0.05). These increases were seen only after 3 days of co-culture with umbilicus-derived cells. These results suggest that umbilicus-derived cell treatment had an impact on the expression of genes associated with phagocytosis, proteosomal degradation and inflammation.

Summary:

Current physical treatments fail to improve visual function for those affected by AMD. Retinal repair may require the transplantation of healthy cells for the treatment of this disease. Co-culture of umbilicus-derived cells on aged hRPE has shown to impact the expression of genes associated with phagocytosis, proteosomal degradation and inflammation.

Accumulating evidence suggests that immunological factors, such as CFH, may play an important role in the development of macular degeneration development. It has been shown in vitro that freshly plated human RPE cells express high levels of CFH. However, when human RPE cells are exposed to prolonged incubation with oxidized photoreceptors rod outer segments or with pro-inflammatory cytokines such as, TNF-alpha and IL-6, CFH is down regulated (M. Chen et al., 2006). This study suggests that the co-culture of umbilicus-derived cells could be used for treatment of macular degeneration as well as other ocular indications where phagocytosis or inflammation may be affected.

Example 27 Gene Profiling Approach to Identify Potential Mechanisms by which Umbilicus-Derived Cells Preserve Vision in the Royal College of Surgeons Rat Model of Retinal Degeneration Methods and Materials Cell Culture for Trophic Factor Secretion:

Umbilicus-derived cells (population doubling 20) was plated at a seeding density of 10,000/cm$^2$ into gelatin-coated 6-well plates in Growth Media as described in the previous example. After 24 hrs, the culture media was replaced with 1 ml fresh growth media. The supernatant of the culture was collected at day 1, 3, 7 and saved frozen at −80° C. Cell number counts were performed for each individual sample. These culture media were sent to Pierce Biotechnology Inc. (Worcester, Mass.) for the analysis described below.

ELISA:

ELISA for HGF and IGF followed the instruction from R&D systems.

Briefly, working standards were prepared as directed in the instruction manual (HGF: 125 pg/ml-4000 pg/ml; IGF: 94 pg/ml-6000 pg/ml). Standards, control, or sample (50 µl) were added to each well and were incubated for 2 hours at room temperature for HGF and at 4° C. for IGF. The plate was washed four times. 200 µL of HGF or IGF conjugate was added to each well and incubated for 1.75 hours at room temperature for HGF and for 1 hour at 4° C. for IGF. The plates were washed for 4 times, then 200 µL of Substrate Solution was added to each well and incubated for 30 minutes at room temperature for HGF and IGF. 50 µL of stop solution was added to each well. The optical density of each well was determined using a microplate reader set to 450 nm.

Cell Transplants.

The transplantation procedure has been described above. Briefly, 20,000 umbilicus-derived cells in 2 µl PBS were injected into the dorso-temporal subretinal space of anesthetized 3-week old dystrophic-pigmented RCS rats. As controls, sets of RCS animals underwent either a sham injection procedure containing PBS only, or were left untreated.

After cell injections were performed, animals were injected with dexamethasone (2 mg/kg) for 10 days post transplantation. For the duration of the study, animals were maintained on oral cyclosporine A (210 mg/L of drinking water; resulting blood concentration: 250-300 micrograms/L) (Bedford Labs, Bedford, Ohio) from 2 days pre-transplantation until end of the study. Food and water were available ad libitum. Animals were sacrificed at day 7, 30 and 60 post transplantation (dystrophic-untreated, dystrophic-cell injected) for microarray study. Sham-operated animals were only collected at day 7 post injection RNA Sample Collection.

Animals were sacrificed at day 7, day 30- and day 60 post cell transplantation, with an overdose of urethane (12.5 g/kg). Eyes were extracted from the animals and fixed in RNALater to prevent RNA degradation. RNA extraction was performed following Invitrogen Trizol protocol. RNA concentration and quality were examined by BIO-RAD Experion Bioanalyzer. From each sample, 2 µg total RNA was used for Affimetrix rat 230 version 2 chips. Three sets of comparisons were done: day 7 treated vs. sham; day 30 treated vs. non-treated; day 60 treated vs. non-treated. In each group, three individual samples were used.

Microarray analysis:

The RNA samples were sent to Johnson & Johnson Pharmaceutical Research and Development in La Jolla, Calif. where the Affymetrix rat chip was used for microarray analysis. The raw micro array data was normalized across the 16 chips using Quantile-Quantile normalization. ANOVA and Multiple test correction (FDR; p-value <=0.01), two methods provided in the Partek Pro (St. Louis, Mo.) software, were used to determine differences between treatment and time factors after normalization. Differentially expressed genes were identified for each time point using the t-test method (p-value less than or equal to 0.05) in conjunction with fold changes (greater than or equal to 1.5) between the mean values of each group. With differentially expressed genes determined, relevant pathway analysis was constructed using Ingenuity systems (IPA) from Ingenuity Systems (Redwood City, Calif.).

Results

Gene Profiling Revealed Protected Photoreceptor Function:

In order to understand the possible mechanisms resulting in the preserved visual function in the umbilicus-derived cell treated eyes, we conducted a microarray study to identify the differentially expressed genes and the canonical pathways in the treated versus non-treated rat eyes to guide further in vitro studies. This study was designed to recognize differential rat gene expression and pathway networks in response to umbilicus-derived cell treatment in the eyes. Total RNA was obtained from treated and non-treated rat eyes at different time points (Days 7, 30 and 60 post cell transplantation, n=3). At each time point, the non-treated fellow eyes were used as controls. Eyes from sham-operated rats were collected at day 7 and were used as controls for Day 7 time point. Standard hybridization procedures were performed for Affimetrix Rat 230 chip. 23,000 gene expression data were obtained from the Affimetrix Rat 230 chip. Raw data were normalized across all chips. 987 genes were differentially expressed in treated eyes vs. controls with statistic significance (p<0.05). Hierarchical clustering was performed and the heat map was generated. The heat map demonstrated that individual sample at the same time point tends to cluster together, suggesting an evident time effect for the treatment and at the same time point, treatment groups differ from the control groups.

Based on the analysis described above, different predominating gene networks were identified at different time points after cell transplantation. At day 7, in the analysis of umbilicus-derived cell-treated vs. sham-operated eyes, genes involved in cell proliferation and growth such as FOS, CSNKID, and RPS6KA2 were up regulated in cell-treated eyes, as shown in Table 27-1. FOS is a transcription factor that regulates cell proliferation in many cell types. Increased FOS expression has been documented in RPE cells during proliferation. FOS activation is regulated by MAP kinase cascade, which links the growth factor receptor activation at cell surface to the transcription factor such as FOS in the nucleus. RPS6KA2, also known as pp90$^{rsk}$, is a kinase involved in the activation of FOS in the MAPK cascade.

The increased expression of a kinase cascade component-pp90$^{rsk}$ and a down-stream transcription factor-FOS strongly suggests the impact of umbilicus-derived cells on cell proliferation in the RCS rat eyes. RPE cell proliferation potentially can increase RPE cell number in the retina and potentially enhance phagocytosis, thus, protect photoreceptors from apoptosis, and preserve visual function.

More over, genes involved in insulin-like growth factor (IGF) pathway, such as IGFBP5, IGF2BP3, were also up-regulated as shown in Table 27-1. A wide range of biological processes are modulated by IGF-1 signaling pathway, including, for example, cell proliferation, tissue-specific differentiation, and protection against apoptosis. In RPE cells, activation of IGF cascade is related with reduction of apoptosis-induced by hydrogen peroxide IGF pathway members such as IGF1 binding protein (IGFBP)5 and IGFBP3 are well documented to inhibit apoptosis in multiple cell types, including RPE cells. IGFBP5 and IGFBP3 promote the activation of IGF1 receptor by carrying IGF1 in the circulation and facilitating binding between IGF1 and its receptor. The up regulation of IGFBP5 and IGF2BP3 in the treated rat eyes demonstrated that activation of IGF pathway is one of the protection mechanisms induced by umbilicus-derived cells against cell death.

Another molecule that umbilicus-derived cells impacted was TXNL1. TXNL is thioredoxin-related protein, a member of the thioredoxin pathway, which regulates oxygen stress and protects cells against oxygen stress-induced cell death. Oxygen stress stimulation such as hydrogen peroxide treatment induced apoptosis in cultured RPE cells. Thus, the increased activity of thioredoxin pathway potentially could release the oxygen stress and protect RPE. Indeed, this pathway has been shown up regulated in non-apoptotic RPE cell line compared to apoptosis RPE. At day 7-post cell transplantation, the up-regulation of cell proliferation and protection against cell death, either by increasing the activity of IGF signaling pathway or by releasing oxygen stress, paves the way for preserved photoreceptors in the outer nuclear layer and preserved visual function in RCS rats.

The predominant anti-apoptosis pathways at day 7 continued to be the dominant signaling network at day 30 as shown in Table 27-2. The platelet-derived growth factor C (PDGFC) is unregulated at day 30 in the cell-treated eyes. PDGFC is a member of PDGF family. Similar to IGF1, PDGF family members also demonstrate a broad biological functions in many cell types, including proliferation and survival.

Down-stream to the PDGF receptor, SH2B was up regulated in the treated eyes. SH2B is a cytoplasmic adaptor protein that connects the growth factor receptor to the kinase cascade. The up regulation of both the growth factor PDGFC and the adaptor protein SH2B demonstrated the impact by umbilicus-derived cells on this growth factor pathway. The continuation of the growth factor activation by the initial treatment demonstrated the long-lasting trophic effect from umbilicus-derived cells in the treated eyes and correlated with the retention of umbilicus-derived cells in the eyes.

Figure 6:
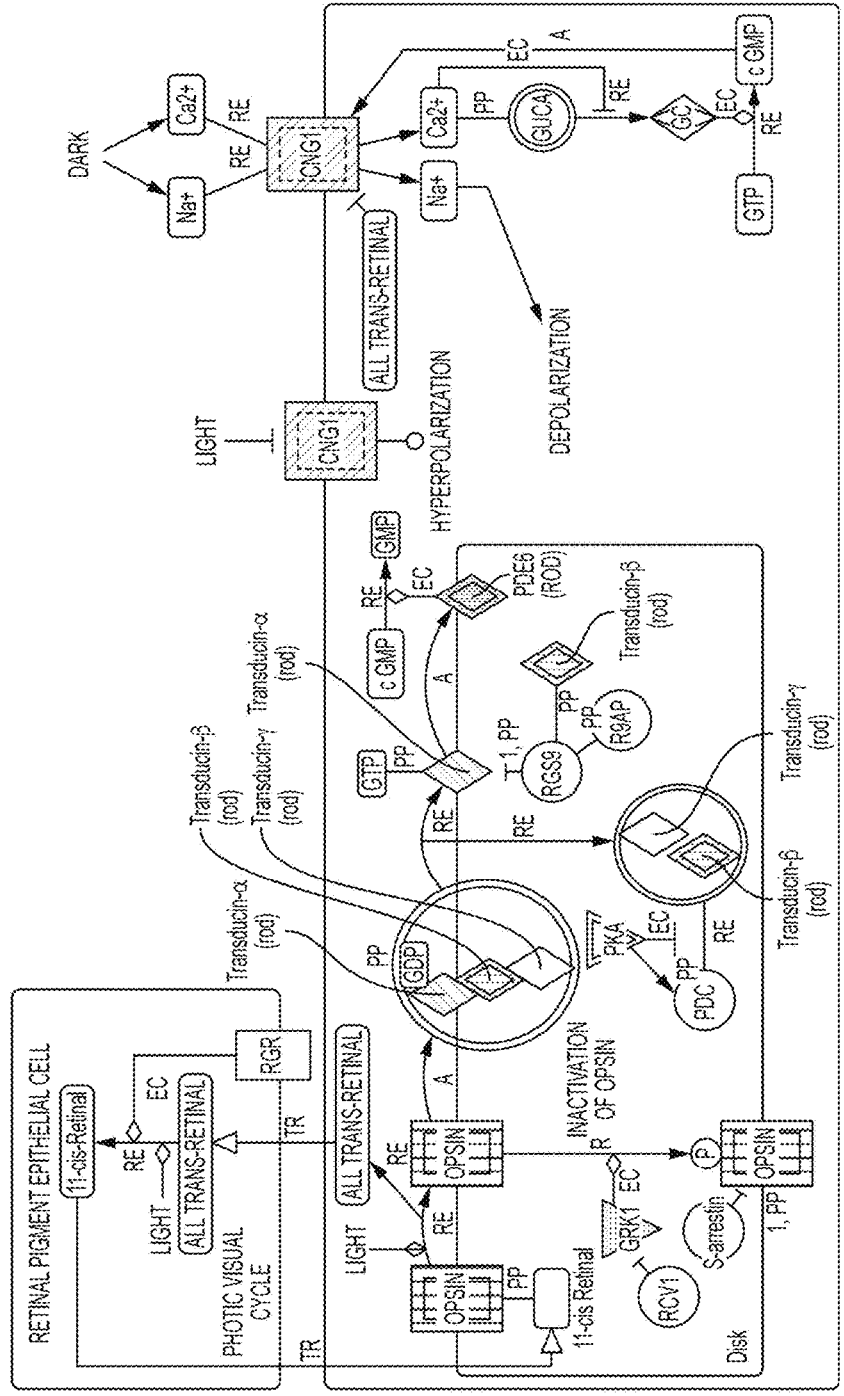
FIG. 6 shows the phototransduction pathway in cone and rod cells. Shading denotes up-regulated expression.

Pathway analysis from Day 60 data revealed a predominant phototransduction pathway in the treated eyes (Table 27-3). The phototransduction pathway is shown in FIG. 6. Briefly, light activation causes a graded change in cell surface membrane potential. The transmission of the pulses is mediated by opening or closing of ion channels, which are regulated by cyclic guanosine monophosphate (cGMP). The series of biochemical changes that ultimately leads to a reduction in cGMP levels begins when a photon is absorbed by the photo pigment in the receptor disks, which contain proteins called opsins. One of opsins in rod cells that mediate the molecular events post light perception is rhodopsin (RHO). When the retinal moiety in the rhodopsin molecule absorbs a photon, its configuration changes. This change then triggers a series of alterations in the protein component of the molecule, and leads to the activation of an intracellular messenger called transducin, which activates a phosphodiesterase that reduces the concentration cGMP and leads to channel closure at cell surface membrane (FIG. 6).

Molecules involved in the phototransduction pathway such as CNGA1, GNAT1, GNB1, RHO, and PDE6B were up regulated. These genes distributed in the entire photoreceptor transduction network. Cyclic nucleotide-gated (CNG) ion channel subunit CNGA1 expression is increased more than 6 fold in the treated eyes and located at photoreceptor outer segment in the transduction pathway to eventually mediate the membrane potential pulses in photo receptors as shown in FIG. 6. RHO is one of the proteins in opsins, which is a complex of molecules to receive and process photons from the light. The up-regulation of RHO suggests preserved light perception function in rod cells. GNAT1 and GNB1 are alpha and beta units in transducin that couple RHO and cGMP-phoshodiesterase during visual impulses. The expression of other visual function regulatory molecules, PDE6B and ROCK1, which directly regulate cGMP were also up regulated. Interestingly, the predominating pathway transition from anti-apoptotic pathway at day 7 and 30 to phototransduction pathway at day 60, suggests a direct impact of umbilicus-derived cell treatment on the protection of photoreceptors.

Trophic Factors Secreted by Umbilicus-Derived Cells:

From the microarray results, it is evident that umbilicus-derived cells may playa role in promoting proliferation and reducing apoptosis at early stage. Additionally, umbilicus-derived cells may playa role in preventing photoreceptor cell death, and maintaining phototransduction at later stage. To determine the cytokines secreted by umbilicus-derived cells that can impact on proliferation and protection, we looked into the trophic factors that are secreted by umbilicus-derived cells in vitro.

From the growth factor analysis, IL-8, IL-6, HGF, and IGF-1 are highly secreted by umbilicus-derived cells in vitro (Table 27-4 and Table 27-5). The pathway analysis described above has demonstrated the involvement of IGF pathway in the umbilicus-derived cell treated eyes. Other cytokines that are secreted by umbilicus-derived cells in vitro include basic FGF, BDNF, CNTF, NT3 as shown in Table 27-4. The trophic factor profiles correlated with the findings from microarray.

Example 28 Conditioned Medium from Umbilicus-Derived Cells Protected ARPE-19 from $H_2O_2$-Induced Apoptosis Apoptosis may be involved in the development of retinal degeneration diseases such as RP and AMD. Apoptosis in photoreceptors is derived from multiple pathophysiologies, including defects in the process of phagocytosis and oxygen stress. Studies from animal models have shown a deleterious effect in photoreceptors and RPE from oxidative damages. The oxidative damage can form a cycle of cell death initiated from the rod undergoing apoptosis. The apoptotic rod cells created environment with increased blood flow and higher oxygen in the retina, which lead to deterioration of RPE, rods, and cones, which is the major cell type for vision.

In the previous example, a gene profiling study (Microarray) revealed anti-apoptosis as a key signaling pathway at early stage post cell transplantation and preservation of photo transduction at later stage. Follow-up trophic factor assessment in the umbilicus-derived cell conditioned media has confirmed the microarray results and identified several cytokines as anti-apoptotic agents based on literatures. In this study, we intend to evaluate if umbilicus-derived cell conditioned media can protect RPE cell line from apoptosis induced by hydrogen peroxide ($H_2O_2$) and to develop a cell-based apoptosis assay.

Materials and Methods

Umbilicus-Derived Cell Culture for Conditioned Media Collection:

Frozen vials of previously expanded umbilicus-derived cells (population doubling 20) were plated at 5,000 cells/$cm^2$ on T75 flasks in Growth Medium as described above. The flasks were incubated in a 37° C. incubator for 24 hours. The supernatant of the culture was collected after 24 hour culture, and saved frozen at −80° C. or applied to ARPE cultures immediately.

ARPE-19 Culture:

Frozen vials of previously expanded ARPE-19 cells (CRL2502, American Type Culture Collection, Manassas, Va.) were seeded onto 24-well plates in Growth Medium at 40,000 cells/well or in 96-well plate at 5000/well for 24 hours. Cells were washed with PBS and treated with media containing $H_2O_2$.

$H_2O_2$ Treatment:

$H_2O_2$ was prepared by adding $H_2O_2$ at different concentrations (0, 0.125 mM, 0.25 mM, 0.5 mM, 1.0 mM, 1.2 mM) to the growth media (GM) or conditioned media (CM) from umbilicus-derived cell culture. ARPE-I9 were cultured in $H_2O_2$ containing media for 0, 0.5 hr, 1 hr, 2 hr, 3 hr, then the $H_2O_2$ media was removed and cells were used for further apoptosis assays.

For Annexin V assay, ARPE-19 cells were treated with wither growth media or conditioned media for 24 hours before assessment of apoptosis.

Colometric Apoptosis Assay:

The apoptosis assay was performed according to the instruction in the Cell Death Detection ELISA$^{plus}$ kit from Roche (Cat #11 774 425 001). Briefly, the cells still attached to the plate was lysed and incubated with an antibody against histone to pull histone from the whole lysates. Another antibody, linked with HRP, recognizing the DNA fragments will be used to identify the DNA components within the histone section. The apoptotic complex of histone and DNA fragments will be recognized by HRP substrates.

Annexin Vapoptosis Assay:

After a 24 hour incubation period, the culture medium was removed and the plate was washed with PBS. Trypsin (Gibco) was added to dislodge the cells from the individual wells. The culture medium from each well and the trypsinized cells from each respective well were combined and centrifuged at 250×g for 5 minutes and the pellet was resuspended in 40 μL cold 1× Nexin buffer. Five microliters Annexin V-PE and 5 μL Nexin 7-AAD were added to each sample and the mixture was vortexed and incubated shielded from light at 4° C. for 20 minutes. Following incubation, 450 μL of cold 1× Nexin buffer was added to each sample and the suspension was vortexed. The stained samples were loaded onto the Guava Personal Cytometer and were acquired and analyzed according to the Guava Personal Cytometer User's Guide.

Results

Figure 7:
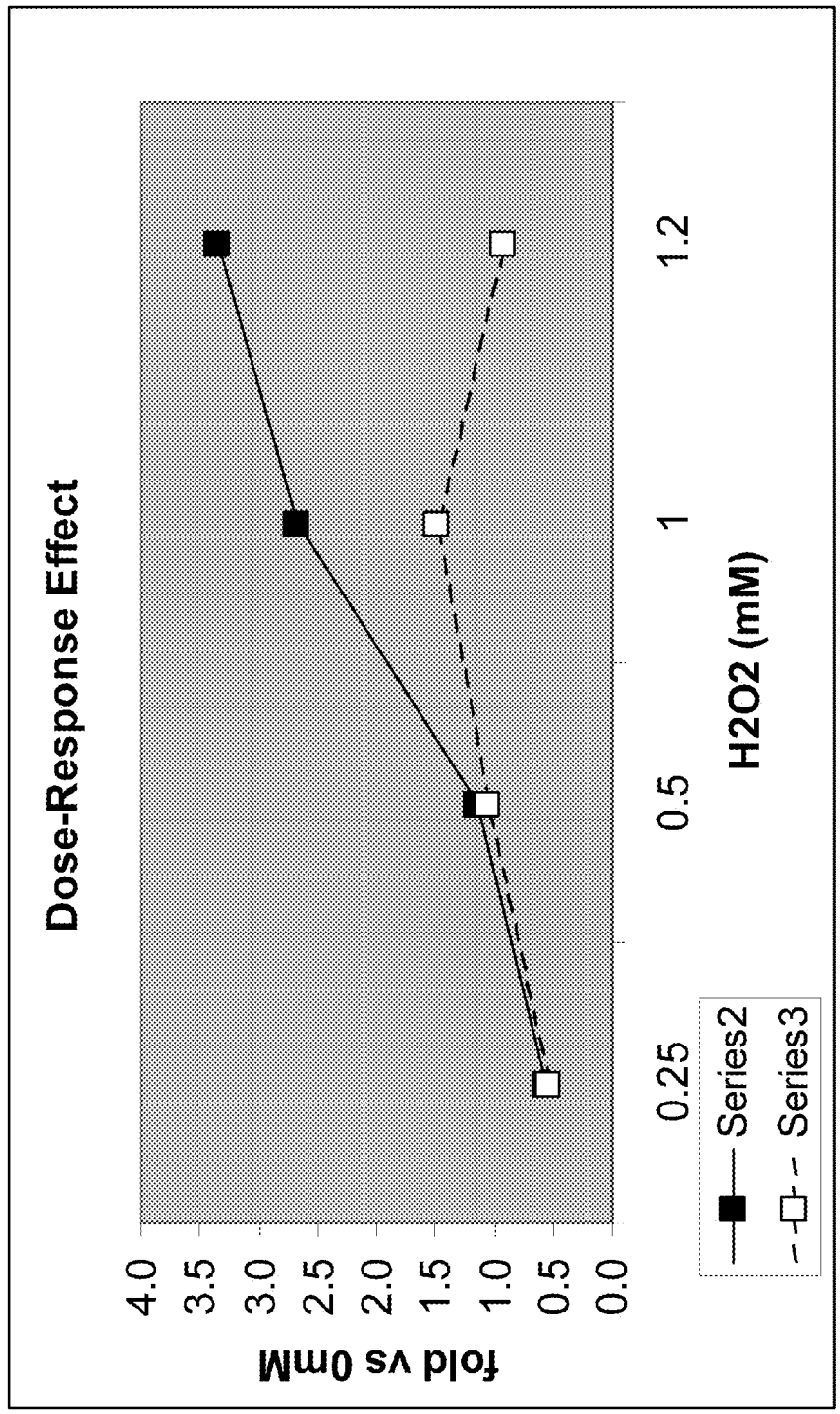
FIG. 7 shows the dose-dependant effect of $H_2O_2$-induced DNA fragmentation in ARPE-19 cells. Filled square and solid line: normal growth media; open square and dotted line: media conditioned using umbilicus-derived cells.

Time- and Dose-Dependent Apoptosis Induction by $H_2O_2$ in ARPE-19 Cells:

$H_2O_2$ induced apoptosis in a time- and dose-dependent manner. Apoptosis measured by DNA fragments associated with histones was determined using ELISA. When ARPE-19 cells were treated with a series of concentrations of $H_2O_2$ from 0.25 mM to 1.2 mM, DNA fragmentation was at 1-fold of negative control (0 mM) at 0.5 mM and was increased to 2.6-fold and 3.3 fold at 1 mM and 1.2 mM respectively, shown in FIG. 7.

In a separate experiment, apoptosis was measured by measuring the percentage of Annexin V(+) cells in the population. One of the early events during apoptosis process is the exposure of a phospholipid-like phosphatidylserine (PS) to the cell surface membrane. Annexin V is a molecule that can bind to PS on the cell surface. Using this feature, apoptotic cells can be detected by staining the cell surface with Annexin V. The percentage of cells in the population that are either in the early stages of apoptosis or the later stages of apoptosis was determined by measuring changes in cell membrane permeability to the DNA dye 7-AAD. At the early stages of apoptosis, when the cell membrane is still intact, 7-AAD is unable to penetrate the cell membrane and will be negative. Therefore early apoptotic cells are typified as being Annexin V(+) and 7-ADD(−). At later stages of apoptosis, when the cell membrane integrity fails, and can be penetrated by 7-ADD, the apoptotic cells are demonstrated as Annexin V(+) and 7-ADD (+).

Figure 8:
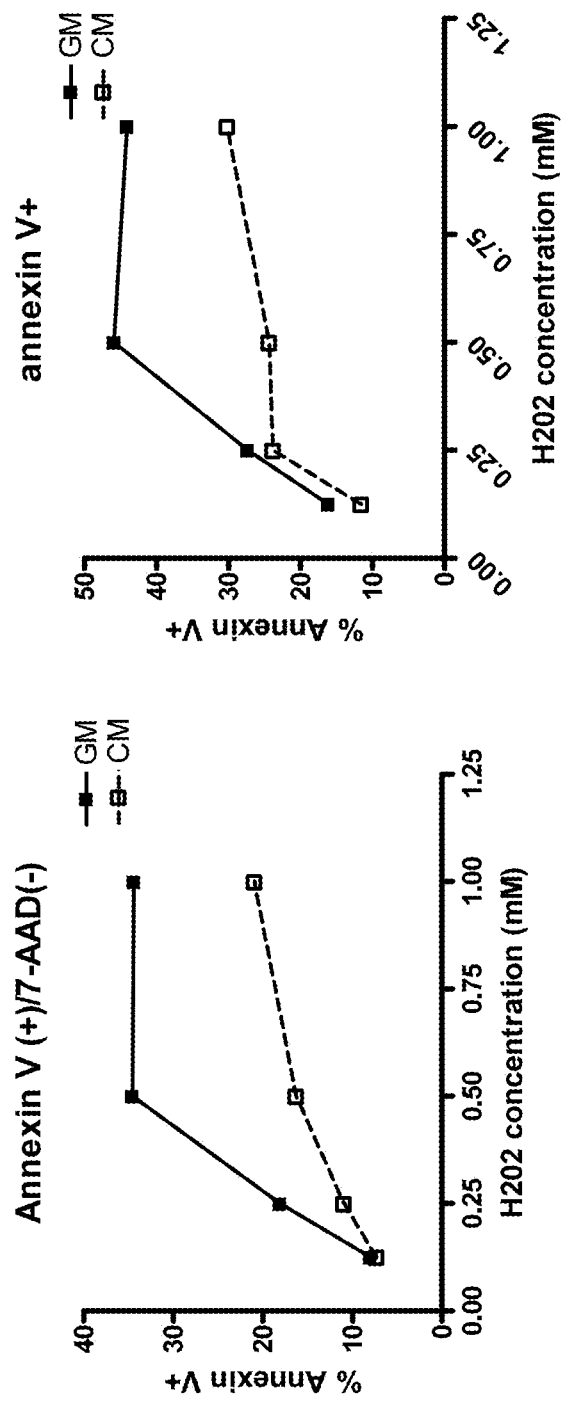
FIG. 8 shows the dose-dependant effect of $H_2O_2$-induced early apoptosis in ARPE-19 cells. Left panel: early apoptotic cells: Annexin V(+) and 7-ADD(−); right panel: total apoptotic cells: Annexin V(+). Filled square and solid line: normal growth media; open square and dotted line: conditioned media.
Figure 9:
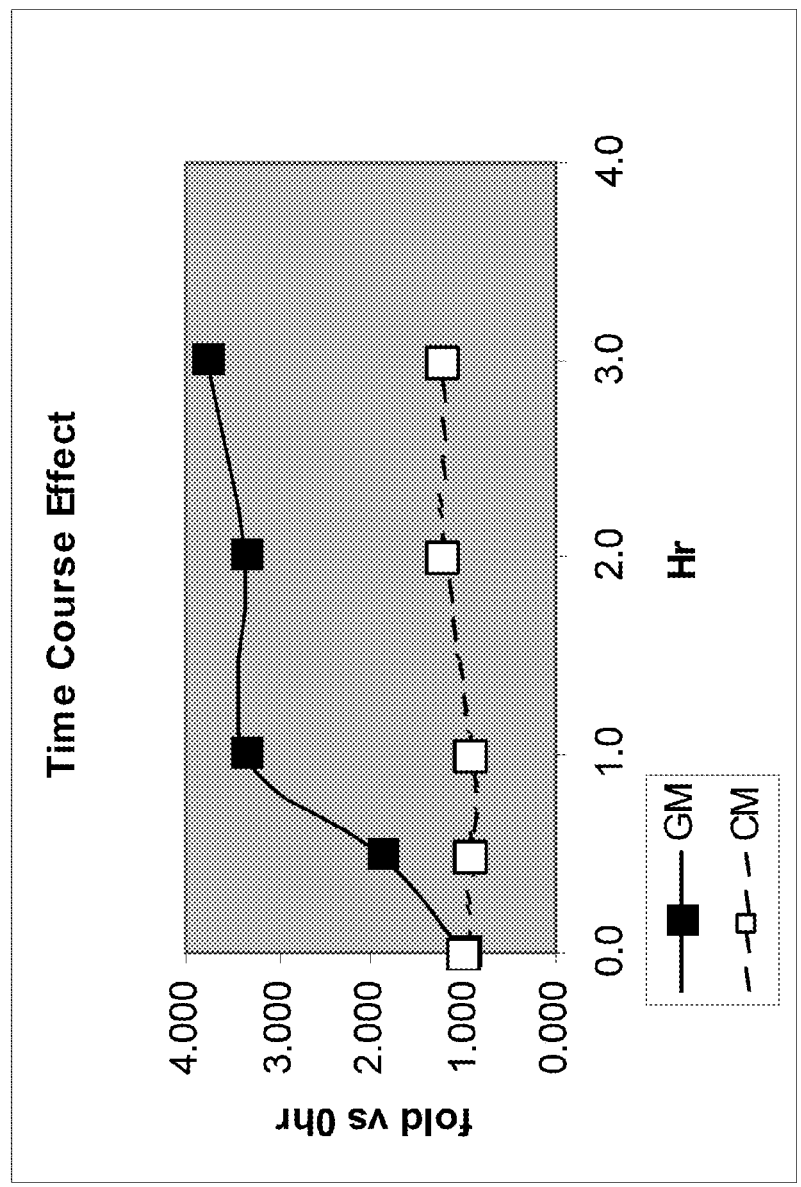
FIG. 9 shows the time course of $H_2O_2$-induced DNA fragmentation in ARPE-19 cells. Filled square and solid line: normal growth media; open square and dotted line: media conditioned using umbilicus-derived cells. Dotted line: media conditioned using c umbilicus-derived cells.

Early apoptotic cells, as determined by the percentage of cells that were Annexin V(+) and 7-AAD(−) increased with the concentration of $H_2O_2$. At 0.125 mM $H_2O_2$, the percentage of cells that were Annexin V(+) and 7-AAD(−) was 8%. This increased to 18% at 0.25 mM $H_2O_2$ and reached a maximum at 34% at 0.5 mM $H_2O_2$. Similarly, total apoptotic cells, as determined by measuring the total Annexin V(+) cells in the population was 16% at 0.125 mM $H_2O_2$, that increased to 27% at 0.25 mM $H_2O_2$. The erect of $H_2O_2$ on the total number of apoptotic cells was maximal at 0.5 mM $H_2O_2$ (FIG. 8). When ARPE-19 was treated at 1.2 mM but with different incubation time, a time course effect was evident. DNA fragmentation reached its plateau by 1 hr, about 3.3-fold versus 0 hr incubation, and remained at this level to 3 hrs as shown in FIG. 9.

Umbilicus-Derived Cell Conditioned Media Reduced Apoptosis Both Dose- and Time-Dependently:

The DNA fragmentation induced by $H_2O_2$ was decreased when cells were treated with conditioned media from umbilicus-derived cells. DNA fragment levels at different doses and different incubation time in conditioned media were maintained at the similar level as the negative control from 0.25 mM to 1.2 mM (0.5-fold to 1.5-fold vs. control), shown in FIGS. 7 and 9.

Similar results were seen using the Annexin V assay. Early apoptosis events and total apoptotic cells were reduced in umbilicus-derived cell conditioned media-treated ARPE-19 cells at 0.25 mM, 0.5 mM, and 1.0 mM as shown in FIG. 8.

These results confirmed the findings in literature that $H_2O_2$ is a potent stimulator of apoptosis for RPE cells. Most importantly, conditioned media from umbilicus-derived cells reduced apoptosis measured by both DNA fragmentation and Annexin V positivity. The dose- and time-dependent inhibition of apoptosis by the conditioned media strongly suggests that cytokines secreted by umbilicus-derived cells can rescue RPE cells from oxygen stress-induced apoptosis.

Example 29 Preservation of Multiple Cell Types in the Retina of a Preclinical Model of Retinitis Pigmentosa The Royal College of Surgeons (RCS) rat is a preclinical model of retinitis pigmentosa in which there is progressive degeneration of the rod and cone photoreceptors resulting from a specific defect in the retinal pigmented epithelial cells (RPE). In this model, a mutation in the allele of the gene for the receptor tyrosine kinase Mertk results in an inability of the RPE to phagocytose shed rod outer segments (ROS). This defect results in apoptotic photoreceptor cell death, beginning around post-natal day 20 (P20), and by P60 the outer nuclear layer (ONL) of these animals, which contains the photoreceptor cell nuclei, is only 1-2 layers in thickness.

Umbilicus-derived cells are an allogeneic cell type with potential for cell therapy applications. Umbilicus-derived cells are obtained from an ethical cell source and can be readily expanded to yield at least $1 \times 10^{17}$ cells from a single donor without karyotypic or phenotypic changes. A single dose of 20,000 umbilicus-derived cells into the subretinal space of RCS rats can preserve visual function as assessed by the use of electroretinogram, optomoter and luminance threshold testing (See, for example, Lund et al. 2007). Umbilicus-derived cells have also demonstrated superior efficacy in preserving visual function compared to two other allogeneic expandable tissue-derived cell types; placental-derived cells and human bone marrow mesenchymal stem cells (hMSC) (Lund et al. 2007). Furthermore, anatomical analysis demonstrated that umbilicus-derived cells at 80 days post cell injection can preserve 4-5 layers of cell nuclei in the outer nuclear layer (ONL) of the subretinal space compared to sham or untreated controls which at the same time point only have 1 layer of cells retained in the ONL.

While histology has been used to visualize the effects of umbilicus-derived cell therapy on the retina, it has been mostly anecdotal in nature and not quantitative. The goal of this study was to use quantitative morphometry to characterize the preservation of various cell types in the retina important in rod photoreceptor connectivity and signaling following subretinal umbilicus-derived cell administration in RCS rats.

Materials and Methods

Animals:

Experiments were performed on male and female pigmented dystrophic RCS rats (rdy-/p-), which were individually housed with a 12-hour light/dark cycle at the Moran Eye Center (University of Utah, Salt Lake City, Utah). All procedures were approved and monitored by the University of Utah Institutional Animal Care and Use Committee and have been conducted in accordance with the Policies on the Use of Animals and Humans in Neuroscience Research, revised and approved by the Society for Neuroscience in January 1995. The rats weighed approximately 30-40 grams at age of dosing (post-natal day 21). Food and water were available ad libitum.

Preparation of Donor Cells:

Human umbilical cords were obtained with donor consent following live births from the National Disease Research Interchange (Philadelphia, PA) and umbilicus-derived cells were isolated, tested and cryopreserved as described in Examples 1-5 above. Prior to injection, umbilicus-derived cells were thawed rapidly in a 37° C. water bath, washed twice in sterile PBS and resuspended at a final concentration of $1 \times 10^4$ cells/µL.

Injection Procedure:

On Day 0 (post-natal Day 21) the rats received a subretinal injection of 20K umbilicus-derived cells in a volume of 2 µL. RCS rats were anesthetized with an intraperitoneal injection of xylazine-ketamine (1 mg/kg of the following mixture: 2.5 ml xylazine at 20 mg/ml, 5 m ketamine at 100 mg/ml, and 0.5 ml distilled water). 20K umbilicus-derived cells were injected through a fine glass pipette (internal diameter 75-150 µm) into the eye through a small scleral incision. The incision was closed with a small suture after injection was completed. All animals received daily dexamethasone injections (1.6 mg/kg, i.p.) for 2 weeks post-injection, and received cyclosporine-A (Bedford Labs, Bedford Mass.) administered in the drinking water (210 mg/L; resulting blood concentration: 250-300 µg/L) from 1-2 days prior to cell injection until euthanasia. Rats were sacrificed at the following time points after surgery: 1, 7, 14, 30 and 60 days. Euthanasia was performed by anesthesia with a ketamine:xylazine: acepromazine mixture, followed by exsanguination.

Collection of Eyes and Extraction of RNA for RT-PCR:

Following euthanasia, the eyes were extracted and placed in RNAlater solution (Ambion, Austin, Tex.). All eyes were kept at 4° C. in RNAlater solution for up to 3 days, then stored at −80° C. until processing. Eyes were placed in Lysing Matrix tubes (Qbiogene, Carlsbad, Calif.) containing 1.4 ml Trizol (Invitrogen, Carlsbad, Calif.) and centrifuged in a Fast Prep FP120 homogenizer (Qbiogene, Carlsbad, Calif.) at speed #6 for 45 sec. The supernatant was transferred to a 5ml round bottom tube. Trizol (2-4 ml) was added to the supernatant and samples were then centrifuged at 9000 rpm for 10 min. Chloroform (2-3 ml) was added to the supernatant and incubated at room temperature then centrifuged at 9000 rpm for 10 min at room temperature. Isopropanol (3-4 ml) was added to the supernatant to precipitate total RNA. The RNA pellet was obtained by centrifuging at 9000 rpm for 10 min. The pellet was washed with 70% ethanol and air-dried at room temperature, then resuspended in 100 µl RNase-free water and stored at −80° C. The RNA quality and quantity was analyzed using the Experion automated electrophoresis system (Bio-Rad Laboratories, Hercules, Calif.).

2-Step RT-PCR:

First-strand cDNA synthesis was performed using the First-Strand cDNA Synthesis Kit (Invitrogen, Carlsbad, Calif.). Briefly, 10 µg total RNA was mixed with 2 µl oligo(dT)20 (50 µm) and 2 µl dNTP (10 mM), incubated at 65° C. for 5 min, then added 4 µl 10× reaction buffer, 8 µl 25 mM MgCl2.4 µl 0.1M DTT, 2 µl RNaseOUT and 2 µl SUPERSCRIPT II RT enzyme, incubated at 50° C. for 50 min, and 65° C. for 5 min. Template RNA was removed by addition of 1 µl RNase H for 20 min at 37° C. Real-time PCR was performed on the 7900HT Fast Real Time PCR System (Applied Biosystems, Foster City, Calif.) using human β-2 micro globulin (hβ2M) TaqMan® Gene Expression Assay with the TaqMan® Fast Universal PCR Master Mix (Applied Biosystems, Foster City, Calif.). All samples were analyzed in triplicate. RNA standards were run alongside samples for quantitation of the number of cells present in injected eyes. To generate RNA standards, eyes from Sprague-Dawley rats were collected as described above. The eyes were injected with 160, 800, 4K, 10K, and 20K umbilicus-derived cells (n=3). RNA extraction and two-step real-time RT-PCR was performed as described above. The threshold cycle value was obtained and analyzed against the injected cell numbers.

Figure 10:
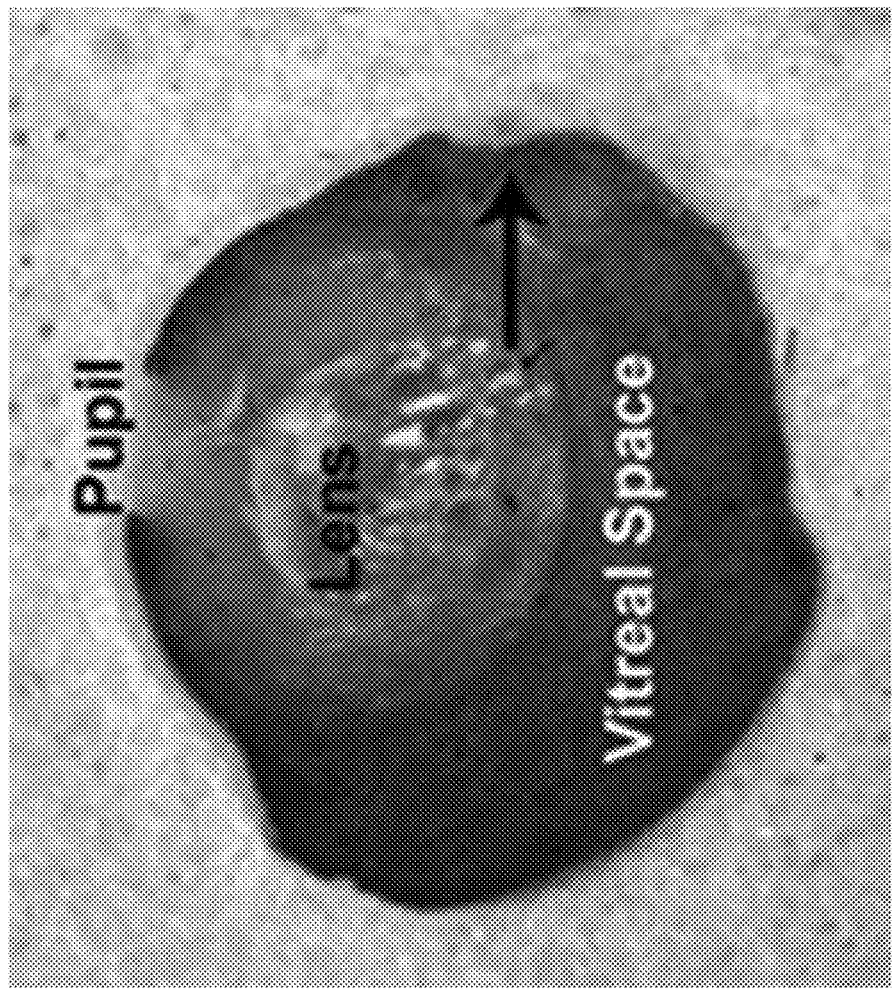
FIG. 10 shows a representative image of an injected eye. This eye was embedded in paraffin and sectioned until the suture was visible on a stereomicroscope and the image was collected. The eye shown was a vehicle-injected eye 1 day post-injection. The suture placed following the injection procedure can be seen on the right side of the eye (arrow).

Collection and Processing of Eyes Fro Histology:

Following euthanasia, the rat was flushed with phosphate buffered saline under low pressure via the aorta. The eyes were carefully removed, and surrounding tissue from the eye trimmed. Both the right and the left eye from each animal were collected and immersed in Pen-Fix fixative (Richard Allan Scientific) for 24-48 h. After fixation, the eyes were processed for histology including dehydration, clearing in xylene and infiltration with paraffin. Each eye was specifically oriented during embedding in paraffin: the superior pole of the eye was embedded down in the paraffin block and the suture marking the injection site rotated in a clockwise manner until it was approximately in the 3 o'clock position on the globe. This orientation was maintained during embedding. This resulted in the injection site residing approximately in the central plane of the eye for the majority of the eyes processed. For injected eyes, collection of 5 μm sections began after facing into the block until the suture marking the injection site is identified on a stereomicroscope (FIG. 10). If no suture was identified, the eye was excluded from further analysis, as was its uninjected counterpart (left eye from same animal). If the suture was identified after sectioning through the central plane of the eye and it was determined that it resided near the pole of the eye, it was excluded from further analysis, as was its uninjected counterpart. For uninjected eyes, sectioning began after the area/depth of interest is identified in the injected (right) eye. The corresponding uninjected (left) eye from the same animal was sectioned to a similar depth, collecting sections from approximately the same area of the eye.

Antibodies:

The following antibodies were used for immunohistochemistry: rabbit-anti-Rhodopsin (Chemic on), rabbit anti-Calretinin (Chemicon), rabbit anti-Recoverin (Chemicon), mouse-anti-human nuclear matrix antigen (NuMA, Calbiochem). Antibodies for secondary detection were biotinylated anti-rabbit (Chemicon), and biotinylated goat-anti-mouse (Jackson Immunoresearch).

Immunocytochemistry:

Sections for IRC staining were incubated for 1 hr at 59° C. followed by deparaffinization through a series of changes in xylene, 100% alcohol, 95% alcohol, and water on a TISSUE TEK® DRS™ 2000 Slide Stainer (Sakura, Torrance, Calif.). Slides were rinsed with tap water for approximately 5 minutes. All immunohistochemical staining was performed on the i6000™ Automated Staining System (BioGenex, San Ramon, Calif.). Antigen retrieval was performed when necessary using a Decloaking Chamber (BioCare Medical, Concord, Calif.) and Reveal HIER Solution (BioCare Medical) or microwaved using Antigen Retrieval Citra Solution (BioGenex). Endogenous activity of peroxidase and antigenic sites were blocked and normal goat serum (BioGenex) reduced background staining due to non-specific binding of the primary or secondary antibody. Sections were incubated with primary antibody at room temperature, detection of the bound primary is achieved by the addition of a biotinylated secondary antibody+peroxidase-conjugated streptavidin (BioGenex) and peroxidase activity was made visible with diaminobenzidine (DAB) (BioGenex). Counterstaining with Mayer's Hematoxylin (BioGenex) for 1 min.

Image Acquisition and Analysis:

A Nikon Eclipse E800 (Nikon Corporation, Tokyo, Japan) microscope was equipped with an Evolution™ MP 5.0 RTV color camera (Media Cybernetics, Inc. Silver Spring, Md.), interfaced with an IBM computer (International Business Machines Corporation, Armonk, N.Y.) running Windows 2000 (Microsoft Corporation, Redmond, Wash.). Images were captured and analyzed using Image-Pro Plus software version 5.1 (Media Cybernetics, Inc. Silver Spring, Md.). Microsoft Excel 2000 (Microsoft Corporation, Redmond, Wash.) and GraphPad Prism version 4.03 (GraphPad Software, Inc. San Diego, Calif.) were used to interpret, analyze and graph the raw data. SigmaStat Statistical Software version 2.03 (SPSS, Inc. Chicago, Ill.) was used to perform statistical analysis on the collected data. Using the Auto-Pro tool within the Image-Pro Plus software, custom written macros were used to perform the analysis consistently.

Morphometry of Day 60 Eyes:

Three umbilicus-derived cell injected and three control (uninjected) eyes from the day 60 group (4 animals) were imaged and analyzed with morphometry. The images captured were 24-bit RGB images, 2560×1920 pixels in size, with a resolution of 300×300 dots/inch. The images were captured with a 60×objective Nikon lens. No imaging or analysis was performed on areas of the retina that were torn, damaged, folded or missing.

Measurement of Area of Outer Nuclear Layer (ONL) Per Length:

From each eye, three hematoxylin and eosin (H&E) stained sections, each separated by 20 μm in depth were imaged and analyzed for the ONL measurements. The areas where the images were collected were defined as regions 1 and 2. Region 1 is an area near the injection site and region 2 is an area away from the injection site. Up to ten images (five from each region) were collected from each section. Using Image-Pro Plus, the ONL was selected as the area of interest (AOI). The AOI was extracted and transformed into an 8-bit grayscale image, referred to as a mask. Area and length (to normalize the data) of the ONL were measured and used to calculate the area per length of the ONL for each image.

Measurement of Amount of Rhodopsin Immunostaining in the Neuroepithelial Layer:

One section per eye immunohistochemically stained for rhodopsin was imaged and analyzed. The area where the images were collected was defined as region 1, an area near the injection site. Up to eight images were collected from each section. Using Image-Pro Plus, the saturation channel of the color model HSI was extracted from the RGB image. Using various acquired images with mixed saturation levels, a threshold was set to the most intensely stained colors or the most dominant hues. This set threshold was used to analyze each image. The AOI was defined as the neuroepithelial layer in each image. The measurement calculated for each image was the percent area of the AOI that was within the set threshold.

Measurement of Area of the Calretinin Immunostaining Per Length:

One section per eye, immunohistochemically stained for calretinin was imaged and analyzed. The area where the images were collected was defined as region 1, an area near the injection site. Up to eight images were collected from each section. Using Image-Pro Plus, three AOIs were defined as: all recoverinpositive areas, the inner nuclear layer and the outer ganglion cell layer (each analysis was performed separately) and were extracted from the image and transformed into an 8-bit grayscale image, referred to as a mask. Area and length (to normalize the data) of the calretinin staining were measured and used to calculate the area per length of the calretinin staining for each image.

Measurement of Area of the Recoverin Immunostaining Per Length:

One section per eye, immunohistochemically stained for recoverin, was imaged and analyzed. The area where the images were collected was defined as region 1, an area near the injection site. Up to eight images were collected from each section. Using Image-Pro Plus, three AOIs were defined as: all recoverin-positive areas, the inner nuclear layer and the outer nuclear layer (each analysis was performed separately). Each AOI was extracted from the image and transformed into an 8-bit grayscale image, referred to as a mask. Area and length (to normalize the data) of the recoverin staining within each AOI was measured and used to calculate the area per length of the recoverin staining for each image.

Results

Figure 12:
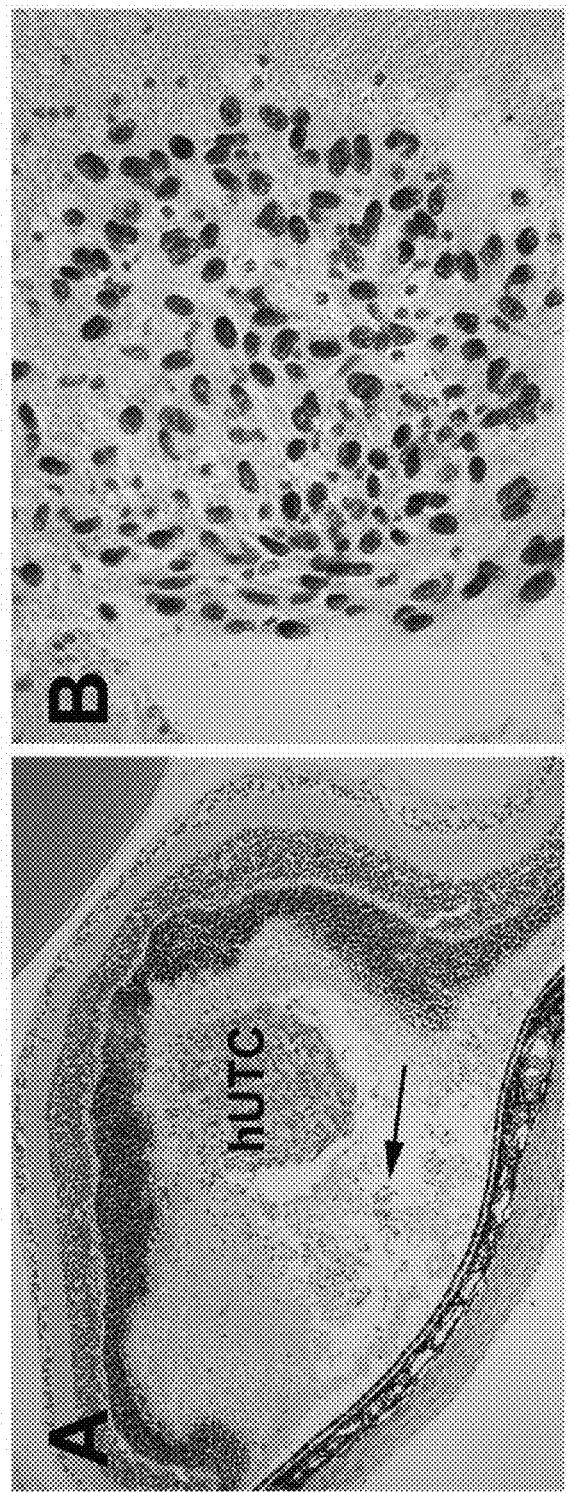
FIG. 12 shows the identification of umbilicus-derived cells in subretinal space, day 1 post-injection. Panel A: H&E stained section of a day 1 eye at 20× magnification. Injected umbilicus-derived cells can be seen in subretinal space. Panel B: an adjacent section immunostained for NuMA, 40× magnification. Infiltrating neutrophils can also be identified amongst NuMA-positive umbilicus-derived cells.

Identification of Umbilicus-Derived Cells in Day 1 Post Injection:

Umbilicus-derived cell injected (right) eyes from day 1 post-injection were sectioned for the purposes of identifying injected umbilicus-derived cells to confirm their placement in the eye. Using this method, injected human cells were positively identified using immunohistochemistry for human nuclear matrix antigen (NuMA, FIG. 12).

Figure 13:
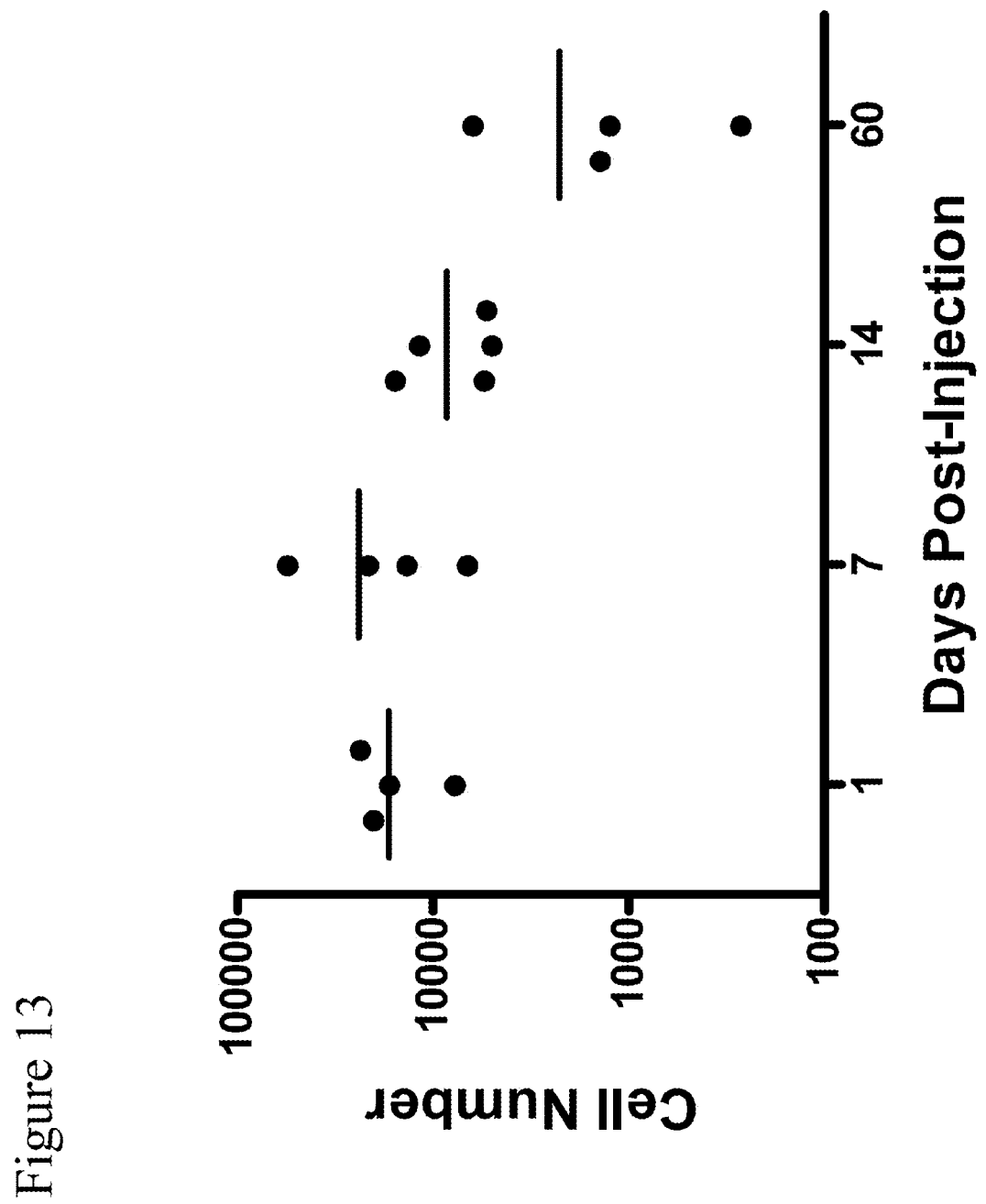
FIG. 13 shows cell retention in the RCS rat eye. Cell retention in the RCS rat eyes from Day 1 to Day 60; the Y-axis is on logarithmic scale. Human β2M mRNA was detected in eyes 1, 7, 14, and 60 days after subretinal injection. The cell number reduced gradually from 18227±3227 (mean+/−standard error of the mean; n=4) at Day 1 to 2266±1328 (mean+/−standard error of the mean; n=4) at Day 60.

Umbilicus-Derived Cell Retention in the Res Rat Eyes:

Umbilicus-derived cell retention in the RCS eyes was investigated using RT-PCR for a human-specific antigen, (32 micro globulin W2M) mRNA. Total RNA from injected eyes was amplified using (32M specific primers. Values are converted to cell number using a standard curve generated using total RNA isolated from eyes injected intravitreally with known numbers of umbilicus-derived cells. Despite variability between specimens, eyes at all time points had detectable levels of (32M mRNA. This indicated that the umbilicus-derived cells were retained in the RCS eye through the course of the study, although the cell number decline substantially by Day 60, with only approximately 10% of the injected cells detected (FIG. 13).

Figure 14:
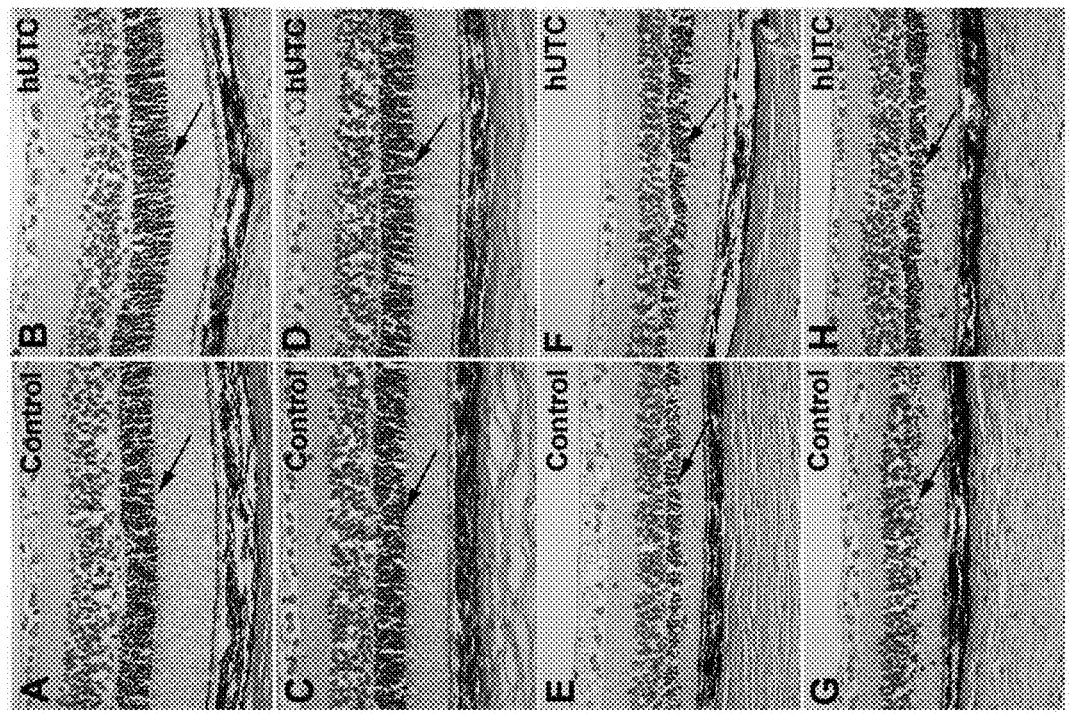
FIG. 14 shows the time course of ONL degeneration. H&E stained sections of control and umbilicus-derived cell injected eyes from the following time points post-injection: Day 7 (A and B), Day 14 (C and D), Day 30 (E and F), and Day 60 (G and H). Images were acquired using 40× magnification near the injection site region. Arrows mark the outer nuclear layer.

Morphometry of the Outer Nuclear Layer:

H&E-stained sections of both control (uninjected) and umbilicus-derived cell-injected eyes from the following time points were examined: 7, 14, 30 and 60 days post-injection (FIG. 14). The earliest time point in which ONL degeneration could be detected in control eyes was Day 30. At this time point, the effect of umbilicus-derived cell injection was subtle. However, at Day 60, the effect of umbilicus-derived cell injection was evident. In control eyes, the ONL had thinned to a discontinuous layer 1-2 nuclei in thickness. In the eyes that had received a subretinal injection of umbilicus-derived cells, the ONL was approximately 3-4 nuclei in thickness near the injection site region, looking comparable to the ONL in the Day 30 specimens. This suggested a preservation of the ONL by umbilicus-derived cells.

Figure 11:
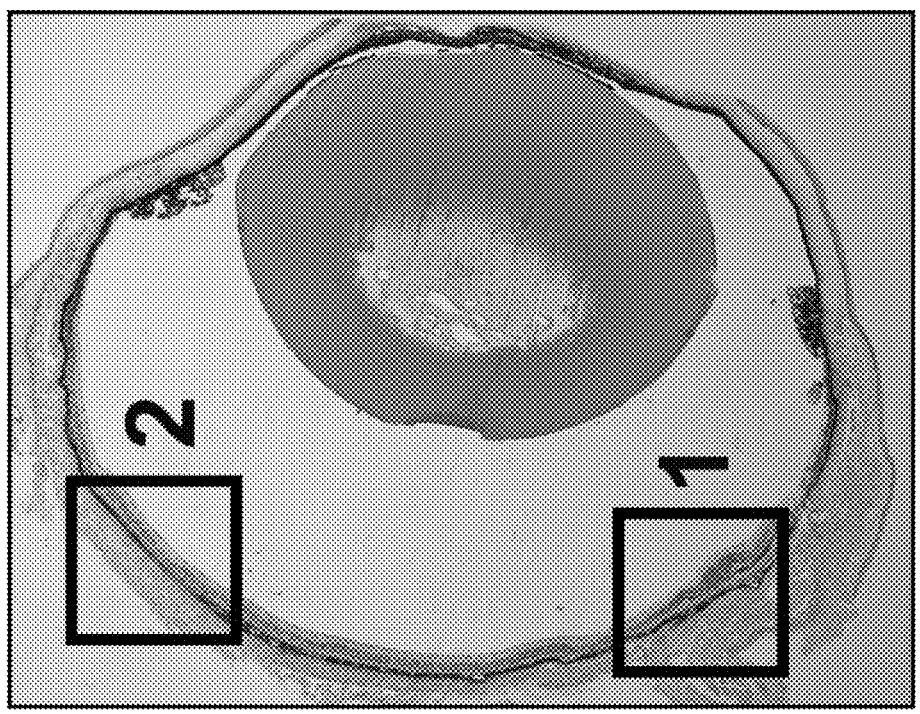
FIG. 11 shows the morphometric analysis of the outer nuclear layer (ONL). Shown is an eye 60 days post-injection, 2× magnification. The regions of ONL analysis are outlined in boxes. Region 1 (bottom box) is local to the injection site, and region 2 (top box) is distal to the injection site, on the opposite side of the eye.
Figure 15:
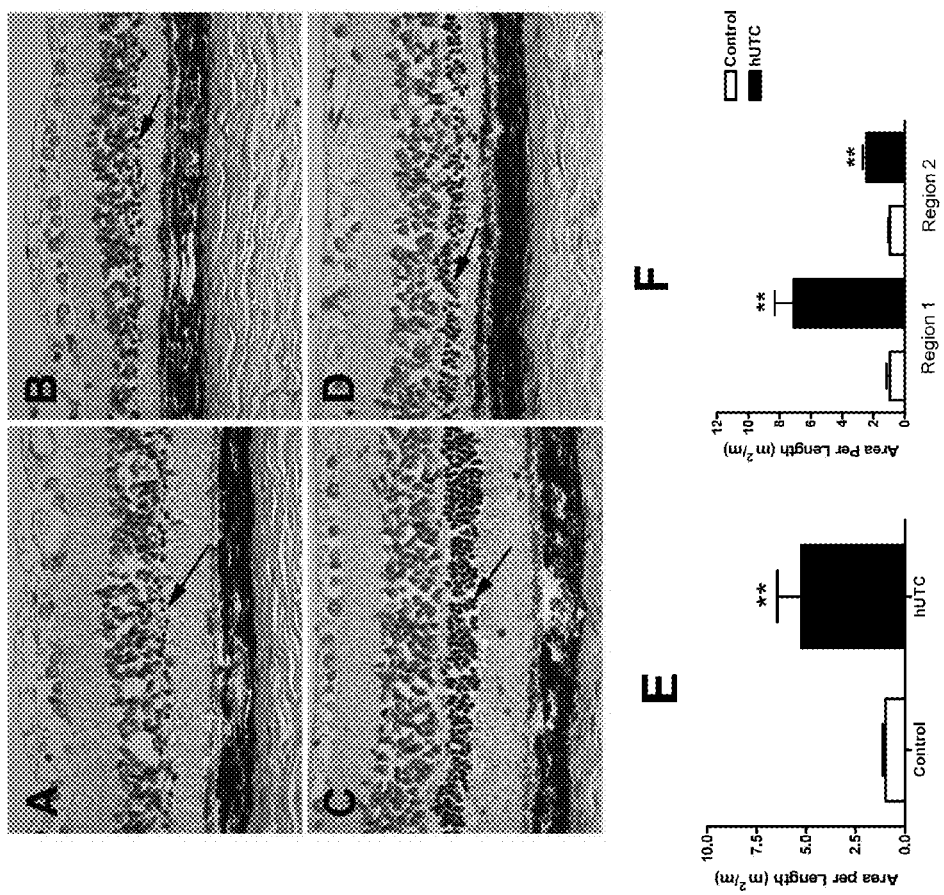
FIG. 15 demonstrates the injection of umbilicus-derived cells preserves ONL thickness at Day 60 post-injection. Representative images from H&E stained sections from umbilicus-derived cell injected and control eyes 60 days post-injection, 60× magnification. Panels A and B: Control eye, images taken from areas near and far from injection site, respectively. ONL (arrows) appears as a single discontinuous layer in both regions. Panels C and D: umbilicus-derived cell injected eye, areas near and far from injection site, respectively. ONL is visibly thicker in both regions, although the area near the injection site is thicker than that further away (approximately 4 nuclei thick near injection site compared to 2 nuclei thick far from injection site in these images). Panels E and F: morphometric results. Panel E: All data from both regions analyzed (near to and far from injection site) were combined for each animal (n=3 animals per group). Values graphed are the mean+/−standard deviation. Means were significantly different between control eyes and eyes injected with umbilicus-derived cells (p<0.001, t-test). Panel F: Regional ONL rescue. The two columns on the left side of the graph are from region 1 (close to injection site), the two columns on the right side are from region 2 (far from the injection site). Values graphed are the mean+/−standard deviation of all tissue sections analyzed (for region 1, the number of images were n=6 and 9 and region 2, the number of images were n=9 and 6 for control and umbilicus-derived cells, respectively). The means for both groups were significantly different in each region (p=0.002 using Mann-Whitney rank sum test for region 1, and p<0.001 using t-test for region 2. Mann-Whitney test was used for region 1 because the umbilicus-derived cells group did not have a normal distribution).

Eyes from day 60 post-injection were evaluated for the effect of umbilicus-derived cells on outer nuclear layer (ONL) thickness, as a measure of photoreceptor rescue. Images were taken at 60× magnification from two regions of the retina, near and far from the injection site in H&E stained sections (see FIG. 11). Two eyes were excluded from analysis due to poor morphology and loss of the majority of the retina, presumably caused by inadequate fixation. The ONL was visibly thicker in umbilicus-derived cell injected eyes compared with control (uninjected) eyes in both regions examined (FIG. 15A-D). Analysis of the images using morphometry supported this observation: the area per length occupied by ONL nuclei was 7.5 times higher near the injection site, 2.6 times higher in areas far from the injection site in umbilicus-derived cell injected eyes compared with control eyes, and 5 times higher overall when the results from both regions were combined, suggesting that the umbilicus-derived cells are preserving photoreceptors in the RCS rat (FIGS. 15E and F). This also shows that the effect is greatest local to the injection site, however there is an overall effect of umbilicus-derived cell injection.

Figure 16:
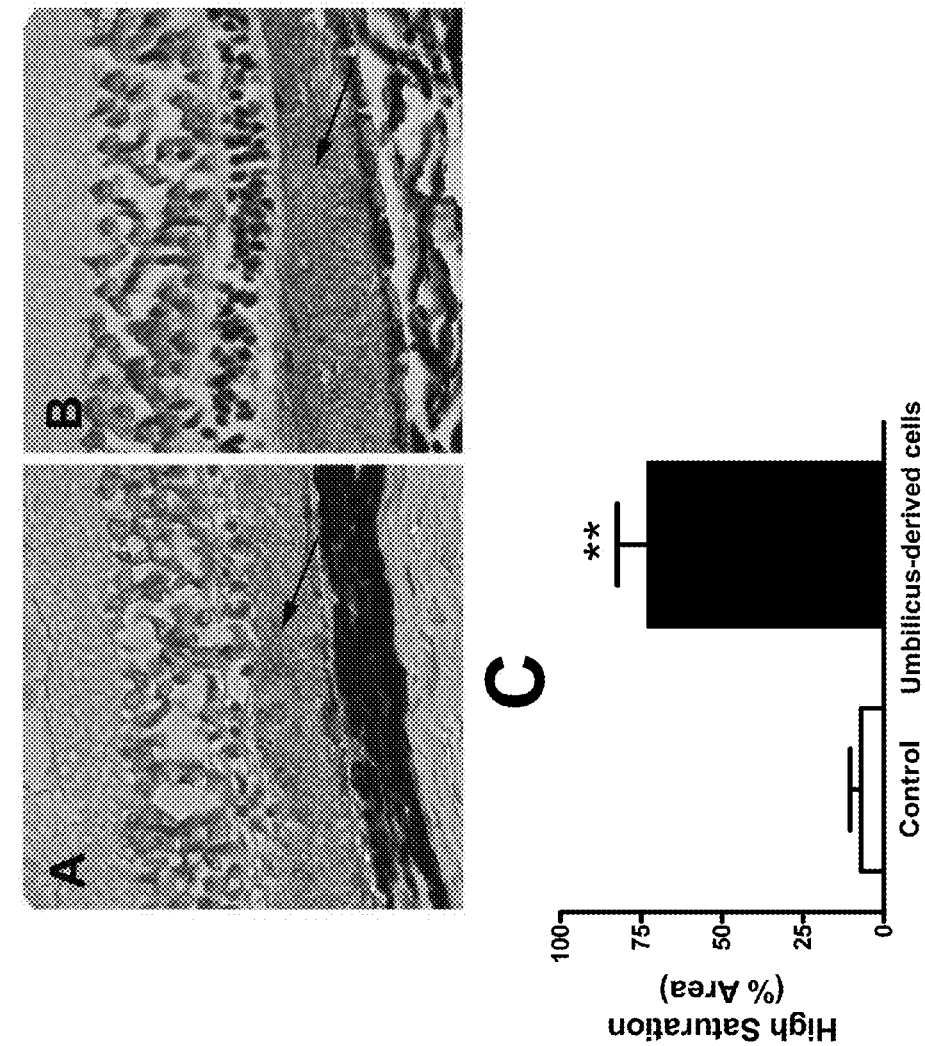
FIG. 16 demonstrates injection of umbilicus-derived cells preserves rhodopsin immunostaining at Day 60 post-injection. Panels A and B: representative images from Day 60 control and umbilicus-derived cell injected animals at 60× magnification near the injection site. Panel A: control, panel B: umbilicus-derived cells. Rhodopsin immunostaining is specific to the neuroepithelial layer (arrows) and is visibly increased in the umbilicus-derived cell injected eye compared with control. Panel C: morphometric results, values graphed are the mean+/−standard deviation (n=3 animals per group). Means were significantly different between control eyes and eyes injected with umbilicus-derived cells: 7.04+/−5.96 and 72.83+/−16.63, respectively (p=0.003, t-test). Values represent raw data multiplied by 100 to be expressed as a percentage.

Image Analysis of Rhodopsin Immunostaining:

Eyes from day 60 post-injection were evaluated for the effect of umbilicus-derived cells on expression of rhodopsin using immunohistochemistry and image analysis. As with the ONL analysis, a visible difference could be seen in the level of rhodopsin immunostaining in umbilicus-derived cell injected eyes compared with control eyes (FIGS. 16A and B). Images at 60× magnification were acquired from regions near the injection site of these eyes. For quantitation of rhodopsin immunostaining, the saturation channel of the color model HSI was extracted from the RGB image. Saturation refers to the dominance of hue in the color. A dominant hue is considered a pure color and a less dominant hue is a lighter shade of a pure color, for instance pink is red with a low degree of saturation or dominance. The saturation value, or amount of rhodopsin staining, translates to how densely packed the rods and cones are within the neuroepithelial layer. A highly saturated area is most likely an area of tightly packed rods and cones. Near the injection site region, the rhodopsin immunostaining was 10 fold higher in umbilicus-derived cell injected eyes compared with controls (FIG. 16C), translating to more densely packed rod outer segments containing rhodopsin and indicating preservation of rod photoreceptors.

Figure 17:
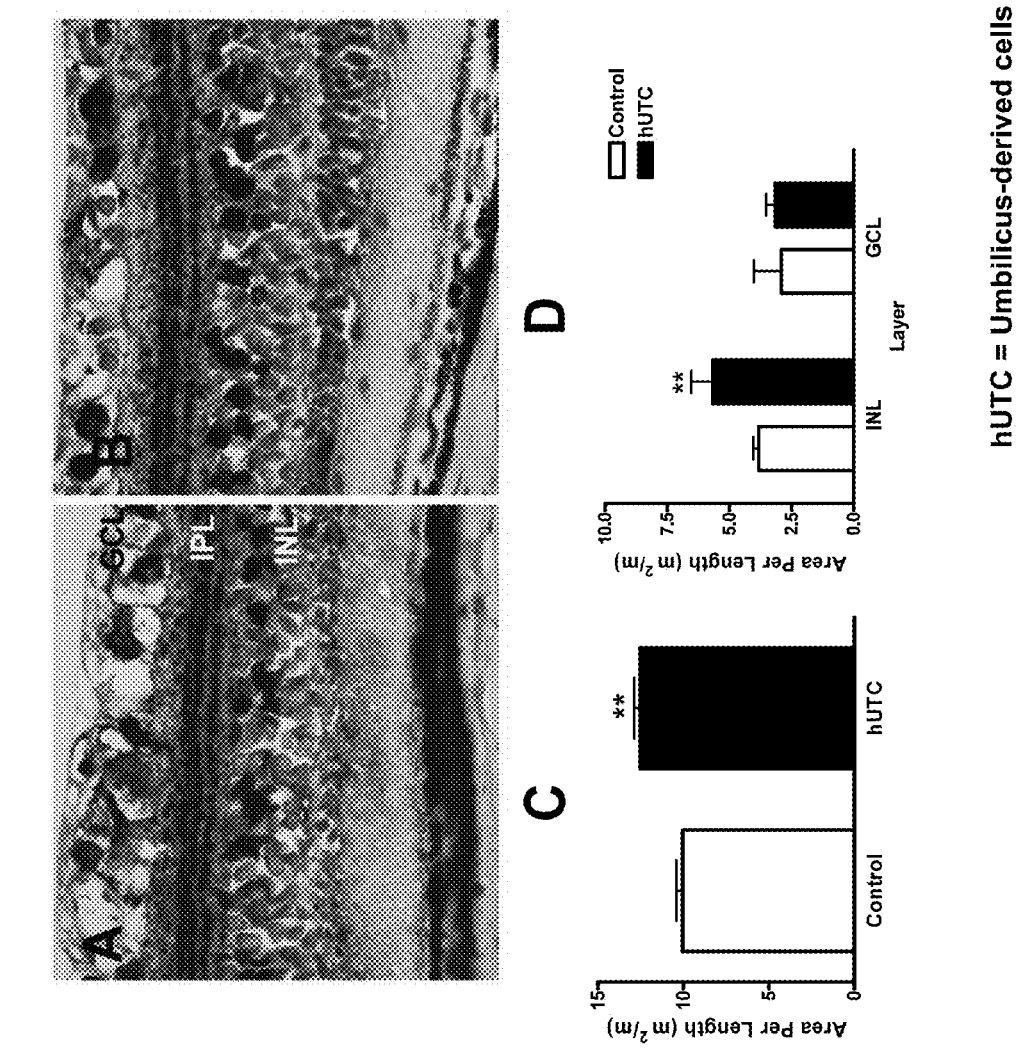
FIG. 17 demonstrates injection of umbilicus-derived cells preserves calretinin immunostaining at Day 60 post-injection. Shown are representative images from Day 60 control and umbilicus-derived cell injected animals at 60× magnification near the injection site. Panel A: control, panel B: umbilicus-derived cells. Calretinin immunostaining is specific to the inner nuclear layer (INL), inner plexiform layer (IPL), and the retinal ganglion cell layer (GCL). Panels C and D: morphometric results, values graphed are the mean+/−standard deviation (n=3 animals per group). Panel C: total calretinin staining (GCL, IPL, INL). Means were significantly different between control eyes and eyes injected with umbilicus-derived cells: 10.05+/−0.66 and 12.52+/−0.60, respectively (p=0.009, t-test). Panel D: calretinin staining of INL and GCL. Means were significantly different between control and umbilicus-derived cell injected eyes in the INL but not in the GCL: 3.82+/−0.22 and 5.67+/−0.85 (INL, p=0.014, t-test) and 2.91+/−1.11 and 3.16+/−0.37 (GCL, p=0.629, t-test), respectively.

Image Analysis of Calreticulin Immunostaining:

Eyes from day 60 post-injection were evaluated for the effect of umbilicus-derived cells on expression of calretinin using immunohistochemistry and image analysis. Unlike the ONL and rhodopsin immunostaining, there was not a marked difference visible in the images of calretinin immunostaining in control and umbilicus-derived cell injected eyes, however upon quantitation there was a small but statistically significant difference between the two groups. Images at 60× magnification were acquired from regions near the injection site of these eyes (FIGS. 17 A and B). Quantitation of calretinin immunostaining was performed in the following layers: inner nuclear layer (INL), inner plexiform layer (IPL) and retinal ganglion cell layer (GCL) together, and the INL and GCL individually. Near the injection site region, overall calretinin immunostaining in all 3 layers was 1.2 fold higher in umbilicus-derived cell injected eyes compared with controls. In the GCL, there was no difference between control eyes and umbilicus-derived cell-injected eyes, however there was a 1.5 fold increase in calretinin immunostaining in the INL of umbilicus-derived cell-injected eyes compared to controls (FIGS. 17C and D), indicating preservation of calretinin-expressing cells in the INL.

Figure 18:
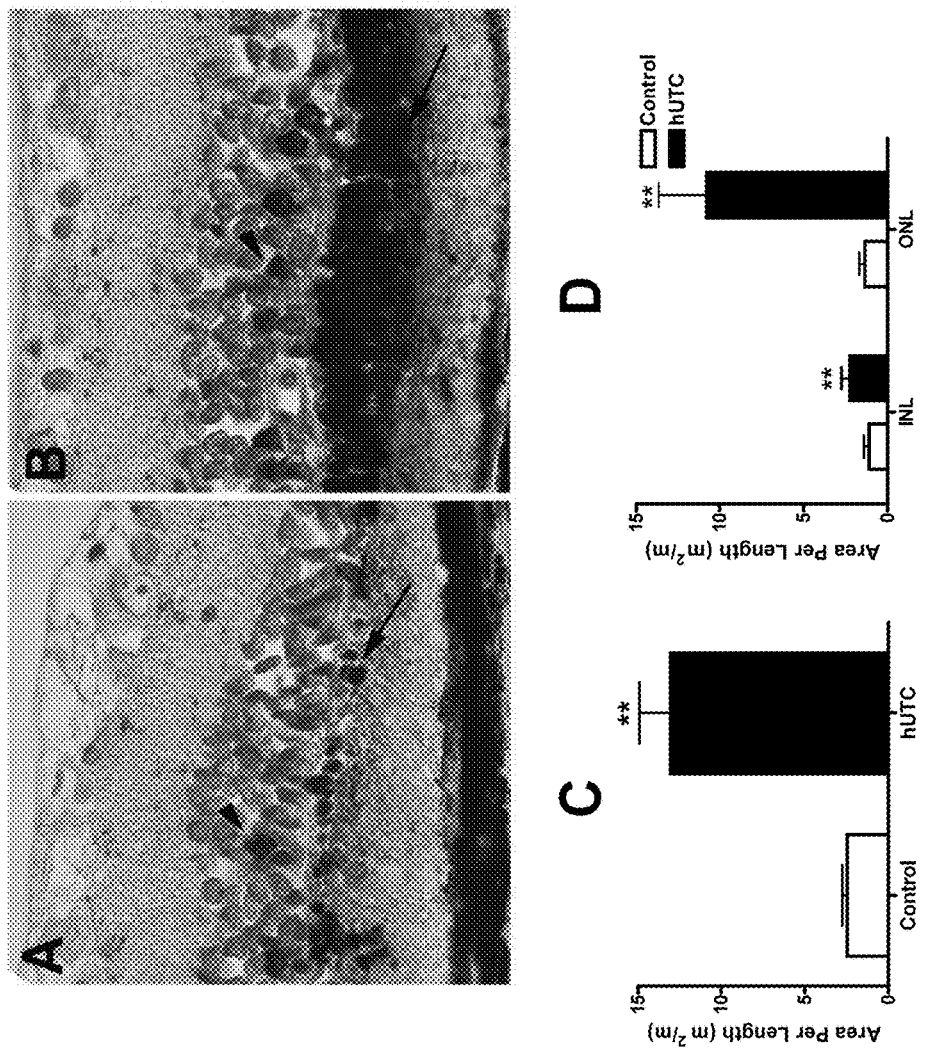
FIG. 18 demonstrates injection of umbilicus-derived cells preserves recoverin immunostaining at Day 60 post-injection. umbilicus-derived cells significantly preserves recoverin immunostaining at day 60 post-injection. Panels A and B: representative images from Day 60 control and umbilicus-derived cell injected animals at 60× magnification near the injection site. Panel A: control, panel B: umbilicus-derived cells. Recoverin immunostaining is specific to the outer nuclear layer (arrows) and a subpopulation of cells in the inner nuclear layer (arrow heads). Panels C and D: morphometric results, values graphed are the mean+/−standard deviation (n=3 animals per group). Panel C: total recoverin staining (INL, ONL). Means were significantly different between control eyes and eyes injected with umbilicus-derived cells: 2.47+/−0.50 and 13.03+/−3.28, respectively (P=0.001, t-test). Panel D: recoverin staining of INL and ONL. Means were significantly different between control and umbilicus-derived cell injected eyes in both the INL and ONL 1.11+/−0.31 and 2.24+/−0.51 (INL, p=0.031, t-test) and 1.36+/−0.34 and 10.78+/−2.87 (ONL, p=0.001, t-test), respectively.

Image Analysis of Recover in Immunostaining:

Eyes from day 60 post-injection were evaluated for the effect of umbilicus-derived cells on expression of recoverin using immunohistochemistry and image analysis. Images at 60× magnification were acquired from regions near the injection site of these eyes (FIGS. 18A and B). Quantitation of recover in immunostaining was performed on the inner nuclear layer (INL) and the outer nuclear layer (ONL). Near the injection site region, the recoverin immunostaining was 2 fold higher in the INL and 7.9 fold higher in the ONL of the umbilicus-derived cell injected eyes compared with controls (FIGS. 18C and D), indicating preservation of recoverin-expressing cells.

Discussion

Umbilicus-derived cell injection into the subretinal space of RCS rats has been demonstrated to sustain visual function for several months after injection into the subretinal space of RCS rats (Lund et al. 2007). It has also been shown to preserve photoreceptor nuclei in the ONL, however this was not done quantitatively. The goal of this study was to quantitate the effects of umbilicus-derived cell injection on the retina using morphometry. To analyze both ONL thickness as well as quantitation of various retinal cell types using immunohistochemistry, it was crucial to orient the eyes identically in the paraffin block. Additionally, it was necessary to obtain sections near the midline/central plane of the eye, so that the retinal layers to be analyzed would not appear artificially thick due to taking a slice through the curvature of the eye. Great care was taken to attain both of these requirements. By using such a careful approach in maintaining orientation of the eyes during processing, embedding and sectioning, the location of the injection site region was known in every eye.

Only the 60 days post-injection time point in this study was selected for morphometric analysis, as this time point clearly showed an effect of the injected hUTC on ONL thickness in H&E stained sections. The effect of hUTC injection on the ONL was evaluated morphometric ally. The ONL contains the cell bodies of the photoreceptor cells, and is ordinarily packed with nuclei arranged in 10-12 rows. In retinal degenerative diseases such as retinitis pigmentosa, photoreceptor cell death results in a thinning of the ONL to approximately 1 layer of nuclei in thickness. There was a visible difference in ONL thickness between control (uninjected) and umbilicus-derived cell injected eyes 60 days post-injection, and this difference was supported morphometric ally. Areas both near and far from the injection site were significantly increased in umbilicus-derived cell injected eyes, suggesting umbilicus-derived cell injected animals preserved greater numbers of nucleated cells in the ONL compared with control animals, thus photoreceptor rescue in these animals. This effect was greatest in the region near the injection site; therefore this region was selected for analysis of rhodopsin, calretinin and recoverin immunostaining.

Rhodopsin immunostaining in the neuroepithelial layer was also visibly increased in the eyes that received injection of umbilicus-derived cells. The neuroepithelial layer contains the rods and cones' outer segments, which are specialized processes of the photoreceptor neurons located in the ONL. Rod outer segments (ROS) convert and amplify the light signal. Mammalian ROS are packed with stack of 1000-2000 flattened disks that are formed by invaginations of the plasma membrane. The discs of the ROS are responsible for trapping photons and express a high level of rhodopsin, also known as visual purple. Rhodopsin is also expressed at a lower level on the plasma membrane. ROS are renewed and shed by the rod photoreceptors daily, and the shed ROS are phagocytosed and recycled by the RPE. Highly saturated rhodopsin immunostaining was significantly increased in umbilicus-derived cell injected animals compared with controls, indicating the presence of greater numbers of tightly packed rhodopsin-expressing ROS in the neuroepithelial layer of the retina. This further suggests the rescue/preservation of rod photo receptors containing functional outer segments and is consistent with the result that there is photoreceptor rescue in the ONL.

Immunostaining for the calcium-binding protein, calretinin, was also evaluated. Calretinin is expressed in neurons of the central nervous system, but its precise function has not yet been elucidated. In the rat, calretinin expression has been demonstrated in amacrine cells located in the INL, retinal ganglion cells in the GCL, and labels 3 bands in the IPL, the site for synaptic junctions between the INL and GCL. All three layers staining positively for calretinin were quantitated. While there was not an impressive difference that could be detected visually in the calretinin staining between control and umbilicus-derived cell injected eyes, there was a small but statistically significant increase found morphometric ally. This 1.2 fold increase in overall calretinin immunostaining suggested a preservation of calretinin-expressing cells in the retina. Quantitation of calretinin immunostaining was subsequently performed on the INL and GCL individually to determine if this effect was specific to a particular layer of the retina. There was no difference in the calretinin staining in the GCL, however there was a 1.5 fold increase in staining in the INL, suggesting a preservation of calretinin-expressing cells in the inner nuclear layer, possibly amacrine cells.

Recoverin immunostaining was performed on the day 60 specimens. Recoverin is a calcium-binding protein localized to photoreceptor cell bodies in the outer nuclear layer, as well as midget cone bipolar cells in the inner nuclear layer. Recoverin immunostaining was visibly increased in umbilicus-derived cell-injected eyes compared with controls, suggesting a preservation of one or more cell types. Morphometry was performed on recoverin staining in the INL and ONL. There was a statistically significant increase in recoverin immunostaining in umbilicus-derived cell injected eyes compared with controls in both layers evaluated, suggesting a preservation of photoreceptors in the ONL and of recover in-expressing cells in the INL, possibly cone bipolar cells.

Taken together, the increase in ONL thickness, rhodopsin, calretinin, and recoverin immunostaining in umbilicus-derived cell-injected eyes compared with controls suggest preservation in the structure of the retina through rescue of photoreceptors, functional rod outer segments and possibly bipolar neurons responsible for relaying information from the retina to the brain. These results provide support for the functional findings that umbilicus-derived cell subretinal injection preserves vision in dystrophic RCS rats. The mechanism of action of umbilicus-derived cells remains to be elucidated. There has been no evidence of differentiation of umbilicus-derived cells into photoreceptors or other retinal cell types. In fact, only a small fraction (less than 10%) of injected umbilicus-derived cells are detectable by quantitative RT-PCR for a human-specific gene 60 days post-injection. If the cells do not survive over the course of time in which there is a therapeutic effect, perhaps the mechanism is that the cells secrete a neurotrophic factor which slows the apoptotic wave in the photoreceptor population, thereby allowing for preservation of not only photoreceptors, but their supporting cells as well. Umbilicus-derived cells are currently being characterized in vitro to address secretory factors and mechanistic studies are in progress.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE 1-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success under conditions tested

TABLE 1-2

Isolation and culture expansion of postpartum cells under varying conditions:

| Condition | Medium | 15% FBS | BME | Gelatin | 20% O2 | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |
| 7 | DMEM-Lg | N (2%) | Y | N (Fibrone) | Y | PDGF/VEGF |
| 8 | DMEM-Lg | N (2%) | Y | N (Fibrone) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibrone) | Y | PDGF/VEGF |
| 16 | DMEM-Lg | N (2%) | N | N (Fibrone) | N (5%) | PDGF/VEGF |

TABLE 2-1

Growth characteristics for different cell populations grown to senescence

| Cell Type | Senescence | Total Population Doublings | Total Cell Yield |
|---|---|---|---|
| MSC | 24 d | 8 | 4.72 E7 |
| Adipose | 57 d | 24 | 4.5 E12 |
| Fibroblasts | 53 d | 26 | 2.82 E13 |
| Umbilicus | 65 d | 42 | 6.15 E17 |
| Placenta | 80 d | 46 | 2.49 E19 |

TABLE 2-2

Growth characteristics for different cell populations using low density growth expansion from passage 10 till senescence

| Cell Type | Senescence | Total Population Doublings | Total Cell Yield |
|---|---|---|---|
| Fibroblast (P10) | 80 d | 43.68 | 2.59 E11 |
| Umbilicus (P10) | 80 d | 53.6 | 1.25 E14 |
| Placenta (P10) | 60 d | 32.96 | 6.09 E12 |

TABLE 3-1

Culture Media

| Culture Medium | Supplier | Added fetal bovine serum % (v/v) |
|---|---|---|
| DMEM low glucose | Gibco Carlsbad CA | 0, 2 10 |
| DMEM high glucose | Gibco | 0, 2 10 |
| RPMI 1640 | Mediatech, Inc. Herndon, VA | 0, 2 10 |
| Cell gro-free (Serum-free, Protein-free | Mediatech, Inc. | — |
| Ham's F10 | Mediatech, Inc. | 0, 2 10 |

TABLE 3-1-continued

Culture Media

| Culture Medium | Supplier | Added fetal bovine serum % (v/v) |
|---|---|---|
| MSCGM (complete with serum) | Cambrex, Walkersville, MD | 0, 2 10 |
| Complete-serum free w/albumin | Mediatech, Inc. | — |
| Growth Medium | NA | — |
| Ham's F12 | Mediatech, Inc. | 0, 2 10 |
| Iscove's | Mediatech, Inc. | 0, 2 10 |
| Basal Medium Eagle's | Mediatech, Inc. | |
| DMEM/F12 (1:1) | Mediatech, Inc. | 0, 2 10 |

TABLE 6-1

Results of PPDC karyotype analysis

| Tissue | passage | Metaphase cells counted | Metaphase cells analyzed | Number of karyotypes | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |

Key:
N—Neonatal aspect;
V—villous region;
M—maternal aspect;
C—clone

TABLE 7.1

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

TABLE 9-1

Cells analyzed by the microarray study. Cell lines are listed by identification code along with passage at time of analysis, cell growth substrate and growth medium.

| Cell Population | Passage | Substrate | Medium |
|---|---|---|---|
| Umbilicus (022803) | 2 | Gelatin | DMEM, 15% FBS, 2-ME |
| Umbilicus (042103) | 3 | Gelatin | DMEM, 15% FBS, 2-ME |
| Umbilicus (071003) | 4 | Gelatin | DMEM, 15% FBS, 2-ME |
| Placenta (042203) | 12 | Gelatin | DMEM, 15% FBS, 2-ME |
| Placenta (042903) | 4 | Gelatin | DMEM, 15% FBS, 2-ME |
| Placenta (071003) | 3 | Gelatin | DMEM, 15% FBS, 2-ME |
| ICBM (070203) (5% 02) | 3 | Plastic | MEM, 10% FBS |
| ICBM (062703) (std. O2) | 5 | Plastic | MEM, 10% FBS |
| ICBM (062703) (5% 02) | 5 | Plastic | MEM, 10% FBS |
| hMSC (Lot 2F1655) | 3 | Plastic | MSCGM |
| hMSC (Lot 2F1656) | 3 | Plastic | MSCGM |
| hMSC (Lot 2F 1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

TABLE 9-2

The Euclidean Distances for the Cell Pairs.

| Cell Pair | Euclidean Distance |
|---|---|
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

TABLE 9-3

Genes shown to have specifically increased expression in the placenta-derived cells as compared to other cell lines assayed
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |

TABLE 9-3-continued

Genes shown to have specifically increased expression in the placenta-derived cells as compared to other cell lines assayed
Genes Increased in Placenta-Derived Cells

| Probe Set ID | Gene Name | NCBI Accession Number |
|---|---|---|
| 206067_s_at | Wilms tumor 1 | NM_024426 |
| 207016_s_at | aldehyde dehydrogenase 1 family, member A2 | AB015228 |
| 206367_at | renin | NM_000537 |
| 210004_at | oxidized low density lipoprotein (lectin-like) receptor 1 | AF035776 |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 9-4

Genes shown to have specifically increased expression in the umbilicus-derived cells as compared to other cell lines assayed
Genes Increased in Umbilicus-Derived Cells

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 9-5

Genes shown to have decreased expression in umbilicus- and placenta-derived cells as compared to other cell lines assayed
Genes Decreased in Umbilicus- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | *Homo sapiens* mRNA; cDNA DKFZp586M2022 (from clone DKFZp586M2022) | N91149 |
| 206201_s_at | mesenchyme homeobox 2 (growth arrest-specific homeo box) | NM_005924.1 |
| 205817_at | sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_nt | a rc homology three (SH3) and cysteine rich donatia | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (*Drosophila*) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |

TABLE 9-5-continued

Genes shown to have decreased expression in umbilicus- and placenta-derived cells as compared to other cell lines assayed
Genes Decreased in Umbilicus- and Placenta-Derived Cells

| Probe Set ID | Gene name | NCBI Accession Number |
|---|---|---|
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeo box 5 | NM_005221.3 |
| 218181_s_at | hypothetical protein FLJ20373 | NM_017792.1 |
| 209160_at | aido-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

TABLE 9-6

Genes that were shown to have increased expression in fibroblasts as compared to the other cell lines assayed.
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 9-7

Genes that were shown to have increased expression in the ICBM-derived cells as compared to the other cell lines assayed.
Genes Increased in ICBM Cells cardiac ankyrin repeat protein
MHC class I region ORF
integrin, alpha 10
hypothetical protein FLJ22362
UDP-N-acetyl-alpha-D-galactosamine: polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 9-8

Genes that were shown to have increased expression in the MSC cells as compared to the other cell lines assayed.
Genes Increased in MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42

TABLE 9-8-continued

Genes that were shown to have increased expression in the MSC cells as compared to the other cell lines assayed.
Genes Increased in MSC Cells nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

TABLE 10-1

Primers used

| Primer name | Primers |
|---|---|
| Oxidized LDL receptor | S: 5'-GAGAAATCCAAAGAGCAAATGG-3' (SEQ ID NO: 1)<br>A: 5'-AGAATGGAAAACTGGAATAGG-3' (SEQ ID NO: 2) |
| Renin | S: 5'-TCTTCGATGCTTCGGATTCC-3' (SEQ ID NO: 3)<br>A: 5'-GAATTCTCGGAATCTCTGTTG-3' (SEQ ID NO: 4) |
| Reticulon | S: 5'-TTACAAGCAGTGCAGAAAACC-3' (SEQ ID NO: 5)<br>A: 5'-AGTAAACATTGAAACCACAGCC-3' (SEQ ID NO: 6) |
| Interleukin-8 | S: 5'-TCTGCAGCTCTGTGTGAAGG-3' (SEQ ID NO: 7)<br>A: 5'-CTTCAAAAACTTCTCCACAACC-3' (SEQ ID NO: 8) |
| Chemokine (CXC) ligand 3 | S: 5'-CCCACGCCACGCTCTCC-3' (SEQ ID NO: 9)<br>A: 5'-TCCTGTCAGTTGGTGCTCC-3' (SEQ ID NO: 10) |

TABLE 10-2

IL-8 protein amount measured by ELISA

| Cell type | IL-8 |
|---|---|
| hFibro | ND |
| Placenta Isolate 1 | ND |
| Umb Isolate 1 | 2058.42 ± 144.67 |
| Placenta Isolate 2 | ND |
| Umb Isolate 2 | 2368.86 ± 22.73 |
| Placenta Isolate3 (normal $O_2$) | 17.27 ± 8.63 |
| Placenta Isolate 3 (low $O_2$, W/O BME) | 264.92 ± 9.88 |

Results of the ELISA assay for interleukin-8 (IL-8) performed on placenta- and umbilicus-derived cells as well as human skin fibroblasts. Values are presented here are picograms/million cells, n = 2, sem.
ND: Not Detected

TABLE 11-1

Antibodies

| Antibody | Manufacturer | Catalog Number |
|---|---|---|
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

TABLE 11-2

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| | Plate ID: Plate1 | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |

TABLE 11-2-continued

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 | Proliferation baseline of receiver | 84 | 242 | 208 | 178.0 | 83.16 | 46.7 |
| (allogenic donor) | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |

Plate ID: Plate 2

| | | | | | | | |
|---|---|---|---|---|---|---|---|
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 11-3

Average stimulation index of placenta cells and an allogeneic donor in a mixed lymphocyte reaction with six individual allogeneic receivers
Average Stimulation Index

| | Recipient | Placenta |
|---|---|---|
| Plate 1 (receivers 1-3) | 279 | 3 |
| Plate 2 (receivers 4-6) | 46.25 | 1.3 |

TABLE 11-4

Mixed Lymphocyte Reaction Data- Cell Line A (Umbilicus)
DPM for Proliferation Assay

| Analytical number | Culture System | Replicates 1 | 2 | 3 | Mean | SD | CV |
|---|---|---|---|---|---|---|---|

Plate ID: Plate1

| | | | | | | | |
|---|---|---|---|---|---|---|---|
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |

TABLE 11-4-continued

Mixed Lymphocyte Reaction Data- Cell Line A (Umbilicus)
DPM for Proliferation Assay

| Analytical number | Culture System | Replicates 1 | 2 | 3 | Mean | SD | CV |
|---|---|---|---|---|---|---|---|
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 11-5

Average stimulation index of umbilicus-derived cells and an allogeneic donor in a mixed lymphocyte reaction with five individual allogeneic receivers.

| | Average Stimulation Index | |
|---|---|---|
| | Recipient | Umbilicus |
| Plate 1 (receivers 1-4) | 42.75 | 6.5 |
| Plate 2 (receiver 5) | 70 | 9 |

TABLE 12-1

ELISA assay results

| | MCP-1 | IL-6 | VEGF | SDF-1α | GCP-2 | IL-8 | TGF-β2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilicus (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilicus (071003) | 2794 ± 84 | 1356 ± 43 | ND | ND | 2184 ± 98 | 2369 ± 23 | ND |
| Placenta (101503) BME | 21 ± 10 | 67 ± 3 | ND | ND | 44 ± 9 | 17 ± 9 | ND |
| Placenta (101503) 5% O$_2$, W/O BME | 77 ± 16 | 339 ± 21 | ND | 1149 ± 137 | 54 ± 2 | 265 ± 10 | ND |

(values presented are picograms/milliliter/million cells (n = 2, sem)
Key: ND: Not Detected.

TABLE 12-2

SearchLight Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key:
hFB (human fibroblasts), P1 (placenta-derived cells (042303)), U1 (umbilicus-derived cells (022803)), P3 (placenta-derived cells(071003)), U3 (umbilicus-derived cells (071003)).
ND: Not Detected.

TABLE 12-3

SearchLight Multiplexed ELISA assay results

| | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key:
hFB (human fibroblasts), P1 (placenta-derived PPDC (042303)), U1 (umbilicus-derived PPDC (022803)), P3 (placenta-derived PPDC (071003)), U3 (umbilicus-derived PPDC (071003)).
ND: Not Detected.

TABLE 13-1

Summary of Primary Antibodies Used

| Antibody | Concentration | Vendor |
|---|---|---|
| Rat 401 (nestin) | 1:200 | Chemicon, Temecula, CA |
| Human Nestin | 1:100 | Chemicon |
| TuJ1 (BIII Tubulin) | 1:500 | Sigma, St. Louis, MO |
| GFAP | 1:2000 | DakoCytomation, Carpinteria, CA |
| Tyrosine hydroxylase (TH) | 1:1000 | Chemicon |
| GABA | 1:400 | Chemicon |
| Desmin (mouse) | 1:300 | Chemicon |
| alpha - alpha-smooth muscle actin | 1:400 | Sigma |
| Human nuclear protein (hNuc) | 1:150 | Chemicon |

TABLE 13-2

Summary of Conditions for Two-Stage Differentiation Protocol

| COND. # | A<br>PRE-DIFFERENTIATION | B<br>2$^{nd}$ STAGE DIFF |
|---|---|---|
| 1 | NPE + F (20 ng/ml) + E (20 ng/ml) | NPE + SHH (200 ng/ml) + F8 (100 ng/ml) |
| 2 | NPE + F (20 ng/ml) + E (20 ng/ml) | NPE + SHH (200 ng/ml) + F8 (100 ng/ml) + RA (1 μM) |
| 3 | NPE + F (20 ng/ml) + E (20 ng/ml) | NPE + RA (1 μM) |
| 4 | NPE + F (20 ng/ml) + E (20 ng/ml) | NPE + F (20 ng/ml) + E (20 ng/ml) |
| 5 | NPE + F (20 ng/ml) + E (20 ng/ml) | Growth Medium |
| 6 | NPE + F (20 ng/ml) + E (20 ng/ml) | Condition 1B + MP52 (20 ng/ml) |
| 7 | NPE + F (20 ng/ml) + E (20 ng/ml) | Condition 1B + BMP7 (20 ng/ml) |
| 8 | NPE + F (20 ng/ml) + E (20 ng/ml) | Condition 1B + GDNF (20 ng/ml) |
| 9 | NPE + F (20 ng/ml) + E (20 ng/ml) | Condition 2B + MP52 (20 ng/ml) |
| 10 | NPE + F (20 ng/ml) + E (20 ng/ml) | Condition 2B + BMP7 (20 ng/ml) |
| 11 | NPE + F (20 ng/ml) + E (20 ng/ml) | Condition 2B + GDNF (20 ng/ml) |
| 12 | NPE + F (20 ng/ml) + E (20 ng/ml) | Condition 3B + MP52 (20 ng/ml) |
| 13 | NPE + F (20 ng/ml) + E (20 ng/ml) | Condition 3B + BMP7 (20 ng/ml) |
| 14 | NPE + F (20 ng/ml) + E (20 ng/ml) | Condition 3B + GDNF (20 ng/ml) |
| 15 | NPE + F (20 ng/ml) + E (20 ng/ml) | NPE + MP52 (20 ng/ml) |
| 16 | NPE + F (20 ng/ml) + E (20 ng/ml) | NPE + BMP7 (20 ng/ml) |
| 17 | NPE + F (20 ng/ml) + E (20 ng/ml) | NPE + GDNF (20 ng/ml) |

TABLE 14-1

Summary of Primary Antibodies Used

| Antibody | Concentration | Vendor |
|---|---|---|
| TuJ1 (βIII Tubulin) | 1:500 | Sigma, St. Louis, MO |
| GFAP | 1:2000 | DakoCytomation, Carpinteria, CA |

TABLE 15-1

Summary of Primary Antibodies Used

| Antibody | Concentration | Vendor |
|---|---|---|
| Rat 401 (nestin) | 1:200 | Chemicon, Temecula, CA |
| TuJ1 (βIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpinteria, CA |
| Myelin Basic Protein (MBP) | 1:400 | Chemicon |

TABLE 15-2

Quantification of progenitor differentiation in control vs transwell co-culture with umbilical-derived cells (E = EGF, F = bFGF)

| Antibody | F + E/Umb [Cond. 1] | F + E/F + E [Cond. 4] | F + E/removed [Cond. 5] |
|---|---|---|---|
| TuJ1 | 8.7% | 2.3% | 3.6% |
| GFAP | 47.2% | 30.2% | 10.9% |
| MBP | 23.0% | 0% | 0% |
| Nestin | 13.4% | 71.4% | 39.4% |

TABLE 18-1

ERG data

| Group | a-wave Untreated | a-wave Treated | mixed b-wave Untreated | mixed b-wave Treated | cone b-wave Untreated | cone b-wave Treated | % rod contribution Untreated | % rod contribution Treated |
|---|---|---|---|---|---|---|---|---|
| Sham 60d | 0 | 0 | 7 ± 9 | 0 | 23 ± 5 | 12 ± 16 | N/A | N/A |
| 1 (n = 4) 60d | 0 | 20 ± 20 | 1.5 ± 2 | 81 ± 72 | 7 ± 7 | 50 ± 19 | N/A | 30 |
| 3 (n = 6) 60d | 0 | 27 ± 11 | 18 ± 13 | 117 ± 67 | 28 ± 11 | 55 ± 25 | 6 ± 7 | 49 ± 16 |
| 3 (n = 6) 90d | 0 | 15 ± 7 | 0 | 37 ± 15 | 7 ± 5 | 16 ± 11 | 0 | 58 ± 39 |

N.B. Sham = control (medium only),
1 = Placental cell transplant,
3 = Umbilical cell transplant

TABLE 19.1

Summary of Primary Antibodies Used

| Antibody | Concentration | Vendor |
|---|---|---|
| Rat 401 (nestin) | 1:200 | Chemicon, Temecula, CA |
| TuJ1 (βIII Tubulin) | 1:500 | Sigma, St. Louis, MO |
| Tyrosine hydroxylase (TH) | 1:1000 | Chemicon |
| GABA | 1:400 | Chemicon |
| GFAP | 1:2000 | DakoCytomation, Carpinteria, CA |
| Myelin Basic Protein (MBP) | 1:400 | Chemicon |

TABLE 19-2

Quantification of progenitor differentiation in control vs transwell co-culture with umbilical-derived cells (E = EGF, F = bFGF)

| Antibody | F + E/Umb [Cond. 1] | F + E/F + E [Cond. 4] | F + E/removed [Cond. 5] |
|---|---|---|---|
| TuJ1 | 8.7% | 2.3% | 3.6% |
| GFAP | 47.2% | 30.2% | 10.9% |
| MBP | 23.0% | 0% | 0% |
| Nestin | 13.4% | 71.4% | 39.4% |

TABLE 22-1

TUNEL Area Analysis at Post Natal Day 29

| Group | P29 (8 days post treatment) DAPI+ area (pixels) | P29 (8 days post treatment) % TUNEL+ |
|---|---|---|
| Congenic untreated (healthy) | 373,812 ± 12,832 | 0.2 ± 0.2% |
| Dystrophic-untreated | — | — |
| Dystrophic-sham (vehicle only) | 222,016 ± 23,242 | 16.0 ± 2.3% |
| Dystrophic-hUTC injected (20,000 cells) | 229,666 ± 6,383 | 6.6 ± 0.5% |

TABLE 25-1

| Integrin | hUTC | ARPE-19 | Fetal RPE * |
|---|---|---|---|
| α1 | − | − | + |
| α2 | + | − | + |

TABLE 25-1-continued

| Integrin | hUTC | ARPE-19 | Fetal RPE * |
|---|---|---|---|
| α3 | + | + | + |
| α4 | + | + | + |
| α5 | + | + | + |
| β1 | + | + | + |
| α5 β1 | − | − | + |
| α2β1 | + | + | + |

TABLE 26-1

Reagents used in first step in SuperScript III First-Strand Synthesis:

| | Component: | | | |
|---|---|---|---|---|
| | Total RNA | 50 μM oligo (dT)20 | 10 mM dNTP mix | DEPC-treated water |
| Amount: | 2 μg | 2 μL | 2 μL | To raise volume to 20 μL |

TABLE 26-2

Reagents used in cDNA Synthesis Mix:

| | Component: | | | | |
|---|---|---|---|---|---|
| | 10X RT buffer | 25 mM MgCl$_2$ | 0.1M DTT | RNaseOUT. (40 U/μl) | SuperScript. III RT |
| Amount: | 4 μL | 8 μL | 4 μL | 2 μL | 2 μL |

TABLE 26-3

Reagents used in Master Mix for the RT-PCR reaction:

| | Component: | | | |
|---|---|---|---|---|
| | Master Mix | cDNA | dH$_2$0 | TaqMan ® Gene Expression Assays |
| Amount: | 10 μL | 3 μL | 6 μL | 1 μL |

TABLE 26-4

TaqMan ® gene expression assays for real time RT-PCR analysis:

| Abbreviation | Name | Taqman Gene Expression Assay | Proposed function in the eye |
|---|---|---|---|
| CRALBP | Cellular retinaldehyde-binding protein | HS00165632_m1 | Regeneration of visual pigment in RPE |
| MERTK | c-mer proto oncogene tyrosine kinase | HS00179024_m1 | ROS phagocytosis (ROS internalization) |
| GAS6 | growth arrest specific-6 (ligand for MERTK) | Hs00181323_m1 | ROS phagocytosis (ROS internalization) |
| CD36 | lipid scavenger receptor CD36 | HS00169627_m1 | ROS phagocytosis (ROS internalization) |
| INTaV | Integrin alpha V | Hs00233808_m1 | ROS phagocytosis (ROS binding) |
| INTB5 | Integrin beta 5 | Hs00174435_m1 | ROS phagocytosis (ROS binding) |
| CATD | Cathepsin D | Hs00157205_m1 | ROS degradation (lysosomal enzyme) |
| CFH | Complement Factor H | HS00164830_m1 | Mediates inflammation |

TABLE 26-5

Calculated ΔCT values for each target. Values were normalized to GAPDH (endogenous control). Fold change is $2^{\Delta\Delta Ct}$. Smaller ΔCT values represent increased gene expression.

| | MERTK | CRALBP | GAS6 | INTAV | INTB5 | CD36 | CATHD | CFH |
|---|---|---|---|---|---|---|---|---|
| Untreated | 16.6 ± 1.2 | 21 ± 3.9 | 3.5 ± 0.3 | 5.5 ± 2.2 | 2.9 ± 0.4 | 14.4 ± 1.0 | 2.1 ± 1.5 | 8.2 ± 0.2 |
| hUTC Treatment | 11.8 ± 0.6 | 14.3 ± 2.6 | 5.0 ± 1.1 | 2.5 ± 0.5 | 3.0 ± 1.5 | 15.3 ± 1.3 | 0.3 ± 0.6 | 2.8 ± 0.2 |

TABLE 27-4

Trophic Factor Secretion by hUTC

| Sample | | hUTC | hUTC | hFIb. | hFIb. |
|---|---|---|---|---|---|
| FGF-b | pg/ml/million | 64.06 | 74.00 | 7.43 | 7.64 |
| HGF | pg/ml/million | 980.23 | 703.24 | 37.76 | 30.54 |
| KGF | pg/ml/million | 50.78 | 41.15 | 81.28 | 63.43 |
| VEGF | pg/ml/million | 118.00 | 90.80 | 202.52 | 165.96 |
| GRO-a | pg/ml/million | 3758.52 | 2398.48 | 795.43 | 760.72 |
| MCP1 | pg/ml/million | 948.56 | 625.71 | 218.83 | 182.95 |
| GMCSF | pg/ml/million | 400.16 | 267.54 | 129.11 | 150.81 |
| IL6 | pg/ml/million | 103.57 | 69.23 | 75.39 | 55.46 |
| IL8 | pg/ml/million | 7308.60 | 3832.09 | 3843.18 | 2781.39 |
| TNFa | pg/ml/million | 21.72 | 6.91 | 6.91 | 6.91 |
| B-NGF | pg/ml/million | 5.16 | 1.18 | 10.06 | 8.28 |
| BDNF | pg/ml/million | 525.38 | 432.08 | 220.41 | 191.69 |
| CNTF | pg/ml/million | 102.11 | 74.58 | 55.06 | 10.00 |
| NT-3 | pg/ml/million | 33.29 | 16.78 | 22.87 | 21.38 |
| NT-proBN | pg/ml/million | 24.14 | 21.91 | 14.92 | 12.56 |
| TGFb | pg/ml/million | 662.45 | 718.24 | 1144.50 | 298.62 |

TABLE 27-5

IGF Secretion buy hUTC

| | IGF(ng/ml/million) | SD |
|---|---|---|
| hUTC | 43529.41 | 43.53 |
| Fib | 24759.26 | 24.70 |

What is claimed is:

1. A method for promoting axonal regeneration in an optic nerve in a patient having optic nerve trauma comprising administering to the optic nerve isolated umbilicus-derived cells isolated from human umbilical cord tissue substantially free of blood, in an amount effective to promote axonal regeneration, wherein the isolated umbilicus-derived cells are capable of self-renewal and expansion in culture, have the potential to differentiate into cells of at least a neural phenotype, maintain a normal karyotype upon passaging and lack production of CD117.

2. The method of claim 1, wherein the isolated umbilicus-derived cells further have the following characteristics:
   a) potential for at least 40 population doublings in culture;
   b) production of CD10, CD13, CD44, CD73, and CD90;
   c) lack of production of CD31, CD34, CD45, and CD141; and
   d) increased expression of genes encoding interleukin 8 and reticulon 1 relative to a human cell that is a fibroblast, a mesenchymal stem cell, or an iliac crest bone marrow cell.

3. The method of claim 2, wherein the isolated umbilicus-derived cells are positive for HLA-A,B,C, and negative for HLA-DR,DP,DQ.

4. The method of claim 1, wherein the isolated umbilicus-derived cells are expanded in culture prior to administering to the optic nerve.

5. The method of claim 1, wherein the isolated umbilicus-derived cells are administered with at least one other agent.

6. The method of claim 5, wherein the at least one other agent is administered simultaneously with, or before, or after, the isolated umbilicus-derived cells.

7. The method of claim 1, wherein the isolated umbilicus-derived cells are administered through a cannula or from a device inserted in the patient's eye.

8. The method of claim 1, wherein the isolated umbilicus-derived cells are administered by insertion of a matrix or scaffold containing the cells.

9. A method for preserving the outer nuclear layer of a retina in a patient with retinal degeneration comprising administering to the interior of the patient's eye isolated umbilicus-derived cells isolated from human umbilical cord tissue substantially free of blood, in an amount effective to preserve the outer nuclear layer, wherein the isolated umbilicus-derived cells are capable of self-renewal and expansion in culture, have the potential to differentiate into cells of at least a neural phenotype, maintain a normal karyotype upon passaging and lack production of CD117.

10. The method of claim 9, wherein the isolated umbilicus-derived cells further have the following characteristics:
    a) potential for at least 40 population doublings in culture;
    b) production of CD10, CD13, CD44, CD73, and CD90;
    c) lack of production of CD31, CD34, CD45, and CD141; and
    d) increased expression of genes encoding interleukin 8 and reticulon 1 relative to a human cell that is a fibroblast, a mesenchymal stem cell, or an iliac crest bone marrow cell.

11. The method of claim 10, wherein the isolated umbilicus-derived cells are positive for HLA-A,B,C, and negative for HLA-DR,DP,DQ.

12. The method of claim 9, wherein the isolated umbilicus-derived cells are expanded in culture prior to administering to the interior of the patient's eye.

13. The method of claim 9, wherein the isolated umbilicus-derived cells are administered with at least one other agent.

14. The method of claim 13, wherein the at least one other agent is administered simultaneously with, or before, or after, the isolated umbilicus-derived cells.

15. The method of claim 9, wherein the isolated umbilicus-derived cells are administered through a cannula or from a device inserted in the patient's eye.

16. The method of claim 9, wherein the isolated umbilicus-derived cells are administered by insertion of a matrix or scaffold containing the cells.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
gagaaatcca aagagcaaat gg                                            22

<210> SEQ ID NO 2
<211> LENGTH: 21
<212> TYPE: DNA
<213> ORGANISM: Artificial Sequence
<220> FEATURE:
<223> OTHER INFORMATION: Synthetic primer

<400> SEQUENCE: 2
agaatggaaa actggaatag g                                             21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tcttcgatgc ttcggattcc                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
gaattctcgg aatctctgtt g                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
ttacaagcag tgcagaaaac c                                             21

<210> SEQ ID NO 6
<211> LENGTH: 22
<212> TYPE: DNA
<213> ORGANISM: Artificial Sequence
<220> FEATURE:
<223> OTHER INFORMATION: Synthetic primer

<400> SEQUENCE: 6
agtaaacatt gaaaccacag cc                                            22

<210> SEQ ID NO 7
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 7
tctgcagctc tgtgtgaagg                                               20

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8
cttcaaaaac ttctccacaa cc                                            22

<210> SEQ ID NO 9
<211> LENGTH: 17
<212> TYPE: DNA
<213> ORGANISM: Artificial Sequence
<220> FEATURE:
<223> OTHER INFORMATION: Synthetic primer

<400> SEQUENCE: 9
cccacgccac gctctcc                                                  17

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
tcctgtcagt tggtgctcc                                                19

<210> SEQ ID NO 11
<211> LENGTH: 36
<212> TYPE: PRT
<213> ORGANISM: Artificial Sequence
<220> FEATURE:
<223> OTHER INFORMATION: Synthetic Construct

<400> SEQUENCE: 11

Ala Arg Gly Ala Leu Ala Ala Ser Pro Ala Leu Ala Ala Arg Gly Ala
1               5                   10                  15

Leu Ala Ala Ser Pro Ala Leu Ala Ala Arg Gly Ala Leu Ala Ala Ser
            20                  25                  30

Pro Ala Leu Ala
        35

<210> SEQ ID NO 12
<211> LENGTH: 30
<212> TYPE: PRT
<213> ORGANISM: Artificial Sequence
<220> FEATURE:
<223> OTHER INFORMATION: Synthetic Construct

<400> SEQUENCE: 12

Leu Tyr Ser Leu Glu Ala Ser Pro Leu Glu Leu Tyr Ser Leu Glu Ala
1               5                   10                  15

Ser Pro Leu Glu Leu Tyr Ser Leu Glu Ala Ser Pro Leu Glu
            20                  25                  30
```